US009526777B2

(12) United States Patent
Sullivan et al.

(10) Patent No.: US 9,526,777 B2
(45) Date of Patent: Dec. 27, 2016

(54) METHODS FOR THE INDUCTION OF EBOLA VIRUS-SPECIFIC IMMUNE RESPONSES COMPRISING ADMINISTERING A REPLICATION-DEFECTIVE CHIMPANZEE ADENOVIRUS VECTOR EXPRESSING THE EBOLA VIRUS GLYCOPROTEIN

(75) Inventors: Nancy J. Sullivan, Kensington, MD (US); Gary J. Nabel, Washington, DC (US); Clement Asiedu, Olney, MD (US); Cheng Cheng, Rockville, MD (US); Alfredo Nicosia, Rome (IT); Riccardo Cortese, Rome (IT); Virginia Ammendola, Naples (IT); Stefano Colloca, Rome (IT)

(73) Assignees: The United States of America as Represented by the Department of Health and Human Services, Washington, DC (US); Glaxosmithkline Biologicals SA, Rixensart (BE)

( * ) Notice: Subject to any disclaimer, the term of this patent is extended or adjusted under 35 U.S.C. 154(b) by 27 days.

(21) Appl. No.: 13/641,655

(22) PCT Filed: Apr. 15, 2011

(86) PCT No.: PCT/US2011/032682
§ 371 (c)(1),
(2), (4) Date: Jan. 2, 2013

(87) PCT Pub. No.: WO2011/130627
PCT Pub. Date: Oct. 20, 2011

(65) Prior Publication Data
US 2013/0101618 A1 Apr. 25, 2013

Related U.S. Application Data

(60) Provisional application No. 61/325,166, filed on Apr. 16, 2010.

(51) Int. Cl.
*A61K 39/295* (2006.01)
*A61K 39/12* (2006.01)
*A61K 39/00* (2006.01)

(52) U.S. Cl.
CPC ....... *A61K 39/12* (2013.01); *A61K 2039/5254* (2013.01); *A61K 2039/5256* (2013.01); *A61K 2039/545* (2013.01); *C12N 2710/10343* (2013.01); *C12N 2760/14134* (2013.01)

(58) Field of Classification Search
CPC .............. A61K 39/12; A61K 2039/545; A61K 2039/5254; A61K 2039/5256; C12N 2710/10343; C12N 2760/14134
See application file for complete search history.

(56) References Cited

U.S. PATENT DOCUMENTS

| 8,101,739 B2* | 1/2012 | Sullivan et al. ........... 536/23.72 |
| 2006/0211115 A1 | 9/2006 | Roy et al. |
| 2009/0215871 A1 | 8/2009 | Wilson et al. |
| 2011/0129498 A1* | 6/2011 | Cortese et al. ............ 424/228.1 |

FOREIGN PATENT DOCUMENTS

| WO | 2006/133911 A2 | 12/2006 |
| WO | 2010/086189 A2 | 8/2010 |

OTHER PUBLICATIONS

Roy, S., et al., 2006, Generation of an adenoviral vaccine vector based on simian adenovirus 21, J. Gen. Virol. 87:2477-2485.*
Reyes-Sandoval, A., et al., Jan. 2010, Prime-boost immunization with adenoviral and modified vaccinia virus ankara vectors enhances the durability and polyfunctionality of protective malaria CD8+ T-cell responses, Infect. Immun. 78(1):145-153.*
Martin, J. E., et al., Nov. 2006, A DNA vaccine for Ebola virus is safe and immunogenic in a phase I clinical trial, Clin. Vacc. Immunol. 13(11):1267-1277.*
Falzarano, D., et al., 2011, Progress in filovirus vaccine development: evaluating the potential for clinical use, Expert Rev. Vaccines 10(1):63-77.*
Hoenen, T., et al., 2012, Current ebola vaccines, Expert Opin. Biol. Ther. 12(7):859-872.*
Hoenen, T., et al., May 2006, Ebola virus: unravelling pathogenesis to combat a deadly disease, TRENDS in Mol. Med. 12(5):206-215.*
Richardson, J. S., et al., Jun. 2010, Recent advances in Ebolavirus vaccine development, Human Vaccines 6(6):439-449.*
Roy, S., et al., "Generation of an adenoviral vaccine vector based on simian adenovirus 21," *Journal of General Virology*, vol. 87, pp. 2477-2485 (2006).
Extended European Search Report dated Feb. 2, 2015 for EP Patent Application No. 11769662.5, 12 pages.
Kobinger et al., "Chimpanzee adenovirus vaccine protects against Zaire Ebola virus", *Virology*, (346): 394-401 (2006).
Lee et al., "Viral vectors for use in the development of biodefense vaccines", *Advanced Drug Delivery Reviews*, (57): 1293-1314 (2005).
Reed et al., "Status and challenges of filovirus vaccines", *Vaccines*, (25): 1923-1934 (2007).

* cited by examiner

*Primary Examiner* — Jeffrey Parkin
(74) *Attorney, Agent, or Firm* — Kilpatrick Townsend & Stockton LLP

(57) ABSTRACT

This invention provides vaccines for inducing an immune response and protection against filovirus infection for use as a preventative vaccine in humans. In particular, the invention provides chimpanzee adenoviral vectors expressing filovirus proteins from different strains of Ebola virus (EBOV) or Marburg virus (MARV).

5 Claims, 13 Drawing Sheets

Figure 1A
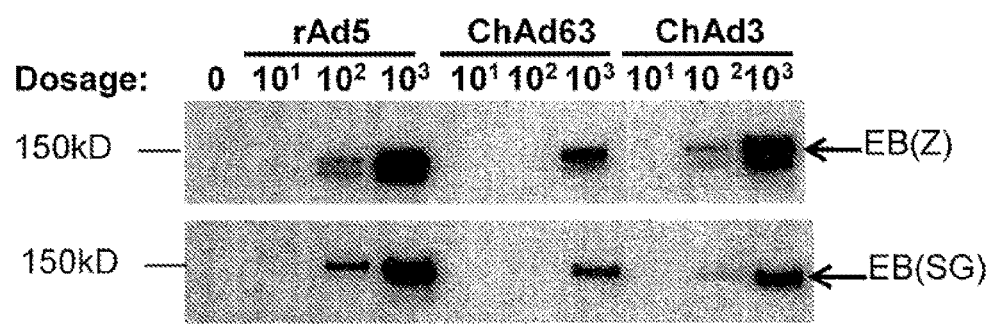
Figure 1B

Figure 6A
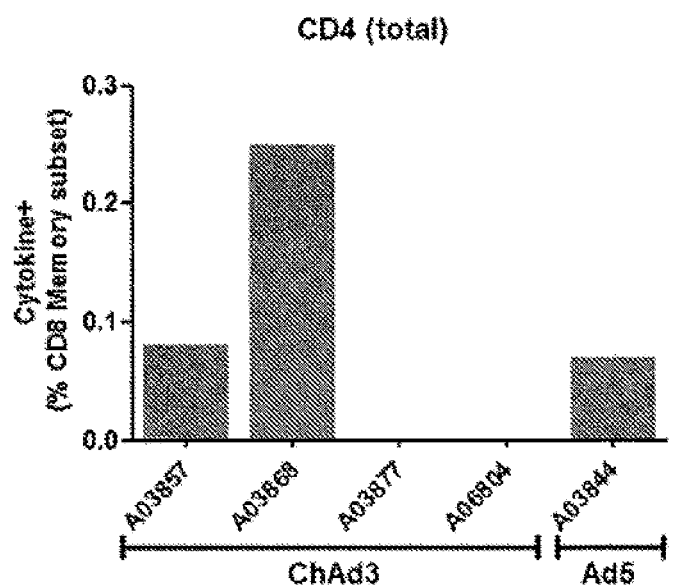
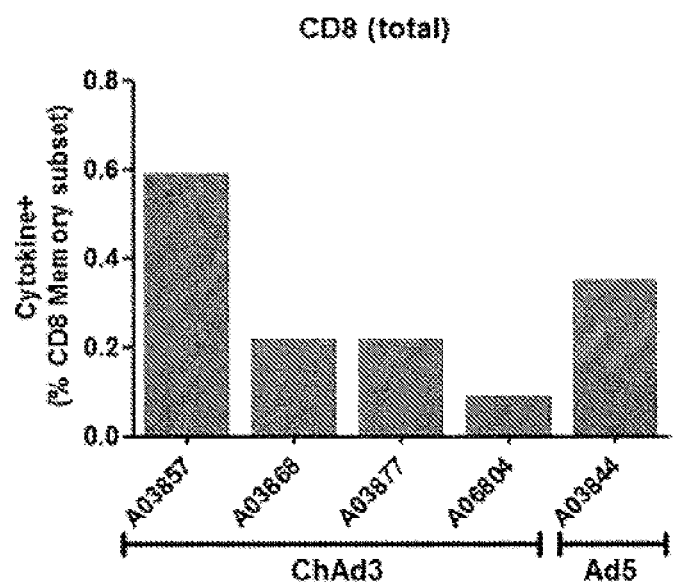
Figure 6B

Figure 7

| Vaccine | N | Survival |
|---|---|---|
| ChAd3-EBOV-GP | 4 | 100% |
| rAd5-EBOV-GP | 1 | 100%* |
| None | 1 | 0%** |

Figure 9A
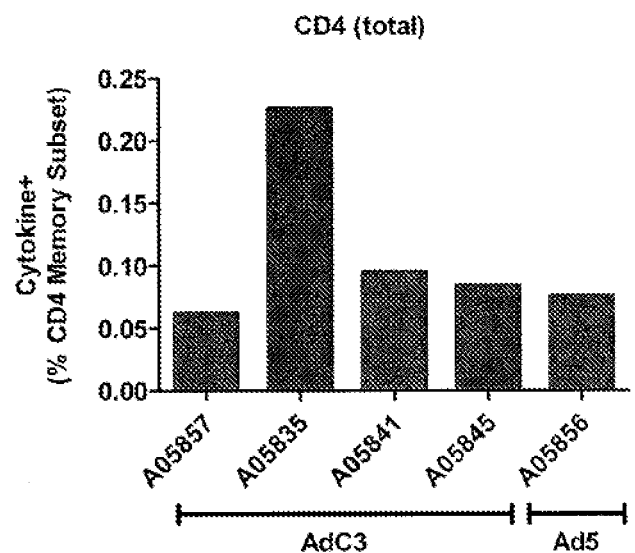
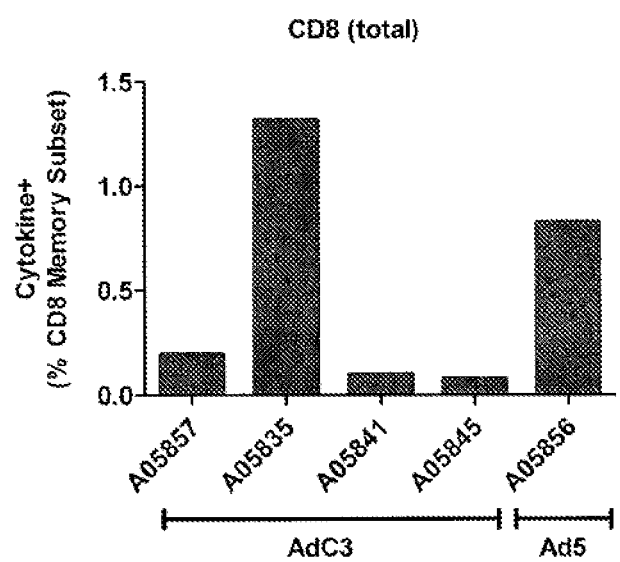
Figure 9B

Figure 10

| Vaccine | N | Survival |
|---|---|---|
| rChAd3-EBOV-GP | 4 | % |
| rAd5-EBOV-GP | 1 | 100%* |
| None | 1 | 0%** |

METHODS FOR THE INDUCTION OF EBOLA VIRUS-SPECIFIC IMMUNE RESPONSES COMPRISING ADMINISTERING A REPLICATION-DEFECTIVE CHIMPANZEE ADENOVIRUS VECTOR EXPRESSING THE EBOLA VIRUS GLYCOPROTEIN

CROSS-REFERENCES TO RELATED APPLICATIONS

This application is a US National Phase of PCT Application No. PCT/US2011/032682, filed Apr. 15, 2011, which claims the benefit of U.S. Patent Application No. 61/325,166, filed Apr. 16, 2010, each of which are incorporated herein by reference in their entirety.

REFERENCE TO SEQUENCE LISTING

This application includes a Sequence Listing as a text file named "77867-591100US-854933_SEQLIST.txt" created Oct. 15, 2012, and containing 387,507 bytes. The material contained in this text file is incorporated by reference in its entirety for all purposes.

FIELD OF THE INVENTION

This invention relates generally to viral vaccines and, more particularly, to filovirus vaccines based on chimpanzee adenoviral vectors.

BACKGROUND OF THE INVENTION

The Ebola viruses, and the genetically-related Marburg virus, viruses of the Filoviridae family, are associated with outbreaks of highly lethal hemorrhagic fever in humans and primates in North America, Europe, and Africa (Peters, C. J. et al. in: Fields Virology, eds. Fields, B. N. et al. 1161-1176, Philadelphia, Lippincott-Raven, 1996; Peters, C. J. et al. 1994 Semin Virol 5:147-154). Ebola viruses are negative-stranded RNA viruses comprised of five subtypes, including those described in the Zaire, Sudan, Reston, Ivory Coast and Bundibugyo episodes (Sanchez, A. et al. 1996 PNAS USA 93:3602-3607). The Ebola virus, was first recognized during an outbreak in 1976 in the Ebola River valley of Zaire (currently the Democratic Republic of the Congo), Africa. Mortality rates vary between different species, spanning from approximately 35 to 90% for the most virulent ones, Zaire and Sudan. The development of effective vaccines and/or drugs is a high priority. The Ebola (EBOV) and Marburg (MARV) viruses have also been categorized as priority class A pathogens due to their virulence, ease of dissemination, lack of effective countermeasures to prevent or treat them, and their potential to cause public panic and social disruption.

Although several subtypes have been defined, the genetic organization of Ebola viruses is similar, each containing seven linearly arrayed genes. Among the viral proteins, the envelope glycoprotein exists in two alternative forms, a 50-70 kilodalton (kDa) secreted protein of unknown function encoded by the viral genome and a 130 kDa transmembrane glycoprotein generated by RNA editing that mediates viral entry (Peters, C. J. et al. in: Fields Virology, eds. Fields, B. N. et al. 1161-1176, Philadelphia, Lippincott-Raven, 1996; Sanchez, A. et al. 1996 PNAS USA 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: Fields Virology, eds. Fields, B. N. et al. 1161-1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 PNAS USA 93:3602-3607), suggesting that immunization may be useful in protecting against this disease. Previous attempts to elicit protective immune responses against Ebola virus using traditional active and passive immunization approaches have, however, not succeeded in primates (Peters, C. J. et al. in: Fields Virology, eds. Fields, B. N. et al. 1161-1176, Philadelphia, Lippincott-Raven, 1996; Clegg, J. C. S. et al. 1997 New Generation Vaccines, eds.: Levine, M. M. et al. 749-765, New York, N.Y. Marcel Dekker, Inc.; Jahrling, P. B. et al. 1996 Arch Virol Suppl 11:135-140).

Replication-defective adenovirus vectors (rAd) are powerful inducers of cellular immune responses and have therefore come to serve as useful vectors for gene-based vaccines, particularly for lentiviruses and filoviruses, as well as other nonviral pathogens (Shiver, et al., (2002) Nature 415(6869): 331-5; (Hill, et al., Hum Vaccin 6(1): 78-83; Sullivan, et al., (2000) Nature 408(6812): 605-9; Sullivan et al., (2003) Nature 424(6949): 681-4; Sullivan, et al., (2006) PLoS Med 3(6): e177; Radosevic, et al., (2007); Santra, et al., (2009) Vaccine 27(42): 5837-45. Adenovirus-based vaccines have several advantages as human vaccines since they can be produced to high titers under GMP conditions and have proven to be safe and immunogenic in humans (Asmuth, et al., J Infect Dis 201(1): 132-41; Kibuuka, et al., J Infect Dis 201(4): 600-7; Koup, et al., PLoS One 5(2): e9015; Catanzaro, et al., (2006) J Infect Dis 194(12): 1638-49; Harro, et al., (2009) Clin Vaccine Immunol 16(9): 1285-92). While most of the initial vaccine work was conducted using rAd5 due to its significant potency in eliciting broad antibody and CD8+ T cell responses, pre-existing immunity to rAd5 in humans may limit efficacy (Catanzaro, (2006); Cheng, et al., (2007) PLoS Pathog 3(2): e25; McCoy, et al., (2007) J Virol 81(12): 6594-604; Buchbinder, et al., (2008) Lancet 372 (9653): 1881-93). This property might restrict the use of rAd5 in clinical applications for many vaccines that are currently in development including Ebola virus (EBOV) and Marburg virus (MARV).

To circumvent the issue of pre-existing immunity to rAd5, several alternative vectors are currently under investigation. These include adenoviral vectors derived from rare human serotypes and vectors derived from other animals such as chimpanzees (Vogels, et al., (2003) J Virol 77(15): 8263-71; Abbink, et al., (2007) J Virol 81: 4654-63; Santra, (2009) Vaccine 27(42): 5837-45). Chimpanzee adenoviral vectors are also described in WO 2010/086189, WO 2005/071093 and WO 98/10087.

It would thus be desirable to provide a vaccine to elicit an immune response against a filovirus or disease caused by infection with filovirus using improved adenoviral vectors. It would further be desirable to provide methods of making and using said vaccine. The present invention addresses these and other needs.

BRIEF SUMMARY OF THE INVENTION

This invention provides vaccines for inducing an immune response and protection against filovirus infection for use as a preventative vaccine in humans. In particular, the invention provides chimpanzee adenoviral vectors (adenoviral vectors derived from chimpanzees) expressing filovirus proteins. For example, these vaccines include chimpanzee adenovirus serotypes ChAd3, ChAd63, PanAd3, PanAd1, PanAd2, or ChAd83 expressing filovirus envelope glycoprotein (GP), including different strains of Ebola virus (EBOV) or Marburg (MARV). Exemplary Chimp Adenoviral Ebola and Marburg sequences are provided in SEQ ID NOs:1-9.

DEFINITIONS

An "adenovirus capsid protein" refers to a protein on the capsid of an adenovirus (e.g., chimpanzee adenovirus) that is involved in determining the serotype and/or tropism of a particular adenovirus. Adenoviral capsid proteins typically include the fiber, penton and/or hexon proteins. As used herein an "adenovirus capsid protein" may be, for example, a chimeric capsid protein that includes capsid protein sequences from two adenoviral iolates.

The terms "adjuvant" and "immune stimulant" are used interchangeably herein, and are defined as one or more substances that cause stimulation of the immune system. In this context, an adjuvant is used to enhance an immune response to the adenovirus vectors of the invention.

The term "corresponding to", when applied to positions of amino acid residues in sequences, means corresponding positions in a plurality of sequences when the sequences are optimally aligned.

The terms "identical" or percent "identity," in the context of two or more nucleic acids or polypeptide sequences, (e.g., adenovirus capsid proteins of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An "isolated" nucleic acid molecule or adenovirus vector is a nucleic acid molecule (e.g., DNA or RNA) or virus, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

"Operably linked" indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs".

A "polypeptide" is a polymer of amino acid residues joined by peptide bonds, whether produced naturally or synthetically. Polypeptides of less than about 50 amino acid residues are commonly referred to as "oligopeptides".

The term "promoter" is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The phrase "substantially identical," in the context of two nucleic acids or polypeptides of the invention (e.g., adenovirus capsid proteins or filovirus antigens), refers to two or more sequences or subsequences that have at least 60%, 65%, 70%, 75%, 80%, 85%, 90%, and 95% nucleotide or amino acid residue identity, when compared and aligned for maximum correspondence, as measured using one of the following sequence comparison algorithms or by visual inspection. In some embodiments, the substantial identity exists over a region of the sequences that is at least about 50 residues, at least about 100 residues, or at least about 150 residues in length. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

A further indication that two nucleic acid sequences or polypeptides of the invention are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

BRIEF DESCRIPTION OF THE DRAWINGS

FIGS. 1A-1B Transgene expression by rAd5, ChAd63 and ChAd3 vectors. FIG. 1A is a schematic of the genomic features of rAd vector. FIG. 1B shows Ebola GP expression in HEK 293 cells. The cells were transduced with rAd5, ChAd63 or ChAd3 vectors at 0, or $10^1$ to $10^3$ vp/cell as indicated. The cell lysates were harvested at 20 hours post transduction and subjected to SDS-PAGE and Western blot analysis.

FIGS. 2A and 2B show % IFN-γ-producing CD4+ and CD8+ T cells, respectively. FIG. 2C shows detection of IgG by ELISA Serum IgG (sera were diluted at 1:1000). *$p<0.05$; ***$p<0.001$.

FIGS. 3A and 3B show % IFN-γ-producing CD4+ and CD8+ T cells, FIG. 3C shows Serum IgG (serum was diluted at 1:1000). *$p<0.05$; ***$p<0.001$.

FIGS. 4A and 4B show % IFN-γ-producing CD4+ and CD8+ T cells, respectively. FIG. 4C shows Serum IgG (sera were diluted at 1:1000). *$p<0.05$; **$p<0.01$.

FIGS. 6A-6B ChAd3 Ebola GP (Zaire) single immunization generates antigen-specific CD4+ and CD8+ T cell responses. Cynomolgus macaques were immunized with rAd5 or ChAd3 encoding EBOV-GP at a dose of $10^{11}$ vp intramuscularly. Blood cells were collected 4 weeks post immunization to detect cellular immune responses by intracellular cytokine staining after stimulation with EBOV-GP peptides. FIG. 6A shows % cytokine-producing CD4+ T cells, FIG. 6B shows % cytokine-producing CD8+ T cells.

FIG. 7. ChAd3 Ebola GP (Zaire) single immunization protects nonhuman primates against infectious challenge with a lethal dose of EBOV-Zaire. Cynomolgus macaques were immunized with rAd5 or ChAd3 encoding EBOV-GP at a dose of $10^{11}$ vp intramuscularly. Subjects were challenged with 1000 PFU of EBOV-Zaire by the intramuscular route at 5 weeks after vaccination. *Additional 10 historical controls performed with the same vaccine and infectious virus challenge stock have yielded the same survival result, **More than 50 historical controls with the same infectious challenge stock have yielded the same survival result.

FIGS. 9A-9B. A single immunization with $10^{10}$ vp of rAdC3 Ebola (Zaire) elicits antigen-specific CD4+ and CD8+ T cell responses. Cynomolgus macaques were vaccinated with rAdC3 or rAd5 encoding EBOV-GP at a dose of $10^{10}$ vp intramuscularly. Blood cells were collected 4 weeks post immunization to detect cellular immune responses by intracellular cytokine staining after stimulation with EBOV-GP peptides. FIG. 9A shows cytokine producing CD4+ T cells, FIG. 9B shows % cytokine producing CD8+ T cells.

FIG. 10. A single immunization with $10^{10}$ vp of rAdC3 Ebola (Zaire) protects nonhuman primates against infectious challenge with a lethal dose of EBOV-Zaire. Cynomolgus macaques were vaccinated with rAdC3 or rAd5 encoding EBOV-GP at a dose of $10^{10}$ vp intramuscularly. Subjects were challenged with 1000 PFU of EBOV-Zaire by the intramuscular route at 5 weeks post vaccination. *Additional 10 historical controls that received the same vaccine and infectious virus challenge stock have yielded the same survival result. **More than 50 historical controls injected with the same infectious challenge stock have yielded the same survival result.

FIG. 11A shows CD4 cellular immune responses in PBMC. FIG. 11B shows CD8 cellular immune responses in PBMC and FIG. 11C shows humoral responses (IgG) to EBOV-GP. Each were measured at three week post immunization by ICS and ELISA, respectively. Zh: humanized EBOV-GP; Z: non-humanized EBOV-GP; *: $p<0.05$; : $p<0.01$; *: $p<0.001$.

FIG. 12A shows CD4 cellular immune responses in PBMC and FIG. 12B shows CD8 cellular immune responses in PBMC. FIG. 12C shows humoral responses (IgG) to EBOV-GP. Each were measured at week 5 by ICS and ELISA, respectively. 5: rAd5; C3: rChAd3; C63: rChAd63; *: $p<0.05$; : $p<0.01$; *: $p<0.001$.

FIG. 13A shows CD4 cellular immune responses in PBMC and FIG. 13B shows CD8 cellular immune responses in PBMC. FIG. 13C shows humoral responses (IgG) to EBOV-GP. Each were measured at week 6 by ICS and ELISA, respectively. 5: rAd5; C3: rChAd3; C63: rChAd63; *: $p<0.05$; : $p<0.01$; *: $p<0.001$.

DETAILED DESCRIPTION

Figure 2A:
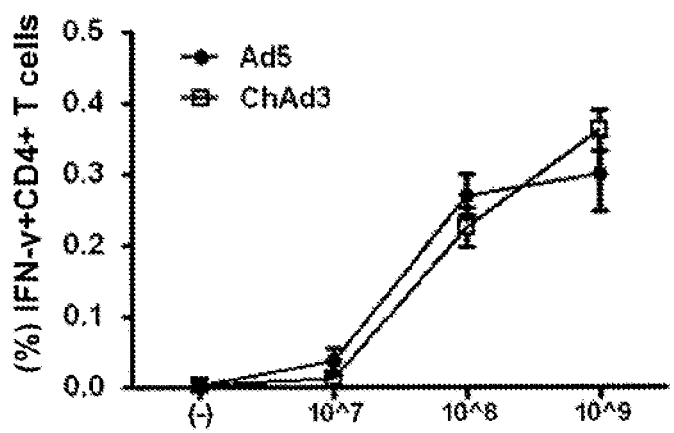
FIGS. 2A-2C ChAd3 Ebola GP (Zaire) single immunization generated comparable CD4+ T cell and IgG responses to rAd5. The mice were immunized with rAd5 Ebola (Zaire) or ChAd3 Ebola (Zaire) at $10^7$, $10^8$ and $10^9$ vp intramuscularly. The spleens and sera were harvested 3 weeks post immunization to detect cellular immune responses by ICS (intracellular cytokine staining) and IgG by ELISA.
Figure 2B:
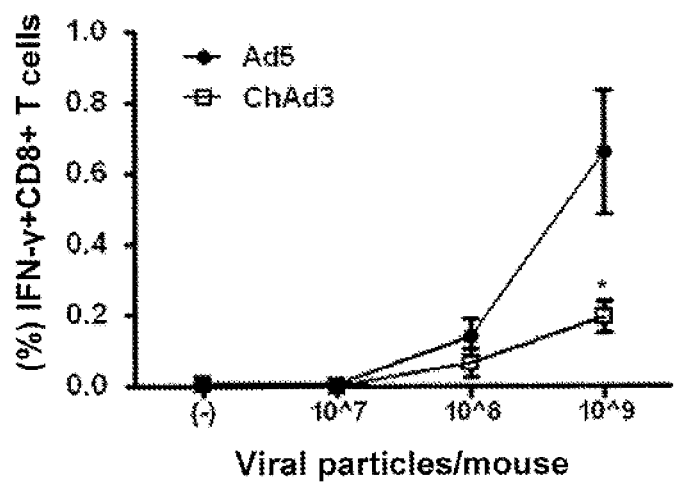
Figure 2C:
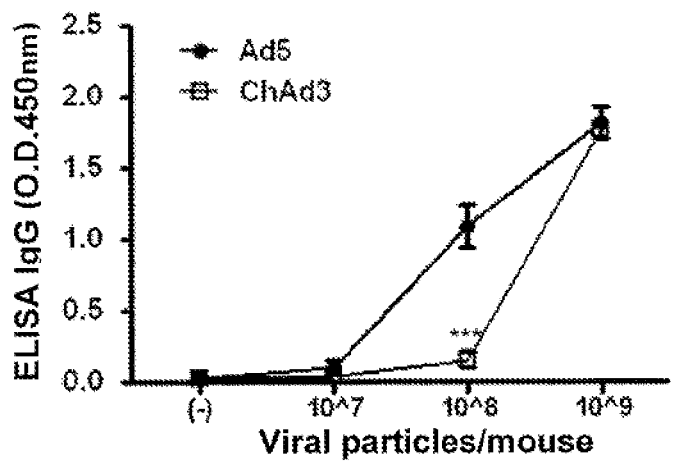
Figure 3A:
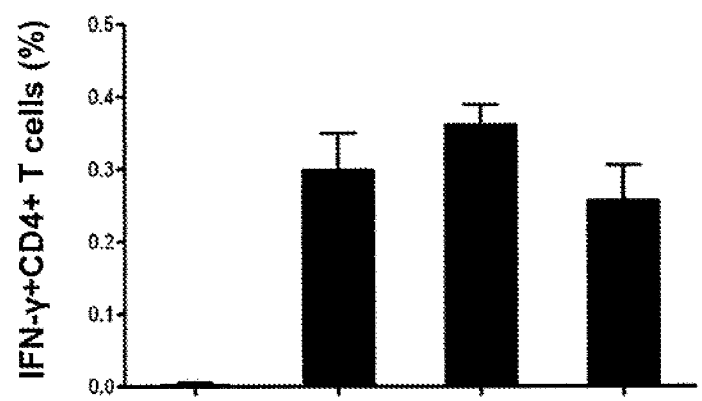
FIGS. 3A-3C ChAd3 Ebola (Zaire) single immunization generated stronger cellular and humoral responses than ChAd63. Mice were immunized with rAd5, ChAd3 or ChAd63 at $10^9$ vp intramuscularly. Spleens and serum were harvested 3 weeks post immunization to detect cellular immune responses by ICS and IgG response by ELISA.
Figure 3B:
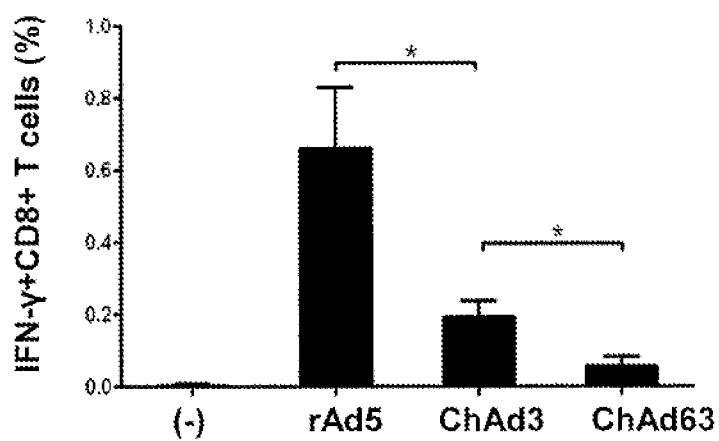
Figure 3C:
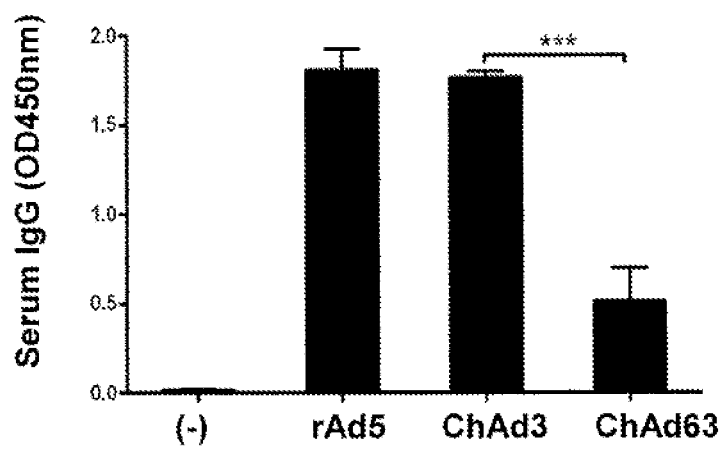
Figure 4A:
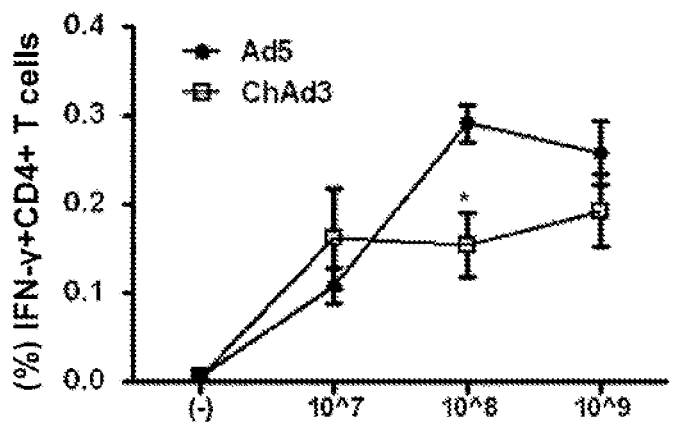
FIGS. 4A-4C ChAd3 Ebola (S/G) single immunization generated comparable cellular and humoral responses to rAd5. Mice were immunized with rAd5 Ebola (S/G) or ChAd3 Ebola (S/G) at 107, 108 and 109 vp intramuscularly. Spleens and sera were harvested 3 weeks post immunization to detect cellular immune responses by ICS and IgG by ELISA.
Figure 4B:
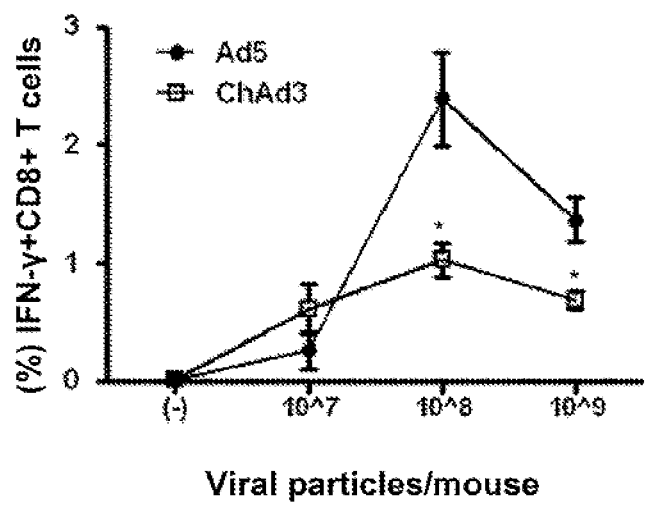
Figure 4C:
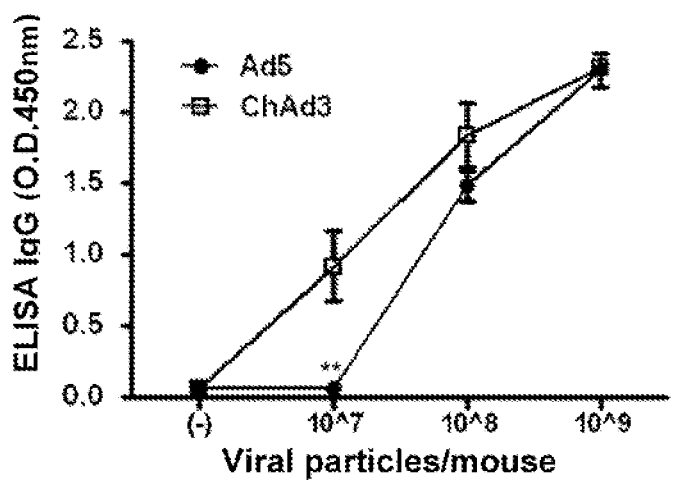
Figure 5:
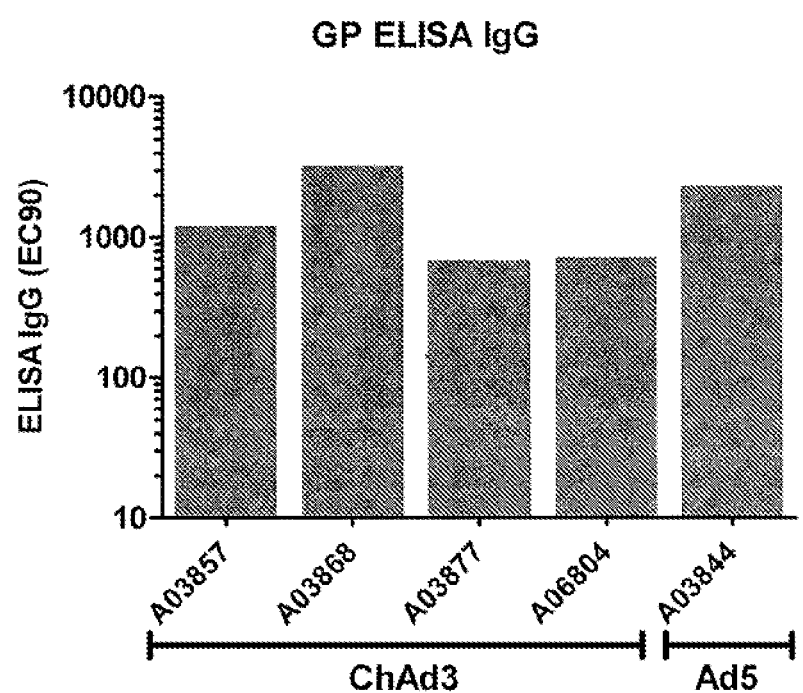
FIG. 5. ChAd3 Ebola (Zaire) single immunization generates antigen-specific antibody responses. Cynomolgus macaques were immunized with rAd5 or ChAd3 encoding EBOV-GP at a dose of 1011 vp intramuscularly. Serum was collected 4 weeks post immunization to detect IgG response by ELISA against EBOV GP.

The present invention also relates to chimpanzee adenovirus vectors which include the nucleic acid molecules of the present invention, host cells which are genetically engineered with the recombinant vectors, the production of filovirus polypeptides or fragments thereof by recombinant techniques and these chimpanzee adenovirus vectors for use in inducing an immune response.

The present invention also relates to pharmaceutical compositions (also referred to as immunogenic compositions) comprising the chimpanzee vectors described above, and a pharmaceutically acceptable diluent, carrier, or excipient carrier as well as to such compositions for use in inducing an immune response. Additionally the compositions may also contain an aqueous medium or a water containing suspension, often mixed with other constituents in order to increase the activity and/or the shelf life. These constituents may be salt, pH buffers, stabilizers (such as skimmed milk or casein hydrolysate), emulsifiers, and preservatives. An adjuvant may be included in the pharmaceutical composition to augment the immune response to the viral antigen expressed from the recombinant virus.

Filovirus Antigens

The nucleic acid molecules of the invention may encode structural gene products of any filovirus species. There are five species of Ebola viruses, Zaire (type species, also referred to herein as ZEBOV), Sudan (also referred to herein as SEBOV), Reston, Bundibugyo, and Ivory Coast. There is a single species of Marburg virus (also referred to herein as MARV).

The particular antigen expressed in the vectors of the invention is not a critical aspect of the present invention. The adenoviral vectors of the invention can be used to express proteins comprising an antigenic determinant of a wide variety of filovirus antigens. In a typical embodiment, the vectors of the invention include nucleic acid encoding the transmembrane form of the viral glycoprotein (GP). In other embodiments, the vectors of the invention may encode the secreted form of the viral glycoprotein (SGP), or the viral nucleoprotein (NP).

One of skill will recognize that the nucleic acid molecules encoding the filovirus antigenic protein may be modified, e.g., the nucleic acid molecules set forth herein may be mutated, as long as the modified expressed protein elicits an immune response against a pathogen or disease. Thus, as used herein, the term "filovirus antigenic protein" refers to a protein that comprises at least one antigenic determinant of a filovirus protein described above. The term encompasses filovirus antigens (i.e., gene products of a filovirus), as well as recombinant proteins that comprise one or more filovirus antigenic determinants.

In some embodiments, the protein may be mutated so that it is less toxic to cells (see e.g., WO2006/037038). The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

Adenoviral Vectors

As noted above, exposure to certain adenoviruses has resulted in immune responses against certain adenoviral serotypes, which can affect efficacy of adenoviral vaccines. The present invention provides adenoviral vectors comprising capsid proteins from chimpanzee adenoviruses.

Thus, the vectors of the invention comprise a chimpanzee adenovirus capsid protein (e.g., a fiber, penton or hexon protein). One of skill will recognize that it is not necessary that an entire chimpanzee capsid protein be used in the vectors of the invention. Thus, chimeric capsid proteins that include at least a part of a chimpanzee capsid protein can be used in the vectors of the invention. The vectors of the invention may also comprise capsid proteins in which the fiber, penton, and hexon proteins are each derived from a different serotype, so long as at least one capsid protein is derived from a chimpanzee adenovirus. For example, the fiber protein can be derived from PanAd3, the penton from ChAd3, and the hexon from ChAd63. In other embodiments, the fiber, penton and hexon proteins can be those provided in SEQ ID NOS:1-9.

In certain embodiments the recombinant adenovirus vector of the invention is derived mainly or entirely from a chimpanzee adenovirus. Exemplary chimpanzee adenoviruses are known in the art and include, for example, ChAd3 and ChAd63 (described in WO 2005/071093), and PanAd3, PanAd1, PanAd2, and ChAd83 (described in WO 2010/086189). ChAd3, ChAd63, and ChAd83 were isolated from the common chimpanzee (*Pan troglodytes*) and PanAd3, PanAd1, PanAd2 were isolated from the bonobo or pygmy chimpanzee (*Pan paniscus*).

In some embodiments, the adenovirus is replication deficient, e.g. because it contains a deletion in the E1 region of the genome. This allows propagation of such adenoviruses in well known complementing cell lines that express the E1 genes, such as for example 293 cells, PER.C6 cells, and the like. In certain embodiments, the adenovirus is a chimpanzee adenovirus, with a deletion in the E1 and E3 region into which an expression cassette encoding the antigen has been cloned. The construction of chimpanzee adenovirus comprising heterologous sequences encoding antigens is described in WO 2005/071093 and WO 2010/086189.

Typically, a vector of the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention may be in the form of RNA or in the form of DNA obtained by cloning or produced synthetically. The DNA may be double-stranded or single-stranded.

The adenovirus vectors of the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As noted above, a wide variety of filovirus antigenic proteins can be expressed in the vectors of the invention. If required, the heterologous gene encoding the filovirus antigenic protein can be codon-optimized to ensure proper expression in the treated host (e.g., human). Thus, codon-optimized antigens are also referred to as humanized antigens. In some embodiments, the viral GP, SGP or NP protein is codon-optimized. For example, codon-optimized antigens include those of SEQ ID NOS: 11, 12, and 14. Codon-optimization is a technology widely applied in the art. Typically, the heterologous gene is cloned into the E1 and/or the E3 region of the adenoviral genome.

The heterologous filovirus gene may be under the control of (i.e., operably linked to) an adenovirus-derived promoter (e.g., the Major Late Promoter) or may be under the control of a heterologous promoter. Examples of suitable heterologous promoters include the CMV promoter and the RSV promoter. In some embodiments, the promoter is located upstream of the heterologous gene of interest within an expression cassette.

As noted above, the adenovirus vectors of the invention can comprise a wide variety of filovirus antigens known to those of skill in the art.

Immunogenic Compositions

Purified or partially purified adenovirus vectors of the invention may be formulated as a vaccine (also referred to as an "immunogenic composition") according to methods well known in the art. Such compositions may include adjuvants to enhance immune responses. The optimal ratios of each component in the formulation may be determined by techniques well known to those skilled in the art.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The compositions are suitable for single administrations or a series of administrations. When given as a series, inoculations subsequent to the initial (priming) administration are given to boost the immune response and are typically referred to as booster inoculations. The compositions of the invention can be used as a boosting composition primed by antigen using any of a variety of different priming compositions, or as the priming composition. Thus, one aspect of the present invention provides a method of priming and/or boosting an immune response to an antigen in an individual. For example, in some embodiments, a priming administration of one adenoviral vector of the invention is followed by a booster inoculation of the second adenoviral vector.

The timing of the administration of boosting compositions is well within the skill in the art. Boosting compositions are generally administered weeks or months after administration of the priming composition, for example, about 2-3 weeks or 4 weeks, or 8 weeks, or 16 weeks, or 20 weeks, or 24 weeks, or 28 weeks, or 32 weeks or one to two years. Methods of accelerated vaccination by administering a single dose of a recombinant adenovirus are described for example in U.S. Pat. No. 7,635,485.

The compositions of the invention may comprise other filovirus antigens or the priming or boosting inoculations may comprise other antigens. The other antigens used in combination with the adenovirus vectors of the invention are not critical to the invention and may be, for example, filovirus antigens, nucleic acids expressing them, virus like particles (VLPs), or prior art viral vectors. Such viral vectors include, for example, other adenoviral vectors, vaccinia virus vectors, avipox vectors such as fowlpox or canarypox, herpes virus vectors, vesicular stomatitis virus vectors, or alphavirus vectors. One of skill will recognize that the immunogenic compositions of the invention may comprise multiple antigens and vectors.

The antigens in the respective priming and boosting compositions (however many boosting compositions are employed) need not be identical, but should share antigenic determinants.

In some embodiments, heterologous prime-boost approaches can be used, for example, priming with Pan3-EBOV and boosting with ChAd3EBOV, priming with ChAd3EBOV and boosting with rLCMV (recombinant lymphocytic choriomeningitis virus), or priming with ChAd63EBOV and boosting with rLCMV. The rLCMV can be constructed as described in Flatz, L. et al., Nature Medicine, 16:339-345, 2010, except that the sequence encoding the antigenic protein is a sequence encoding a filovirus GP protein of the invention. In other embodiments, the boost can be rMVA (modified vaccinia virus Ankara) encoding an Ebola GP protein. Preparation and use of rMVA vectors is known and described for example in Ourmanov et al. *J. Virol.* 83:5388-5400, 2009 and Martinon et al. *Vaccine* 26:532-545, 2008. The vaccines of the invention can be used to generate protection against all human EBOV threats including Bundibugyo and Ivory Coast in a single vaccine. Finally, the vaccines against EBOV and MARV may also be mixed into a single inoculation in order to provide protection against both filoviruses simultaneously. In "prime and boost" immunization regimes, the immune response induced by administration of a priming composition is boosted by administration of a boosting composition. Effective boosting can be achieved using replication-defective adenovirus vectors, following priming with any of a variety of different types of priming compositions, as described for example in U.S. Pat. No. 7,094,598, which is incorporated herein by reference.

As noted above, the immunogenic compositions of the invention may comprise adjuvants. Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that may be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-10, and IL-12 or encoding nucleic acids therefore.

As noted above, the compositions of the invention may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Administration is typically intramuscular.

Intramuscular administration of the immunogenic compositions may be achieved by using a needle to inject a suspension of the adenovirus vector. An alternative is the use of a needless injection device to administer the composition (using, e.g., Biojector™ or a freeze-dried powder containing the vaccine.

For intravenous, cutaneous or subcutaneous injection, or injection at the site of affliction, the adenovirus vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, or Lactated Ringer's Injection. Preservatives, stabilizers, buffers, antioxidants and/or other additives may be included, as required. A slow-release formulation may also be employed.

Typically, administration will have a prophylactic aim to generate an immune response against a filovirus antigen before infection or development of symptoms. Diseases and disorders that may be treated or prevented in accordance with the present invention include those in which an immune response may play a protective or therapeutic role. In other embodiments, the adenovirus vectors can be administered for post-exposure prophylactics.

The immunogenic compositions containing the adenovirus vectors are administered to a subject, giving rise to an anti-filovirus immune response in the subject. An amount of a composition sufficient to induce a detectable immune response is defined to be an "immunologically effective dose." As shown below, the immunogenic compositions of the invention induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the adenovirus vectors may be administered to an individual, particularly human or other primate. Administration may be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but may be for use in an experimental context, for instance in investigation of mechanisms of immune responses to the adenovirus vector.

In one exemplary regimen, the adenovirus vector is administered (e.g., intramuscularly) in the range of from about 100 µl to about 10 ml of saline solution containing concentrations of from about $10^4$ to $10^{12}$ virus particles/ml. Typically, the adenovirus vector is administered in an amount of about $10^9$ to about $10^{12}$ viral particles (vp) to a human subject during one administration. For example, the adenovirus vector can be administered in an amount of about $10^9$, $10^{10}$, $10^{11}$, or $10^{12}$ vp per administration. In some embodiments, the dose administered is from about $10^{10}$ to about $10^{12}$ vp. An initial vaccination can be followed by a boost as described above. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The present invention also provides kits for enhancing the immunity of a host to a pathogen. These kits may include any one ore more vaccines according to the present invention in combination with a composition for delivering the vaccine to a host and/or a device, such as a syringe, for delivering the vaccine to a host.

The vaccine according to the invention is administered as a pre-exposure (or post-exposure) single dose in a manner compatible with the dosage formulation, and in such amount as will be prophylactively effective. Immunity is defined as the induction of a significant level of protection after vaccination compared to an unvaccinated human or other host.

The vaccine of the present invention, i.e., the recombinant virus, may be administered to a host, such as a human subject, via any pharmaceutically acceptable routes of administration. The routes of administration include, but are not limited to, intramuscular, intratracheal, subcutaneous, intranasal, intradermal, rectal, oral and parental route of administration. Routes of administration may be combined, if desired, or adjusted depending upon the type of the pathogenic virus to be immunized against and the desired body site of protection.

Doses or effective amounts of the recombinant virus may depend on factors such as the condition, the selected viral antigen, the age, weight and health of the host, and may vary among hosts. The appropriate titer of the recombinant virus of the present invention to be administered to an individual is the titer that can modulate an immune response against the viral antigen and elicits antibodies against the pathogenic virus from which the antigen is derived. An effective titer can be determined using an assay for determining the activity of immunoeffector cells following administration of the vaccine to the individual or by monitoring the effectiveness of the therapy using well known in vivo diagnostic assays.

The chimp Ad vectors of the invention can be used as single inoculations to provide either immediate (e.g., 2-4 weeks) or long-term (e.g., one year) immune protection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand. By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a modified or wild-type filovirus or adenovirus structural gene product; and DNA molecules which comprise a sequence substantially different from those described above but which, due to the degeneracy of the genetic code, still encode an ORF of a filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus or adenovirus structural gene product is intended fragments at least about 15 nt., at least about 20 nt., at least about 30 nt., or at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus or adenovirus structural gene product. By a fragment at least 20 nt. in length, for example, is intended fragments which include 20 or more contiguous bases from the nucleotide sequence of the ORF of a wild-type filovirus or adenovirus structural gene product.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), at least about 20 nt., at least about 30 nt., or about 30-70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids; such as those which provide additional functionalities.

The present invention further relates to variants of the nucleic acid molecules of the present invention, which encode portions, analogs or derivatives of the filovirus or adenovirus structural gene product. Variants may occur naturally, such as a natural allelic variant. By an "allelic variant" is intended one of several alternate forms of a gene occupying a given locus on a genome of an organism. (*Genes II*, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. In some embodiments, the variations are silent substitutions, additions and deletions, which do not alter the properties and activities of the filovirus or adenovirus structural gene product or portions thereof. In some embodiments the variants are conservative substitutions.

Further embodiments of the invention include nucleic acid molecules comprising a polynucleotide having a nucleotide sequence at least 95% identical, or at least 96%, 97%, 98% or 99% identical to a nucleotide sequence encoding a polypeptide having the amino acid sequence of a wild-type filovirus or adenovirus structural gene product or fragment thereof or a nucleotide sequence complementary thereto.

By a polynucleotide having a nucleotide sequence at least, for example, 95% "identical" to a reference nucleotide sequence encoding a filovirus or adenovirus structural gene product is intended that the nucleotide sequence of the polynucleotide is identical to the reference sequence except that the polynucleotide sequence may include up to five point mutations per each 100 nucleotides of the reference nucleotide sequence encoding the virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981 *Advances in Applied Mathematics* 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide of the invention. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having the desired activity. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306-1310, wherein the authors indicate that proteins are surprisingly tolerant of amino acid substitutions.

Polypeptides and Fragments

The invention further provides filovirus and adenovirus polypeptides having the amino acid sequence encoded by an open reading frame (ORF) of a wild-type or modified filovirus or adenovirus structural gene, or a peptide or polypeptide comprising a portion thereof.

It will be recognized in the art that some amino acid sequences of the filovirus polypeptides can be varied without significant effect on the structure or function of the protein. If such differences in sequence are contemplated, it should be remembered that there will be critical areas on the protein which determine activity.

Thus, the invention further includes variations of the filovirus or adenovirus polypeptides which show substantial antigenic or other relevant biological activity. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue and such substituted amino acid residue may or may not be one encoded by the genetic code, or (ii) one in which one or more of the amino acid residues include a substituent group, or (iii) one in which additional amino acids are fused to the mature polypeptide. Such fragments, derivatives and analogs are deemed to be within the scope of those skilled in the art from the teachings herein.

Of course, the number of amino acid substitutions a skilled artisan would make depends on many factors, including those described above. Generally speaking, the number of amino acid substitutions for any given filovirus or adenovirus polypeptide will not be more than 50, 40, 30, 20, 10, 5 or 3.

Amino acids in the filovirus or adenovirus polypeptides of the present invention that are essential for the desired function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus or adenovirus polypeptide can be substantially purified by the one-step method described in Smith and Johnson 1988 *Gene* 67:31-40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, or at least 96%, 97%, 98%, or 99% identical to those described above.

By a polypeptide having an amino acid sequence at least, for example, 95% "identical" to a reference amino acid sequence of an filovirus or adenovirus polypeptide is intended that the amino acid sequence of the polypeptide is identical to the reference sequence except that the polypeptide sequence may include up to five amino acid alterations per each 100 amino acids of the reference amino acid of the filovirus or adenovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

EXAMPLES

The following examples are offered to illustrate, but not to limit the claimed invention.

Example 1

This example shows that humoral and cellular responses generated by ChAdC3 Ebola (S/G) and ChAdC3 Ebola (Zaire) were comparable to those generated by rAd 5Ebola (S/G) and rAd5 Ebola (Zaire) respectively.

Immunization of cynomologous macaques with ChAdC3 Ebola (Zaire) produced antigen-specific antibody and Cd4+ and Cd8+ T cell responses. Protection against infection with a lethal dose of EBOV-Zaire was also demonstrated, as 4 macaques survived the challenge after immunization with ChAdC3 Ebola (Zaire) (see FIGS. 1-7).

Example 2

This example shows that a single immunization with rChAdC3 Ebola (Zaire) elicited humoral and cellular immune responses comparable to those generated by rAd5 Ebola (Zaire).

Figure 8:
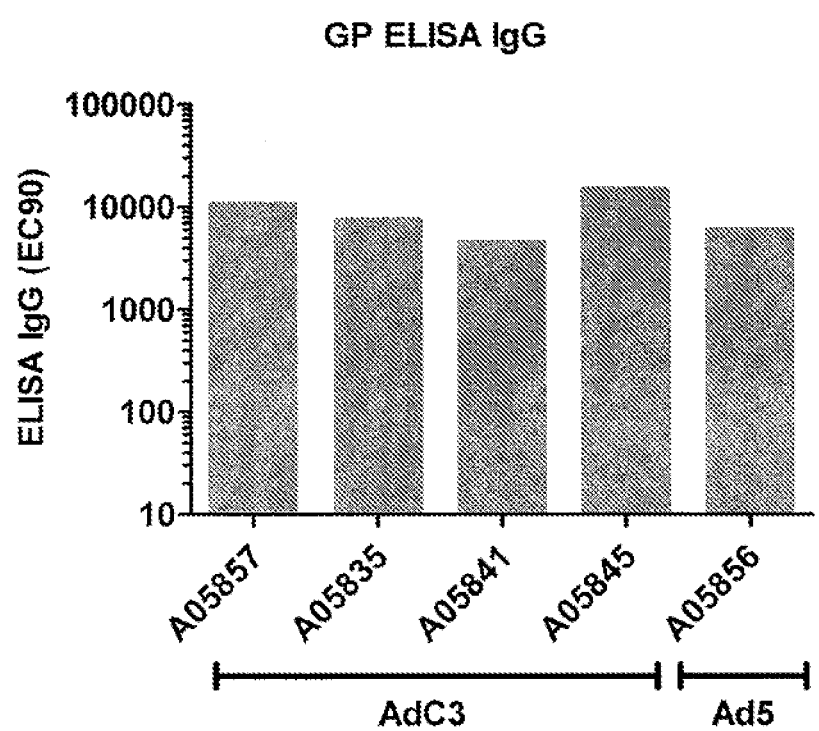
FIG. 8. A single immunization with $10^{10}$ vp of rAdC3 Ebola (Zaire) elicits antigen-specific Antibody responses. Cynomolgus macaques were vaccinated with rAdC3 or rAd5 encoding EBOV-GP at a dose of $10^{10}$ vp intramuscularly. Serum was collected at 4 weeks post Immunization to detect IgG responses against EBOV GP by ELISA.

Immunization of cynomologous macaques with rChAdC3 Ebola (Zaire) produced antigen-specific antibody and Cd4+ and Cd8+ T cell responses. Protection against infection with a lethal dose of EBOV-Zaire was also demonstrated, as 4 out of 4 macaques survived the challenge after immunization with rChAdC3 Ebola (Zaire) (see FIGS. 8-10).

Example 3

This example shows that a single immunization with adenoviral vectors encoding humanized Ebola glycoprotein (EBOV-GP) induced stronger cellular and humoral responses in mice than adenoviral vectors encoding non-humanized EBOV-GP.

Figure 11A:
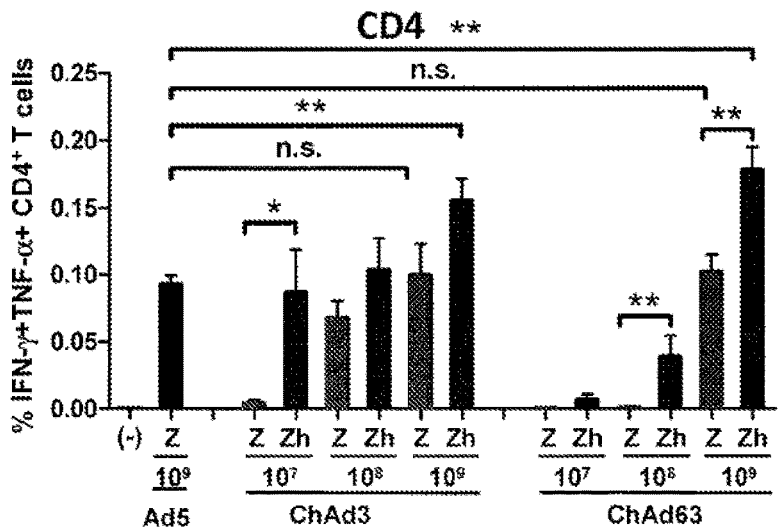
FIGS. 11A-11C rChAd vectors encoding humanized EBOV-GP or non-humanized EBOV-GP elicited potent immune responses in mice. Five 6-8 weeks female Balb/C mice in each group were immunized with rAd EBOV-GP at indicated $10^7$ or $10^8$ or $10^9$ viral particles through intramuscular injection.
Figure 11B:
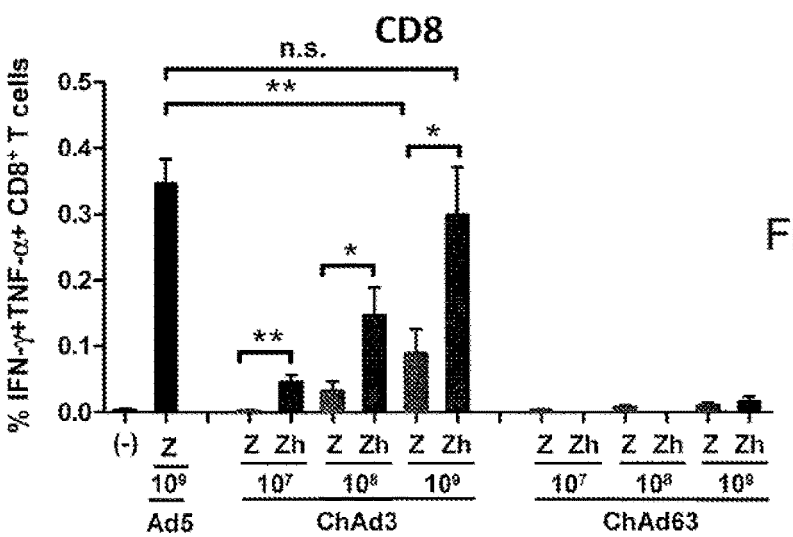
Figure 11C:
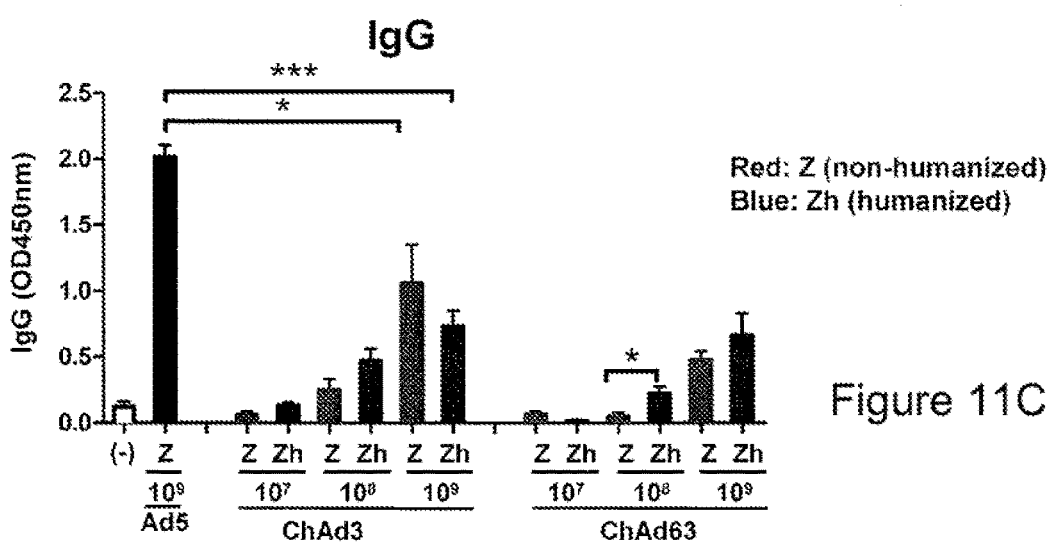

Groups of female Balb/C mice were immunized with rAd EBOV-GP (Z) at a dose of $10^7$, $10^8$, and $10^9$ viral particles via intramuscular injection. Cellular immune responses (Cd4+ and Cd8+ T cell responses) in PBMC and humoral responses (IgG) to EBOV-GP were measured at three weeks post immunization by ICS (intracellular cytokine staining) and ELISA, respectively. As shown in FIG. 11, immunization with adenoviral vectors rChAd3 and rChAd63 encoding EBOV-GP (Zh) codon optimized for expression in humans produced significantly higher percentages of CD4+ T cells that express cytokines IFN-γ and TNF-α than the same vectors encoding non-humanized (wild-type) EBOV-GP (Z) (SEQ ID NO:10), and these responses were significantly greater than the response due to rAd5 at $10^9$ viral particles.

Immunization with rChAd3 encoding humanized EBOV-GP produced significantly higher percentages of CD8+ T cells that express cytokines IFN-γ and TNF-α than the same vector encoding non-humanized EBOV-GP, and the percentage of cytokine positive cells was comparable, although not significantly different, to the percentage of cytokine positive CD8+ T cells produced by rAd5 at $10^9$ viral particles (see FIG. 11). There was no significant difference in the CD8+ response produced by rChAd63 encoding humanized and non-humanized EBOV-GP.

Immunization with rChAd63 encoding humanized EBOV-GP produced significantly higher IgG when compared to the same vector encoding non-humanized EBOV-GP at $10^8$ viral particles. There was no significant difference in the IgG response by rChAd3 encoding humanized and non-humanized EBOV-GP. Further, the IgG response by rChAd3 and rChAd63 encoding humanized and non-humanized EBOV-GP was significantly lower than response generated by Ad5 (see FIG. 11).

Example 4

This example shows that a prime/boost regimen using adenoviral vectors encoding EBOV-GP generated potent immune responses in mice.

Groups of female Balb/C mice were immunized with $10^8$ and $10^9$ rAd EBOV-GP (Z) viral particles via intramuscular injection at week 0 and boosted at week 3. Cellular and humoral immune responses were measured as described above at week 5.

Figure 12A:
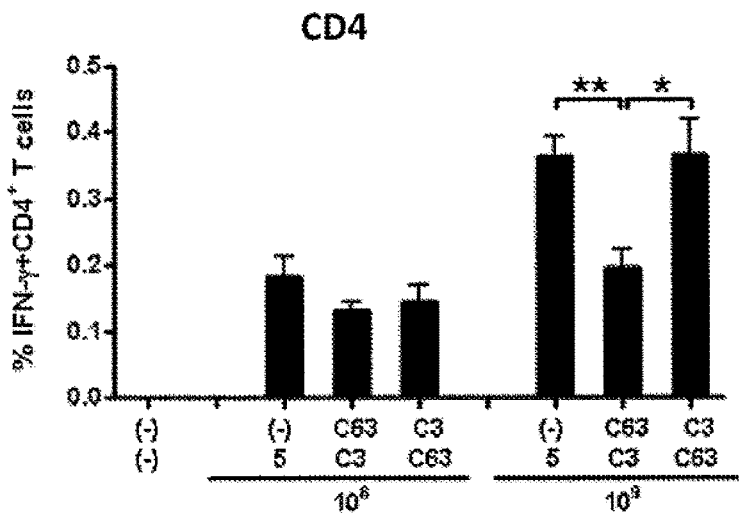
FIGS. 12A-12C rChAd prime and boost regimen generated potent immune responses in mice. Five 6-8 weeks female Balb/C mice in each group were immunized with rAd EBOV-GP at week 0 and boosted at week 3, at $10^8$ or $10^9$ viral particles as indicated through intramuscular injection.
Figure 12B:
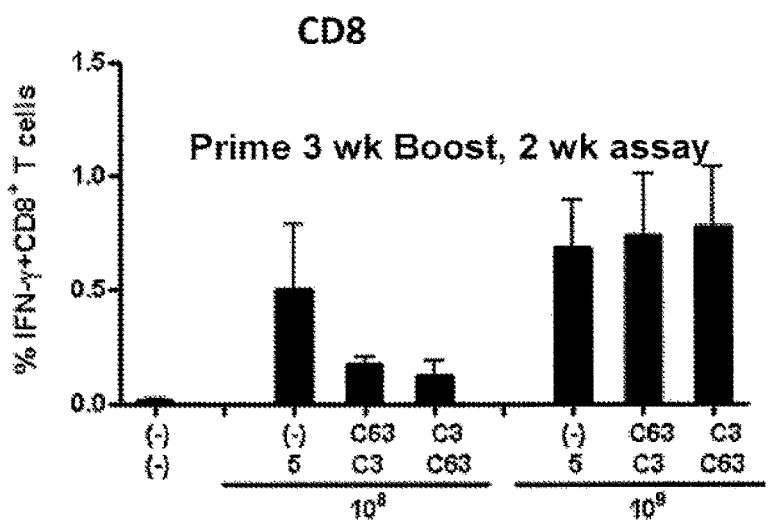
Figure 12C:
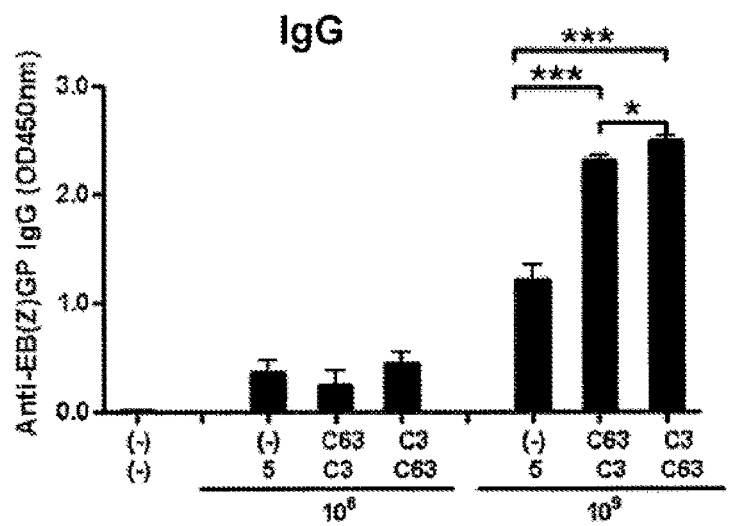

As shown in FIG. 12, prime with $10^9$ particles of rChAd3 and boost with $10^9$ particles of rChAd63 generated similar CD4+ and CD8+ responses as a single immunization at 3 weeks with rAd5. Likewise, prime with $10^9$ particles of rChAd63 and boost with $10^9$ particles of rChAd3 generated a similar CD8+ response as a single immunization at 3 weeks with rAd5, whereas this regimen produced a significantly lower CD4+ response.

Prime with $10^9$ particles of rChAd3 and boost with $10^9$ particles of rChAd63 generated a significantly higher IgG response than a single rAd5 immunization at 3 weeks. Similarly, prime with $10^9$ particles of rChAd63 and boost with $10^9$ particles of rChAd3 generated a significantly higher IgG response than a single rAd5 immunization at 3 weeks.

Figure 13A:
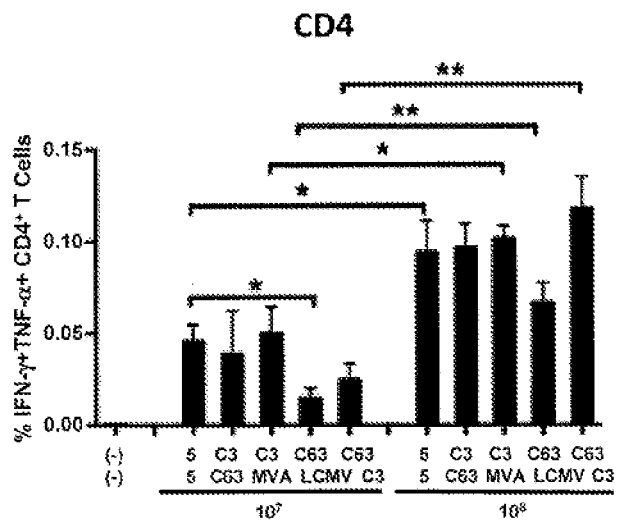
FIGS. 13A-13C rAd, rMVA and rLCMV vectors used in prime and boost regimen generated potent immune responses in mice. Five 6-8 weeks female Balb/C mice in each group were immunized with vectors encoding EBOV-GP at week 0 and boosted at week 4. rAd vectors were dosed at $10^7$ or $10^8$ viral particles as indicated, and MVA vectors at $10^5$ pfu, LCMV at $10^6$ pfu, through intramuscular injection.
Figure 13B:
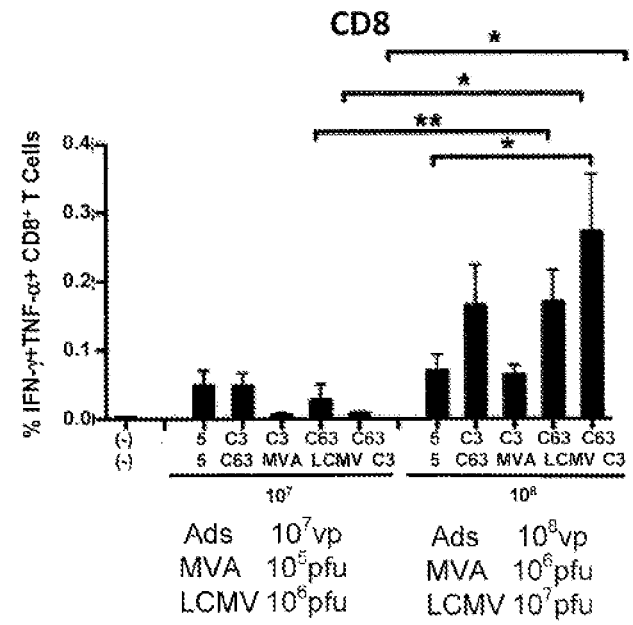
Figure 13C:
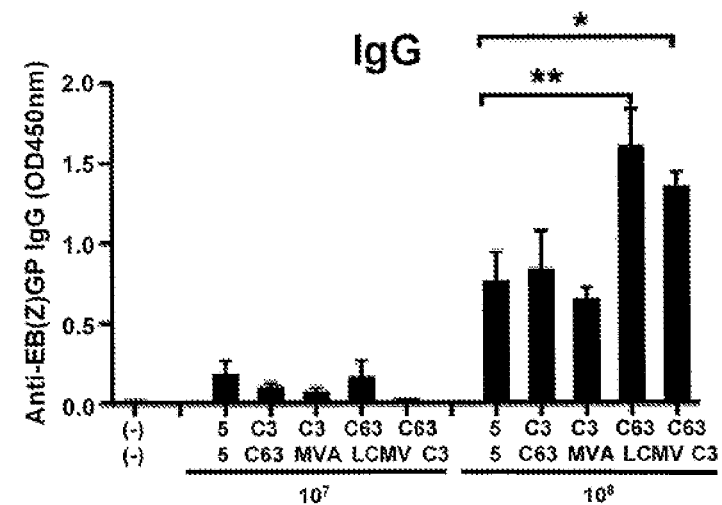

As shown in FIG. 13, prime with $10^8$ particles of rChAd63 and boost with $10^8$ particles of rChAd3 induced higher CD8+ and IgG responses than prime and boost with rAd5. The LCMV and MVA vectors were prepared as described above.

In summary, the above examples demonstrate that rChAd3 consistently generated comparable immune responses as rAd5 for single administration. Further, prime and boost with rChAd3/rChAd63, ChAd63/ChAd3, and ChAd3/LCMV are useful candidates for a combination regimen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing a protective immune response against an Ebola virus infection in a subject, the method comprising intramuscularly administering to the subject $10^{10}$ to $10^{12}$ viral particles of a recombinant chimpanzee adenovirus type 3 (ChAd3) vector comprising a nucleic acid encoding an Ebola virus glycoprotein, followed by administering to the subject a prophylactically effective amount of a modified vaccinia virus Ankara (MVA) vector comprising a nucleic acid encoding the Ebola virus glycoprotein.

2. The method of claim 1, wherein the Ebola virus is of species Zaire.

3. The method of claim 2, wherein the Ebola virus glycoprotein is encoded by a polynucleotide sequence as shown in SEQ ID NO:10 (Z GP wild-type).

4. The method of claim 1, wherein the Ebola virus is of species Sudan/Gulu.

5. The method of claim 4, wherein the Ebola virus glycoprotein is encoded by a polynucleotide sequence as shown in SEQ ID NO: 11 or 13 (S/G GP codon-optimized or wild-type).

* * * * *

SEQUENCE LISTING

```
<160> NUMBER OF SEQ ID NOS: 14

<210> SEQ ID NO 1
<211> LENGTH: 33104
<212> TYPE: DNA
<213> ORGANISM: Artificial Sequence
<220> FEATURE:
<223> OTHER INFORMATION: synthetic chimpanzee adenovirus serotype ChAd3
      with Ebola virus Zaire wild type transmembrane
      envelope glycoprotein (GP) insert (ChAd3 Ebola
      Zaire (PB/6001))
<220> FEATURE:
<221> NAME/KEY: CDS
<222> LOCATION: (2143)...(4444)
<223> OTHER INFORMATION: Ebola virus Zaire wild type transmembrane
      envelope glycoprotein (GP) insert in ChAd3 Ebola Zaire (PB/6001)
<220> FEATURE:
<221> NAME/KEY: CDS
<222> LOCATION: (15413)...(17194)
<223> OTHER INFORMATION: chimpanzee adenovirus serotype ChAd3 penton
<220> FEATURE:
<221> NAME/KEY: CDS
<222> LOCATION: (19086)...(21968)
<223> OTHER INFORMATION: chimpanzee adenovirus serotype ChAd3 hexon
<220> FEATURE:
<221> NAME/KEY: CDS
<222> LOCATION: (29962)...(31647)
<223> OTHER INFORMATION: chimpanzee adenovirus serotype ChAd3 fiber

<400> SEQUENCE: 1
catcatcaat aatatacctt attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgcccccg ggaagtgaca ttttcccgc ggttttttacc     240 ggatgttgta gtgaatttgg gcgtaaccaa gtaagatttg gccattttcg cgggaaaact     300
gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctccgtttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660 cgaccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgccccctat tgacgtcaat gacggtaaat ggcccgcctg     840
gcattatgcc cagtacatga ccttatggga ctttcctact tggcagtaca tctacgtatt     900
```

```
agtcatcgct attaccatgg tgatgcggtt ttggcagtac atcaatgggc gtggatagcg    960
gtttgactca cggggatttc caagtctcca ccccattgac gtcaatggga gtttgttttg   1020
gaaccaaaat caacgggact ttccaaaatg tcgtaacaac tccgcccat tgacgcaaat    1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg aacggtgca ttggaacgcg gattccccgt gccaagagtg acgtaagtac    1320
cgcctataga ctctataggc acccccttt ggctcttatg catgctatac tgttttggc     1380
ttggggccta tacaccccg cttccttatg ctataggtga tggtatagct tagcctatag    1440
gtgtgggtta ttgaccatta ttgaccactc ccctattggt gacgatactt tccattacta   1500
atccataaca tggctctttg ccacaactat ctctattggc tatatgccaa tactctgtcc   1560
ttcagagact gacacggact ctgtattttt acaggatggg gtcccattta ttatttacaa   1620
attcacatat acaacaacgc cgtcccccgt gcccgcagtt tttattaaac atagcgtggg   1680
atctccacgc gaatctcggg tacgtgttcc ggacatgggc tcttctccgg tagcggcgga   1740
gcttccacat ccgagccctg gtcccatgcc tccagcggct catggtcgct cggcagctcc   1800
ttgctcctaa cagtggaggc cagacttagg cacagcacaa tgcccaccac caccagtgtg   1860
ccgcacaagg ccgtggcggt agggtatgtg tctgaaaatg agcgtggaga ttgggctcgc   1920
acggctgacg cagatggaag acttaaggca gcggcagaag aagatgcagg cagctgagtt   1980
gttgtattct gataagagtc agaggtaact cccgttgcgg tgctgttaac ggtggagggc   2040
agtgtagtct gagcagtact cgttgctgcc gcgcgcgcca ccagacataa tagctgacag   2100
actaacagac tgttcctttc catgggtctt ttctgcagtc accgtcgtcg acacgtgtga   2160
tcagatatcg cggccgctct agaccaggcc ctggatcgat ccaacaacac aatgggcgtt   2220
acaggaatat tgcagttacc tcgtgatcga ttcaagagga catcattctt tctttgggta   2280
attatccttt tccaaagaac attttccatc ccacttggag tcatccacaa tagcacatta   2340
caggttagtg atgtcgacaa actagtttgt cgtgacaaac tgtcatccac aaatcaattg   2400
agatcagttg gactgaatct cgaagggaat ggagtggcaa ctgacgtgcc atctgcaact   2460
aaaagatggg gcttcaggtc cggtgtccca ccaaaggtgg tcaattatga agctggtgaa   2520
tgggctgaaa actgctacaa tcttgaaatc aaaaaacctg acgggagtga gtgtctacca   2580
gcagcgccag acgggattcg ggccttcccc cggtgccggt atgtgcacaa agtatcagga   2640
acgggaccgt gtgccggaga cttttgccttc cataaagagg gtgctttctt cctgtatgat   2700
cgacttgctt ccacagttat ctaccgagga acgactttcg ctgaaggtgt cgttgcattt   2760
ctgatactgc cccaagctaa gaaggacttc ttcagctcac accccttgag agagccggtc   2820
aatgcaacgg aggacccgtc tagtggctac tattctacca caattagata tcaggctacc   2880
ggttttggaa ccaatgagac agagtacttg ttcgaggttg acaatttgac ctacgtccaa   2940
cttgaatcaa gattcacacc acagtttctg ctccagctga atgagacaat atatacaagt   3000
gggaaaagga gcaataccac gggaaaacta atttggaagg tcaaccccga aattgataca   3060
acaatcgggg agtgggcctt ctgggaaact aaaaaaaacc tcactagaaa aattcgcagt   3120
gaagagttgt cttcacagt tgtatcaaac ggagccaaaa acatcagtgg tcagagtccg   3180
gcgcgaactt cttccgaccc agggaccaac acaacaactg aagaccacaa aatcatggct   3240
tcagaaaatt cctctgcaat ggttcaagtg cacagtcaag gaagggaagc tgcagtgtcg   3300
```

```
catctaacaa cccttgccac aatctccacg agtccccaat ccctcacaac caaaccaggt    3360
ccggacaaca gcacccataa tacacccgtg tataaacttg acatctctga ggcaactcaa    3420
gttgaacaac atcaccgcag aacagacaac gacagcacag cctccgacac tccctctgcc    3480
acgaccgcag ccggaccccc aaaagcgag aacaccaaca cgagcaagag cactgacttc    3540
ctggaccccg ccaccacaac aagtccccaa aaccacagcg agaccgctgg caacaacaac    3600
actcatcacc aagataccgg agaagagagt gccagcagcg ggaagctagg cttaattacc    3660
aatactattg ctggagtcgc aggactgatc acaggcggga gaagaactcg aagagaagca    3720
attgtcaatg ctcaacccaa atgcaaccct aatttacatt actggactac tcaggatgaa    3780
ggtgctgcaa tcggactggc ctggatacca tatttcgggc cagcagccga gggaatttac    3840
atagaggggc taatgcacaa tcaagatggt ttaatctgtg ggttgagaca gctgccaac    3900 gagacgactc aagctcttca actgttcctg agagccacaa ctgagctacg cacctttca    3960 atcctcaacc gtaaggcaat tgatttcttg ctgcagcgat ggggcggcac atgccacatt    4020
ctgggaccgg actgctgtat cgaaccacat gattggacca agaacataac agacaaaatt    4080
gatcagatta ttcatgattt tgttgataaa acccttccgg accaggggga caatgacaat    4140
tggtggacag gatggagaca atggataccg gcaggtattg gagttacagg cgttgtaatt    4200
gcagttatcg ctttattctg tatatgcaaa tttgtcttt agtttttctt cagattgctt    4260
catggaaaag ctcagcctca aatcaatgaa accaggattt aattatatgg attacttgaa    4320
tctaagatta cttgacaaat gataatataa tacactggag ctttaaacat agccaatgtg    4380
attctaactc ctttaaactc acagttaatc ataaacaagg tttgaggtac cgagctcgaa    4440
ttgatctgct gtgccttcta gttgccagcc atctgttgtt tgcccctccc ccgtgccttc    4500
cttgaccctg gaaggtgcca ctcccactgt cctttcctaa taaaatgagg aaattgcatc    4560
gcattgtctg agtaggtgtc attctattct ggggggtggg gtgggcagg acagcaaggg    4620 ggaggattgg gaagacaata gcaggcatgc tggggatgcg gtgggcgata tcagcgatcg    4680
ctgaggtggg tgagtgggcg tggcctgggg tggtcatgaa aatatataag ttggggggtct    4740 tagggtctct ttatttgtgt tgcagagacc gccggagcca tgagcgggag cagcagcagc    4800
agcagtagca gcagcgcctt ggatggcagc atcgtgagcc cttatttgac gacgcggatg    4860
ccccactggg ccggggtgcg tcagaatgtg atgggctcca gcatcgacgg ccgacccgtc    4920
ctgcccgcaa attccgccac gctgacctat gcgaccgtcg cggggacgcc gttggacgcc    4980
accgccgccg ccgccgccac cgcagccgcc tcggccgtgc gcagcctggc cacggacttt    5040
gcattcctgg gaccactggc gacaggggct acttctcggg ccgctgctgc cgccgttcgc    5100
gatgacaagc tgaccgccct gctggcgcag ttggatgcgc ttactcggga actgggtgac    5160
ctttctcagc aggtcatggc cctgcgccag caggtctcct ccctgcaagc tggcgggaat    5220
gcttctccca caaatgccgt ttaagataaa taaaaccaga ctctgtttgg attaaagaaa    5280
agtagcaagt gcattgctct ctttatttca taattttccg cgcgcgatag gccctagacc    5340
agcgttctcg gtcgttgagg gtgcggtgta tcttctccag gacgtggtag aggtggctct    5400
ggacgttgag atacatgggc atgagcccgt cccgggggtg gaggtagcac cactgcagag    5460
cttcatgctc cggggtggtg ttgtagatga tccagtcgta gcaggagcgc tgggcatggt    5520
gcctaaaaat gtccttcagc agcaggccga tggccagggg gaggcccttg gtgtaagtgt    5580
ttacaaaacg gttaagttgg gaagggtgca ttcggggaga gatgatgtgc atcttggact    5640
```

```
gtattttag attggcgatg tttccgccca gatcccttct gggattcatg ttgtgcagga      5700
ccaccagtac agtgtatccg gtgcacttgg ggaatttgtc atgcagctta gagggaaaag      5760
cgtggaagaa cttggagacg cccttgtggc ctcccagatt ttccatgcat tcgtccatga      5820
tgatggcaat gggcccgcgg gaggcagctt gggcaaagat atttctgggg tcgctgacgt      5880
cgtagttgtg ttccagggtg aggtcgtcat aggccatttt tacaaagcgc gggcggaggg      5940
tgcccgactg ggggatgatg gtcccctctg gccctgggc gtagttgccc tcgcagatct      6000
gcatttccca ggccttaatc tcggaggggg gaatcatatc cacctgcggg gcgatgaaga      6060
aaacggtttc cggagccggg gagattaact gggatgagag caggttttcta agcagctgtg      6120 attttccaca accggtgggc ccataaataa cacctataac cggttgcagc tggtagttta      6180
gagagctgca gctgccgtcg tcccggagga gggggccac ctcgttgagc atgtccctga      6240
cgcgcatgtt ctccccgacc agatccgcca gaaggcgctc gccgcccagg acagcagct      6300 cttgcaagga agcaaagttt ttcagcggct tgaggccgtc cgccgtgggc atgttttttca      6360 gggtctggct cagcagctcc aggcggtccc agagctcggt gacgtgctct acggcatctc      6420
tatccagcat atctcctcgt ttcgcgggtt ggggcgactt tcgctgtagg gcaccaagcg      6480
gtggtcgtcc agcggggcca aagtcatgtc cttccatggg gcagggtcc tcgtcagggt      6540 ggtctgggtc acggtgaagg ggtgcgctcc gggctgagcg cttgccaagg tgcgcttgag      6600
gctggttctg ctggtgctga agcgctgccg gtcttcgccc tgcgcgtcgg ccaggtagca      6660
tttgaccatg gtgtcatagt ccagcccctc cgcggcgtgt cccttggcgc gcagcttgcc      6720
cttggaggtg gcgccgcacg aggggcagag caggctcttg agcgcgtaga gcttgggggc      6780
gaggaagacc gattcggggg agtaggcgtc cgcgccgcag accccgcaca cggtctcgca      6840
ctccaccagc caggtgagct cggggcgcgc cgggtcaaaa accaggttttc ccccatgctt      6900 tttgatgcgt ttcttacctc gggtctccat gaggtggtgt cccgctcgg tgacgaagag      6960 gctgtccgtg tctccgtaga ccgacttgag gggtcttttc tccaggggg tccctcggtc      7020 ttcctcgtag aggaactcgg accactctga gacgaaggcc cgcgtccagg ccaggacgaa      7080
ggaggctatg tgggagggt agcggtcgtt gtccactagg gggtccacct tctccaaggt      7140
gtgaagacac atgtcgcctt cctcggcgtc caggaaggtg attggcttgt aggtgtaggc      7200
cacgtgaccg ggggttcctg acggggggt ataaaagggg gtggggcgc gctcgtcgtc      7260 actctcttcc gcatcgctgt ctgcgagggc cagctgctgg ggtgagtatt ccctctcgaa      7320
ggcgggcatg acctccgcgc tgaggttgtc agtttccaaa aacgaggagg atttgatgtt      7380
cacctgtccc gaggtgatac ctttgagggt acccgcgtcc atctggtcag aaaacacgat      7440
ctttttattg tccagcttgg tggcgaacga cccgtagagg gcgttggaga gcagcttggc      7500
gatggagcgc agggtctggt tcttgtccct gtcggcgcgc tccttggccg cgatgttgag      7560
ctgcacgtac tcgcgcgcga cgcagcgcca ctcggggaag acggtggtgc gctcgtcggg      7620
caccaggcgc acgcgccagc cgcggttgtg cagggtgacc aggtccacgc tggtggcgac      7680
ctcgccgcgc aggcgctcgt tggtccagca gagacggccg cccttgcgcg agcagaaggg      7740
gggcaggggg tcgagctggg tctcgtccgg ggggtccgcg tccacggtga aaaccccggg      7800
gcgcaggcgc gcgtcgaagt agtctatctt gcaaccttgc atgtccagcg cctgctgcca      7860
gtcgcggggc gcgagcgcgc gctcgtaggg gttgagcggc gggccccagg gcatggggtg      7920
ggtgagtgcg gaggcgtaca tgccgcagat gtcatagacg tagaggggct cccgcaggac      7980
cccgatgtag gtggggtagc agcggccgcc gcggatgctg gcgcgcacgt agtcatacag      8040
```

```
ctcgtgcgag ggggcgagga ggtcggggcc caggttggtg cgggcggggc gctccgcgcg    8100
gaagacgatc tgcctgaaga tggcatgcga gttggaagag atggtggggc gctggaagac    8160
gttgaagctg gcgtcctgca ggccgacggc gtcgcgcacg aaggaggcgt aggagtcgcg    8220
cagcttgtgt accagctcgg cggtgacctg cacgtcgagc gcgcagtagt cgagggtctc    8280
gcggatgatg tcatatttag cctgccccctt cttttccac agctcgcggt tgaggacaaa    8340
ctcttcgcgg tctttccagt actcttggat cgggaaaccg tccggttccg aacggtaaga    8400
gcctagcatg tagaactggt tgacggcctg gtaggcgcag cagcccttct ccacggggag    8460
ggcgtaggcc tgcgcggcct tgcggagcga ggtgtgggtc agggcgaagg tgtccctgac    8520
catgactttg aggtactggt gcttgaagtc ggagtcgtcg cagccgcccc gctcccagag    8580
cgagaagtcg gtgcgcttct tggagcgggg gttgggcaga gcgaaggtga catcgttgaa    8640
gaggattttg cccgcgcggg gcatgaagtt gcgggtgatg cggaagggcc ccggcacttc    8700
agagcggttg ttgatgacct gggcggcgag cacgatctcg tcgaagccgt tgatgttgtg    8760
gcccacgatg tagagttcca ggaagcgggg ccggcccttt acggtgggca gcttctttag    8820
ctcttcgtag gtgagctcct cgggcgaggc gaggccgtgc tcggccaggg cccagtccgc    8880
gaggtgcggg ttgtctctga ggaaggactc ccagaggtcg cgggccagga gggtctgcag    8940
gcggtccctg aaggtcctga actggcggcc cacggccatt ttttcggggg tgatgcagta    9000
gaaggtgagg gggtcttgct gccagcggtc ccagtcgagc tgcagggcga ggtcgcgcgc    9060
ggcggtgacc aggcgctcgt cgcccccgaa tttcatgacc agcatgaagg gcacgagctg    9120 cttttccgaag gcccccatcc aagtgtaggt ctctacatcg taggtgacaa agaggcgctc    9180
cgtgcgagga tgcgagccga tcgggaagaa ctggatctcc cgccaccagt tggaggagtg    9240
gctgttgatg tggtggaagt agaagtcccg tcgccgggcc gaacactcgt gctggctttt    9300
gtaaaagcga gcgcagtact ggcagcgctg cacgggctgt acctcctgca cgagatgcac    9360 cttttcgcccg cgcacgagga agccgagggg aaatctgagc cccccgcctg gctcgcggca    9420
tggctggtgc tcttctactt tggatgcgtg tccgtctccg tctggctcct cgaggggtgt    9480
tacggtggag cggaccacca cgccgcgcga gccgcaggtc cagatatcgg cgcgcggcgg    9540
tcggagtttg atgacgacat cgcgcagctg ggagctgtcc atggtctgga gctcccgcgg    9600
cggcggcagg tcagccggga gttcttgcag gttcacctcg cagagtcggg ccagggcgcg    9660
gggcaggtct aggtggtacc tgatctctag gggcgtgttg gtggcggcgt cgatggcttg    9720
caggagcccg catccccggg gggcgacgac ggtgccccgc ggggtggtgg tggtggtggt    9780
ggtggtggtg gtggcggtgc agctcagaag cggtgccgcg ggcgggcccc cggaggtagg    9840
gggggctccg gtcccgccgg cagggcggc agcggcacgt cggcgtggag gcgggcagg    9900 agttggtgct gtgcccggag gttgctggcg aaggcgacga cgcggcggtt gatctcctgg    9960
atctggcgcc tctgcgtgaa gacgacgggc ccggtgagct tgaacctgaa agagagttcg   10020
acagaatcaa tctcggtgtc attgaccgcg gcctggcgca ggatctcctg cacgtctccc   10080
gagttgtctt ggtaggcgat ctcggccatg aactgctcga tctcttcctc ctggaggtct   10140
ccgcgtccgg cgcgttccac ggtggccgcc aggtcgttgg agatgcgccc catgagctgc   10200
gagaaggcgt tgagtccgcc ctcgttccag actcggctgt agaccacgcc ccctggtca   10260 tcgcgggcgc gcatgaccac ctgcgcgagg ttgagctcca cgtgccgcgc gaagacggcg   10320
tagttgcgca gacgctggaa gaggtagttg agggtggtgg cggtgtgctc ggccacgaag   10380
```

```
aagttcatga cccagcggcg caacgtggat tcgttgatgt cccccaaggc ctccagccgt  10440
tccatggcct cgtagaagtc cacggcgaag ttgaaaaact gggagttgcg cgccgacacg  10500
gtcaactcct cctccagaag acggatgagc tcggcgacgg tgtcgcgcac ctcgcgctcg  10560
aaggctatgg ggatctcttc ctccgctagc atcaccacct cctcctcttc ctcctcttct  10620
ggcacttcca tgatggcttc ctcctcttcg gggggcggcg gcggcggcgg tgggggaggg  10680
ggcgctctgc gccggcggcg gcgcaccggg aggcggtcca cgaagcgcgc gatcatctcc  10740
ccgcggcggc ggcgcatggt ctcggtgacg gcgcggccgt tctcccgggg gcgcagttgg  10800
aagacgccgc cggacatctg tgctgggcg ggtggccgt gaggcagcga acggcgctg   10860
acgatgcatc tcaacaattg ctgcgtaggt acgccgccga gggacctgag ggagtccata  10920
tccaccggat ccgaaaacct ttcgaggaag gcgtctaacc agtcgcagtc gcaaggtagg  10980
ctgagcaccg tggcgggcgg cggggggtgg ggggagtgtc tggcggaggt gctgctgatg  11040
atgtaattga agtaggcgga cttgacacgg cggatggtcg acaggagcac catgtccttg  11100
ggtccggcct gctggatgcg gaggcggtcg gctatgcccc aggcttcgtt ctggcatcgg  11160
cgcaggtcct tgtagtagtc ttgcatgagc ctttccaccg gcacctcttc tccttcctct  11220
tctgcttctt ccatgtctgc ttcggccctg ggcggcgcc gcgcccccct gccccccatg   11280
cgcgtgaccc cgaaccccct gagcggttgg agcagggcca ggtcggcgac gacgcgctcg  11340
gccaggatgg cctgctgcac ctgcgtgagg gtggtttgga agtcatccaa gtccacgaag  11400
cggtggtagg cgcccgtgtt gatggtgtag gtgcagttgg ccatgacgga ccagttgacg  11460
gtctggtggc ccggttgcga catctcggtg tacctgagtc gcgagtaggc gcgggagtcg  11520
aagacgtagt cgttgcaagt ccgcaccagg tactggtagc ccaccaggaa gtgcggcggc  11580
ggctggcggt agaggggcca gcgcagggtg cggggggctc cggggccag gtcttccagc   11640
atgaggcggt ggtaggcgta gatgtacctg gacatccagg tgatacccgc ggcggtggtg  11700
gaggcgcgcg ggaagtcgcg cacccggttc cagatgttgc gcaggggcag aaagtgctcc  11760
atggtaggcg tgctctgtcc agtcagacgc gcgcagtcgt tgatactcta gaccagggaa  11820
aacgaaagcc ggtcagcggg cactcttccg tggtctggtg aatagatcgc aagggtatca  11880
tggcggaggg cctcggttcg agccccgggt ccggccgga cggtccgcca tgatccacgc   11940
ggttaccgcc cgcgtgtcga acccaggtgt gcgacgtcag acaacggtgg agtgttcctt  12000
ttggcgtttt tctggccggg cgccggcgtc gcgtaagaga ctaagccgcg aaagcgaaag  12060
cagtaagtgg ctcgctcccc gtagccgag ggatccttgc taagggttgc gttgcggcga   12120
accccggttc gaatcccgta ctcgggccgg ccggacccgc ggctaaggtg ttggattggc  12180
ctcccccctcg tataaagacc ccgcttgcgg attgactccg gacacgggga cgagccccctt 12240
ttatttttgc tttccccaga tgcatccggt gctgcggcag atgcgccccc cgccccagca  12300
gcagcaacaa caccagcaag agcggcagca acagcagcgg gagtcatgca gggcccctc   12360
acccacccctc ggcgggccgg ccacctcggc gtccgcggcc gtgtctggcg cctgcggcgg  12420
cggcgggggg ccggctgacg accccgagga gccccgcgg cgcagggcca gacactacct   12480
ggacctggag gagggcgagg gcctggcgcg ctgggggcg ccgtctcccg agcgccaccc   12540
gcgggtgcag ctgaagcgcg actcgcgcga ggcgtacgtg cctcggcaga acctgttcag  12600
ggaccgcgcg ggcgaggagc ccgaggagat gcgggacagg aggttcagcg cagggcggga  12660
gctgcggcag gggctgaacc gcgagcggct gctgcgcgag gaggactttg agcccgacgc  12720
gcggacgggg atcagccccg cgcgcgcgca cgtggcggcc gccgacctgg tgacggcgta  12780
```

```
cgagcagacg gtgaaccagg agatcaactt ccaaaagagt ttcaacaacc acgtgcgcac   12840
gctggtggcg cgcgaggagg tgaccatcgg gctgatgcac ctgtgggact ttgtaagcgc   12900
gctggtgcag aaccccaaca gcaagcctct gacggcgcag ctgttcctga tagtgcagca   12960
cagcagggac aacgaggcgt ttagggacgc gctgctgaac atcaccgagc ccagggtcg    13020 gtggctgctg gacctgatta acatcctgca gagcatagtg gtgcaggagc gcagcctgag   13080
cctggccgac aaggtggcgg ccatcaacta ctcgatgctg agcctgggca agttttacgc   13140
gcgcaagatc taccagacgc cgtacgtgcc catagacaag gaggtgaaga tcgacggttt   13200
ttacatgcgc atggcgctga aggtgctcac cctgagcgac gacctgggcg tgtaccgcaa   13260
cgagcgcatc cacaaggccg tgagcgtgag ccggcggcgc gagctgagcg accgcgagct   13320
gatgcacagc ctgcagcggg cgctggcggg cgccggcagc ggcgacaggg aggcggagtc   13380
ctacttcgat gcggggcgg acctgcgctg gcgcccagc cggcgggccc tggaggccgc     13440
gggggtccgc gaggactatg acgaggacg cgaggaggat gaggagtacg agctagagga    13500
gggcgagtac ctggactaaa ccgcgggtgg tgtttccggt agatgcaaga cccgaacgtg   13560
gtggacccgg cgctgcgggc ggctctgcag agccagccgt ccggccttaa ctcctcagac   13620
gactggcgac aggtcatgga ccgcatcatg tcgctgacgg cgcgtaaccc ggacgcgttc   13680
cggcagcagc cgcaggccaa caggctctcc gccatcctgg aggcggtggt gcctgcgcgc   13740
tcgaacccca cgcacgagaa ggtgctggcc atagtgaacg cgctggccga gaacagggcc   13800
atccgcccgg acgaggccgg gctggtgtac gacgcgctgc tgcagcgcgt ggcccgctac   13860
aacagcggca acgtgcagac caacctggac cggctggtgg gggacgtgcg cgaggcggtg   13920
gcgcagcgcg agcgcgcgga tcggcagggc aacctgggct ccatggtggc gctgaatgcc   13980
ttcctgagca cgcagccggc caacgtgccg cgggggcagg aagactacac caactttgtg   14040
agcgcgctgc ggctgatggt gaccgagacc ccccagagcg aggtgtacca gtcgggcccg   14100
gactacttct tccagaccag cagacagggc ctgcagacgg tgaacctgag ccaggctttc   14160
aagaacctgc gggggctgtg gggcgtgaag gcgcccaccg cgaccgggc gacggtgtcc    14220 agcctgctga cgcccaactc gcgcctgctg ctgctgctga tcgcgccgtt cacggacagc   14280
ggcagcgtgt cccgggacac ctacctgggg cacctgctga ccctgtaccg cgaggccatc   14340
gggcaggcgc aggtggacga gcacaccttc caggagatca ccagcgtgag ccgcgcgctg   14400
gggcaggagg acacgagcag cctggaggcg actctgaact acctgctgac caaccggcgg   14460
cagaagattc cctcgctgca cagcctgacc tccgaggagg agcgcatctt gcgctacgtg   14520
cagcagagcg tgagcctgaa cctgatgcgc gacggggtga cgcccagcgt ggcgctggac   14580
atgaccgcgc gcaacatgga accgggcatg tacgccgcgc accggcctta catcaaccgc   14640
ctgatggact acctgcatcg cgcggcggcc gtgaacccg agtactttac caacgccatc   14700
ctgaacccgc actggctccc gccgcccggg ttctacagcg ggggcttcga ggtcccggag   14760
gccaacgatg gcttcctgtg ggacgacatg gacgacagcg tgttctcccc gcggccgcag   14820
gcgctggcgg aagcgtccct gctgcgtccc aagaaggagg aggaggaggc gagtcgccgc   14880
cgcggcagca gcgcgtggc ttctctgtcc gagctggggg cggcagccgc cgcgcgcccc    14940
gggtccctgg gcggcagccc ctttccgagc ctggtggggt ctctgcacag cgagcgcacc   15000
acccgccctc ggctgctggg cgaggacgag tacctgaata actccctgct gcagccggtg   15060
cgggagaaaa acctgccccc cgccttcccc aacaacggga tagagagcct ggtggacaag   15120
```

```
atgagcagat ggaagaccta tgcgcaggag cacagggacg cgcccgcgct ccggccgccc    15180
acgcggcgcc agcgccacga ccggcagcgg gggctggtgt gggatgacga ggactccgcg    15240
gacgatagca gcgtgctgga cctgggaggg agcggcaacc cgttcgcgca cctgcgcccc    15300
cgcctgggga ggatgtttta aaaaaaaaa aagcaagaag catgatgcaa aattaaataa    15360
aactcaccaa ggccatggcg accgagcgtt ggtttcttgt gttcccttca gtatgcggcg    15420
cgcggcgatg taccaggagg gacctcctcc ctcttacgag agcgtggtgg gcgcggcggc    15480
ggcggcgccc tcttctccct ttgcgtcgca gctgctggag ccgccgtacg tgcctccgcg    15540
ctacctgcgg cctacggggg ggagaaacag catccgttac tcggagctgg cgcccctgtt    15600
cgacaccacc cgggtgtacc tggtggacaa caagtcggcg gacgtggcct ccctgaacta    15660
ccagaacgac cacagcaatt ttttgaccac ggtcatccag aacaatgact acagcccgag    15720
cgaggccagc acccagacca tcaatctgga tgaccggtcg cactggggcg gcgacctgaa    15780
aaccatcctg cacaccaaca tgcccaacgt gaacgagttc atgttcacca ataagttcaa    15840
ggcgcgggtg atggtgtcgc gctcgcacac caaggaagac cgggtggagc tgaagtacga    15900
gtgggtggag ttcgagctgc cagagggcaa ctactccgag accatgacca ttgacctgat    15960
gaacaacgcg atcgtggagc actatctgaa agtgggcagg caaaacgggg tcctggagag    16020
cgacatcggg gtcaagttcg acaccaggaa cttccgcctg gggctggacc ccgtgaccgg    16080
gctggttatg cccggggtgt acaccaacga ggccttccat cccgacatca tcctgctgcc    16140
cggctgcggg gtggacttca cttacagccg cctgagcaac ctcctgggca tccgcaagcg    16200
gcagcccttc caggagggct tcaggatcac ctacgaggac ctggaggggg gcaacatccc    16260
cgcgctcctc gatgtggagg cctaccagga tagcttgaag gaaaatgagg cgggacagga    16320
ggataccacc cccgccgcct ccgccgccgc cgagcagggc gaggatgctg ctgacaccgc    16380
ggccgcggac ggggcagagg ccgaccccgc tatggtggtg gaggctcccg agcaggagga    16440
ggatatgaat gacagtgcgg tgcgcggaga caccttcgtc acccgggggg aggaaaagca    16500
agcggaggcc gaggccgcgg ccgaggaaaa gcaactggcg gcagcagcgg cggcggcggc    16560
gttggccgcg gcggaggctg agtctgaggg gaccaagccc gccaaggagc ccgtgattaa    16620
gcccctgacc gaagatagca agaagcgcag ttacaacctg ctcaaggaca gcaccaacac    16680
cgcgtaccgc agctggtacc tggcctacaa ctacggcgac ccgtcgacgg gggtgcgctc    16740
ctggaccctg ctgtgcacgc cggacgtgac ctgcggctcg gagcaggtgt actggtcgct    16800
gcccgacatg atgcaagacc ccgtgacctt ccgctccacg cggcaggtca gcaacttccc    16860
ggtggtgggc gccgagctgc tgcccgtgca ctccaagagc ttctacaacg accaggccgt    16920
ctactcccag ctcatccgcc agttcacctc tctgacccac gtgttcaatc gctttcctga    16980
gaaccagatt ctggcgcgcc cgcccgcccc caccatcacc accgtcagtg aaaacgttcc    17040
tgctctcaca gatcacggga cgctaccgct gcgcaacagc atcggaggag tccagcgagt    17100
gaccgttact gacgccagac gccgcacctg cccctacgtt tacaaggcct tgggcatagt    17160
ctcgccgcgc gtcctttcca gccgcacttt ttgagcaaca ccaccatcat gtccatcctg    17220
atctcaccca gcaataactc cggctgggga ctgctgcgcg cgcccagcaa gatgttcgga    17280
ggggcgagga agcgttccga gcagcacccc gtgcgcgtgc gcgggcactt ccgcgccccc    17340
tggggagcgc acaaacgcgg ccgcgcgggg cgcaccaccg tggacgacgc catcgactcg    17400
gtggtggagc aggcgcgcaa ctacaggccc gcggtctcta ccgtgacgcg gccatccag    17460 accgtggtgc gggcgcgcg gcggtacgcc aagctgaaga gccgccggaa gcgcgtggcc    17520
```

```
cgccgccacc gccgccgacc cggggccgcc gccaaacgcg ccgccgcggc cctgcttcgc   17580
cgggccaagc gcacgggccg ccgcgccgcc atgagggccg cgcgccgctt ggccgccggc   17640
atcaccgccg ccaccatggc cccccgtacc cgaagacgcg cggccgccgc cgccgccgcc   17700
gccatcagtg acatggccag caggcgccgg ggcaacgtgt actgggtgcg cgactcggtg   17760
accggcacgc gcgtgcccgt gcgcttccgc ccccgcgga cttgagatga tgtgaaaaaa   17820
caacactgag tctcctgctg ttgtgtgtat cccagcggcg gcggcgcgcg cagcgtcatg   17880
tccaagcgca aaatcaaaga agagatgctc caggtcgtcg cgccggagat ctatgggccc   17940
ccgaagaagg aagagcagga ttcgaagccc cgcaagataa agcgggtcaa aaagaaaaag   18000
aaagatgatg acgatgccga tggggaggtg gagttcctgc gcgccacggc gcccaggcgc   18060
ccggtgcagt ggaagggccg gcgcgtaaag cgcgtcctgc gccccggcac cgcggtggtc   18120
ttcacgcccg gcgagcgctc caccggact ttcaagcgcg tctatgacga ggtgtacggc   18180
gacgaagacc tgctggagca ggccaacgag cgcttcggag agtttgctta cgggaagcgt   18240
cagcgggcgc tggggaagga ggacctgctg gcgctgccgc tggaccaggg caaccccacc   18300
cccagtctga gcccgtgac cctgcagcag gtgctgccga gcagcgcacc ctccgaggcg   18360
aagcggggtc tgaagcgcga gggcggcgac ctggcgccca ccgtgcagct catggtgccc   18420
aagcggcaga ggctggagga tgtgctggag aaaatgaaag tagacccccgg tctgcagccg   18480 gacatcaggg tccgtcccat caagcaggtg gcgccgggcc tcggcgtgca gaccgtggac   18540
gtggtcatcc ccaccggcaa ctccccccgcc gccaccacca ctaccgctgc ctccacggac   18600
atggagacac agaccgatcc cgccgcagcc gcagccgccg ccgcagccgc gacctcctcg   18660
gcggaggtgc agacggaccc ctggctgccg ccggcgatgt cagctccccg cgcgcgccgc   18720
ggacgcagaa agtacggcgc cgccaacgcg ctcctgcccg agtacgcctt gcatccttcc   18780
atcgcgccca ccccccggcta ccgaggctat acctaccgcc cgcgaagagc caagggttcc   18840 accccgccgtc cccgccgacg cgccgccgcc accaccccgcc gccgccgccg cagacgccag   18900
cccgcactgg ctccagtctc cgtgaggaga gtggcgcgcg acggacacac cctggtgctg   18960
cccagggcgc gctaccaccc cagcatcgtt taaaagcctg ttgtggttct tgcagatatg   19020
gccctcactt gccgcctccg tttccggtg ccgggatacc gaggaggaag atcgcgccgc   19080
aggaggggtc tggccggccg cggcctgagc ggaggcagcc gccgcgcgca ccggcggcga   19140
cgcgccacca gccgacgcat gcgcggcggg gtgctgcccc tgttaatccc cctgatcgcc   19200
gcggcgatcg gcgccgtgcc cgggatcgcc tccgtggcct tgcaagcgtc ccagaggcat   19260
tgacagactt gcaaacttgc aaatatggaa aaaaaaaaa aaccccaata aaaagtctag   19320
actctcacgc tcgcttggtc ctgtgactat tttgtagaat ggaagacatc aactttgcgt   19380
cgctggcccc gcgtcacggc tcgcgcccgt tcctgggaca ctggaacgat atcggcacca   19440
gcaacatgag cggtggcgcc ttcagttggg gctctctgtg gagcggcatt aaaagtatcg   19500
ggtctgccgt taaaaattac ggctcccggg cctggaacag cagcacgggc cagatgttga   19560
gagacaagtt gaaagagcag aacttccagc agaaggtggt ggagggcctg gcctccggca   19620 tcaacgggt ggtggacctg gccaaccagg ccgtgcagaa taaaatcaac agcagactgg   19680 accccggcc gccggtggag gaggtgccgc cggcgctgga cggtgtcc cccgatgggc   19740 gtggcgagaa gcgccgcgg cccgataggg aagagaccac tctggtcacg cagaccgatg   19800
agccgccccc gtatgaggag gccctaaagc aaggtctgcc caccacgcgg cccatcgcgc   19860
```

```
ccatggccac cggggtggtg ggccgccaca cccccgccac gctggacttg cctccgcccg    19920
ccgatgtgcc gcagcagcag aaggcggcac agccgggccc gcccgcgacc gcctcccgtt    19980
cctccgccgg tcctctgcgc cgcgcggcca gcggcccccg cggggggggtc gcgaggcacg    20040
gcaactggca gagcacgctg aacagcatcg tgggtctggg ggtgcggtcc gtgaagcgcc    20100
gccgatgcta ctgaatagct tagctaacgt gttgtatgtg tgtatgcgcc ctatgtcgcc    20160
gccagaggag ctgctgagtc gccgccgttc gcgcgccac caccaccgcc actccgcccc    20220
tcaagatggc gaccccatcg atgatgccgc agtggtcgta catgcacatc tcgggccagg    20280
acgcctcgga gtacctgagc cccgggctgg tgcagttcgc ccgcgccacc gagagctact    20340
tcagcctgag taacaagttt aggaaccccca cggtggcgcc cacgcacgat gtgaccaccg    20400
accggtctca gcgcctgacg ctgcggttca ttcccgtgga ccgcgaggac accgcgtact    20460
cgtacaaggc gcggttcacc ctggccgtgg gcgacaaccg cgtgctggac atggcctcca    20520
cctactttga catccgcggg gtgctggacc ggggtcccac tttcaagccc tactctggca    20580
ccgcctacaa ctccctggcc cccaagggcg ctcccaactc ctgcgagtgg gagcaagagg    20640
aaactcaggc agttgaagaa gcagcagaag aggaagaaga agatgctgac ggtcaagctg    20700
aggaagagca agcagctacc aaaaagactc atgtatatgc tcaggctccc ctttctggcg    20760
aaaaaattag taaagatggt ctgcaaatag aacggacgc tacagctaca gaacaaaaac    20820
ctatttatgc agaccctaca ttccagcccg aaccccaaat cggggagtcc cagtggaatg    20880
aggcagatgc tacagtcgcc ggcggtagag tgctaaagaa atctactccc atgaaaccat    20940
gctatggttc ctatgcaaga cccacaaatg ctaatggagg tcagggtgta ctaacggcaa    21000
atgcccaggg acagctagaa tctcaggttg aaatgcaatt cttttcaact tctgaaaacg    21060
cccgtaacga ggctaacaac attcagccca aattggtgct gtatagtgag gatgtgcaca    21120
tggagacccc ggatacgcac ctttcttaca gcccgcaaa aagcgatgac aattcaaaaa    21180
tcatgctggg tcagcagtcc atgcccaaca gacctaatta catcggcttc agagacaact    21240
ttatcggcct catgtattac aatagcactg gcaacatggg agtgcttgca ggtcaggcct    21300
ctcagttgaa tgcagtggtg gacttgcaag acagaaacac agaactgtcc taccagctct    21360
tgcttgattc catgggtgac agaaccagat acttttccat gtggaatcag gcagtggaca    21420
gttatgaccc agatgttaga attattgaaa atcatggaac tgaagacgag ctccccaact    21480
attgtttccc tctgggtggc atagggggtaa ctgacactta ccaggctgtt aaaaccaaca    21540
atggcaataa cggggggccag gtgacttgga caaaagatga aacttttgca gatcgcaatg    21600
aaatagggt gggaaacaat ttcgctatgg agatcaacct cagtgccaac ctgtggagaa    21660
acttcctgta ctccaacgtg gcgctgtacc taccagacaa gcttaagtac aaccccctcca    21720
atgtggacat ctctgacaac cccaacacct acgattacat gaacaagcga gtggtggccc    21780
cggggctggt ggactgctac atcaacctgg gcgcgcgctg gtcgctggac tacatggaca    21840
acgtcaaccc cttcaaccac caccgcaatg cgggcctgcg ctaccgctcc atgctcctgg    21900
gcaacgggcg ctacgtgccc ttccacatcc aggtgcccca gaagttcttt gccatcaaga    21960
acctcctcct cctgccgggc tcctacacct acgagtggaa cttcaggaag gatgtcaaca    22020
tggtcctcca gagctctctg gtaacgatct caggtgtgga cggggccagc atcaagttcg    22080
agagcatctg cctctacgcc accttcttcc ccatggccca aacacggcc tccacgctcg    22140
aggccatgct caggaacgac accaacgacc agtccttcaa tgactacctt tccgccgcca    22200
acatgctcta ccccatacccc gccaacgcca ccaacgtccc catctccatc ccctcgcgca    22260
```

```
actgggcggc cttccgcggc tgggccttca cccgcctcaa gaccaaggag acccctccc   22320
tgggctcggg attcgacccc tactacacct actcgggctc tattccctac ctggacggca   22380
ccttctacct caaccacact ttcaagaagg tctcggtcac cttcgactcc tcggtcagct   22440
ggccgggcaa cgaccgtctg ctcaccccca acgagttcga gatcaagcgc tcggtcgacg   22500
gggaaggcta caacgtggcc cagtgcaaca tgaccaagga ctggttcctg gtccagatgc   22560
tggccaacta caacatcggc taccagggct tctacatccc agagagctac aaggacagga   22620
tgtactcctt cttcaggaac ttccagccca tgagccggca ggtggtggac cagaccaagt   22680
acaaggacta ccaggaggtg ggcatcatcc accagcacaa caactcgggc ttcgtgggct   22740
acctcgcccc caccatgcgc gagggacagg cctaccccgc caacttcccc tacccgctca   22800
taggcaagac cgcggtcgac agcatcaccc agaaaaagtt cctctgcgac cgcaccctct   22860
ggcgcatccc cttctccagc aacttcatgt ccatgggtgc gctctcggac ctgggccaga   22920
acttgctcta cgccaactcc gcccacgccc tcgacatgac cttcgaggtc gaccccatgg   22980
acgagcccac ccttctctat gttctgttcg aagtctttga cgtggtccgg gtccaccagc   23040
cgcaccgcgg cgtcatcgag accgtgtacc tgcgtacgcc cttctcggcc ggcaacgcca   23100
ccacctaaag aagcaagccg cagtcatcgc cgcctgcatg ccgtcgggtt ccaccgagca   23160
agagctcagg gccatcgtca gagacctggg atgcgggccc tattttttgg gccacttcga   23220
caagcgcttc cctggctttg tctccccaca caagctggcc tgcgccatcg tcaacacggc   23280
cggccgcgag accgggggcg tgcactggct ggccttttgcc tggaacccgc gctccaaaac   23340
atgcttcctc tttgacccct tcggcttttc ggaccagcgg ctcaagcaaa tctacgagtt   23400
cgagtacgag ggcttgctgc gtcgcagcgc catcgcctcc tcgcccgacc gctgcgtcac   23460
cctcgaaaag tccacccaga ccgtgcaggg gcccgactcg gccgcctgcg gtctcttctg   23520
ctgcatgttt ctgcacgcct ttgtgcactg gcctcagagt cccatggacc gcaaccccac   23580
catgaacttg ctgacgggg tgcccaactc catgctccaa agccccagg tcgagcccac    23640
cctgcgccgc aaccaggagc agctctacag cttcctggag cgccactcgc cctacttccg   23700
ccgccacagc gcacagatca ggagggccac ctccttctgc cacttgcaag agatgcaaga   23760
agggtaataa cgatgtacac acttttttct caataaatgg catttttttt ttatttatac   23820
aagctctctg gggtattcat ttcccaccac caccacccgc cgttgtcgcc atctggctct   23880
atttagaaat cgaagggtt ctgccgggag tcgccgtgcg ccacgggcag ggacacgttg    23940
cgatactggt agcgggtgcc ccacttgaac tcgggcacca ccaggcgagg cagctcgggg   24000
aagttttcgc tccacaggct gcgggtcagc accagcgcgt tcatcaggtc gggcgccgag   24060
atcttgaagt cgcagttggg gccgccgccc tgcgcgcgcg agttgcggta caccgggttg   24120
cagcactgga acaccaacag cgccgggtgc ttcacgctgg ccagcacgct gcggtcggag   24180
atcagctcgg cgtccaggtc ctccgcgttg ctcagcgcga acgggtcat cttgggcact    24240
tgccgcccca ggaagggcgc gtgccccggt ttcgagttgc agtcgcagcg cagcgggatc   24300
agcaggtgcc cgtgcccgga ctcggcgttg gggtacagcg cgcgcatgaa ggcctgcatc   24360
tggcggaagg ccatctgggc cttggcgccc tccgagaaga acatgccgca ggacttgccc   24420
gagaactggt ttgcggggca gctggcgtcg tgcaggcagc agcgcgcgtc ggtgttggcg   24480
atctgcacca cgttgcgccc ccaccggttc ttcacgatct tggccttgga cgattgctcc   24540
ttcagcgcgc gctgccgtt ctcgctggtc acatccatct cgatcacatg ttccttgttc    24600
```

```
accatgctgc tgccgtgcag acacttcagc tcgccctccg tctcggtgca gcggtgctgc   24660
cacagcgcgc agcccgtggg ctcgaaagac ttgtaggtca cctccgcgaa ggactgcagg   24720
tacccctgca aaaagcggcc catcatggtc acgaaggtct tgttgctgct gaaggtcagc   24780
tgcagcccgc ggtgctcctc gttcagccag gtcttgcaca cggccgccag cgcctccacc   24840
tggtcgggca gcatcttgaa gttcaccttc agctcattct ccacgtggta cttgtccatc   24900
agcgtgcgcg ccgcctccat gcccttctcc caggccgaca ccagcggcag gctcacgggg   24960
ttcttcacca tcaccgtggc cgccgcctcc gccgcgcttt cgctttccgc cccgctgttc   25020
tcttcctctt cctcctcttc ctcgccgccg cccactcgca gccccgcac cacgggtcg   25080 tcttcctgca ggcgctgcac cttgcgcttg ccgttgcgcc cctgcttgat gcgcacgggc   25140
gggttgctga agcccaccat caccagcgcg gcctcttctt gctcgtcctc gctgtccaga   25200
atgacctccg gggaggggg gttggtcatc ctcagtaccg aggcacgctt cttttcttc   25260 ctgggggcgt tcgccagctc cgcggctgcg gccgctgccg aggtcgaagg ccgagggctg   25320
ggcgtgcgcg gcaccagcgc gtcttgcgag ccgtcctcgt cctcctcgga ctcgagacgg   25380
aggcgggccc gcttcttcgg gggcgcgcgg ggcggcggag gcggcggcgg cgacggagac   25440
ggggacgaga catcgtccag ggtgggtgga cggcgggccg cgccgcgtcc gcgctcgggg   25500
gtggtttcgc gctggtcctc ttcccgactg gccatctccc actgctcctt ctcctatagg   25560
cagaaagaga tcatggagtc tctcatgcga gtcgagaagg aggaggacag cctaaccgcc   25620
ccctctgagc cctccaccac cgccgccacc accgccaatg ccgccgcgga cgacgcgccc   25680
accgagacca ccgccagtac caccctcccc agcgacgcac ccccgctcga gaatgaagtg   25740
ctgatcgagc aggacccggg tttttgtgagc ggagaggagg atgaggtgga tgagaaggag   25800
aaggaggagg tcgccgcctc agtgccaaaa gaggataaaa agcaagacca ggacgacgca   25860
gataaggatg agacagcagt cgggcggggg aacggaagcc atgatgctga tgacggctac   25920
ctagacgtgg gagacgacgt gctgcttaag cacctgcacc gccagtgcgt catcgtctgc   25980
gacgcgctgc aggagcgctg cgaagtgccc ctggacgtgg cggaggtcag ccgcgcctac   26040
gagcggcacc tcttcgcgcc gcacgtgccc cccaagcgcc gggagaacgg cacctgcgag   26100
cccaacccgc gtctcaactt ctacccggtc ttcgcggtac ccgaggtgct ggccacctac   26160
cacatcttct tccaaaactg caagatcccc ctctcctgcc gcgctaaccg cacccgcgcc   26220
gacaaaaccc tgaccctgcg gcagggcgcc cacatacctg atattgcctc tctggaggaa   26280
gtgcccaaga tcttcgaggg tctcggtcgc gacgagaaac gggcggcgaa cgctctgcac   26340
ggagacagcg aaaacgagag tcactcgggg gtgctggtgg agctcgaggg cgacaacgcg   26400
cgcctggccg tactcaagcg cagcatagag gtcaccccact ttgcctaccc ggcgctcaac   26460 ctgccccccca aggtcatgag tgtggtcatg ggcgagctca tcatgcgccg cgctcagccc   26520
ctggccgcga tgcaaaactt gcaagagtcc tccgaggaag gcctgccgc ggtcagcgac   26580 gagcagctag cgcgctggct ggagacccgc gaccccgcgc agctgaggga gcggcgcaag   26640
ctcatgatgg ccgcggtgct ggtcaccgtg gagctcgagt gtctgcagcg cttcttcgcg   26700
gaccccgaga tgcagcgcaa gctcgaggag accctgcact acaccttccg ccagggctac   26760
gtgcgccagg cctgcaagat ctccaacgtg gagctctgca acctggtctc ctacctgggc   26820
atcctgcacg agaaccgcct cgggcagaac gtcctgcact ccaccctcaa aggggaggcg   26880
cgccgcgact acatccgcga ctgcgcctac ctcttcctct gctacacctg gcagacggcc   26940
atgggggtct ggcagcagtg cctggaggag cgcaacctca aggagctgga aaagctactc   27000
```

```
aagcgcaccc tcagggacct ctggacgggc ttcaacgagc gctcggtggc cgccgcgctg   27060
gcggacatca tcttccccga gcgcctgctc aagaccctgc agcagggcct gcccgacttc   27120
accagccaga gcatgctgca gaactttagg actttcatcc tggagcgctc gggcatcctg   27180
cctgccactt gctgcgcgct gcccagcgac ttcgtgccca tcaagtacag ggagtgcccg   27240
ccgccgctct ggggccactg ctacctcttc cagctggcca actacctcgc ctaccactcg   27300
gacctcatgg aagacgtgag cggcgagggc ctgctcgagt gccactgccg ctgcaacctc   27360
tgcacgcccc accgctctct agtctgcaac ccgcagctgc tcagcgagag tcagattatc   27420
ggtaccttcg agctgcaggg tccctcgcct gacgagaagt ccgcggctcc ggggctgaaa   27480
ctcactccgg ggctgtggac ttccgcctac ctacgcaaat ttgtacctga ggactaccac   27540
gcccacgaga tcaggttcta cgaagaccaa tcccgcccgc caaggcgga gctcaccgcc   27600 tgcgtcatca cccaggggca catcctgggc caattgcaag ccatcaacaa gcccgccga   27660 gagttcttgc tgaaaaaggg tcgggggggtg tacctggacc cccagtccgg cgaggagcta   27720
aacccgctac ccccgccgcc gccccagcag cgggaccttg cttcccagga tggcacccag   27780
aaagaagcag cagccgccgc cgccgcagcc atacatgctt ctggaggaag aggaggagga   27840
ctgggacagt caggcagagg aggtttcgga cgaggagcag gaggagatga tggaagactg   27900
ggaggaggac agcagcctag acgaggaagc ttcagaggcc gaagaggtgg cagacgcaac   27960
accatcaccc tcggtcgcag cccctcgcc ggggcccctg aaatcctccg aacccagcac   28020
cagcgctata acctccgctc ctccggcgcc ggcgccaccc gcccgcagac caaccgtag   28080 atgggacacc acaggaaccg gggtcggtaa gtccaagtgc ccgccgccgc caccgcagca   28140
gcagcagcag cgccagggct accgctcgtg gcgcgggcac aagaacgcca tagtcgcctg   28200
cttgcaagac tgcgggggca acatctcttt cgcccggcgc ttcctgctat tccaccacgg   28260
ggtcgccttt ccccgcaatg tcctgcatta ctaccgtcat ctctacagcc cctactgcag   28320
cggcgaccca gaggcggcag cggcagccac agcggcgacc accacctagg aagatatcct   28380
ccgcgggcaa gacagcggca gcagcggcca ggagacccgc ggcagcagcg gcggagcgg   28440 tgggcgcact gcgcctctcg cccaacgaac ccctctcgac ccgggagctc agacacagga   28500
tcttccccac tttgtatgcc atcttccaac agagcagagg ccaggagcag gagctgaaaa   28560
taaaaaacag atctctgcgc tccctcaccc gcagctgtct gtatcacaaa agcgaagatc   28620
agcttcggcg cacgctggag gacgcggagg cactcttcag caaatactgc gcgctcactc   28680
ttaaagacta gctccgcgcc cttctcgaat ttaggcggga gaaaactacg tcatcgccgg   28740
ccgccgccca gcccgcccag ccgagatgag caaagagatt cccacgccat acatgtggag   28800
ctaccagccg cagatgggac tcgcggcggg agcggcccag gactactcca cccgcatgaa   28860
ctacatgagc gcgggacccc acatgatctc acaggtcaac gggatccgcg cccagcgaaa   28920
ccaaatactg ctggaacagg cggccatcac cgccacgccc cgcctataatc tcaacccccg   28980 aaattggccc gccgccctcg tgtaccagga acccctcc gccaccaccg tactacttcc   29040
gcgtgacgcc caggccgaag tccagatgac taactcaggg gcgcagctcg cgggcggctt   29100
tcgtcacggg gcgcggccgc tccgaccagg tataagacac ctgatgatca gaggccgagg   29160
tatccagctc aacgacgagt cggtgagctc ttcgctcggt ctccgtccgg acggaacttt   29220
ccagctcgcc ggatccggcc gctcttcgtt cacgcccgc caggcgtacc tgactctgca   29280
gacctcgtcc tcggagccc gctccggagg catcggaacc ctccagttcg tggaggagtt   29340
```

```
cgtgccctcg gtctacttca accccttctc gggacctccc ggacgctacc ccgaccagtt   29400
cattccgaac tttgacgcgg tgaaggactc ggcggacggc tacgactgaa tgtcaggtgc   29460
cgaggcagag cagcttcgcc tgagacacct cgagcactgc cgccgccaca agtgcttcgc   29520
ccgcggttcc ggtgagttct gctactttca gctacccgag gagcataccg aggggccggc   29580
gcacggcgtc cgcctgacca cccagggcga ggttacctgt tccctcatcc gggagttcac   29640
cctccgtccc ctgctagtgg agcgggagcg gggtccctgt gtcctaacta tcgcctgcaa   29700
ctgccctaac cctggattac atcaagatct ttgctgtcat ctctgtgctg agtttaataa   29760
acgctgagat cagaatctac tgggaattcg atttagtccc ctttaactaa tcaaacactg   29820
gaatcaataa aaagaatcac ttacttaaaa tcagacagca ggtctctgtc cagtttattc   29880
agcagcacct ccttcccctc ctcccaactc tggtactcca aacgccttct ggcggcaaac   29940
ttcctccaca ccctgaaggg aatgtcagat tcttgctcct gtccctccgc acccactatc   30000
ttcatgttgt tgcagatgaa gcgcaccaaa acgtctgacg agagcttcaa ccccgtgtac   30060
ccctatgaca cggaaagcgg ccctcccctcc gtccctttcc tcacccctcc cttcgtgtct   30120
cccgatggat tccaagaaag ccccccgggg gtcctgtctc tgaacctggc cgagcccctg   30180
gtcacttccc acggcatgct cgccctgaaa atgggaagtg gcctctccct ggacgacgct   30240
ggcaacctca cctctcaaga tatcaccacc gctagccctc ccctcaaaaa aaccaagacc   30300
aacctcagcc tagaaacctc atccccccta actgtaagca cctcaggcgc cctcaccgta   30360
gcagccgccg ctcccctggc agtggccggc acctccctca ccatgcaatc agaggccccc   30420
ctgacagtac aggatgcaaa actcaccctg gccaccaaag gcccctgac cgtgtctgaa   30480 ggcaaactgg ccttgcaaac atcggccccg ctgacggccg ctgacagcag cacccctcacc   30540 gttagcgcca caccaccaat taatgtaagc agtggaagtt taggcttaga catggaagac   30600
cctatgtata ctcacgatgg aaaactggga ataagaattg ggggtccact aagagtagta   30660
gacagcttgc acacactcac tgtagttacc ggaaatggac taactgtaga taacaatgcc   30720
ctccaaacta gagttacggg cgccctaggt tatgacacat caggaaatct acaattgaga   30780
gctgcaggag gtatgcgaat tgatgcaaat ggccaactta tccttaatgt ggcatacccca   30840 tttgatgctc agaacaatct cagccttaga cttggtcagg gaccctgta tataaacaca   30900 gaccacaacc tggatttgaa ttgcaacaga ggtctaacca caactaccac caacaacaca   30960
aaaaaacttg agactaaaat tagctcaggc ttagactatg acaccaatgg tgctgtcatt   31020
attaaacttg gcactggtct aagcttcgac aacacaggcg ccctaactgt gggaaacact   31080
ggtgatgata aactgactct gtggacgacc ccagacccat ctccaaattg cagaattcac   31140
tcagacaaag actgcaagtt tactctagtc ctaactaagt gtggaagcca aatcctggcc   31200
tctgtcgccg ccctagcggt atcaggaaat ctggcttcga taacaggcac cgttgccagc   31260
gttaccatct ttctcagatt tgatcagaat ggagtgctta tggaaaactc ctcgctagac   31320
aggcagtact ggaacttcag aaatggcaac tcaactaacg ctgcccccta caccaatgca   31380
gttgggttca tgccaaacct cgcagcatac cccaaaacgc aaagccagac tgctaaaaac   31440
aacattgtaa gtcaggttta cttgaatgga gacaaatcca aacccatgac ccttaccatc   31500
accctcaatg gaactaatga atccagtgaa actagccagg tgagtcacta ctccatgtca   31560
tttacatggg cttgggaaag tgggcaatat gccactgaaa cctttgccac caactccttc   31620
acctttcttt acattgctga acaataaaaa gcatgacact gatgttcatt tctgattctt   31680
attttattat tttcaaacac aacaaaatca ttcaagtcat tcttccatct tagcttaata   31740
```

```
gacacagtag cttaatagac ccagtagtgc aaagccccat tctagcttat aactagtgga     31800
gaagtactcg cctacatggg ggtagagtca taatcgtgca tcaggatagg gcggtggtgc     31860
tgcagcagcg cgcgaataaa ctgctgccgc cgccgctccg tcctgcagga atacaacatg     31920
gcagtggtct cctcagcgat gattcgcacc gcccgcagca taaggcgcct tgtcctccgg     31980
gcacagcagc gcaccctgat ctcacttaaa tcagcacagt aactgcagca cagcaccaca     32040
atattgttca aaatcccaca gtgcaaggcg ctgtatccaa agctcatggc ggggaccaca     32100
gaacccacgt ggccatcata ccacaagcgc aggtagatta agtggcgacc cctcataaac     32160
acgctggaca taaacattac ctcttttggc atgttgtaat tcaccacctc ccggtaccat     32220
ataaacctct gattaaacat ggcgccatcc accaccatcc taaaccagct ggccaaaacc     32280
tgcccgccgg ctatacactg cagggaaccg ggactggaac aatgacagtg gagagcccag     32340
gactcgtaac catggatcat catgctcgtc atgatatcaa tgttggcaca acacaggcac     32400
acgtgcatac acttcctcag gattacaagc tcctcccgcg ttagaaccat atcccaggga     32460
acaacccatt cctgaatcag cgtaaatccc acactgcagg gaagacctcg cacgtaactc     32520
acgttgtgca ttgtcaaagt gttacattcg ggcagcagcg gatgatcctc cagtatggta     32580
gcgcgggttt ctgtctcaaa aggaggtaga cgatccctac tgtacggagt gcgccgagac     32640
aaccgagatc gtgttggtcg tagtgtcatg ccaaatggaa cgccggacgt agtcatattt     32700
cctgaagtct tagatctctc aacgcagcac cagcaccaac acttcgcagt gtaaaaggcc     32760
aagtgccgag agagtatata taggaataaa aagtgacgta aacgggcaaa gtccaaaaaa     32820
cgcccagaaa aaccgcacgc gaacctacgc cccgaaacga aagccaaaaa acactagaca     32880
ctcccttccg gcgtcaactt ccgctttccc acgctacgtc acttgcccca gtcaaacaaa     32940
ctacatatcc cgaacttcca agtcgccacg cccaaaacac cgcctacacc tccccgcccg     33000
ccggcccgcc cccaaacccg cctcccgccc cgcgccccgc ccgcgccgc ccatctcatt     33060 atcatattgg cttcaatcca aaataaggta tattattgat gatg                     33104
```

<210> SEQ ID NO 2
<211> LENGTH: 32337
<212> TYPE: DNA
<213> ORGANISM: Artificial Sequence
<220> FEATURE:
<223> OTHER INFORMATION: synthetic chimpanzee adenovirus serotype ChAd3
      with Ebola virus Sudan/Gulu codon optimized
      transmembrane envelope glycoprotein (GP) insert
      (ChAd3 GP Ebola S/G (PB/6611))
<220> FEATURE:
<221> NAME/KEY: CDS
<222> LOCATION: (1634)...(3664)
<223> OTHER INFORMATION: Ebola virus Sudan/Gulu codon optimized
      transmembrane envelope glycoprotein (GP) insert in ChAd3 GP Ebola
      S/G (PB/6611)
<220> FEATURE:
<221> NAME/KEY: CDS
<222> LOCATION: (14646)...(16427)
<223> OTHER INFORMATION: chimpanzee adenovirus serotype ChAd3 penton
<220> FEATURE:
<221> NAME/KEY: CDS
<222> LOCATION: (19459)...(22338)
<223> OTHER INFORMATION: chimpanzee adenovirus serotype ChAd3 hexon
<220> FEATURE:
<221> NAME/KEY: CDS
<222> LOCATION: (29195)...(30881)
<223> OTHER INFORMATION: chimpanzee adenovirus serotype ChAd3 fiber

<400> SEQUENCE: 2

```
catcatcaat aatataccct attttggatt gaagccaata tgataatgag atgggcggcg          60
```

```
cggggcgggg cgcggggcgg gaggcgggtt tggggcggg ccggcgggcg ggcggtgtg      120 gcggaagtgg actttgtaag tgtggcggat gtgacttgct agtgccgggc gcggtaaaag    180
tgacgttttc cgtgcgcgac aacgccccg ggaagtgaca ttttccccgc ggttttacc     240 ggatgttgta gtgaatttgg gcgtaaccaa gtaagatttg gccattttcg cgggaaaact   300
gaaacgggga agtgaaatct gattaatttt gcgttagtca taccgcgtaa tatttgtcta   360
gggccgaggg actttggccg attacgtgga ggactcgccc aggtgttttt tgaggtgaat   420
ttccgcgttc cgggtcaaag tctccgtttt attattatag gatatcccat tgcatacgtt   480
gtatccatat cataatatgt acatttatat tggctcatgt ccaacattac cgccatgttg   540
acattgatta ttgactagtt attaatagta atcaattacg gggtcattag ttcatagccc   600
atatatggag ttccgcgtta cataacttac ggtaaatggc ccgcctggct gaccgcccaa   660
cgacccccgc ccattgacgt caataatgac gtatgttccc atagtaacgc caatagggac   720
tttccattga cgtcaatggg tggagtattt acggtaaact gcccacttgg cagtacatca   780
agtgtatcat atgccaagta cgccccctat tgacgtcaat gacggtaaat ggcccgcctg   840
gcattatgcc cagtacatga ccttatggga ctttcctact tggcagtaca tctacgtatt   900
agtcatcgct attaccatgg tgatgcggtt ttggcagtac atcaatgggc gtggatagcg   960
gtttgactca cggggatttc caagtctcca ccccattgac gtcaatggga gtttgttttg   1020
gaaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acagctcgt ttagtgaacc gtcagatcgc    1200
ctggagacgc catccacgct gttttgacct ccatagaaga caccgggacc gatccagcct   1260
ccatcggctc gcatctctcc ttcacgcgcc cgccgcccta cctgaggccg ccatccacgc   1320
cggttgagtc gcgttctgcc gcctcccgcc tgtggtgcct cctgaactgc gtccgccgtc   1380
taggtaagtt taaagctcag gtcgagaccg ggcctttgtc cggcgctccc ttggagccta   1440
cctagactca gccggctctc cacgctttgc ctgaccctgc ttgctcaact ctagttaacg   1500
gtggagggca gtgtagtctg agcagtactc gttgctgccg cgcgcgccac cagacataat   1560
agctgacaga ctaacagact gttccttttcc atgggtcttt tctgcagtca ccgtcgtcga   1620
cgatatcgcc gccatggagg gcctgagcct gctgcagctg cccagggaca gttcaggaa    1680 gagcagcttc ttcgtgtggg tgatcatcct gttccagaag gccttcagca tgccccctggg  1740 cgtggtgacc aacagcaccc tggaggtgac cgagatcgac cagctggtgt gcaaggacca    1800
cctggccagc accgaccagc tgaagagcgt gggcctgaac ctggagggca gcggcgtgag    1860
caccgacatc cccagcgcca ccaagaggtg gggcttcagg agcggcgtgc ctcccaaggt    1920
ggtgagctac gaggccggcg agtgggccga gaactgctac aacctggaga tcaagaagcc   1980
cgacggcagc gagtgcctgc ctcctcctcc tgacggcgtg aggggcttcc ccaggtgcag    2040
gtacgtgcac aaggcccagg gcaccggccc ctgccccggc gactacgcct tccacaagga   2100
cggcgccttc ttcctgtacg acaggctggc cagcaccgtg atctacaggg gcgtgaactt   2160
cgccgagggc gtgatcgcct tcctgatcct ggccaagccc aaggagacct tcctgcagag   2220
ccctcccatc agggaggccg tgaactacac cgagaacacc agcagctact acgccaccag   2280
ctatctagag tacgagatcg agaacttcgg cgcccagcac agcaccaccc tgttcaagat   2340
cgacaacaac accttcgtga ggctggacag gccccacacc cctcagttcc tgttccagct   2400
```

```
gaacgacacc atccacctgc accagcagct gagcaacacc accggcaggc tgatctggac    2460
cctggacgcc aacatcaacg ccgacatcgg cgagtgggcc ttctgggaga caagaagaa     2520
cctgagcgag cagctgaggg gcgaggagct gagcttcgag gccctgagcc tgaacgagac    2580
cgaggacgac gacgccgcca gcagcaggat caccaagggc aggatcagcg acagggccac    2640
caggaagtac agcgacctgg tgcccaagaa cagccccggc atggtgcccc tgcacatccc    2700
cgagggcgag accaccctgc ccagccagaa cagcaccgag gcaggagggt gggcgtgaa     2760
cacccaggag accatcaccg agaccgccgc caccatcatc ggcaccaacg caaccacat     2820
gcagatcagc accatcggca tcaggcccag cagcagccag atcccagca gcagccccac     2880
caccgcccct agccccgagg cccagacccc caccacccac accagcggac ccagcgtgat    2940
ggccaccgag gagcccacca cccctcccgg cagcagcccc ggacccacca ccgaggcccc    3000
taccctgacc acccctgaga acatcaccac cgccgtgaag accgtgctgc cccaggagag    3060
caccagcaac ggcctgatca ccagcaccgt gaccggcatc ctgggcagcc tgggcctgag    3120
gaagaggagc aggaggcaga ccaacaccaa ggccaccggc aagtgcaacc caacctgca    3180
ctactggacc gcccaggagc agcacaacgc cgccggcatc gcctggattc cctacttcgg    3240
ccccggcgcc gagggcatct acaccgaggg cctgatgcac aaccagaacg ccctggtgtg    3300
cggcctgagg cagctggcca acgagaccac ccaggccctg cagctgttcc tgagggccac    3360
caccgagctg aggacctaca ccatcctgaa caggaaggcc atcgacttcc tgctgaggag    3420
gtggggcggc acctgcagga ttctgggccc cgactgctgc atcgagcccc acgactggac    3480
caagaacatc accgacaaga tcaaccagat catccacgac ttcatcgaca accctctgcc    3540
caaccaggac aacgacgaca actggtggac cggctggcgg cagtggatac ctgccggcat    3600
cggcatcacc ggcatcatca tcgccatcat cgctctgctg tgcgtgtgca agctgctgtg    3660
ctgagaattc agatctgctg tgccttctag ttgccagcca tctgttgttt gcccctcccc    3720
cgtgccttcc ttgaccctgg aaggtgccac tcccactgtc cttcctaat aaaatgagga    3780
aattgcatcg cattgtctga gtaggtgtca ttctattctg gggggtgggg tggggcagga    3840
cagcaagggg gaggattggg aagacaatag caggcatgct ggggatgcgg tgggctctag    3900
atatcagcga tcgctgaggt gggtgagtgg gcgtggcctg gggtggtcat gaaaatatat    3960
aagttggggg tcttagggtc tctttatttg tgttgcagag accgccggag ccatgagcgg    4020
gagcagcagc agcagcagta gcagcagcgc cttggatggc agcatcgtga gccttatttt    4080
gacgacgcgc atgccccact gggccgggt gcgtcagaat gtgatgggct ccagcatcga    4140
cggccgaccc gtcctgcccg caaattccgc cacgctgacc tatgcgaccg tcgcggggac    4200
gccgttggac gccaccgccg ccgccgccgc caccgcagcc gcctcggccg tgcgcagcct    4260
ggccacggac tttgcattcc tgggaccact ggcgacaggg gctacttctc gggccgctgc    4320
tgccgccgtt cgcgatgaca agctgaccgc cctgctggcg cagttggatg cgcttactcg    4380
ggaactgggt gacctttctc agcaggtcat ggccctgcgc cagcaggtct cctccctgca    4440
agctggcggg aatgcttctc ccacaaatgc cgtttaagat aaataaaacc agactctgtt    4500
tggattaaag aaaagtagca agtgcattgc tctctttatt tcataatttt ccgcgcgcga    4560
taggccctag accagcgttc tcggtcgttg agggtgcggt gtatcttctc caggacgtgg    4620
tagaggtggc tctggacgtt gagatacatg gcatgagcc cgtcccgggg gtggaggtag    4680
caccactgca gagcttcatg ctccggggtg gtgttgtaga tgatccagtc gtagcaggag    4740
cgctgggcat ggtgcctaaa aatgtccttc agcagcaggc cgatggccag ggggaggccc    4800
```

```
ttggtgtaag tgtttacaaa acggttaagt tgggaagggt gcattcgggg agagatgatg    4860
tgcatcttgg actgtatttt tagattggcg atgtttccgc ccagatccct tctgggattc    4920
atgttgtgca ggaccaccag tacagtgtat ccggtgcact tggggaattt gtcatgcagc    4980
ttagagggaa aagcgtggaa gaacttggag acgcccttgt ggcctccag  attttccatg    5040 cattcgtcca tgatgatggc aatgggcccg cgggaggcag cttgggcaaa gatatttctg    5100
gggtcgctga cgtcgtagtt tgttccagg  gtgaggtcgt cataggccat ttttacaaag    5160
cgcgggcgga gggtgcccga ctggggatg  atggtcccct ctggccctgg ggcgtagttg    5220
ccctcgcaga tctgcatttc ccaggcctta atctcggagg ggggaatcat atccacctgc    5280
ggggcgatga agaaaacggt tccggagcc  ggggagatta actgggatga gagcaggttt    5340
ctaagcagct gtgattttcc acaaccggtg ggcccataaa taacacctat aaccggttgc    5400
agctggtagt ttagagagct gcagctgccg tcgtcccgga ggagggggc  cacctcgttg    5460 agcatgtccc tgacgcgcat gttctccccg accagatccg ccagaaggcg ctcgccgccc    5520
agggacagca gctcttgcaa ggaagcaaag ttttcagcg  gcttgaggcc gtccgccgtg    5580
ggcatgtttt tcagggtctg gctcagcagc tccaggcggt cccagagctc ggtgacgtgc    5640
tctacggcat ctctatccag catatctcct cgtttcgcgg gttggggcga cttcgctgt     5700 agggcaccaa gcgtggtcg  tccagcgggg ccaaagtcat gtccttccat gggcgcaggg    5760
tcctcgtcag ggtggtctgg gtcacggtga aggggtgcgc tccgggctga gcgcttgcca    5820
aggtgcgctt gaggctggtt ctgctggtgc tgaagcgctg ccggtcttcg ccctgcgcgt    5880
cggccaggta gcatttgacc atggtgtcat agtccagccc ctccgcggcg tgtcccttgg    5940
cgcgcagctt gcccttggag gtggcgccgc acgaggggca gagcaggctc ttgagcgcgt    6000
agagcttggg ggcgaggaag accgattcgg gggagtaggc gtccgcgccg cagacccgc     6060 acacggtctc gcactccacc agccaggtga gctcggggcg cgccgggtca aaaaccaggt    6120
ttcccccatg cttttgatg  cgtttcttac ctcgggtctc catgaggtgg tgtccccgct    6180
cggtgacgaa gaggctgtcc gtgtctccgt agaccgactt gagggtgtct ttctccaggg    6240
gggtccctcg gtcttcctcg tagaggaact cggaccactc tgagacgaag gcccgcgtcc    6300
aggccaggac gaaggaggct atgtgggagg ggtagcggtc gttgtccact aggggtccca    6360
ccttctccaa ggtgtgaaga cacatgtcgc cttcctcggc gtccaggaag gtgattggct    6420
tgtaggtgta ggccacgtga ccggggttc  ctgacggggg ggtataaaag ggggtgggg     6480 cgcgctcgtc gtcactctct tccgcatcgc tgtctgcgag ggccagctgc tggggtgagt    6540
attccctctc gaaggcgggc atgacctccg cgctgaggtt gtcagtttcc aaaaacgagg    6600
aggatttgat gttcacctgt cccgaggtga tacctttgag ggtacccgcg tccatctggt    6660
cagaaaacac gatcttttta ttgtccagct tggtggcgaa cgacccgtag agggcgttgg    6720
agagcagctt ggcgatggag cgcagggtct ggttcttgtc cctgtcggcg cgctccttgg    6780
ccgcgatgtt gagctgcacg tactcgcgcg cgacgcagcg ccactcgggg aagacggtgg    6840
tgcgctcgtc gggcaccagg cgcacgcgcc agccgcggtt gtgcagggtg accaggtcca    6900
cgctggtggc gacctcgccg cgcaggcgct cgttggtcca gcagagacgg ccgcccttgc    6960
gcgagcagaa gggggggcagg gggtcgagct gggtctcgtc cgggggggtcc gcgtccacgg    7020 tgaaaacccc gggggcgcagg cgcgcgtcga agtagtctat cttgcaacct tgcatgtcca    7080
gcgcctgctg ccagtcgcgg gcggcgagcg cgcgctcgta gggggttgagc ggcgggcccc    7140
```

```
agggcatggg gtgggtgagt gcggaggcgt acatgccgca gatgtcatag acgtagaggg    7200
gctcccgcag gacccgatg taggtgggt agcagcggcc gccgcggatg ctggcgcgca     7260
cgtagtcata cagctcgtgc gagggggcga ggaggtcggg gcccaggttg gtgcgggcgg    7320
ggcgctccgc gcggaagacg atctgcctga agatggcatg cgagttggaa gagatggtgg    7380
ggcgctggaa gacgttgaag ctggcgtcct gcaggccgac ggcgtcgcgc acgaaggagg    7440
cgtaggagtc gcgcagcttg tgtaccagct cggcggtgac ctgcacgtcg agcgcgcagt    7500
agtcgagggt ctcgcggatg atgtcatatt tagcctgccc cttcttttc cacagctcgc    7560 ggttgaggac aaactcttcg cggtctttcc agtactcttg gatcgggaaa ccgtccggtt    7620
ccgaacggta agagcctagc atgtagaact ggttgacggc ctggtaggcg cagcagccct    7680
tctccacggg gagggcgtag gcctgcgcgc ccttgcggag cgaggtgtgg gtcagggcga    7740
aggtgtccct gaccatgact ttgaggtact ggtgcttgaa gtcggagtcg tcgcagccgc    7800
cccgctccca gagcgagaag tcggtgcgct tcttggagcg ggggttgggc agagcgaagg    7860
tgacatcgtt gaagaggatt ttgcccgcgc ggggcatgaa gttgcgggtg atgcggaagg    7920
gccccggcac ttcagagcgg ttgttgatga cctgggcggc gagcacgatc tcgtcgaagc    7980
cgttgatgtt gtggcccacg atgtagagtt ccaggaagcg gggccggccc tttacggtgg    8040
gcagcttctt tagctcttcg taggtgagct cctcgggcga ggcgaggccg tgctcggcca    8100
gggcccagtc cgcgaggtgc gggttgtctc tgaggaagga ctcccagagg tcgcgggcca    8160
ggagggtctg caggcggtcc ctgaaggtcc tgaactggcg gcccacggcc attttttcgg    8220
gggtgatgca gtagaaggtg agggggtctt gctgccagcg gtcccagtcg agctgcaggg    8280
cgaggtcgcg cgcggcggtg accaggcgct cgtcgccccc gaatttcatg accagcatga    8340
agggcacgag ctgcttttccg aaggccccca tccaagtgta ggtctctaca tcgtaggtga    8400
caaagaggcg ctccgtgcga ggatgcgagc cgatcgggaa gaactggatc tcccgccacc    8460
agttggagga gtgctgttg atgtggtgga agtagaagtc ccgtcgccgg gccgaacact    8520
cgtgctggct tttgtaaaag cgagcgcagt actggcagcg ctgcacgggc tgtacctcct    8580
gcacgagatg cacctttcgc ccgcgcacga ggaagccgag gggaaatctg agccccccgc    8640
ctggctcgcg gcatggctgg tgctcttcta cttttggatgc gtgtccgtct ccgtctggct    8700
cctcgagggg tgttacggtg gagcggacca ccacgccgcg cgagccgcag gtccagatat    8760
cggcgcgcgg cggtcggagt ttgatgacga catcgcgcag ctgggagctg tccatggtct    8820
ggagctcccg cggcggcggc aggtcagccg ggagttcttg caggttcacc tcgcagagtc    8880
gggccagggc gcggggcagg tctaggtggt acctgatctc taggggcgtg ttggtggcgg    8940
cgtcgatggc ttgcaggagc ccgcatcccc gggggcgac gacggtgccc cgcggggtgg    9000
tggtggtggt ggtggtggtg gtggtggcgg tgcagctcag aagcggtgcc gcgggcgggc    9060
ccccggaggt aggggggct ccggtcccgc cggcaggggc ggcagcggca cgtcggcgtg    9120
gagcgcgggc aggagttggt gctgtgcccg gaggttgctg gcgaaggcga cgacgcggcg    9180
gttgatctcc tggatctggc gcctctgcgt gaagacgacg ggcccggtga gcttgaacct    9240
gaaagagagt tcgacagaat caatctcggt gtcattgacc gcggcctggc gcaggatctc    9300
ctgcacgtct cccgagttgt cttggtaggc gatctcggcc atgaactgct cgatctcttc    9360
ctcctggagg tctccgcgtc cggcgcgttc cacggtggcc gccaggtcgt tggagatgcg    9420
ccccatgagc tgcgagaagg cgttgagtcc gccctcgttc cagactcggc tgtagaccac    9480 gccccctgg tcatcgcggg cgcgcatgac cacctgcgcg aggttgagct ccacgtgccg    9540
```

```
cgcgaagacg gcgtagttgc gcagacgctg gaagaggtag ttgagggtgg tggcggtgtg   9600
ctcggccacg aagaagttca tgacccagcg gcgcaacgtg gattcgttga tgtcccccaa   9660
ggcctccagc cgttccatgg cctcgtagaa gtccacggcg aagttgaaaa actgggagtt   9720
gcgcgccgac acggtcaact cctcctccag aagacggatg agctcggcga cggtgtcgcg   9780
cacctcgcgc tcgaaggcta tggggatctc ttcctccgct agcatcacca cctcctcctc   9840
ttcctcctct tctggcactt ccatgatggc ttcctcctct tcgggggggcg gcggcggcgg   9900
cggtggggga gggggcgctc tgcgccggcg gcggcgcacc gggaggcggt ccacgaagcg   9960
cgcgatcatc tccccgcggc ggcggcgcat ggtctcggtg acggcgcggc cgttctcccg  10020
ggggcgcagt tggaagacgc cgccggacat ctggtgctgg ggcgggtggc cgtgaggcag  10080
cgaaacggcg ctgacgatgc atctcaacaa ttgctgcgta ggtacgccgc cgagggacct  10140
gagggagtcc atatccaccg gatccgaaaa cctttcgagg aaggcgtcta accagtcgca  10200
gtcgcaaggt aggctgagca ccgtggcggg cggcggggg tgggggagt gtctggcgga  10260
ggtgctgctg atgatgtaat tgaagtaggc ggacttgaca cggcggatgg tcgacaggag  10320
caccatgtcc ttgggtccgg cctgctggat gcggaggcgg tcggctatgc cccaggcttc  10380
gttctggcat cggcgcaggt ccttgtagta gtcttgcatg agccttttcca ccggcacctc  10440
ttctccttcc tcttctgctt cttccatgtc tgcttcggcc ctggggcggc gccgcgcccc  10500
cctgcccccc atgcgcgtga ccccgaaccc cctgagcggt tggagcaggg ccaggtcggc  10560
gacgacgcgc tcggccagga tggcctgctg cacctgcgtg agggtggttt ggaagtcatc  10620
caagtccacg aagcggtggt aggcgcccgt gttgatggtg taggtgcagt tggccatgac  10680
ggaccagttg acggtctggt ggcccggttg cgacatctcg gtgtacctga gtcgcgagta  10740
ggcgcgggag tcgaagacgt agtcgttgca agtccgcacc aggtactggt agcccaccag  10800
gaagtgcggc ggcggctggc ggtagagggg ccagcgcagg gtggcggggg ctccgggggc  10860
caggtcttcc agcatgaggc ggtggtaggc gtagatgtac ctggacatcc aggtgatacc  10920
cgcggcggtg gtggaggcgc gcgggaagtc gcgcacccgg ttccagatgt tgcgcagggg  10980
cagaaagtgc tccatggtag gcgtgctctg tccagtcaga cgcgcgcagt cgttgatact  11040
ctagaccagg gaaaacgaaa gccggtcagc gggcactctt ccgtggtctg gtgaatagat  11100
cgcaagggta tcatggcgga gggcctcggt tcgagcgccg gtccgggcc ggacggtccg  11160
ccatgatcca cgcggttacc gcccgcgtgt cgaacccagg tgtgcgacgt cagacaacgg  11220
tggagtgttc cttttggcgt ttttctggcc gggcgccggc gtcgcgtaag agactaagcc  11280
gcgaaagcga aagcagtaag tggctcgctc cccgtagccg gagggatcct tgctaagggt  11340
tgcgttgcgg cgaaccccgg ttcgaatccc gtactcgggc cggccggacc cgcggctaag  11400
gtgttggatt ggcctccccc tcgtataaag accccgcttg cggattgact ccggacacgg  11460
ggacgagccc cttttatttt tgctttcccc agatgcatcc ggtgctgcgg cagatgcgcc  11520
ccccgcccca gcagcagcaa caacaccagc aagagcggca gcaacagcag cgggagtcat  11580
gcagggcccc ctcacccacc ctcggcgggc cggccacctc ggcgtccgcg gccgtgtctg  11640
gcgcctgcgg cggcggcggg gggccggctg acgaccccga ggagccccg cggcgcaggg  11700
ccagacacta cctggacctg gaggagggcg agggcctggc gcggctgggg gcgccgtctc  11760
ccgagcgcca cccgcgggtg cagctgaagc gcgactcgcg cgaggcgtac gtgcctcggc  11820
agaacctgtt cagggaccgc gcgggcgagg agcccgagga gatgcgggac aggaggttca  11880
```

```
gcgcagggcg ggagctgcgg caggggctga accgcgagcg gctgctgcgc gaggaggact    11940
ttgagcccga cgcgcggacg gggatcagcc ccgcgcgcgc gcacgtggcg gccgccgacc    12000
tggtgacggc gtacgagcag acggtgaacc aggagatcaa cttccaaaag agtttcaaca    12060
accacgtgcg cacgctggtg gcgcgcgagg aggtgaccat cgggctgatg cacctgtggg    12120
actttgtaag cgcgctggtg cagaacccca acagcaagcc tctgacggcg cagctgttcc    12180
tgatagtgca gcacagcagg gacaacgagg cgtttaggga cgcgctgctg aacatcaccg    12240
agcccgaggg tcggtggctg ctggacctga ttaacatcct gcagagcata gtggtgcagg    12300
agcgcagcct gagcctggcc gacaaggtgg cggccatcaa ctactcgatg ctgagcctgg    12360
gcaagttttta cgcgcgcaag atctaccaga cgccgtacgt gcccatagac aaggaggtga    12420
agatcgacgg ttttttacatg cgcatggcgc tgaaggtgct cacctgagc gacgacctgg    12480
gcgtgtaccg caacgagcgc atccacaagg ccgtgagcgt gagccggcgg cgcgagctga    12540
gcgaccgcga gctgatgcac agcctgcagc gggcgctggc gggcgccggc agcggcgaca    12600
gggaggcgga gtcctacttc gatgcggggg cggacctgcg ctgggcgccc agccggcggg    12660
ccctggaggc cgcggggggtc cgcgaggact atgacgagga cggcgaggag gatgaggagt    12720
acgagctaga ggagggcgag tacctggact aaaccgcggg tggtgtttcc ggtagatgca    12780
agacccgaac gtggtggacc cggcgctgcg ggcggctctg cagagccagc cgtccggcct    12840
taactcctca gacgactggc gacaggtcat ggaccgcatc atgtcgctga cggcgcgtaa    12900
cccggacgcg ttccggcagc agccgcaggc caacaggctc tccgccatcc tggaggcggt    12960
ggtgcctgcg cgctcgaacc ccacgcacga aaggtgctg gccatagtga acgcgctggc    13020
cgagaacagg gccatccgcc cggacgaggc cgggctggtg tacgacgcgc tgctgcagcg    13080
cgtgccccgc tacaacagcg gcaacgtgca gaccaacctg gaccggctgg tggggacgt     13140
gcgcgaggcg gtggcgcagc gcgagcgcgc ggatcggcag ggcaacctgg gctccatggt    13200
ggcgctgaat gccttcctga gcacgcagcc ggccaacgtg ccgcgggggc aggaagacta    13260
caccaacttt gtgagcgcgc tgcggctgat ggtgaccgag acccccaga gcgaggtgta    13320
ccagtcgggc ccggactact tcttccagac cagcagacag ggcctgcaga cggtgaacct    13380
gagccaggct ttcaagaacc tgcgggggct gtggggcgtg aaggcgccca ccggcgaccg    13440
ggcgacggtg tccagcctgc tgacgcccaa ctcgcgcctg ctgctgctgc tgatcgcgcc    13500
gttcacggac agcggcagcg tgtcccggga cacctacctg gggcacctgc tgaccctgta    13560
ccgcgaggcc atcgggcagg cgcaggtgga cgagcacacc ttccaggaga tcaccagcgt    13620
gagccgcgcg ctggggcagg aggacacgag cagcctggag gcgactctga actacctgct    13680
gaccaaccgg cggcagaaga ttccctcgct gcacagcctg acctccgagg aggagcgcat    13740
cttgcgctac gtgcagcaga gcgtgagcct gaacctgatg cgcgacgggg tgacgcccag    13800
cgtggcgctg gacatgaccg cgcgcaacat ggaaccgggc atgtacgccg cgcaccggcc    13860
ttacatcaac cgcctgatgg actacctgca tcgcgcggcg gccgtgaacc ccgagtactt    13920
taccaacgcc atcctgaacc cgcactggct cccgccgccc gggttctaca gcggggcgctt    13980
cgaggtcccg gaggccaacg atggcttcct gtgggacgac atggacgaca gcgtgttctc    14040
cccgcggccg caggcgctgg cggaagcgtc cctgctgcgt cccaagaagg aggaggagga    14100
ggcgagtcgc cgccgcggca gcagcggcgt ggcttctctg tccgagctgg ggcggcagc    14160
cgccgcgcgc cccgggtccc tgggcggcag cccctttccg agcctggtgg ggtctctgca    14220
cagcgagcgc accacccgcc ctcggctgct gggcgaggac gagtacctga ataactccct    14280
```

```
gctgcagccg gtgcgggaga aaaacctgcc ccccgccttc cccaacaacg ggatagagag    14340
cctggtggac aagatgagca gatggaagac ctatgcgcag gagcacaggg acgcgcccgc    14400
gctccggccg cccacgcggc gccagcgcca cgaccggcag cggggggctgg tgtgggatga   14460 cgaggactcc gcggacgata gcagcgtgct ggacctggga gggagcggca acccgttcgc    14520
gcacctgcgc ccccgcctgg ggaggatgtt ttaaaaaaaa aaaaagcaag aagcatgatg    14580
caaaattaaa taaaactcac caaggccatg gcgaccgagc gttggtttct tgtgttccct    14640
tcagtatgcg gcgcgcggcg atgtaccagg agggacctcc tccctcttac gagagcgtgg    14700
tgggcgcggc ggcggcggcg ccctcttctc cctttgcgtc gcagctgctg gagccgccgt    14760
acgtgcctcc gcgctacctg cggcctacgg gggggagaaa cagcatccgt tactcggagc    14820
tggcgcccct gttcgacacc acccgggtgt acctggtgga caacaagtcg gcggacgtgg    14880
cctccctgaa ctaccagaac gaccacagca attttttgac cacggtcatc cagaacaatg    14940
actacagccc gagcgaggcc agcacccaga ccatcaatct ggatgaccgg tcgcactggg    15000
gcggcgacct gaaaaccatc ctgcacacca acatgcccaa cgtgaacgag ttcatgttca    15060
ccaataagtt caaggcgcgg gtgatggtgt gcgcgctcgca caccaaggaa gacccgggtgg  15120 agctgaagta cgagtgggtg gagttcgagc tgccagaggg caactactcc gagaccatga   15180
ccattgacct gatgaacaac gcgatcgtgg agcactatct gaaagtgggc aggcaaaacg    15240
gggtcctgga gagcgacatc ggggtcaagt tcgacaccag gaacttccgc ctggggctgg    15300
accccgtgac cgggctggtt atgcccgggg tgtacaccaa cgaggccttc catcccgaca    15360
tcatcctgct gcccggctgc ggggtggact tcacttacag ccgcctgagc aacctcctgg    15420
gcatccgcaa gcggcagccc ttccaggagg gcttcaggat cacctacgag gacctggagg    15480
ggggcaacat ccccgcgctc ctcgatgtgg aggcctacca ggatagcttg aaggaaaatg    15540
aggcgggaca ggaggatacc accccgccc cctccgccgc cgccgagcag ggcgaggatg    15600
ctgctgacac cgcggccgcg gacggggcag aggccgaccc cgctatggtg gtggaggctc    15660
ccgagcagga ggaggatatg aatgacagtg cggtgcgcgg agacaccttc gtcacccggg    15720
gggaggaaaa gcaagcggag gccgaggccg cggccgagga aaagcaactg gcggcagcag    15780
cggcggcggc ggcgttggcc gcggcggagg ctgagtctga ggggaccaag cccgccaagg    15840
agcccgtgat taagccccctg accgaagata gcaagaagcg cagttacaac ctgctcaagg    15900
acagcaccaa caccgcgtac cgcagctggt acctggccta caactacggc gacccgtcga    15960 cggggggtgcg ctcctggacc ctgctgtgca cgccggacgt gacctgcggc tcggagcagg    16020
tgtactggtc gctgcccgac atgatgcaag accccgtgac cttccgctcc acgcggcagg    16080
tcagcaactt cccggtggtg ggcgccgagc tgctgcccgt gcactccaag agcttctaca    16140
acgaccaggc cgtctactcc cagctcatcc gccagttcac ctctctgacc cacgtgttca    16200 atcgcttttcc tgagaaccag attctggcgc gcccgcccgc ccccaccatc accaccgtca    16260
gtgaaaacgt tcctgctctc acagatcacg ggacgctacc gctgcgcaac agcatcggag    16320
gagtccagcg agtgaccgtt actgacgcca gacgccgcac ctgccccatac gtttacaagg    16380 ccttgggcat agtctcgccg cgcgtccttt ccagccgcac ttttttgagca acaccaccat    16440 catgtccatc ctgatctcac ccagcaataa ctccggctgg ggactgctgc gcgcgcccag    16500
caagatgttc ggaggggcga ggaagcgttc cgagcagcac cccgtgcgcg tgcgcgggca    16560
cttccgcgcc ccctggggag cgcacaaacg cggccgcgcg gggcgcacca ccgtggacga    16620
```

```
cgccatcgac tcggtggtgg agcaggcgcg caactacagg cccgcggtct ctaccgtgga    16680
cgcggccatc cagaccgtgg tgcgggggcgc gcggcggtac gccaagctga agagccgccg   16740
gaagcgcgtg gcccgccgcc accgccgccg acccggggcc gccgccaaac gcgccgccgc    16800
ggccctgctt cgccgggcca agcgcacggg ccgccgcgcc gccatgaggg ccgcgcgccg    16860
cttggccgcc ggcatcaccg ccgccaccat ggcccccgt  acccgaagac gcgcggccgc    16920
cgccgccgcc gccgccatca gtgacatggc cagcaggcgc cggggcaacg tgtactgggt    16980
gcgcgactcg gtgaccggca cgcgcgtgcc cgtgcgcttc cgccccccgc ggacttgaga    17040
tgatgtgaaa aaacaacact gagtctcctg ctgttgtgtg tatcccagcg gcggcggcgc    17100
gcgcagcgtc atgtccaagc gcaaaatcaa agaagagatg ctccaggtcg tcgcgccgga    17160
gatctatggg cccccgaaga aggaagagca ggattcgaag ccccgcaaga taaagcgggt    17220
caaaaagaaa aagaaagatg atgacgatgc cgatggggag gtggagttcc tgcgcgccac    17280
ggcgcccagg cgcccggtgc agtggaaggg ccggcgcgta agcgcgtcc  tgcgccccgg    17340 caccgcggtg gtcttcacgc ccggcgagcg ctccacccgg actttcaagc gcgtctatga    17400
cgaggtgtac ggcgacgaag acctgctgga gcaggccaac gagcgcttcg agagtttgc    17460 ttacgggaag cgtcagcggg cgctggggaa ggaggacctg ctggcgctgc cgctggacca    17520
gggcaacccc accccccagtc tgaagcccgt gaccctgcag caggtgctgc cgagcagcgc    17580
accctccgag gcgaagcggg gtctgaagcg cgagggcggc gacctggcgc ccaccgtgca    17640
gctcatggtg cccaagcggc agaggctgga ggatgtgctg gagaaaatga agtagaccc     17700 cggtctgcag ccggacatca gggtccgtcc catcaagcag gtggcgccgg gctcggcgt     17760 gcagaccgtg gacgtggtca tccccaccgg caactccccc gccgccacca ccactaccgc    17820
tgcctccacg gacatggaga cacagaccga tcccgccgca gccgcagccg ccgccgcagc    17880
cgcgacctcc tcggcggagg tgcagacgga ccctggctg  ccgccggcga tgtcagctcc    17940
ccgcgcgcgc gcggacgca  gaaagtacgg cgccgccaac gcgctcctgc ccagtacgc     18000 cttgcatcct tccatcgcgc ccaccccgg  ctaccgaggc tatacctacc gcccgcgaag    18060
agccaagggt tccacccgcc gtccccgccg acgcgccgcc gccaccaccc gccgccgccg    18120
ccgcagacgc cagcccgcac tggctccagt ctccgtgagg agagtggcgc gcgacggaca    18180
caccctggtg ctgcccaggg cgcgctacca ccccagcatc gtttaaaagc ctgttgtggt    18240
tcttgcagat atggccctca cttgccgcct ccgtttcccg gtgccgggat accgaggagg    18300
aagatcgcgc cgcaggaggg gtctggccgg ccgcggcctg agcggaggca gccgccgcgc    18360
gcaccggcgg cgacgcgcca ccagccgacg catgcgcggc ggggtgctgc ccctgttaat    18420 cccctgatc  gccgcggcga tcggcgccgt gcccgggatc gcctccgtgg ccttgcaagc    18480
gtcccagagg cattgacaga cttgcaaact tgcaaatatg gaaaaaaaa  aaaaacccca    18540 ataaaaagtc tagactctca cgctcgcttg gtcctgtgac tattttgtag aatgaagac    18600 atcaactttg cgtcgctggc cccgcgtcac ggctcgcgcc cgttcctggg acactggaac    18660
gatatcggca ccagcaacat gagcggtggc gccttcagtt ggggctctct gtggagcggc    18720
attaaaagta tcgggtctgc cgttaaaaat tacggctccc gggcctggaa cagcagcacg    18780
ggccagatgt tgagagacaa gttgaaagag cagaacttcc agcagaaggt ggtggagggc    18840
ctggcctccg gcatcaacgg ggtggtggac ctggccaacc aggccgtgca gaataaaatc    18900
aacagcagac tggacccccg gccgccggtg gaggaggtgc cgccggcgct ggagacggtg    18960
tcccccgatg ggcgtggcga gaagcgcccg cggcccgata gggaagagac cactctggtc    19020
```

```
acgcagaccg atgagccgcc cccgtatgag gaggccctaa agcaaggtct gcccaccacg    19080
cggcccatcg cgcccatggc caccggggtg gtgggccgcc acaccccgc  cacgctggac    19140
ttgcctccgc ccgccgatgt gccgcagcag cagaaggcgg cacagccggg cccgcccgcg    19200
accgcctccc gttcctccgc cggtcctctg cgccgcgcgg ccagcggccc ccgcgggggg    19260
gtcgcgaggc acggcaactg gcagagcacg ctgaacagca tcgtgggtct ggggdtgcgg    19320
tccgtgaagc gccgccgatg ctactgaata gcttagctaa cgtgttgtat gtgtgtatgc    19380
gccctatgtc gccgccagag gagctgctga gtcgccgccg ttcgcgcgcc caccaccacc    19440
gccactccgc ccctcaagat ggcgacccca tcgatgatgc cgcagtggtc gtacatgcac    19500
atctcgggcc aggacgcctc ggagtacctg agccccgggc tggtgcagtt cgcccgcgcc    19560
accgagagct acttcagcct gagtaacaag tttaggaacc ccacggtggc gcccacgcac    19620
gatgtgacca ccgaccggtc tcagcgcctg acgctgcggt tcattcccgt ggaccgcgag    19680
gacaccgcgt actcgtacaa ggcgcggttc accctggccg tgggcgacaa ccgcgtgctg    19740
gacatggcct ccacctactt tgacatccgc ggggtgctgg accggggtcc cacttttcaag   19800
ccctactctg gcaccgccta caactccctg gcccccaagg gcgctcccaa ctcctgcgag    19860
tgggagcaag aggaaactca ggcagttgaa gaagcagcag aagaggaaga agaagatgct    19920
gacggtcaag ctgaggaaga gcaagcagct accaaaaaga ctcatgtata tgctcaggct    19980
ccccttctg  gcgaaaaaat tagtaaagat ggtctgcaaa taggaacgga cgctacagct    20040
acagaacaaa aacctattta tgcagaccct acattccagc ccgaaccca  aatcggggag    20100
tcccagtgga atgaggcaga tgctacagtc gccggcggta gagtgctaaa gaaatctact    20160
cccatgaaac catgctatgg ttcctatgca agacccacaa atgctaatgg aggtcagggt    20220
gtactaacgg caaatgccca gggacagcta gaatctcagg ttgaaatgca attcttttca    20280
acttctgaaa acgcccgtaa cgaggctaac aacattcagc ccaaattggt gctgtatagt    20340
gaggatgtgc acatggagac cccggatacg caccttttctt acaagcccgc aaaaagcgat   20400
gacaattcaa aaatcatgct gggtcagcag tccatgccca acagacctaa ttacatcggc    20460
ttcagagaca actttatcgg cctcatgtat tacaatagca ctggcaacat gggagtgctt    20520
gcaggtcagg cctctcagtt gaatgcagtg gtggacttgc aagacagaaa cacagaactg    20580
tcctaccagc tcttgcttga ttccatgggt gacagaacca gatacttttc catgtggaat    20640
caggcagtgg acagttatga cccagatgtt agaattattg aaaatcatgg aactgaagac    20700
gagctcccca actattgttt ccctctgggt ggcatagggg taactgacac ttaccaggct    20760
gttaaaacca caatggcaa  taacgggggc caggtgactt ggacaaaaga tgaaactttt    20820
gcagatcgca atgaaatagg ggtgggaaac aatttcgcta tggagatcaa cctcagtgcc    20880
aacctgtgga gaaacttcct gtactccaac gtggcgctgt acctaccaga caagcttaag    20940
tacaacccct ccaatgtgga catctctgac aaccccaaca cctacgatta catgaacaag    21000
cgagtggtgg ccccggggct ggtggactgc tacatcaacc tgggcgcgcg ctggtcgctg    21060
gactacatgg acaacgtcaa ccccttcaac caccaccgca atgcgggcct gcgctaccgc    21120
tccatgctcc tgggcaacgg gcgctacgtg cccttccaca tccaggtgcc ccagaagttc    21180
tttgccatca gaacctcct  cctcctgccg ggctcctaca cctacgagtg gaacttcagg    21240
aaggatgtca acatggtcct ccagagctct ctgggtaacg atctcagggt ggacgggggcc   21300
agcatcaagt tcgagagcat ctgcctctac gccaccttct tccccatggc ccacaacacg    21360
```

```
gcctccacgc tcgaggccat gctcaggaac gacaccaacg accagtcctt caatgactac   21420
ctttccgccg ccaacatgct ctaccccata cccgccaacg ccaccaacgt ccccatctcc   21480 atccctcgc gcaactgggc ggccttccgc ggctgggcct tcacccgcct caagaccaag    21540
gagaccccct ccctgggctc gggattcgac ccctactaca cctactcggg ctctattccc   21600
tacctggacg gcaccttcta cctcaaccac actttcaaga aggtctcggt caccttcgac   21660
tcctcggtca gctggccggg caacgaccgt ctgctcaccc caacgagtt cgagatcaag     21720 cgctcggtcg acggggaagg ctacaacgtg gcccagtgca acatgaccaa ggactggttc   21780
ctggtccaga tgctggccaa ctacaacatc ggctaccagg gcttctacat cccagagagc   21840
tacaaggaca ggatgtactc cttcttcagg aacttccagc ccatgagccg gcaggtggtg   21900
gaccagacca agtacaagga ctaccaggag gtgggcatca tccaccagca caacaactcg   21960
ggcttcgtgg gctacctcgc ccccaccatg cgcgagggac aggcctaccc cgccaacttc   22020
ccctacccgc tcataggcaa gaccgcggtc gacagcatca cccagaaaaa gttcctctgc   22080
gaccgcaccc tctggcgcat cccccttctcc agcaacttca tgtccatggg tgcgctctcg   22140
gacctgggcc agaacttgct ctacgccaac tccgcccacg ccctcgacat gaccttcgag    22200
gtcgacccca tggacgagcc caccccttctc tatgttctgt tcgaagtctt tgacgtggtc   22260
cgggtccacc agccgcaccg cggcgtcatc gagaccgtgt acctgcgtac gcccttctcg   22320
gccggcaacg ccaccaccta agaagcaag ccgcagtcat cgccgcctgc atgccgtcgg    22380
gttccaccga gcaagagctc agggccatcg tcagagacct gggatgcggg ccctattttt    22440 tgggcaccttt cgacaagcgc ttccctggct ttgtctcccc acacaagctg gcctgcgcca   22500
tcgtcaacac ggccggccgc gagaccgggg gcgtgcactg gctggccttt gcctggaacc   22560
cgcgctccaa aacatgcttc ctctttgacc ccttcggctt tcggaccag cggctcaagc     22620 aaatctacga gttcgagtac gagggcttgc tgcgtcgcag cgccatcgcc tcctcgcccg   22680
accgctgcgt caccctcgaa aagtccaccc agaccgtgca ggggcccgac tcggccgcct    22740
gcggtctctt ctgctgcatg tttctgcacg cctttgtgca ctggcctcag agtcccatgg   22800
accgcaaccc caccatgaac ttgctgacgg gggtgcccaa ctccatgctc caaagccccc   22860
aggtcgagcc caccctgcgc cgcaaccagg agcagctcta cagcttcctg gagcgccact   22920
cgccctactt ccgccgccac agcgcacaga tcaggagggc cacctccttc tgccacttgc   22980
aagagatgca agaagggtaa taacgatgta cacactttt tctcaataaa tggcattttt     23040
tttttattta tacaagctct ctgggtatt catttcccac caccaccacc cgccgttgtc      23100
gccatctggc tctatttaga aatcgaaagg gttctgccgg gagtcgccgt gcgccacggg   23160
cagggacacg ttgcgatact ggtagcgggt gcccccacttg aactcgggca ccaccaggcg   23220
aggcagctcg gggaagtttt cgctccacag gctgcgggtc agcaccagcg cgttcatcag   23280
gtcgggcgcc gagatcttga agtcgcagtt ggggccgccg ccctgcgcgc gcgagttgcg   23340
gtacaccggg ttgcagcact ggaacaccaa cagcgccggg tgcttcacgc tggccagcac   23400
gctgcggtcg gagatcagct cggcgtccag gtcctccgcg ttgctcagcg cgaacggggt    23460
catcttgggc acttgccgcc ccaggaaggg cgcgtgcccc ggtttcgagt tgcagtcgca    23520
gcgcagcggg atcagcaggt gcccgtgccc ggactcggcg ttggggtaca gcgcgcgcat   23580
gaaggcctgc atctggcgga aggccatctg ggccttggcg ccctccgaga agaacatgcc   23640
gcaggacttg cccgagaact ggtttgcggg gcagctggcg tcgtgcaggc agcagcgcgc    23700
gtcggtgttg gcgatctgca ccacgttgcg cccccaccgg ttcttcacga tcttggcctt   23760
```

```
ggacgattgc tccttcagcg cgcgctgccc gttctcgctg gtcacatcca tctcgatcac   23820
atgttccttg ttcaccatgc tgctgccgtg cagacacttc agctcgccct ccgtctcggt   23880
gcagcggtgc tgccacagcg cgcagcccgt gggctcgaaa gacttgtagg tcacctccgc   23940
gaaggactgc aggtacccct gcaaaaagcg gcccatcatg gtcacgaagg tcttgttgct   24000
gctgaaggtc agctgcagcc gcggtgctc ctcgttcagc caggtcttgc acacggccgc    24060
cagcgcctcc acctggtcgg gcagcatctt gaagttcacc ttcagctcat tctccacgtg   24120
gtacttgtcc atcagcgtgc gcgccgcctc catgcccttc tcccaggccg acaccagcgg   24180
caggctcacg gggttcttca ccatcaccgt ggccgccgcc tccgccgcgc tttcgctttc   24240
cgccccgctg ttctcttcct cttcctcctc ttcctcgccg ccgcccactc gcagcccccg   24300
caccacgggg tcgtcttcct gcaggcgctg caccttgcgc ttgccgttgc gccctgctt    24360
gatgcgcacg ggcgggttgc tgaagcccac catcaccagc gcggcctctt cttgctcgtc   24420
ctcgctgtcc agaatgacct ccggggaggg ggggttggtc atcctcagta ccgaggcacg   24480
cttcttttc ttcctggggg cgttcgccag ctccgcggct gcggccgctg ccgaggtcga    24540
aggccgaggg ctgggcgtgc gcggcaccag cgcgtcttgc gagccgtcct cgtcctcctc   24600
ggactcgaga cggaggcggg cccgcttctt cggggggcgcg cggggcggcg gaggcggcgg  24660
cggcgacgga gacggggacg agacatcgtc caggtgggt ggacggcggg ccgcgccgcg    24720
tccgcgctcg ggggtggttt cgcgctggtc ctcttcccga ctggccatct cccactgctc   24780
cttctcctat aggcagaaag agatcatgga gtctctcatg cgagtcgaga aggaggagga   24840
cagcctaacc gcccctctg agccctccac caccgccgcc accaccgcca atgccgccgc    24900
ggacgacgcg cccaccgaga ccaccgccag taccaccctc cccagcgacg caccccgct    24960
cgagaatgaa gtgctgatcg agcaggaccc gggttttgtg agcggagagg aggatgaggt   25020
ggatgagaag gagaaggagg aggtcgccgc ctcagtgcca aaagaggata aaaagcaaga   25080
ccaggacgac gcagataagg atgagacagc agtcgggcgg gggaacggaa gccatgatgc   25140
tgatgacggc tacctagacg tgggagacga cgtgctgctt aagcacctgc accgccagtg   25200
cgtcatcgtc tgcgacgcgc tgcaggagcg ctgcgaagtg cccctggacg tggcggaggt   25260
cagccgcgcc tacgagcggc acctcttcgc gccgcacgtg cccccaagc gccgggagaa    25320
cggcacctgc gagcccaacc gcgtctcaa cttctacccg gtcttcgcgg tacccgaggt    25380
gctggccacc taccacatct tcttccaaaa ctgcaagatc ccctctcct gccgcgctaa    25440
ccgcacccgc gccgacaaaa ccctgaccct gcggcagggc gcccacatac ctgatattgc   25500
ctctctggag gaagtgccca agatcttcga gggtctcggt cgcgacgaga acgggcggc    25560
gaacgctctg cacggagaca gcgaaaacga gagtcactcg ggggtgctgg tggagctcga   25620
gggcgacaac gcgcgcctgg ccgtactcaa gcgcagcata gaggtcaccc actttgccta   25680
cccgcgctc aacctgcccc ccaaggtcat gagtgtggtc atgggcgagc tcatcatgcg    25740
ccgcgctcag cccctggccg cggatgcaaa cttgcaagag tcctccgagg aaggcctgcc   25800
cgcggtcagc gacgagcagc tagcgcgctg gctggagacc cgcgaccccg cgcagctgga   25860
ggagcggcgc aagctcatga tggccgcggt gctggtcacc gtggagctcg agtgtctgca   25920
gcgcttcttc gcggaccccg agatgcagcg caagctcgag gagaccctgc actacacctt   25980
ccgccagggc tacgtgcgcc aggcctgcaa gatctccaac gtggagctct gcaacctggt   26040
ctcctacctg ggcatcctgc acgagaaccg cctcgggcag aacgtcctgc actccaccct   26100
```

```
caaaggggag gcgcgccgcg actacatccg cgactgcgcc tacctcttcc tctgctacac   26160
ctggcagacg gccatggggg tctggcagca gtgcctggag gagcgcaacc tcaaggagct   26220
ggaaaagcta ctcaagcgca ccctcaggga cctctggacg ggcttcaacg agcgctcggt   26280
ggccgccgcg ctggcggaca tcatcttccc cgagcgcctg ctcaagaccc tgcagcaggg   26340
cctgcccgac ttcaccagcc agagcatgct gcagaacttt aggactttca tcctggagcg   26400
ctcgggcatc ctgcctgcca cttgctgcgc gctgcccagc gacttcgtgc ccatcaagta   26460
cagggagtgc ccgccgccgc tctggggcca ctgctacctc ttccagctgg ccaactacct   26520
cgcctaccac tcggacctca tggaagacgt gagcggcgag ggcctgctcg agtgccactg   26580
ccgctgcaac ctctgcacgc cccaccgctc tctagtctgc aacccgcagc tgctcagcga   26640
gagtcagatt atcggtacct tcgagctgca gggtccctcg cctgacgaga agtccgcggc   26700
tccggggctg aaactcactc cggggctgtg gacttccgcc tacctacgca aatttgtacc   26760
tgaggactac cacgcccacg agatcaggtt ctacgaagac caatcccgcc cgcccaaggc   26820
ggagctcacc gcctgcgtca tcacccaggg gcacatcctg ggccaattgc aagccatcaa   26880
caaagcccgc cgagagttct tgctgaaaaa gggtcggggg gtgtacctgg acccccagtc   26940
cggcgaggag ctaaacccgc tacccccgcc gccgccccag cagcgggacc ttgcttccca   27000
ggatggcacc cagaaagaag cagcagccgc cgccgccgca gccatacatg cttctggagg   27060
aagaggagga ggactgggac agtcaggcag aggaggtttc ggacgaggag caggaggaga   27120
tgatggaaga ctgggaggag gacagcagcc tagacgagga agcttcagag gccgaagagg   27180
tggcagacgc aacaccatca ccctcggtcg cagcccctc gccggggccc ctgaaatcct   27240
ccgaacccag caccagcgct ataacctccg ctcctccggc gccggcgcca cccgcccgca   27300
gacccaaccg tagatgggac accacaggaa ccggggtcgg taagtccaag tgcccgccgc   27360
cgccaccgca gcagcagcag cagcgccagg gctaccgctc gtggcgcggg cacaagaacg   27420
ccatagtcgc ctgcttgcaa gactgcgggg gcaacatcc tttcgcccgg cgcttcctgc   27480
tattccacca cggggtcgcc ttttccccgca atgtcctgca ttactaccgt catctctaca   27540
gcccctactg cagcggcgac ccagaggcgg cagcggcagc cacagcggcg accaccacct   27600
aggaagatat cctccgcggg caagacagcg gcagcagcgg ccaggagacc cgcggcagca   27660
gcggcgggag cggtgggcgc actgcgcctc tcgcccaacg aaccctctc gacccgggag   27720 ctcagacaca ggatcttccc cactttgtat gccatcttcc aacagagcag aggccaggag   27780
caggagctga aaataaaaaa cagatctctg cgctccctca cccgcagctg tctgtatcac   27840
aaaagcgaag atcagcttcg gcgcacgctg gaggacgcgg aggcactctt cagcaaatac   27900
tgcgcgctca ctcttaaaga ctagctccgc gcccttctcg aatttaggcg ggagaaaact   27960
acgtcatcgc cggccgccgc ccagcccgcc cagccgagat gagcaaagag attcccacgc   28020
catacatgtg gagctaccag ccgcagatgg gactcgcggc gggagcggcc caggactact   28080
ccacccgcat gaactacatg agcgcgggac cccacatgat ctcacaggtc aacgggatcc   28140
gcgcccagcg aaaccaaata ctgctggaac aggcggccat caccgccacg ccccgccata   28200
atctcaaccc ccgaaattgg cccgccgccc tcgtgtacca ggaaaccccc tccgccacca   28260
ccgtactact tccgcgtgac gcccaggccg aagtccagat gactaactca ggggcgcagc   28320
tcgcgggcgg ctttcgtcac ggggcgcggc cgctccgacc aggtataaga cacctgatga   28380
tcagaggcca aggtatccag ctcaacgacg agtcggtgag ctcttcgctc ggtctccgtc   28440
cggacggaac tttccagctc gccggatccg gccgctcttc gttcacgccc cgccaggcgt   28500
```

```
acctgactct gcagacctcg tcctcggagc cccgctccgg aggcatcgga accctccagt    28560
tcgtggagga gttcgtgccc tcggtctact tcaaccccctt ctcgggacct cccggacgct    28620
accccgacca gttcattccg aactttgacg cggtgaagga ctcggcggac ggctacgact    28680
gaatgtcagg tgccgaggca gagcagcttc gcctgagaca cctcgagcac tgccgccgcc    28740
acaagtgctt cgcccgcggt tccggtgagt tctgctactt tcagctaccc gaggagcata    28800
ccgaggggcc ggcgcacggc gtccgcctga ccacccaggg cgaggttacc tgttccctca    28860
tccgggagtt caccctccgt cccctgctag tggagcggga gcggggtccc tgtgtcctaa    28920
ctatcgcctg caactgccct aaccctggat tacatcaaga tctttgctgt catctctgtg    28980
ctgagtttaa taaacgctga gatcagaatc tactgggaat tcgatttagt ccccttttaac    29040 taatcaaaca ctggaatcaa taaaaagaat cacttactta aaatcagaca gcaggtctct    29100
gtccagttta ttcagcagca cctccttccc ctcctcccaa ctctggtact ccaaacgcct    29160
tctggcggca aacttcctcc acaccctgaa gggaatgtca gattcttgct cctgtccctc    29220
cgcacccact atcttcatgt tgttgcagat gaagcgcacc aaaacgtctg acgagagctt    29280
caaccccgtg taccccctatg acacggaaag cggccctccc tccgtcccctt tcctcacccc    29340 tcccttcgtg tctcccgatg gattccaaga aagccccccc ggggtcctgt ctctgaacct    29400
ggccgagccc ctggtcactt cccacggcat gctcgcccctg aaaatgggaa gtggcctctc    29460
cctggacgac gctggcaacc tcacctctca agatatcacc accgctagcc ctcccctcaa    29520
aaaaaccaag accaacctca gcctagaaac ctcatccccc ctaactgtaa gcacctcagg    29580
cgccctcacc gtagcagccg ccgctccccct ggcagtggcc ggcacctccc tcaccatgca    29640
atcagaggcc cccctgacag tacaggatgc aaaactcacc ctggccacca aggcccccct    29700
gaccgtgtct gaaggcaaac tggccttgca acatcggcc ccgctgacgg ccgctgacag    29760 cagcacccctc accgttagcg ccacaccacc aattaatgta agcagtggaa gtttaggctt    29820
agacatggaa gaccctatgt atactcacga tggaaaactg ggaataagaa ttgggggtcc    29880
actaagagta gtagacagct tgcacacact cactgtagtt accggaaatg gactaactgt    29940
agataacaat gccctccaaa ctagagttac gggcgcccta ggttatgaca catcaggaaa    30000
tctacaattg agagctgcag gaggtatgcg aattgatgca aatggccaac ttatccttaa    30060
tgtggcatac ccatttgatg ctcagaacaa tctcagcctt agacttggtc agggacccct    30120
gtatataaac acagaccaca acctggattt gaattgcaac agaggtctaa ccacaactac    30180
caccaacaac acaaaaaaac ttgagactaa aattagctca ggcttagact atgacaccaa    30240
tggtgctgtc attattaaac ttggcactgg tctaagcttc gacaacacag gcgccctaac    30300
tgtgggaaac actggtgatg ataaactgac tctgtggacg accccagacc catctccaaa    30360
ttgcagaatt cactcagaca aagactgcaa gtttactcta gtcctaacta agtgtggaag    30420
ccaaatcctg gcctctgtcg ccgccctagc ggtatcagga atctggctt cgataacagg    30480 caccgttgcc agcgttacca tctttctcag atttgatcag aatggagtgc ttatggaaaa    30540
ctcctcgcta gacaggcagt actgaacctt cagaaatggc aactcaacta acgctgcccc    30600
ctacaccaat gcagttgggt tcatgccaaa cctcgcagca tacccccaaaa cgcaaagcca    30660 gactgctaaa aacaacattg taagtcaggt ttacttgaat ggagacaaat ccaaacccat    30720
gacccttacc atcacccctca atggaactaa tgaatccagt gaaactagcc aggtgagtca    30780
ctactccatg tcatttacat gggcttggga aagtgggcaa tatgccactg aaacctttgc    30840
```

```
caccaactcc ttcacctttt cttacattgc tgaacaataa aaagcatgac actgatgttc    30900
atttctgatt cttattttat tattttcaaa cacaacaaaa tcattcaagt cattcttcca    30960
tcttagctta atagacacag tagcttaata gacccagtag tgcaaagccc cattctagct    31020
tataactagt ggagaagtac tcgcctacat gggggtagag tcataatcgt gcatcaggat    31080
agggcggtgg tgctgcagca gcgcgcgaat aaactgctgc cgccgccgct ccgtcctgca    31140
ggaatacaac atggcagtgg tctcctcagc gatgattcgc accgcccgca gcataaggcg    31200
ccttgtcctc cgggcacagc agcgcaccct gatctcactt aaatcagcac agtaactgca    31260
gcacagcacc acaatattgt tcaaaatccc acagtgcaag cgctgtatc caaagctcat     31320 ggcggggacc acagaaccca cgtggccatc ataccacaag cgcaggtaga ttaagtggcg    31380
acccctcata acacgctgg acataaacat tacctctttt ggcatgttgt aattcaccac     31440
ctcccggtac catataaacc tctgattaaa catggcgcca tccaccacca tcctaaacca    31500
gctggccaaa acctgcccgc cggctataca ctgcagggaa ccgggactgg aacaatgaca    31560
gtggagagcc caggactcgt aaccatggat catcatgctc gtcatgatat caatgttggc    31620
acaacacagg cacacgtgca tacacttcct caggattaca agctcctccc gcgttagaac    31680
catatcccag ggaacaaccc attcctgaat cagcgtaaat cccacactgc agggaagacc    31740
tcgcacgtaa ctcacgttgt gcattgtcaa agtgttacat tcgggcagca gcggatgatc    31800
ctccagtatg gtagcgcggg tttctgtctc aaaaggaggt agacgatccc tactgtacgg    31860
agtgcgccga gacaaccgag atcgtgttgg tcgtagtgtc atgccaaatg gaacgccgga    31920
cgtagtcata tttcctgaag tcttagatct ctcaacgcag caccagcacc aacacttcgc    31980
agtgtaaaag gccaagtgcc gagagagtat atataggaat aaaaagtgac gtaaacgggc    32040
aaagtccaaa aaacgcccag aaaaaccgca cgcgaaccta cgccccgaaa cgaaagccaa    32100
aaaacactag acactcccct tccggcgtcaa cttccgcttt cccacgctac gtcacttgcc    32160
ccagtcaaac aaactacata tcccgaactt ccaagtcgcc acgcccaaaa caccgcctac    32220
acctccccgc ccgccggccc gccccccaaac ccgcctcccg cccccgcgccc cgccccgcgc    32280 cgcccatctc attatcatat tggcttcaat ccaaaataag gtatattatt gatgatg       32337
```

<210> SEQ ID NO 3
<211> LENGTH: 32381
<212> TYPE: DNA
<213> ORGANISM: Artificial Sequence
<220> FEATURE:
<223> OTHER INFORMATION: synthetic chimpanzee adenovirus serotype ChAd3
      with Marburg virus Angola codon optimized
      transmembrane envelope glycoprotein (GP) insert
      (ChAd3 Marburg (PB/6712))
<220> FEATURE:
<221> NAME/KEY: CDS
<222> LOCATION: (1666)...(3708)
<223> OTHER INFORMATION: Marburg virus Angola codon optimized
      transmembrane envelope glycoprotein (GP) insert in ChAd3 Marburg
      (PB/6712)
<220> FEATURE:
<221> NAME/KEY: CDS
<222> LOCATION: (14690)...(16470)
<223> OTHER INFORMATION: chimpanzee adenovirus serotype ChAd3 penton
<220> FEATURE:
<221> NAME/KEY: CDS
<222> LOCATION: (19503)...(22382)
<223> OTHER INFORMATION: chimpanzee adenovirus serotype ChAd3 hexon
<220> FEATURE:
<221> NAME/KEY: CDS
<222> LOCATION: (29239)...(30924)
<223> OTHER INFORMATION: chimpanzee adenovirus serotype ChAd3 fiber

<400> SEQUENCE: 3

```
catcatcaat aatatacctt attttggatt gaagccaata tgataatgag atgggcggcg      60
cggggcgggg cgcggggcgg gaggcgggtt tggggggcggg ccggcgggcg ggcggtgtg     120
gcggaagtgg actttgtaag tgtggcggat gtgacttgct agtgccgggc gcggtaaaag    180
tgacgttttc cgtgcgcgac aacgcccccg ggaagtgaca ttttttcccgc ggtttttacc   240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctccgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gaaccaaaat caacgggact ttccaaaatg tcgtaacaac tccgcccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccatcggctc gcatctctcc ttcacgcgcc cgccgcccta cctgaggccg ccatccacgc   1320
cggttgagtc gcgttctgcc gcctcccgcc tgtggtgcct cctgaactgc gtccgccgtc   1380
taggtaagtt taaagctcag gtcgagaccg ggcctttgtc cggcgctccc ttggagccta   1440
cctagactca gccggctctc cacgctttgc ctgaccctgc ttgctcaact ctagttaacg   1500
gtggagggca gtgtagtctg agcagtactc gttgctgccg cgcgcgccac cagacataat   1560
agctgacaga ctaacagact gttcctttcc atgggtcttt tctgcagtca ccgtcgtcga   1620
cacgtgtgat cagatatcgc ggccgctcta gagatatcgg ccgccatgaa gaccacctgc   1680
ctgctgatca gcctgatcct gatccagggc gtgaagaccc tgcccatcct ggagatcgcc   1740
agcaacatcc agccccagaa cgtggacagc gtgtgcagcg gcaccctgca gaagaccgag   1800
gacgtgcacc tgatgggctt caccctgagc ggccagaagg tggccgacag ccctctggag   1860
gccagcaaga ggtgggcctt cagggccggc gtgccccccca gaacgtgga gtacaccgag   1920
ggcgaggagg ccaagacctg ctacaacatc agcgtgaccg accccagcgg caagagcctg   1980
ctgctggacc ctcccaccaa catcagggac taccctaagt gcaagaccat ccaccacatc   2040
cagggccaga accctcacgc ccagggcatc gccctgcacc tgtggggcgc cttcttcctg   2100
tacgacagga tcgccagcac caccatgtac agaggaaaag tgttcacaga gggaaacatc   2160
gctgctatga tcgtgaacaa gaccgtgcat aagatgatct tcagcagaca gggacaggga   2220
tatagacata tgaacctgac atccacaaac aagtactgga caagcagcaa cggaacacag   2280
acaaacgata caggatgttt tggaacactg caggaataca actccaccaa gaaccagaca   2340
```

```
tgtgcccta gcaagaagcc tctgcctctg cctacagctc atcctgaagt gaagctgaca    2400
tccacaagca cagatgccac aaagctgaac acaacagatc taatagcga cgacgaggat    2460 ctgacaacaa gcggatccgg atccggagaa caggaacctt atacaacaag cgacgctgct    2520
acaaaacagg gactgtcctc cacaatgcct cctacaccta gccctcagcc tagcacacct    2580
cagcagggag gcaacaacac aaaccattcc cagggagtgg tgacagaacc tggaaagaca    2640
aacacaacag cccagcctag catgcctcct cataacacaa caacaatcag cacaaacaac    2700
acctccaagc acaatctgag cacacctagc gtgcctattc agaatgccac caactacaac    2760
acacagtcca cagcccctga aaacgaacag acctccgccc cttccaaaac aaccctgctg    2820
cctacagaaa accctacaac agccaagagc acaaacagca caaagagccc tacaacaaca    2880
gtgcctaaca acaaacaa gtatagcaca agccctagcc ctacacctaa ttccacagct    2940
cagcatctgg tgtattttag aagaaagaga acatcctgt ggagagaagg agatatgttc    3000
ccttttctgg atggactgat caacgctcct atcgattttg atcctgtgcc taacacaaag    3060
acaatctttg atgaaagcag cagcagcgga gcctccgccg aagaagatca gcatgcctcc    3120
cctaacatca gcctgacact gagctatttt cctaaggtga cgaaaacac agcccattcc    3180 ggagaaaacg aaaacgattg tgatgccgaa ctgagaatct ggagcgtgca ggaagatgat    3240
ctggccgccg gactgagctg gatcccttt tttgggcccg gaattgaagg actgtacacc    3300
gccggcctga tcaagaacca gaacaacctg gtgtgcaggc tgaggaggct ggccaaccag    3360
accgccaaga gcctggagct gctgctgagg gtgaccaccg aggagaggac cttcagcctg    3420
atcaacaggc acgccatcga cttcctgctg ctaggtggg gcggcacctg caaggtgctg    3480
ggccccgact gctgcatcgg catcgaggac ctgagcagga acatcagcga gcagatcgac    3540
cagatcaaga aggacgagca aaggagggc accggctggg gcctgggcgg caagtggtgg    3600
accagcgact ggggagtgct gacaaacctg ggaatcctgc tgctgctgag cattgccgtg    3660
ctcattgctc tgtcctgtat ctgtagaatc tttaccaagt acatcggatg atagatccag    3720
atctgctgtg ccttctagtt gccagccatc tgttgtttgc ccctccccg tgccttcctt    3780 gaccctggaa ggtgccactc ccactgtcct ttcctaataa aatgaggaaa ttgcatcgca    3840
ttgtctgagt aggtgtcatt ctattctggg gggtggggtg gggcaggaca gcaaggggga    3900
ggattgggaa gacaatagca ggcatgctgg ggatgcggtg ggcgtatca gcgatcgctg    3960 aggtgggtga gtgggcgtgg cctggggtgg tcatgaaaat atataagttg ggggtcttag    4020 ggtctctta tttgtgttgc agagaccgcc ggagccatga gcgggagcag cagcagcagc    4080
agtagcagca gcgccttgga tggcagcatc gtgagccctt atttgacgac gcggatgccc    4140
cactgggccg ggtgcgtca gaatgtgatg ggctccagca tcgacggccg acccgtcctg    4200
cccgcaaatt ccgccacgct gacctatgcg accgtcgcgg ggacgccgtt ggacgccacc    4260
gccgccgccg ccgccaccgc agccgcctcg gccgtgcgca gcctggccac ggactttgca    4320
ttcctgggac cactggcgac aggggctact tctcggggccg ctgctgccgc cgttcgcgat    4380
gacaagctga ccgccctgct ggcgcagttg gatgcgctta ctcgggaact gggtgacctt    4440
tctcagcagg tcatggccct gcgccagcag gtctcctccc tgcaagctgg cgggaatgct    4500
tctcccacaa atgccgtta agataaataa aaccagactc tgtttggatt aaagaaaagt    4560
agcaagtgca ttgctctctt tatttcataa ttttccgcgc gcgataggcc ctagaccagc    4620
gttctcggtc gttgagggtg cggtgtatct tctccaggac gtggtagagg tggctctgga    4680
```

```
cgttgagata catgggcatg agcccgtccc gggggtggag gtagcaccac tgcagagctt    4740
catgctccgg ggtggtgttg tagatgatcc agtcgtagca ggagcgctgg gcatggtgcc    4800
taaaaatgtc cttcagcagc aggccgatgg ccaggggag gcccttggtg taagtgttta     4860
caaaacggtt aagttgggaa gggtgcattc ggggagagat gatgtgcatc ttggactgta    4920
tttttagatt ggcgatgttt ccgcccagat cccttctggg attcatgttg tgcaggacca    4980
ccagtacagt gtatccggtg cacttgggga atttgtcatg cagcttagag ggaaaagcgt    5040
ggaagaactt ggagacgccc ttgtggcctc ccagattttc catgcattcg tccatgatga    5100
tggcaatggg cccgcgggag gcagcttggg caaagatatt tctggggtcg ctgacgtcgt    5160
agttgtgttc cagggtgagg tcgtcatagg ccatttttac aaagcgcggg cggagggtgc    5220
ccgactgggg gatgatggtc ccctctggcc ctggggcgta gttgccctcg cagatctgca    5280
tttcccaggc cttaatctcg gagggggaa tcatatccac ctgcggggcg atgaagaaaa     5340
cggtttccgg agccggggag attaactggg atgagagcag gtttctaagc agctgtgatt    5400
ttccacaacc ggtgggccca taataacac ctataaccgg ttgcagctgg tagtttagag     5460
agctgcagct gccgtcgtcc cggaggaggg gggccacctc gttgagcatg tccctgacgc    5520
gcatgttctc cccgaccaga tccgccagaa ggcgctcgcc gcccagggac agcagctctt    5580
gcaaggaagc aaagttttc agcggcttga ggccgtccgc cgtgggcatg ttttccaggg     5640
tctggctcag cagctccagg cggtcccaga gctcggtgac gtgctctacg gcatctctat    5700
ccagcatatc tcctcgtttc gcgggttggg gcgactttcg ctgtagggca ccaagcggtg    5760
gtcgtccagc ggggccaaag tcatgtcctt ccatgggcgc agggtcctcg tcaggtggt    5820 ctgggtcacg gtgaagggt gcgctccggg ctgagcgctt gccaaggtgc gcttgaggct     5880
ggttctgctg gtgctgaagc gctgccggtc ttcgccctgc gcgtcggcca ggtagcattt    5940
gaccatggtg tcatagtcca gcccctccgc ggcgtgtccc ttggcgcgca gcttgccctt    6000
ggaggtggcg ccgcacgagg ggcagagcag gctcttgagc gctagagct tgggggcgag     6060 gaagaccgat tcggggagt aggcgtccgc gccgcagacc ccgcacacgg tctcgcactc     6120
caccagccag gtgagctcgg ggcgcgccgg gtcaaaaacc aggtttcccc catgcttttt    6180
gatgcgtttc ttacctcggg tctccatgag gtggtgtccc cgctcggtga cgaagaggct    6240
gtccgtgtct ccgtagaccg acttgagggg tcttttctcc agggggtcc ctcggtcttc     6300 ctcgtagagg aactcggacc actctgagac gaaggcccgc gtccaggcca ggacgaagga    6360
ggctatgtgg gaggggtagc ggtcgttgtc cactaggggg tccaccttct ccaaggtgtg    6420
aagacacatg tcgccttcct cggcgtccag gaaggtgatt ggcttgtagg tgtaggccac    6480
gtgaccgggg gttcctgacg gggggtata aaaggggtg ggggcgcgct cgtcgtcact      6540
ctcttccgca tcgctgtctg cgagggccag ctgctggggt gagtattccc tctcgaaggc    6600
gggcatgacc tccgcgctga ggttgtcagt ttccaaaaac gaggaggatt tgatgttcac    6660
ctgtcccgag gtgatacctt tgagggtacc cgcgtccatc tggtcagaaa acacgatctt    6720
tttattgtcc agcttggtgg cgaacgaccc gtagagggcg ttggagagca gcttggcgat    6780
ggagcgcagg gtctggttct tgtccctgtc ggcgcgctcc ttggccgcga tgttgagctg    6840
cacgtactcg cgcgcgacgc agcgccactc ggggaagacg gtggtgcgct cgtcgggcac    6900
caggcgcacg cgccagccgc ggttgtgcag ggtgaccagg tccacgctgg tggcgacctc    6960
gccgcgcagg cgctcgttgg tccagcagag acggccgccc ttgcgcgagc agaagggggg    7020 caggggtcg agctgggtct cgtccggggg gtccgcgtcc acggtgaaaa ccccggggcg     7080
```

```
caggcgcgcg tcgaagtagt ctatcttgca accttgcatg tccagcgcct gctgccagtc    7140
gcgggcggcg agcgcgcgct cgtaggggtt gagcggcggg ccccagggca tggggtgggt    7200
gagtgcggag gcgtacatgc cgcagatgtc atagacgtag aggggctccc gcaggacccc    7260
gatgtaggtg gggtagcagc ggccgccgcg gatgctggcg cgcacgtagt catacagctc    7320
gtgcgagggg gcgaggaggt cggggcccag gttggtgcgg gcggggcgct ccgcgcggaa    7380
gacgatctgc ctgaagatgg catgcgagtt ggaagagatg gtgggcgct ggaagacgtt     7440 gaagctggcg tcctgcaggc cgacggcgtc gcgcacgaag gaggcgtagg agtcgcgcag    7500
cttgtgtacc agctcggcgg tgacctgcac gtcgagcgcg cagtagtcga gggtctcgcg    7560
gatgatgtca tatttagcct gccccttctt tttccacagc tcgcggttga ggacaaactc    7620
ttcgcggtct ttccagtact cttggatcgg gaaaccgtcc ggttccgaac ggtaagagcc    7680
tagcatgtag aactggttga cggcctggta ggcgcagcag cccttctcca cggggagggc    7740
gtaggcctgc gcggccttgc ggagcgaggt gtgggtcagg gcgaaggtgt ccctgaccat    7800
gactttgagg tactggtgct tgaagtcgga gtcgtcgcag ccgccccgct cccagagcga    7860
gaagtcggtc gcttcttgg agcggggtt gggcagagcg aaggtgacat cgttgaagag      7920
gattttgccc gcgcggggca tgaagttgcg ggtgatgcgg aagggccccg gcacttcaga    7980
gcggttgttg atgacctggg cggcgagcac gatctcgtcg aagccgttga tgttgtggcc    8040
cacgatgtag agttccagga agcggggccg gcccttacg gtgggcagct tctttagctc     8100
ttcgtaggtg agctcctcgg gcgaggcgag gccgtgctcg gccagggccc agtccgcgag    8160
gtgcgggttg tctctgagga aggactccca gaggtcgcgg gccaggaggg tctgcaggcg    8220
gtccctgaag gtcctgaact ggcggcccac ggccattttt tcggggtga tgcagtagaa     8280 ggtgaggggg tcttgctgcc agcggtccca gtcgagctgc agggcgaggt cgcgcgcggc    8340
ggtgaccagg cgctcgtcgc ccccgaattt catgaccagc atgaagggca cgagctgctt    8400
tccgaaggcc cccatccaag tgtaggtctc tacatcgtag gtgacaaaga ggcgctccgt    8460
gcgaggatgc gagccgatcg ggaagaactg gatctcccgc caccagttgg aggagtggct    8520
gttgatgtgg tggaagtaga agtcccgtcg ccgggccgaa cactcgtgct ggcttttgta    8580
aaagcgagcg cagtactggc agcgctgcac gggctgtacc tcctgcacga gatgcacctt    8640
tcgcccgcgc acgaggaagc cgaggggaaa tctgagcccc ccgcctggct cgcggcatgg    8700
ctggtgctct tctactttgg atgcgtgtcc gtctccgtct ggctcctcga ggggtgttac    8760
ggtggagcgg accaccacgc cgcgcgagcc gcaggtccag atatcggcgc gcggcggtcg    8820
gagtttgatg acgacatcgc gcagctggga gctgtccatg gtctggagct cccgcggcgg    8880
cggcaggtca gccgggagtt cttgcaggtt cacctcgcag agtcgggcca gggcgcgggg    8940
caggtctagg tggtacctga tctctagggg cgtgttggtg gcggcgtcga tggcttgcag    9000
gagcccgcat ccccgggggg cgacgacggt gccccgcggg gtggtggtgg tggtggtggt    9060
ggtggtggtg gcggtgcagc tcagaagcgg tgccgcgggc gggcccccgg aggtagggg    9120 ggctccggtc ccgccggcag gggcggcagc ggcacgtcgg cgtggagcgc gggcaggagt    9180
tggtgctgtg cccggaggtt gctggcgaag gcgacgacgc ggcggttgat ctcctggatc    9240
tggcgcctct gcgtgaagac gacgggcccg gtgagcttga acctgaaaga gagttcgaca    9300
gaatcaatct cggtgtcatt gaccgcgcc tggcgcagga tctcctgcac gtctcccgag     9360
ttgtcttggt aggcgatctc ggccatgaac tgctcgatct cttcctcctg gaggtctccg    9420
```

```
cgtccggcgc gttccacggt ggccgccagg tcgttggaga tgcgccccat gagctgcgag   9480
aaggcgttga gtccgccctc gttccagact cggctgtaga ccacgccccc ctggtcatcg   9540
cgggcgcgca tgaccacctg cgcgaggttg agctccacgt gccgcgcgaa gacggcgtag   9600
ttgcgcagac gctggaagag gtagttgagg gtggtggcgg tgtgctcggc cacgaagaag   9660
ttcatgaccc agcggcgcaa cgtggattcg ttgatgtccc ccaaggcctc cagccgttcc   9720
atggcctcgt agaagtccac ggcgaagttg aaaaactggg agttgcgcgc cgacacggtc   9780
aactcctcct ccagaagacg gatgagctcg gcgacggtgt cgcgcacctc gcgctcgaag   9840
gctatgggga tctcttcctc cgctagcatc accacctcct cctcttcctc ctcttctggc   9900
acttccatga tggcttcctc ctcttcgggg ggcggcggcg gcggcggtgg gggaggggggc   9960
gctctgcgcc ggcggcggcg caccgggagg cggtccacga agcgcgcgat catctccccg  10020
cggcggcggc gcatggtctc ggtgacggcg cggccgttct cccgggggcg cagttggaag  10080
acgccgccgg acatctggtg ctggggcggg tggccgtgag gcagcgaaac ggcgctgacg  10140
atgcatctca acaattgctg cgtaggtacg ccgccgaggg acctgaggga gtccatatcc  10200
accggatccg aaaaccttc gaggaaggcg tctaaccagt cgcagtcgca aggtaggctg  10260
agcaccgtgg cggcggcgg ggggtggggg gagtgtctgg cggaggtgct gctgatgatg  10320
taattgaagt aggcggactt gacacggcgg atggtcgaca ggagcaccat gtccttgggt  10380
ccggcctgct ggatgcggag gcggtcggct atgcccagg cttcgttctg gcatcggcgc  10440
aggtccttgt agtagtcttg catgagcctt ccaccggca cctcttctcc ttcctcttct  10500
gcttcttcca tgtctgcttc ggccctgggg cggcgccgcg ccccccctgcc ccccatgcgc  10560
gtgaccccga accccctgag cggttggagc agggccaggt cggcgacgac gcgctcggcc  10620
aggatggcct gctgcacctg cgtgagggtg gtttggaagt catccaagtc cacgaagcgg  10680
tggtaggcgc ccgtgttgat ggtgtaggtg cagttggcca tgacggacca gttgacggtc  10740
tggtggcccg gttgcgacat ctcggtgtac ctgagtcgcg agtaggcgcg ggagtcgaag  10800
acgtagtcgt tgcaagtccg caccaggtac tggtagccca ccaggaagtg cggcggcggc  10860
tggcggtaga ggggccagcg cagggtggcg ggggctccgg gggccaggtc ttccagcatg  10920
aggcggtggt aggcgtagat gtacctggac atccaggtga tacccgcggc ggtggtggag  10980
gcgcgcggga agtcgcgcac ccggttccag atgttgcgca ggggcagaaa gtgctccatg  11040
gtaggcgtgc tctgtccagt cagacgcgcg cagtcgttga tactctagac cagggaaaac  11100
gaaagccggt cagcgggcac tcttccgtgg tctggtgaat agatcgcaag ggtatcatgg  11160
cggagggcct cggttcgagc cccgggtccg ggccggacgg tccgccatga tccacgcggt  11220
taccgcccgc gtgtcgaacc caggtgtgcg acgtcagaca acgtggagt gttccttttg  11280
gcgttttct ggccgggcgc cggcgtcgcg taagagacta agccgcgaaa gcgaaagcag  11340
taagtggctc gctccccgta gccggaggga tccttgctaa gggttgcgtt gcggcgaacc  11400
ccggttcgaa tcccgtactc gggccggccg gacccgcggc taaggtgttg gattggcctc  11460
cccctcgtat aaagaccccg cttgcggatt gactccggac acgggacga gcccctttta  11520
ttttgctttt cccagatgc atccggtgct gcggcagatg cgccccccgc cccagcagca  11580
gcaacaacac cagcaagagc ggcagcaaca gcagcgggag tcatgcaggg cccctcacc   11640
caccctcggc gggccggcca cctcggcgtc gcggccgtg tctggcgcct gcggcggcgg   11700
cgggggggccg gctgacgacc ccgaggagcc ccgcgcgcg agggcagac actacctgga  11760
cctggaggag ggcgagggcc tggcgcggct gggggcgccg tctcccgagc gccacccgcg  11820
```

```
ggtgcagctg aagcgcgact cgcgcgaggc gtacgtgcct cggcagaacc tgttcaggga  11880
ccgcgcgggc gaggagcccg aggagatgcg ggacaggagg ttcagcgcag ggcgggagct  11940
gcggcagggg ctgaaccgcg agcggctgct gcgcgaggag gactttgagc ccgacgcgcg  12000 gacgggatc agccccgcgc gcgcgcacgt ggcggccgcc gacctggtga cggcgtacga  12060
gcagacggtg aaccaggaga tcaacttcca aaagagtttc aacaaccacg tgcgcacgct  12120 ggtgcgcgc gaggaggtga ccatcgggct gatgcacctg tgggactttg taagcgcgct  12180
ggtgcagaac cccaacagca agcctctgac ggcgcagctg ttcctgatag tgcagcacag  12240
cagggacaac gaggcgttta gggacgcgct gctgaacatc accgagcccg agggtcggtg  12300
gctgctggac ctgattaaca tcctgcagag catagtggtg caggagcgca gcctgagcct  12360
ggccgacaag gtggcggcca tcaactactc gatgctgagc ctgggcaagt tttacgcgcg  12420
caagatctac cagacgccgt acgtgcccat agacaaggag gtgaagatcg acggttttta  12480
catgcgcatg gcgctgaagg tgctcaccct gagcgacgac ctgggcgtgt accgcaacga  12540
gcgcatccac aaggccgtga cgtgagccg gcggcgcgag ctgagcgacc gcgagctgat  12600
gcacagcctg cagcgggcgc tggcgggcgc cggcagcggc gacagggagg cggagtccta  12660
cttcgatgcg ggggcggacc tgcgctgggc gcccagccgg cgggccctgg aggccgcggg  12720
ggtccgcgag gactatgacg aggacggcga ggaggatgag gagtacgagc tagaggaggg  12780
cgagtacctg gactaaaccg cgggtggtgt ttccggtaga tgcaagaccc gaacgtggtg  12840
gacccggcgc tgcgggcggc tctgcagagc cagccgtccg gccttaactc ctcagacgac  12900
tggcgacagg tcatggaccg catcatgtcg ctgacggcgc gtaacccgga cgcgttccgg  12960
cagcagccgc aggccaacag gctctccgcc atcctggagg cggtggtgcc tgcgcgctcg  13020
aaccccacgc acgagaaggt gctggccata gtgaacgcgc tggccgagaa cagggccatc  13080
cgcccggacg aggccgggct ggtgtacgac gcgctgctgc agcgcgtggc ccgctacaac  13140
agcggcaacg tgcagaccaa cctggaccgg ctggtggggg acgtgcgcga ggcggtggcg  13200
cagcgcgagc gcgcggatcg gcagggcaac ctgggctcca tggtggcgct gaatgccttc  13260
ctgagcacgc agccggccaa cgtgccgcgg gggcaggaag actacaccaa ctttgtgagc  13320
gcgctgcggc tgatggtgac cgagaccccc cagagcgagg tgtaccagtc gggcccggac  13380
tacttcttcc agaccagcag acaggcctg cagacggtga acctgagcca ggctttcaag  13440
aacctgcggg ggctgtgggg cgtgaaggcg cccaccggcg accgggcgac ggtgtccagc  13500
ctgctgacgc ccaactcgcg cctgctgctg ctgctgatcg cgccgttcac ggacagcggc  13560
agcgtgtccc gggacaccta cctggggcac ctgctgaccc tgtaccgcga ggccatcggg  13620
caggcgcagg tggacgagca caccttccag gagatcacca gcgtgagccg cgcgctgggg  13680
caggaggaca cgagcagcct ggaggcgact ctgaactacc tgctgaccaa ccggcggcag  13740
aagattccct cgctgcacag cctgacctcc gaggaggagc gcatcttgcg ctacgtgcag  13800
cagagcgtga gcctgaacct gatgcgcgac ggggtgacgc ccagcgtggc gctggacatg  13860
accgcgcgca acatggaacc gggcatgtac gccgcgcacc ggccttacat caaccgcctg  13920
atggactacc tgcatcgcgc ggcggccgtg aaccccgagt actttaccaa cgccatcctg  13980
aacccgcact ggctcccgcc gcccgggttc tacagcgggg gcttcgaggt cccggaggcc  14040
aacgatggct tcctgtggga cgacatggac gacagcgtgt ctccccgcg gccgcaggcg  14100 ctggcggaag cgtccctgct gcgtcccaag aaggaggagg aggaggcgag tcgccgccgc  14160
```

```
ggcagcagcg gcgtggcttc tctgtccgag ctggggcgg cagccgccgc gcgcccggg    14220 tccctgggcg gcagcccctt tccgagcctg gtgggtctc tgcacagcga gcgcaccacc    14280
cgccctcggc tgctgggcga ggacgagtac ctgaataact ccctgctgca gccggtgcgg    14340
gagaaaaacc tgccccccgc cttccccaac aacgggatag agagcctggt ggacaagatg    14400
agcagatgga agacctatgc gcaggagcac agggacgcgc ccgcgctccg ccgcccacg    14460 cggcgccagc gccacgaccg gcagcggggg ctggtgtggg atgacgagga ctccgcggac    14520
gatagcagcg tgctggacct gggagggagc ggcaacccgt tcgcgcacct gcgccccgc    14580 ctggggagga tgttttaaaa aaaaaaaaag caagaagcat gatgcaaaat taaataaaac    14640
tcaccaaggc catggcgacc gagcgttggt ttcttgtgtt cccttcagta tgcggcgcgc    14700
ggcgatgtac caggagggac ctcctccctc ttacgagagc gtggtgggcg cggcggcggc    14760
ggcgccctct tctcccttg cgtcgcagct gctggagccg ccgtacgtgc ctccgcgcta    14820
cctgcggcct acggggggga gaaacagcat ccgttactcg gagctggcgc ccctgttcga    14880
caccacccgg gtgtacctgg tggacaacaa gtcggcggac gtggcctccc tgaactacca    14940
gaacgaccac agcaattttt tgaccacggt catccagaac aatgactaca gcccgagcga    15000
ggccagcacc cagaccatca atctggatga ccggtcgcac tggggcggcg acctgaaaac    15060
catcctgcac accaacatgc ccaacgtgaa cgagttcatg ttcaccaata agttcaaggc    15120
gcgggtgatg gtgtcgcgct cgcacaccaa ggaagaccgg gtggagctga agtacgagtg    15180
ggtggagttc gagctgccag agggcaacta ctccgagacc atgaccattg acctgatgaa    15240
caacgcgatc gtggagcact atctgaaagt gggcaggcaa acgggggtcc tggagagcga    15300
catcggggtc aagttcgaca ccaggaactt ccgcctgggg ctggaccccg tgaccgggct    15360
ggttatgccc ggggtgtaca ccaacgaggc cttccatccc gacatcatcc tgctgcccgg    15420
ctgcggggtg gacttcactt acagccgcct gagcaacctc ctgggcatcc gcaagcggca    15480
gcccttccag gagggcttca ggatcaccta cgaggacctg gaggggggca acatccccgc    15540
gctcctcgat gtggaggcct accaggatag cttgaaggaa aatgaggcgg gacaggagga    15600
taccaccccc gccgcctccg ccgccgccga gcagggcgag gatgctgctg acaccgcggc    15660
cgcggacggg gcagaggccg accccgctat ggtggtggag gctcccgagc aggaggagga    15720
tatgaatgac agtgcggtgc gcggagacac cttcgtcacc cgggggggagg aaaagcaagc    15780 ggaggccgag gccgcggccg aggaaaagca actggcggca gcagcggcgg cggcggcgtt    15840
ggccgcggcg gaggctgagt ctgagggac caagcccgcc aaggagcccg tgattaagcc    15900
cctgaccgaa gatagcaaga agcgcagtta caacctgctc aaggacagca ccaacaccgc    15960
gtaccgcagc tggtacctgg cctacaacta cggcgacccg tcgacggggg tgcgctcctg    16020
gaccctgctg tgcacgccgg acgtgacctg cggctcggag caggtgtact ggtcgctgcc    16080
cgacatgatg caagacccg tgaccttccg ctccacgcgg caggtcagca acttcccggt    16140
ggtgggcgcc gagctgctgc ccgtgcactc caagagcttc tacaacgacc aggccgtcta    16200
ctcccagctc atccgccagt tcacctctct gacccacgtg ttcaatcgct ttcctgagaa    16260
ccagattctg gcgcgcccgc ccgccccac catcaccacc gtcagtgaaa cgttcctgc    16320 tctcacagat cacgggacgc taccgctgcg caacagcatc ggaggagtcc agcgagtgac    16380
cgttactgac gccagacgcc gcacctgccc ctacgtttac aaggccttgg gcatagtctc    16440
gccgcgcgtc ctttccagcc gcactttttg agcaacacca ccatcatgtc catcctgatc    16500
tcacccagca ataactccgg ctggggactg ctgcgcgcgc ccagcaagat gttcggaggg    16560
```

```
gcgaggaagc gttccgagca gcaccccgtg cgcgtgcgcg ggcacttccg cgcccctgg    16620 ggagcgcaca aacgcggccg cgcggggcgc accaccgtgg acgacgccat cgactcggtg    16680
gtggagcagg cgcgcaacta caggcccgcg gtctctaccg tggacgcggc catccagacc    16740
gtggtgcggg gcgcgcggcg gtacgccaag ctgaagagcc gccggaagcg cgtggcccgc    16800
cgccaccgcc gccgacccgg ggccgccgcc aaacgcgccg ccgcggccct gcttcgccgg    16860
gccaagcgca cgggccgccg cgccgccatg agggccgcgc gccgcttggc cgccggcatc    16920
accgccgcca ccatggcccc ccgtacccga agacgcgcgg ccgccgccgc cgccgccgcc    16980
atcagtgaca tggccagcag gcgccggggc aacgtgtact gggtgcgcga ctcggtgacc    17040
ggcacgcgcg tgcccgtgcg cttccgcccc ccgcggactt gagatgatgt gaaaaaacaa    17100
cactgagtct cctgctgttg tgtgtatccc agcggcggcg cgcgcgcag cgtcatgtcc    17160 aagcgcaaaa tcaaagaaga gatgctccag gtcgtcgcgc cggagatcta tgggcccccg    17220
aagaaggaag agcaggattc gaagcccgc aagataaagc gggtcaaaaa gaaaagaaa     17280 gatgatgacg atgccgatgg ggaggtggag ttcctgcgcg ccacggcgcc caggcgcccg    17340
gtgcagtgga agggccggcg cgtaaagcgc gtcctgcgcc ccggcaccgc ggtggtcttc    17400
acgcccggcg agcgctccac ccggactttc aagcgcgtct atgacgaggt gtacggcgac    17460
gaagacctgc tggagcaggc caacgagcgc ttcggagagt ttgcttacgg gaagcgtcag    17520
cgggcgctgg ggaaggagga cctgctggcg ctgccgctgg accagggcaa ccccacccc     17580 agtctgaagc ccgtgaccct gcagcaggtg ctgccgagca gcgcaccctc cgaggcgaag    17640
cggggtctga agcgcgaggg cggcgacctg gcgcccaccg tgcagctcat ggtgcccaag    17700
cggcagaggc tggaggatgt gctggagaaa atgaaagtag accccggtct gcagccggac    17760
atcagggtcc gtcccatcaa gcaggtggcg ccgggcctcg gcgtgcagac cgtggacgtg    17820
gtcatcccca ccggcaactc ccccgccgcc accaccacta ccgctgcctc cacgacatg     17880 gagacacaga ccgatcccgc cgcagccgca gccgccgccg cagccgcgac ctcctcggcg    17940
gaggtgcaga cggaccctg gctgccgccg gcgatgtcag ctccccgcgc gcgccgcgga    18000
cgcagaaagt acgcgccgc caacgcgctc ctgcccgagt acgccttgca tccttccatc     18060
gcgcccaccc ccggctaccg aggctatacc taccgcccgc gaagagccaa gggttccacc    18120
cgccgtcccc gccgacgcgc cgccgccacc cccgccgcc gccgccgcag acgccagccc     18180
gcactggctc cagtctccgt gaggagagtg gcgcgcgacg gacacaccct ggtgctgccc    18240
agggcgcgct accaccccag catcgtttaa aagcctgttg tggttcttgc agatatggcc    18300
ctcacttgcc gcctccgttt cccggtgccg ggataccgag gaggaagatc gcgccgcagg    18360
aggggtctgg ccggccgcgg cctgagcgga ggcagccgcc gcgcgcaccg gcggcgacgc    18420
gccaccagcc gacgcatgcg cggcggggtg ctgcccctgt aatccccct gatcgccgcg     18480 gcgatcggcg ccgtgcccgg gatcgcctcc gtggccttgc aagcgtccca gaggcattga    18540
cagacttgca aacttgcaaa tatggaaaaa aaaaaaaaac cccaataaaa agtctagact    18600
ctcacgctcg cttggtcctg tgactatttt gtagaatgga agacatcaac tttgcgtcgc    18660
tggccccgcg tcacggctcg cgcccgttcc tgggacactg aacgatatc ggcaccagca     18720 acatgagcgg tggcgccttc agttgggct ctctgtggag cggcattaaa agtatcgggt     18780
ctgccgttaa aaattacggc tcccgggcct ggaacagcag cacgggccag atgttgagag    18840
acaagttgaa agagcagaac ttccagcaga aggtggtgga gggcctggcc tccggcatca    18900
```

```
acggggtggt ggacctggcc aaccaggccg tgcagaataa aatcaacagc agactggacc   18960
cccggccgcc ggtggaggag gtgccgccgg cgctggagac ggtgtccccc gatgggcgtg   19020
gcgagaagcg cccgcggccc gatagggaag agaccactct ggtcacgcag accgatgagc   19080
cgcccccgta tgaggaggcc ctaaagcaag gtctgcccac cacgcggccc atcgcgccca   19140
tggccaccgg ggtggtgggc cgccacaccc ccgccacgct ggacttgcct ccgcccgccg   19200
atgtgccgca gcagcagaag gcggcacagc cgggcccgcc cgcgaccgcc tcccgttcct   19260
ccgccggtcc tctgcgccgc gcggccagcg gcccccgcgg ggggtcgcg aggcacggca    19320 actggcagag cacgctgaac agcatcgtgg gtctgggggt gcggtccgtg aagcgccgcc   19380
gatgctactg aatagcttag ctaacgtgtt gtatgtgtgt atgcgccta tgtcgccgcc    19440 agaggagctg ctgagtcgcc gccgttcgcg cgcccaccac caccgccact ccgcccctca   19500
agatggcgac cccatcgatg atgccgcagt ggtcgtacat gcacatctcg ggccaggacg   19560
cctcggagta cctgagcccc gggctggtgc agttcgcccg cgccaccgag agctacttca   19620
gcctgagtaa caagtttagg aaccccacgg tggcgcccac gcacgatgtg accaccgacc   19680
ggtctcagcg cctgacgctg cggttcattc ccgtggaccg cgaggacacc gcgtactcgt   19740
acaaggcgcg gttcaccctg gccgtgggcg acaaccgcgt gctggacatg gcctccacct   19800
actttgacat ccgcggggtg ctggaccggg gtcccacttt caagccctac tctggcaccg   19860
cctacaactc cctggccccc aagggcgctc ccaactcctg cgagtgggag caagaggaaa   19920
ctcaggcagt tgaagaagca gcagaagagg aagaagaaga tgctgacggt caagctgagg   19980
aagagcaagc agctaccaaa aagactcatg tatatgctca ggctcccctt tctggcgaaa   20040
aaattagtaa agatggtctg caaataggaa cggacgctac agctacagaa caaaaaccta   20100
tttatgcaga ccctacattc cagcccgaac cccaaatcgg ggagtccag tggaatgagg    20160 cagatgctac agtcgccggc ggtagagtgc taaagaaatc tactcccatg aaaccatgct   20220
atggttccta tgcaagaccc acaaatgcta atggaggtca gggtgtacta acggcaaatg   20280
cccagggaca gctagaatct caggttgaaa tgcaattctt ttcaacttct gaaaacgccc   20340
gtaacgaggc taacaacatt cagcccaaat tggtgctgta tagtgaggat gtgcacatgg   20400
agacccggga tacgcacctt tcttacaagc ccgcaaaaag cgatgacaat tcaaaaatca   20460
tgctgggtca gcagtccatg cccaacagac taattacat cggcttcaga gacaacttta    20520
tcggcctcat gtattacaat agcactggca acatgggagt gcttgcaggt caggcctctc   20580
agttgaatgc agtggtggac ttgcaagaca gaaacacaga actgtcctac cagctcttgc   20640
ttgattccat gggtgacaga accagatact tttccatgtg gaatcaggca gtggacagtt   20700
atgacccaga tgttagaatt attgaaaatc atggaactga agacgagctc cccaactatt   20760
gtttccctct gggtggcata ggggtaactg acacttacca ggctgttaaa accaacaatg   20820
gcaataacgg gggccaggtg acttggacaa aagatgaaac ttttgcagat cgcaatgaaa   20880 tagggtggg aaacaatttc gctatggaga tcaacctcag tgccaacctg tggagaaact    20940
tcctgtactc caacgtggcg ctgtacctac cagacaagct taagtacaac ccctccaatg   21000
tggacatctc tgcaaccccc aacacctacg attacatgaa caagcgagtg gtggcccgg    21060 ggctggtgga ctgctacatc aacctgggcg cgcgctggtc gctggactac atggacaacg   21120
tcaacccctt caaccaccac cgcaatgcgg gcctgcgcta ccgctccatg ctcctgggca   21180
acgggcgcta cgtgcccttc cacatccagg tgccccagaa gttctttgcc atcaagaacc   21240
tcctcctcct gccgggctcc tacacctacg agtggaactt caggaaggat gtcaacatgg   21300
```

```
tcctccagag ctctctgggt aacgatctca gggtggacgg ggccagcatc aagttcgaga  21360
gcatctgcct ctacgccacc ttcttcccca tgcccacaa cacggcctcc acgctcgagg   21420
ccatgctcag gaacgacacc aacgaccagt ccttcaatga ctacctttcc gccgccaaca   21480
tgctctaccc cataccgcc aacgccacca acgtccccat ctccatcccc tcgcgcaact   21540
gggcggcctt ccgcggctgg gccttcaccc gcctcaagac caaggagacc ccctccctgg   21600
gctcgggatt cgacccctac tacacctact cgggctctat tccctacctg gacgcacct   21660
tctacctcaa ccacactttc aagaaggtct cggtcacctt cgactcctcg gtcagctggc   21720
cgggcaacga ccgtctgctc accccaacg agttcgagat caagcgctcg gtcgacgggg   21780
aaggctacaa cgtggcccag tgcaacatga ccaaggactg gttcctggtc cagatgctgg   21840
ccaactacaa catcggctac cagggcttct acatcccaga gagctacaag acaggatgt    21900
actccttctt caggaacttc cagcccatga ccggcaggt ggtggaccag accaagtaca   21960
aggactacca ggaggtgggc atcatccacc agcacaacaa ctcgggcttc gtgggctacc   22020
tcgcccccac catgcgcgag ggacaggcct accccgccaa cttcccctac ccgctcatag   22080
gcaagaccgc ggtcgacagc atcacccaga aaaagttcct ctgcgaccgc accctctggc   22140
gcatcccctt ctccagcaac ttcatgtcca tgggtgcgct ctcggacctg gccagaact    22200
tgctctacgc caactccgcc cacgcctcg acatgacctt cgaggtcgac cccatggacg   22260
agcccaccct tctctatgtt ctgttcgaag tctttgacgt ggtccgggtc caccagccgc   22320
accgcggcgt catcgagacc gtgtacctgc gtacgccctt ctcggccggc aacgccacca   22380
cctaaagaag caagccgcag tcatcgccgc ctgcatgccg tcgggttcca ccgagcaaga   22440
gctcagggcc atcgtcagag acctgggatg cgggccctat tttttgggca ccttcgacaa   22500
gcgcttccct ggctttgtct ccccacacaa gctggcctgc gccatcgtca acacggccgg   22560
ccgcgagacc gggggcgtgc actggctggc ctttgcctgg aacccgcgct ccaaaacatg   22620
cttcctcttt gaccccttcg gcttttcgga ccagcggctc aagcaaatct acgagttcga   22680
gtacgagggc ttgctgcgtc gcagcgccat cgcctcctcg cccgaccgct gcgtcaccct   22740
cgaaaagtcc acccagaccg tgcagggggcc cgactcggcc gcctgcggtc tcttctgctg   22800
catgtttctg cacgccttttg tgcactggcc tcagagtccc atggaccgca accccaccat   22860
gaacttgctg acggggggtgc ccaactccat gctccaaagc ccccaggtcg agcccaccct   22920
gcgccgcaac caggagcagc tctacagctt cctggagcgc cactcgccct acttccgccg   22980
ccacagcgca cagatcagga gggccacctc cttctgccac ttgcaagaga tgcaagaagg   23040
gtaataacga tgtacacact tttttctcaa taaatggcat ttttttttta tttatacaag   23100
ctctctgggg tattcatttc ccaccaccac cacccgccgt tgtcgccatc tggctctatt   23160
tagaaatcga aagggttctg ccgggagtcg ccgtgcgcca cgggcaggga cacgttgcga   23220
tactggtagc gggtgcccca cttgaactcg ggcaccacca ggcgaggcag ctcggggaag   23280
ttttcgctcc acaggctgcg ggtcagcacc agcgcgttca tcaggtcggg cgccgagatc   23340
ttgaagtcgc agttggggcc gccgccctgc gcgcgcgagt tgcggtacac cgggttgcag   23400
cactggaaca ccaacagcgc cggggtgcttc acgctggcca gcacgctgcg gtcggagatc   23460
agctcggcgt ccaggtcctc cgcgttgctc agcgcgaacg gggtcatctt gggcacttgc   23520
cgccccagga agggcgcgtg ccccggtttc gagttgcagt cgcagcgcag cgggatcagc   23580
aggtgcccgt gcccggactc ggcgttgggg tacagcgcgc gcatgaaggc ctgcatctgg   23640
```

```
cggaaggcca tctgggcctt ggcgccctcc gagaagaaca tgccgcagga cttgcccgag   23700
aactggtttg cggggcagct ggcgtcgtgc aggcagcagc gcgcgtcggt gttggcgatc   23760
tgcaccacgt tgcgccccca ccggttcttc acgatcttgg ccttggacga ttgctccttc   23820
agcgcgcgct gcccgttctc gctggtcaca tccatctcga tcacatgttc cttgttcacc   23880
atgctgctgc cgtgcagaca cttcagctcg ccctccgtct cggtgcagcg gtgctgccac   23940
agcgcgcagc ccgtgggctc gaaagacttg taggtcacct ccgcgaagga ctgcaggtac   24000
ccctgcaaaa agcggcccat catggtcacg aaggtcttgt tgctgctgaa ggtcagctgc   24060
agcccgcggt gctcctcgtt cagccaggtc ttgcacacgg ccgccagcgc ctccacctgg   24120
tcgggcagca tcttgaagtt caccttcagc tcattctcca cgtggtactt gtccatcagc   24180
gtgcgcgccg cctccatgcc cttctcccag gccgacacca gcggcaggct cacggggttc   24240
ttcaccatca ccgtggccgc cgcctccgcc gcgctttcgc tttccgcccc gctgttctct   24300
tcctcttcct cctcttcctc gccgccgccc actcgcagcc cccgcaccac ggggtcgtct   24360
tcctgcaggc gctgcacctt gcgcttgccg ttgcgccct gcttgatgcg cacgggcggg   24420
ttgctgaagc ccaccatcac cagcgcggcc tcttcttgct cgtcctcgct gtccagaatg   24480
acctccgggg agggggggtt ggtcatcctc agtaccgagg cacgcttctt tttcttcctg   24540
ggggcgttcg ccagctccgc ggctgcggcc gctgccgagg tcgaaggccg agggctgggc   24600
gtgcgcggca ccagcgcgtc ttgcgagccg tcctcgtcct cctcggactc gagacggagg   24660
cgggcccgct tcttcggggg cgcgcggggc ggcggaggcg gcggcggcga cggagacggg   24720
gacgagacat cgtccagggt gggtggacgg cgggccgcgc cgcgtccgcg ctcggggtg   24780 gtttcgcgct ggtcctcttc ccgactggcc atctcccact gctccttctc ctataggcag   24840
aaagagatca tggagtctct catgcgagtc gagaaggagg aggacagcct aaccgccccc   24900
tctgagccct ccaccaccgc cgccaccacc gccaatgccg ccgcggacga cgcgcccacc   24960
gagaccaccg ccagtaccac cctccccagc gacgcacccc cgctcgagaa tgaagtgctg   25020
atcgagcagg acccgggttt tgtgagcgga gaggaggatg aggtggatga aaggagaag   25080 gaggaggtcg ccgcctcagt gccaaaagag gataaaaagc aagaccagga cgacgcagat   25140
aaggatgaga cagcagtcgg gcggggggaac ggaagccatg atgctgatga cggctaccta   25200
gacgtgggag acgacgtgct gcttaagcac ctgcaccgcc agtgcgtcat cgtctgcgac   25260
gcgctgcagg agcgctgcga agtgccctg gacgtggcgg aggtcagccg cgcctacgag   25320
cggcacctct tcgcgccgca cgtgcccccc aagcgccggg agaacggcac ctgcgagccc   25380
aacccgcgtc tcaacttcta cccggtcttc gcggtacccg aggtgctggc cacctaccac   25440
atcttcttcc aaaactgcaa gatccccctc tcctgccgcg ctaaccgcac ccgcgccgac   25500
aaaaccctga ccctgcggca gggcgcccac atacctgata ttgcctctct ggaggaagtg   25560
cccaagatct tcgagggtct cggtcgcgac gagaaacggg cggcgaacgc tctgcacgga   25620
gacagcgaaa acgagagtca ctcggggtg ctggtggagc tcgagggcga caacgcgcgc   25680
ctggccgtac tcaagcgcag catagaggtc acccactttg cctacccggc gctcaacctg   25740
ccccccaagg tcatgagtgt ggtcatgggc gagctcatca tgcgccgcgc tcagcccctg   25800
gccgcggatg caaacttgca agagtcctcc gaggaaggcc tgcccgcggt cagcgacgag   25860
cagctagcgc gctggctgga gacccgcgac cccgcgcagc tggaggagcg gcgcaagctc   25920
atgatggccg cggtgctggt caccgtggag ctcgagtgtc tgcagcgctt cttcgcggac   25980
cccgagatgc agcgcaagct cgaggagacc ctgcactaca ccttccgcca gggctacgtg   26040
```

```
cgccaggcct gcaagatctc caacgtggag ctctgcaacc tggtctccta cctgggcatc    26100
ctgcacgaga accgcctcgg gcagaacgtc ctgcactcca ccctcaaagg ggaggcgcgc    26160
cgcgactaca tccgcgactg cgcctacctc ttcctctgct acacctggca gacggccatg    26220
ggggtctggc agcagtgcct ggaggagcgc aacctcaagg agctggaaaa gctactcaag    26280 cgcacccctca gggacctctg gacgggcttc aacgagcgct cggtggccgc cgcgctggcg    26340
gacatcatct tccccgagcg cctgctcaag accctgcagc agggcctgcc cgacttcacc    26400
agccagagca tgctgcagaa ctttaggact ttcatcctgg agcgctcggg catcctgcct    26460
gccacttgct gcgcgctgcc cagcgacttc gtgcccatca agtacaggga gtgcccgccg    26520
ccgctctggg gccactgcta cctcttccag ctggccaact acctcgccta ccactcggac    26580
ctcatggaag acgtgagcgg cgagggcctg ctcgagtgcc actgccgctg caacctctgc    26640
acgccccacc gctctctagt ctgcaacccg cagctgctca gcgagagtca gattatcggt    26700
accttcgagc tgcagggtcc ctcgcctgac gagaagtccg cggctccggg gctgaaactc    26760
actccggggc tgtggacttc cgcctaccta cgcaaatttg tacctgagga ctaccacgcc    26820
cacgagatca ggttctacga agaccaatcc cgcccgccca aggcggagct caccgcctgc    26880
gtcatcaccc aggggcacat cctgggccaa ttgcaagcca tcaacaaagc ccgccgagag    26940
ttcttgctga aaaagggtcg gggggtgtac ctggaccccc agtccggcga ggagctaaac    27000
ccgctacccc cgccgccgcc ccagcagcgg gaccttgctt cccaggatgg cacccagaaa    27060
gaagcagcag ccgccgccgc cgcagccata catgcttctg gaggaagagg aggaggactg    27120
ggacagtcag gcagaggagg tttcggacga ggagcaggag gagatgatgg aagactggga    27180
ggaggacagc agcctagacg aggaagcttc agaggccgaa gaggtggcag acgcaacacc    27240
atcaccctcg gtcgcagccc cctcgccggg gcccctgaaa tcctccgaac ccagcaccag    27300
cgctataacc tccgctcctc cggcgccggc gccaccgcc gcagaccca accgtagatg    27360 ggacaccaca ggaaccgggg tcggtaagtc caagtgcccg ccgccgccac cgcagcagca    27420
gcagcagcgc cagggctacc gctcgtggcg cgggcacaag aacgccatag tcgcctgctt    27480
gcaagactgc gggggcaaca tctctttcgc ccggcgcttc ctgctattcc accacggggt    27540
cgcctttccc cgcaatgtcc tgcattacta ccgtcatctc tacagcccct actgcagcgg    27600
cgacccagag gcggcagcgg cagccacagc ggcgaccacc acctaggaag atatcctccg    27660
cgggcaagac agcggcagca gcggccagga gacccgcggc agcagcggcg ggagcggtgg    27720
gcgcactgcg cctctcgccc aacgaacccc tctcgacccg ggagctcaga cacaggatct    27780
tccccacttt gtatgccatc ttccaacaga gcagaggcca ggagcaggag ctgaaaataa    27840
aaaacagatc tctgcgctcc ctcacccgca gctgtctgta tcacaaaagc gaagatcagc    27900
ttcggcgcac gctggaggac gcggaggcac tcttcagcaa atactgcgcg ctcactctta    27960
aagactagct ccgcgccctt ctcgaattta ggcgggagaa aactacgtca tcgcggccgc    28020
ccgcccagcc cgcccagccg agatgagcaa agagattccc acgccataca tgtggagcta    28080
ccagccgcag atgggactcg cggcgggagc ggcccaggac tactccaccc gcatgaacta    28140
catgagcgcg ggaccccaca tgatctcaca ggtcaacggg atccgcgccc agcgaaacca    28200
aatactgctg gaacaggcgg ccatcaccgc cacgcccgc cataatctca ccccgaaa    28260 ttggcccgcc gccctcgtgt accaggaaac ccctccgcc accaccgtac tacttccgcg    28320
tgacgcccag gccgaagtcc agatgactaa ctcagggcg cagctcgcgg gcggctttcg    28380
```

```
tcacggggcg cggccgctcc gaccaggtat aagacacctg atgatcagag gccgaggtat   28440
ccagctcaac gacgagtcgg tgagctcttc gctcggtctc cgtccggacg aactttcca   28500
gctcgccgga tccggccgct cttcgttcac gccccgccag gcgtacctga ctctgcagac   28560
ctcgtcctcg gagccccgct ccggaggcat cggaaccctc cagttcgtgg aggagttcgt   28620
gccctcggtc tacttcaacc ccttctcggg acctcccgga cgctaccccg accagttcat   28680
tccgaacttt gacgcggtga aggactcggc ggacggctac gactgaatgt caggtgccga   28740
ggcagagcag cttcgcctga gacacctcga gcactgccgc cgccacaagt gcttcgcccg   28800
cggttccggt gagttctgct actttcagct acccgaggag cataccgagg ggccggcgca   28860
cggcgtccgc ctgaccaccc agggcgaggt tacctgttcc ctcatccggg agttcaccct   28920
ccgtcccctg ctagtggagc gggagcgggg tccctgtgtc ctaactatcg cctgcaactg   28980
ccctaacccct ggattacatc aagatctttg ctgtcatctc tgtgctgagt ttaataaacg   29040
ctgagatcag aatctactgg gaattcgatt tagtcccctt taactaatca aacactggaa   29100
tcaataaaaa gaatcactta cttaaaatca gacagcaggt ctctgtccag tttattcagc   29160
agcacctcct tcccctcctc ccaactctgg tactccaaac gccttctggc ggcaaacttc   29220
ctccacaccc tgaagggaat gtcagattct tgctcctgtc cctccgcacc cactatcttc   29280
atgttgttgc agatgaagcg caccaaaacg tctgacgaga gcttcaaccc cgtgtacccc   29340
tatgacacgg aaagcggccc tccctccgtc cctttcctca ccccctccctt cgtgtctccc   29400
gatggattcc aagaaagccc cccgggggtc ctgtctctga acctggccga gcccctggtc   29460
acttcccacg gcatgctcgc cctgaaaatg ggaagtggcc tctccctgga cgacgctggc   29520
aacctcacct ctcaagatat caccaccgct agccctcccc tcaaaaaaac caagaccaac   29580
ctcagcctag aaacctcatc cccctaact gtaagcacct caggcgccct caccgtagca   29640
gccgccgctc ccctggcagt ggccggcacc tccctcacca tgcaatcaga ggccccctg   29700
acagtacagg atgcaaaact cacccctggcc accaaaggcc ccctgaccgt gtctgaaggc   29760
aaactggcct tgcaaacatc ggccccgctg acggccgctg acagcagcac cctcaccgtt   29820
agcgccacac caccaattaa tgtaagcagt ggaagtttag gcttagacat ggaagaccct   29880
atgtatactc acgatggaaa actgggaata agaattgggg gtccactaag agtagtagac   29940
agcttgcaca cactcactgt agttaccgga aatggactaa ctgtagataa caatgccctc   30000
caaactagag ttacgggcgc cctaggttat gacacatcag gaaatctaca attgagagct   30060
gcaggaggta tgcgaattga tgcaaatggc caacttatcc ttaatgtggc atacccattt   30120
gatgctcaga acaatctcag ccttagactt ggtcagggac ccctgtatat aaacacagac   30180
cacaacctgg atttgaattg caacagaggt ctaaccacaa ctaccaccaa caacacaaaa   30240
aaacttgaga ctaaaattag ctcaggctta gactatgaca ccaatggtgc tgtcattatt   30300
aaacttggca ctggtctaag cttcgacaac acaggcgccc taactgtggg aaacactggt   30360
gatgataaac tgactctgtg gacgaccccca gacccatctc caattgcag aattcactca   30420
gacaaagact gcaagtttac tctagtccta actaagtgtg aagccaaat cctggcctct   30480
gtcgccgccc tagcggtatc aggaaatctg gcttcgataa caggcaccgt tgccagcgtt   30540
accatctttc tcagatttga tcagaatgga gtgcttatgg aaaactcctc gctagacagg   30600
cagtactgga acttcagaaa tggcaactca actaacgctg cccctacac caatgcagtt   30660
gggttcatgc caaacctcgc agcataccc aaaacgcaaa gccagactgc taaaaacaac   30720
attgtaagtc aggtttactt gaatggagac aaatccaaac ccatgaccct taccatcacc   30780
```

```
ctcaatggaa ctaatgaatc cagtgaaact agccaggtga gtcactactc catgtcattt    30840
acatgggctt gggaaagtgg gcaatatgcc actgaaacct tgccaccaa ctccttcacc     30900 ttttcttaca ttgctgaaca ataaaaagca tgacactgat gttcatttct gattcttatt    30960
ttattatttt caaacacaac aaaatcattc aagtcattct tccatcttag cttaatagac    31020
acagtagctt aatagaccca gtagtgcaaa gccccattct agcttataac tagtggagaa    31080
gtactcgcct acatgggggt agagtcataa tcgtgcatca ggatagggcg gtggtgctgc    31140
agcagcgcgc gaataaactg ctgccgccgc cgctccgtcc tgcaggaata caacatggca    31200
gtggtctcct cagcgatgat tcgcaccgcc cgcagcataa ggcgccttgt cctccgggca    31260
cagcagcgca ccctgatctc acttaaatca gcacagtaac tgcagcacag caccacaata    31320
ttgttcaaaa tcccacagtg caaggcgctg tatccaaagc tcatggcggg gaccacagaa    31380
cccacgtggc catcatacca caagcgcagg tagattaagt ggcgacccct cataaacacg    31440
ctggacataa acattccctc ttttggcatg ttgtaattca ccacctcccg gtaccatata    31500
aacctctgat taaacatggc gccatccacc accatcctaa accagctggc caaaacctgc    31560
ccgccggcta tacactgcag ggaaccggga ctggaacaat gacagtggag agcccaggac    31620
tcgtaaccat ggatcatcat gctcgtcatg atatcaatgt tggcacaaca caggcacacg    31680
tgcatacact tcctcaggat tacaagctcc tcccgcgtta gaaccatatc ccagggaaca    31740
acccattcct gaatcagcgt aaatcccaca ctgcagggaa gacctcgcac gtaactcacg    31800
ttgtgcattg tcaaagtgtt acattcgggc agcagcggat gatcctccag tatggtagcg    31860
cgggtttctg tctcaaaagg aggtagacga tccctactgt acggagtgcg ccgagacaac    31920
cgagatcgtg ttggtcgtag tgtcatgcca aatggaacgc cggacgtagt catatttcct    31980
gaagtcttag atctctcaac gcagcaccag caccaacact tcgcagtgta aaggccaag     32040 tgccgagaga gtatatatag gaataaaaag tgacgtaaac gggcaaagtc caaaaaacgc    32100
ccagaaaaac cgcacgcgaa cctacgcccc gaaacgaaag ccaaaaaaca ctagacactc    32160
ccttccggcg tcaacttccg ctttcccacg ctacgtcact tgcccagtc aaacaaacta    32220 catatcccga acttccaagt cgccacgccc aaaacaccgc ctacacctcc ccgcccgccg    32280
gcccgccccc aaacccgcct cccgccccgc gccccgcccc gcgccgccca tctcattatc    32340
atattggctt caatccaaaa taaggtatat tattgatgat g                       32381
```

<210> SEQ ID NO 4
<211> LENGTH: 31881
<212> TYPE: DNA
<213> ORGANISM: Artificial Sequence
<220> FEATURE:
<223> OTHER INFORMATION: synthetic chimpanzee adenovirus serotype ChAd63
      with Ebola virus Zaire wild type transmembrane
      envelope glycoprotein (GP) insert (ChAd63 Ebola
      Zaire (PB/6001))
<220> FEATURE:
<221> NAME/KEY: CDS
<222> LOCATION: (2139)...(4440)
<223> OTHER INFORMATION: Ebola virus Zaire wild type transmembrane
      envelope glycoprotein (GP) insert in ChAd63 Ebola Zaire
      (PB/6001)
<220> FEATURE:
<221> NAME/KEY: CDS
<222> LOCATION: (15152)...(16771)
<223> OTHER INFORMATION: chimpanzee adenovirus serotype ChAd63 penton
<220> FEATURE:
<221> NAME/KEY: CDS
<222> LOCATION: (19538)...(22414)
<223> OTHER INFORMATION: chimpanzee adenovirus serotype ChAd63 hexon

```
<220> FEATURE:
<221> NAME/KEY: CDS
<222> LOCATION: (28942)...(30219)
<223> OTHER INFORMATION: chimpanzee adenovirus serotype ChAd63 fiber

<400> SEQUENCE: 4
```

| | | | | | |
|---|---|---|---|---|---|
| catcatcaat | aatatacctc | aaacttttgg | tgcgcgttaa | tatgcaaatg | aggtgtttga | 60 |
| atttggggat | gcggggcgct | gattggctga | gagacgggcg | accgttaggg | gcggggcggg | 120 |
| tgacgttttg | atgacgtggc | cgtgaggcgg | agccggtttg | caagttctcg | tgggaaaagt | 180 |
| gacgtcaaac | gaggtgtggt | ttgaacacgg | aaatactcaa | ttttcccgcg | ctctctgaca | 240 |
| ggaaatgagg | tgtttctggg | cggatgcaag | tgaaaacggg | ccattttcgc | gcgaaaactg | 300 |
| aatgaggaag | tgaaaatctg | agtaattccg | cgtttatggc | agggaggagt | atttgccgag | 360 |
| ggccgagtag | actttgaccg | attacgtggg | ggtttcgatt | accgtatttt | tcacctaaat | 420 |
| ttccgcgtac | ggtgtcaaag | tccggtgttt | ttacggatat | ctccattgca | tacgttgtat | 480 |
| ccatatcata | atatgtacat | ttatattggc | tcatgtccaa | cattaccgcc | atgttgacat | 540 |
| tgattattga | ctagttatta | atagtaatca | attacggggt | cattagttca | tagcccatat | 600 |
| atggagttcc | gcgttacata | acttacggta | aatggcccgc | ctggctgacc | gcccaacgac | 660 |
| ccccgcccat | tgacgtcaat | aatgacgtat | gttcccatag | taacgccaat | agggactttc | 720 |
| cattgacgtc | aatgggtgga | gtatttacgg | taaactgccc | acttggcagt | acatcaagtg | 780 |
| tatcatatgc | caagtacgcc | ccctattgac | gtcaatgacg | gtaaatggcc | cgcctggcat | 840 |
| tatgcccagt | acatgacctt | atgggacttt | cctacttggc | agtacatcta | cgtattagtc | 900 |
| atcgctatta | ccatggtgat | gcggttttgg | cagtacatca | atgggcgtgg | atagcggttt | 960 |
| gactcacggg | gatttccaag | tctccacccc | attgacgtca | atgggagttt | gttttggaac | 1020 |
| caaaatcaac | gggactttcc | aaaatgtcgt | aacaactccg | ccccattgac | gcaaatgggc | 1080 |
| ggtaggcgtg | tacggtggga | ggtctatata | agcagagctc | tccctatcag | tgatagagat | 1140 |
| ctccctatca | gtgatagaga | tcgtcgacga | gctcgtttag | tgaaccgtca | gatcgcctgg | 1200 |
| agacgccatc | cacgctgttt | tgacctccat | agaagacacc | gggaccgatc | cagcctccgc | 1260 |
| ggccgggaac | ggtgcattgg | aacgcggatt | ccccgtgcca | agagtgacgt | aagtaccgcc | 1320 |
| tatagactct | ataggcacac | ccctttggct | cttatgcatg | ctatactgtt | tttggcttgg | 1380 |
| ggcctataca | cccccgcttc | cttatgctat | aggtgatggt | atagcttagc | ctataggtgt | 1440 |
| gggttattga | ccattattga | ccactcccct | attggtgacg | atactttcca | ttactaatcc | 1500 |
| ataacatggc | tctttgccac | aactatctct | attggctata | tgccaatact | ctgtccttca | 1560 |
| gagactgaca | cggactctgt | attttttacag | gatggggtcc | catttattat | ttacaaattc | 1620 |
| acatatacaa | caacgccgtc | ccccgtgccc | gcagttttta | ttaaacatag | cgtgggatct | 1680 |
| ccacgcgaat | ctcgggtacg | tgttccggac | atgggctctt | ctccggtagc | ggcggagctt | 1740 |
| ccacatccga | gccctggtcc | catgcctcca | gcggctcatg | gtcgctcggc | agctccttgc | 1800 |
| tcctaacagt | ggaggccaga | cttaggcaca | gcacaatgcc | caccaccacc | agtgtgccgc | 1860 |
| acaaggccgt | ggcggtaggg | tatgtgtctg | aaaatgagcg | tggagattgg | gctcgcacgg | 1920 |
| ctgacgcaga | tggaagactt | aaggcagcgg | cagaagaaga | tgcaggcagc | tgagttgttg | 1980 |
| tattctgata | agagtcagag | gtaactcccg | ttgcggtgct | gttaacggtg | gagggcagtg | 2040 |
| tagtctgagc | agtactcgtt | gctgccgcgc | gcgccaccag | acataatagc | tgacagacta | 2100 |
| acagactgtt | cctttccatg | ggtctttttct | gcagtcaccg | tcgtcgacac | gtgtgatcag | 2160 |

```
atatcgcggc cgctctagac caggccctgg atcgatccaa caacacaatg ggcgttacag    2220
gaatattgca gttacctcgt gatcgattca agaggacatc attctttctt tgggtaatta    2280
tccttttcca aagaacattt tccatcccac ttggagtcat ccacaatagc acattacagg    2340
ttagtgatgt cgacaaacta gtttgtcgtg acaaactgtc atccacaaat caattgagat    2400
cagttggact gaatctcgaa gggaatggag tggcaactga cgtgccatct gcaactaaaa    2460
gatggggctt caggtccggt gtcccaccaa aggtggtcaa ttatgaagct ggtgaatggg    2520
ctgaaaactg ctacaatctt gaaatcaaaa aacctgacgg gagtgagtgt ctaccagcag    2580
cgccagacgg gattcggggc ttcccccggt gccggtatgt gcacaaagta tcaggaacgg    2640
gaccgtgtgc cggagacttt gccttccata agagggtgc tttcttcctg tatgatcgac     2700
ttgcttccac agttatctac cgaggaacga ctttcgctga aggtgtcgtt gcatttctga    2760
tactgcccca agctaagaag gacttcttca gctcacaccc cttgagagag ccggtcaatg    2820
caacggagga cccgtctagt ggctactatt ctaccacaat tagatatcag gctaccggtt    2880
ttggaaccaa tgagacagag tacttgttcg aggttgacaa tttgacctac gtccaacttg    2940
aatcaagatt cacaccacag tttctgctcc agctgaatga gacaatatat acaagtggga    3000
aaaggagcaa taccacggga aaactaattt ggaaggtcaa ccccgaaatt gatacaacaa    3060
tcggggagtg ggccttctgg gaaactaaaa aaaacctcac tagaaaaatt cgcagtgaag    3120
agttgtcttt cacagttgta tcaaacggag ccaaaaacat cagtggtcag agtccggcgc    3180
gaacttcttc cgacccaggg accaacacaa caactgaaga ccacaaaatc atggcttcag    3240
aaaattcctc tgcaatggtt caagtgcaca gtcaaggaag ggaagctgca gtgtcgcatc    3300
taacaaccct tgccacaatc tccacgagtc cccaatccct cacaaccaaa ccaggtccgg    3360
acaacagcac cctaatataca cccgtgtata aacttgacat ctctgaggca actcaagttg    3420
aacaacatca ccgcagaaca gacaacgaca gcacagcctc cgacactccc tctgccacga    3480
ccgcagccgg accccaaaa gcagagaaca ccaacacgag caagagcact gacttcctgg     3540
accccgccac cacaacaagt ccccaaaacc acagcgagac cgctggcaac aacaacactc    3600
atcaccaaga taccggagaa gagagtgcca gcagcgggaa gctaggctta attaccaata    3660
ctattgctgg agtcgcagga ctgatcacag gcgggagaag aactcgaaga gaagcaattg    3720
tcaatgctca acccaaatgc aaccctaatt tacattactg gactactcag gatgaaggtg    3780
ctgcaatcgg actggcctgg ataccatatt tcgggccagc agccgaggga atttacatag    3840
aggggctaat gcacaatcaa gatggtttaa tctgtgggtt gagacagctg ccaacgaga    3900
cgactcaagc tcttcaactg ttcctgagag ccacaactga gctacgcacc ttttcaatcc    3960
tcaaccgtaa ggcaattgat ttcttgctgc agcgatgggg cggcacatgc cacattctgg    4020
gaccggactg ctgtatcgaa ccacatgatt ggaccaagaa cataacagac aaaattgatc    4080
agattattca tgattttgtt gataaaaccc ttccggacca ggggacaat gacaattggt      4140
ggacaggatg gagacaatgg ataccggcag gtattggagt tacaggcgtt gtaattgcag    4200
ttatcgcttt attctgtata tgcaaatttg tcttttagtt tttcttcaga ttgcttcatg    4260
gaaaagctca gcctcaaatc aatgaaacca ggatttaatt atatggatta cttgaatcta    4320
agattacttg acaaatgata atataataca ctggagcttt aaacatagcc aatgtgattc    4380
taactccttt aaactcacag ttaatcataa acaaggtttg aggtaccgag ctcgaattga    4440
tctgctgtgc cttctagttg ccagccatct gttgtttgcc cctcccccgt gccttccttg    4500
accctggaag gtgccactcc cactgtcctt tcctaataaa atgaggaaat tgcatcgcat    4560
```

```
tgtctgagta ggtgtcattc tattctgggg ggtggggtgg ggcaggacag caaggggggag    4620 gattgggaag acaatagcag gcatgctggg gatgcggtgg gctctagata tcagcgatcg    4680
cgtgagtagt gtttgggggt gggtgggagc ctgcatgatg ggcagaatga ctaaaatctg    4740
tgtttttctg tgtgttgcag cagcatgagc ggaagcgcct cctttgaggg aggggtattc    4800
agcccttatc tgacggggcg tctcccctcc tgggcgggag tgcgtcagaa tgtgatggga    4860
tccacggtgg acggccggcc cgtgcagccc gcgaactctt caaccctgac ctacgcgacc    4920
ctgagctcct cgtccgtgga cgcagctgcc gccgcagctg ctgcttccgc cgccagcgcc    4980
gtgcgcggaa tgggccctggg cgccggctac tacagctctc tggtggccaa ctcgagttcc    5040
accaataatc ccgccagcct gaacgaggag aagctgttgc tgctgatggc ccagctcgag    5100
gccctgaccc agcgcctggg cgagctgacc cagcaggtgg ctcagctgca ggcggagacg    5160
cgggccgcgg ttgccacggt gaaaaccaaa taaaaaatga atcaataaat aaacggagac    5220
ggttgttgat tttaacacag agtcttgaat ctttatttga tttttcgcgc gcggtaggcc    5280
ctggaccacc ggtctcgatc attgagcacc cggtggatct tttccaggac ccggtagagg    5340
tgggcttgga tgttgaggta catgggcatg agcccgtccc ggggggtggag gtagctccat    5400 tgcagggcct cgtgctcggg ggtggtgttg taaatcaccc agtcatagca ggggcgcagg    5460
gcgtggtgct gcacgatgtc tttgaggagg agactgatgg ccacgggcag ccccttggtg    5520
taggtgttga cgaacctatt gagctgggag ggatgcatgc ggggggagat gagatgcatc    5580
ttggcctgga tcttgagatt ggcgatgttc ccgcccagat cccgccgggg gttcatgttg    5640
tgcaggacca ccagcacggt gtatccggtg cacttgggga atttgtcatg caacttggaa    5700
gggaaggcgt gaaagaattt ggagacgccc ttgtgaccgc ccaggttttc catgcactca    5760
tccatgatga tggcgatggg cccgtgggcg gcggcctggg caaagacgtt tcgggggtcg    5820
gacacatcgt agttgtggtc ctgggtgagc tcgtcatagg ccattttaat gaatttgggg    5880
cggagggtac ccgactgggg gacaaaggtg ccctcgatcc cggggggcgta gttcccctcg    5940 cagatctgca tctcccaggc cttgagctcg gaggggggga tcatgtccac ctgcggggcg    6000
atgaaaaaaa cggtttccgg ggcgggggag atgagctgcg ccgaaagcag gttccggagc    6060
agctgggact tgccgcagcc ggtggggccg tagatgaccc cgatgaccgg ctgcaggtgg    6120
tagttgaggg agagacagct gccgtcctcg cggaggaggg gggccacctc gttcatcatc    6180
tcgcgcacat gcatgttctc gcgcacgagt tccgccagga ggcgctcgcc ccccagcgag    6240
aggagctctt gcagcgaggc gaagtttttc agcggcttga gcccgtcggc catgggcatt    6300
ttggagaggg tctgttgcaa gagttccaga cggtcccaga gctcggtgat gtgctctagg    6360
gcatctcgat ccagcagacc tcctcgtttc gcgggttggg gcgactgcgg gagtagggca    6420
ccaggcgatg ggcgtccagc gaggccaggg tccggtcctt ccagggtcgc agggtccgcg    6480
tcagcgtggt ctccgtcacg gtgaaggggt gcgcgccggg ctgggcgctt gcagggtgc    6540 gcttcaggct catccggctg gtcgagaacc gctcccggtc ggcgccctgc gcgtcggcca    6600
ggtagcaatt gagcatgagt tcgtagttga gcgcctcggc gcgtggccc ttggcgcgga    6660 gcttaccttt ggaagtgtgt ccgcagacgg gacagaggag ggacttgagg gcgtagagct    6720
tgggggcgag gaagacggac tcgggggcgt aggcgtccgc gccgcagctg gcgcagacgg    6780
tctcgcactc cacgagccag gtgaggtcgg ggcggtcggt gtcaaaaacg aggtttcctc    6840
cgtgcttttt gatgcgtttc ttacctctgg tctccatgag ctcgtgtccc cgctgggtga    6900
```

```
caaagaggct gtccgtgtcc ccgtagaccg actttatggg ccggtcctcg agcggggtgc    6960
cgcggtcctc gtcgtagagg aaccccgccc actccgagac gaaggcccgg gtccaggcca    7020
gcacgaagga ggccacgtgg gaggggtagc ggtcgttgtc caccagcggg tccaccttct    7080
ccagggtatg caagcacatg tccccctcgt ccacatccag gaaggtgatt ggcttgtaag    7140
tgtaggccac gtgaccgggg gtcccggccg ggggggtata aaggggggcg ggcccctgct    7200
cgtcctcact gtcttccgga tcgctgtcca ggagcgccag ctgttggggt aggtattccc    7260
tctcgaaggc gggcatgacc tcggcactca ggttgtcagt ttctagaaac gaggaggatt    7320
tgatattgac ggtgccgttg gagacgcctt tcatgagccc ctcgtccatc tggtcagaaa    7380
agacgatctt tttgttgtcg agcttggtgg cgaaggagcc gtagagggcg ttggagagca    7440
gcttggcgat ggagcgcatg gtctggttct tttccttgtc ggcgcgctcc ttggcggcga    7500
tgttgagctg cacgtactcg cgcgccacgc acttccattc ggggaagacg gtggtgagct    7560
cgtcgggcac gattctgacc cgccagccgc ggttgtgcag ggtgatgagg tccacgctgg    7620
tggccacctc gccgcgcagg ggctcgttgg tccagcagag gcgcccgccc ttgcgcgagc    7680 agaaggggggg cagcgggtcc agcatgagct cgtcgggggg gtcggcgtcc acggtgaaga    7740
tgccgggcag gagctcgggg tcgaagtagc tgatgcaggt gcccagatcg tccagacttg    7800
cttgccagtc gcgcacggcc agcgcgcgct cgtaggggct gagggcgtg ccccagggca    7860 tggggtgcgt gagcgcggag gcgtacatgc cgcagatgtc gtagacgtag aggggctcct    7920
ggaggacgcc gatgtaggtg gggtagcagc gccccccgcg gatgctggcg cgcacgtagt    7980
cgtacagctc gtgcgagggc gcgaggagcc ccgtgccgag attggagcgc tgcggctttt    8040
cggcgcggta gacgatctgg cggaagatgg cgtgggagtt ggaggagatg gtgggcctct    8100
ggaagatgtt gaagtgggca tggggcagtc cgaccgagtc cctgatgaag tgggcgtagg    8160
agtcctgcag cttggcgacg agctcggcgg tgacgaggac gtccagggcg cagtagtcga    8220
gggtctcttg gatgatgtcg tacttgagct ggcccttctg cttccacagc tcgcggttga    8280
gaaggaactc ttcgcggtcc ttccagtact cttcgagggg gaacccgtcc tgatcggcac    8340
ggtaagagcc caccatgtag aactggttga cggccttgta ggcgcagcag cccttctcca    8400
cggggagggc gtaagcttgc gcggccttgc gcagggaggt gtgggtgagg gcgaaggtgt    8460
cgcgcaccat gactttgagg aactggtgct tgaagtcgag gtcgtcgcag ccgccctgct    8520
cccagagctg gaagtccgtg cgcttcttgt aggcggggtt gggcaaagcg aaagtaacat    8580
cgttgaagag gatcttgccc gcgcggggca tgaagttgcg agtgatgcgg aaaggctggg    8640
gcacctcggc ccggttgttg atgacctggg cggcgaggac gatctcgtcg aagccgttga    8700
tgttgtgccc gacgatgtag agttccacga atcgcgggcg gcccttgacg tggggcagct    8760
tcttgagctc gtcgtaggtg agctcggcgg ggtcgctgag cccgtgctgc tcgagggccc    8820
agtcggcgac gtgggggttg gcgctgagga aggaagtcca gagatccacg ccagggcgg    8880 tctgcaagcg gtcccggtac tgacggaact gctggcccac ggccattttt tcggggtga    8940 cgcagtagaa ggtgcggggg tcgccgtgcc agcggtccca cttgagctgg agggcgaggt    9000
cgtgggcgag ctcgacgagc ggcgggtccc cggagagttt catgaccagc atgaagggga    9060
cgagctgctt gccgaaggac cccatccagg tgtaggtttc cacatcgtag gtgaggaaga    9120
gcctttcggt gcgaggatgc gagccgatgg ggaagaactg gatctcctgc caccagttgg    9180
aggaatggct gttgatgtga tggaagtaga aatgccgacg gcgcgccgag cactcgtgct    9240
tgtgtttata caagcgtccg cagtgctcgc aacgctgcac gggatgcacg tgctgcacga    9300
```

```
gctgtacctg ggttcctttg acgaggaatt tcagtgggca gtggagcgct ggcggctgca    9360
tctggtgctg tactacgtcc tggccatcgg cgtggccatc gtctgcctcg atggtggtca    9420
tgctgacgag cccgcgcggg aggcaggtcc agacctcggc tcggacgggt cggagagcga    9480
ggacgagggc gcgcaggccg gagctgtcca gggtcctgag acgctgcgga gtcaggtcag    9540
tgggcagcgg cggcgcgcgg ttgacttgca ggagcttttc cagggcgcgc gggaggtcca    9600
gatggtactt gatctccacg gcgccgttgg tggcgacgtc cacggcttgc agggtcccgt    9660
gccctgggg cgccaccacc gtgccccgtt tcttcttggg cggcggcggc tccatgctta    9720
gaagcggcgc cgaggacgcg cgccgggcgg caggggcggc tcgggcccg gaggcagggg    9780
cggcaggggc acgtcggcgc gcgcgcgggg caggttctgg tactgcgccc ggagaagact    9840
ggcgtgagcg acgacgcgac ggttgacgtc ctggatctga cgcctctggg tgaaggccac    9900
gggacccgtg agtttgaacc tgaaagagag ttcgacagaa tcaatctcgg tatcgttgac    9960
gcggcctgc cgcaggatct cttgcacgtc gcccgagttg tcctggtagg cgatctcggt   10020
catgaactgc tcgatctcct cctcctgaag gtctccgcgg ccggcgcgct cgacggtggc   10080
cgcgaggtcg ttggagatgc ggcccatgag ctgcagaag gcgttcatgc cggcctcgtt   10140
ccagacgcgg ctgtagacca cggctccgtc ggggtcgcgc gcgcgcatga ccacctgggc   10200
gaggttgagc tcgacgtggc gcgtgaagac cgcgtagttg cagaggcgct ggtagaggta   10260
gttgagcgtg gtggcgatgt gctcggtgac gaagaagtac atgatccagc ggcggagcgg   10320
catctcgctg acgtcgccca gggcttccaa gcgctccatg gcctcgtaga agtccacggc   10380
gaagttgaaa aactgggagt tgcgcgccga gacggtcaac tcctcctcca aagacggat   10440
gagctcggcg atggtggcgc gcacctcgcg ctcgaaggcc ccgggggct cctcttccat   10500
ttcctcctct tcctcctcca ctaacatctc ttctacttcc tcctcaggag gcggcggcgg   10560
gggagggcc ctgcgtcgcc ggcggcgcac gggcagacgg tcgatgaagc gctcgatggt   10620
ctccccgcgc cggcgacgca tggtctcggt gacggcgcgc ccgtcctcgc ggggccgcag   10680
cgtgaagacg ccgccgcgca tctccaggtg gccgccgggg gggtctccgt tgggcaggga   10740
gagggcgctg acgatgcatc ttatcaattg acccgtaggg actccgcgca aggacctgag   10800
cgtctcgaga tccacgggat ccgaaaaccg ctgaacgaag gcttcgagcc agtcgcagtc   10860
gcaaggtagg ctgagcccgg tttccttgttc ttcgggtatt tggtcgggag gcgggcgggc   10920
gatgctgctg gtgatgaagt tgaagtaggc ggtcctgaga cggcggatgg tggcgaggag   10980
caccaggtcc ttgggcccgg cttgctggat gcgcagacgg tcggccatgc cccaggcgtg   11040
gtcctgacac ctggcgaggt ccttgtagta gtcctgcatg agccgctcca cgggcacctc   11100
ctcctcgccc gcgcggccgt gcatgcgcgt gagcccgaac ccgcgctgcg gctggacgag   11160
cgccaggtcg gcgacgacgc gctcggcgag gatggcctgc tggatctggg tgagggtggt   11220
ctggaagtcg tcgaagtcga cgaagcggtg gtaggctccg gtgttgatgg tgtaggagca   11280
gttggccatg acgaccagt tgacggtctg gtggccgggg cgcacgagct cgtggtactt   11340
gaggcgcgag taggcgcgcg tgtcgaagat gtagtcgttg caggtgcgca cgaggtactg   11400
gtatccgacg aggaagtgcg gcggcggctg gcggtagagc ggccatcgct cggtggcggg   11460
ggcgccgggc gcgaggtcct cgagcatgag gcggtggtag ccgtagatgt acctggacat   11520
ccaggtgatg ccggcggcgg tggtggaggc gcgcgggaac tcgcggacgc ggttccagat   11580
gttgcgcagc ggcaggaagt agttcatggt ggccgcggtc tggcccgtga ggcgcgcgca   11640
```

```
gtcgtggatg ctctagacat acgggcaaaa acgaaagcgg tcagcggctc gactccgtgg   11700
cctggaggct aagcgaacgg gttgggctgc gcgtgtaccc cggttcgaat ctcgaatcag   11760
gctggagccg cagctaacgt ggtactggca ctcccgtctc gacccaagcc tgctaacgaa   11820
acctccagga tacggaggcg ggtcgttttt tggccttggt cgctggtcat gaaaaactag   11880
taagcgcgga aagcggccgc ccgcgatggc tcgctgccgt agtctggaga agaatcgcc    11940 agggttgcgt tgcggtgtgc cccggttcga gcctcagcgc tcggcgccgg ccggattccg   12000
cggctaacgt gggcgtggct gccccgtcgt ttccaagacc ccttagccag ccgacttctc   12060
cagttacgga gcgagcccct ctttttttct tgtgttttg ccagatgcat cccgtactgc    12120
ggcagatgcg cccccaccct ccaccacaac cgcccctacc gcagcagcag caacagccgg   12180
cgcttctgcc cccgcccag cagcagcagc cagccactac cgcggcggcc gccgtgagcg    12240
gagccggcgt tcagtatgac ctggccttgg aagagggcga ggggctggcg cggctggggg   12300
cgtcgtcgcc ggagcggcac ccgcgcgtgc agatgaaaag ggacgctcgc gaggcctacg   12360
tgcccaagca gaacctgttc agagacagga gcggcgagga gcccgaggag atgcgcgcct   12420
cccgcttcca cgcggggcgg gagctgcggc gcggcctgga ccgaaagcgg gtgctgaggg   12480
acgaggattt cgaggcggac gagctgacgg ggatcagccc cgcgcgcgcg cacgtggccg   12540
cggccaacct ggtcacggcg tacgagcaga ccgtgaagga ggagagcaac ttccaaaaat   12600
ccttcaacaa ccacgtgcgc acgctgatcg cgcgcgagga ggtgaccctg ggcctgatgc   12660
acctgtggga cctgctggag gccatcgtgc agaaccccac gagcaagccg ctgacggcgc   12720
agctgtttct ggtggtgcag cacagtcggg acaacgagac gttcagggag gcgctgctga   12780
atatcaccga gcccgagggc cgctggctcc tggacctggt gaacattctg cagagcatcg   12840
tggtgcagga gcgcggctg ccgctgtccg agaagctggc ggccatcaac ttctcggtgc    12900
tgagcctggg caagtactac gctaggaaga tctacaagac cccgtacgtg cccatagaca   12960
aggaggtgaa gatcgatggg ttttacatgc gcatgaccct gaaagtgctg accctgagcg   13020
acgatctggg ggtgtaccgc aacgacagga tgcaccgcgc ggtgagcgcc agccgccggc   13080
gcgagctgag cgaccaggag ctgatgcaca gcctgcagcg ggccctgacc ggggccggaa   13140
ccgaggggga gagctacttt gacatgggcg cggacctgcg ctggcagccc agccgccggg   13200
ccttggaagc tgccggcggc gtgcccacg tggaggaggt ggacgatgag gaggaggagg    13260
gcgagtacct ggaagactga tggcgcgacc gtattttgc tagatgcagc aacagccacc    13320
gccgccgcct cctgatcccg cgatgcgggc ggcgctgcag agccagccgt ccggcattaa   13380
ctcctcggac gattggaccc aggccatgca acgcatcatg gcgctgacga cccgcaatcc   13440
cgaagccttt agacagcagc ctcaggccaa ccggctctcg gccatcctgg aggccgtggt   13500
gccctcgcgc tcgaacccca cgcacgagaa ggtgctggcc atcgtgaacg cgctggtgga   13560
gaacaaggcc atccgcggcg acgaggccgg gctggtgtac aacgcgctgc tggagcgcgt   13620
ggcccgctac aacagcacca acgtgcagac gaacctggac cgcatggtga ccgacgtgcg   13680
cgaggcggtg tcgcagcgcg agcggttcca ccgcgagtcg aacctgggct ccatggtggc   13740
gctgaacgcc ttcctgagca cgcagcccgc caacgtgccc cggggccagg aggactacac   13800
caacttcatc agcgcgctgc ggctgatggt ggccgaggtg ccccagagcg aggtgtacca   13860
gtcggggccg gactacttct tccagaccag tcgccagggc ttgcagaccg tgaacctgag   13920
ccaggctttc aagaacttgc agggactgtg gggcgtgcag gccccggtcg gggaccgcgc   13980
gacggtgtcg agcctgctga cgccgaactc gcgcctgctg ctgctgctgg tggcgccctt   14040
```

```
cacggacagc ggcagcgtga gccgcgactc gtacctgggc tacctgctta acctgtaccg  14100
cgaggccatc gggcaggcgc acgtggacga gcagacctac caggagatca cccacgtgag  14160
ccgcgcgctg ggccaggagg acccgggcaa cctggaggcc accctgaact tcctgctgac  14220
caaccggtcg cagaagatcc cgccccagta cgcgctgagc accgaggagg agcgcatcct  14280
gcgctacgtg cagcagagcg tggggctgtt cttgatgcag gaggggggcca cgcccagcgc  14340
cgcgctcgac atgaccgcgc gcaacatgga gcccagcatg tacgcccgca accgccgtt  14400
catcaataag ctgatggact acttgcatcg ggcggccgcc atgaactcgg actactttac  14460
caacgccatc ttgaacccgc actggctccc gccgccgggg ttctacacgg gcagtacga  14520
catgcccgac cccaacgacg ggttcctgtg ggacgacgtg gacagcagcg tgttctcgcc  14580
gcggcccacc accaccaccg tgtggaagaa agagggcggg gaccggcggc cgtcctcggc  14640
gctgtccggt cgcgcgggtg ctgccgcggc ggtgcccgag gctgccagcc ccttcccgag  14700
cctgcccttt tcgctgaaca gcgtgcgcag cagcgagctg ggtcggctga cgcggccgcg  14760
cctgctgggc gaggaggagt acctgaacga ctccttgttg aagcccgagc gcgagaagaa  14820
cttccccaat aacgggatag agagcctggt ggacaagatg agccgctgga agacgtacgc  14880
gcacgagcac agggacgagc cccgagctag cagcgcaggc acccgtagac gccagcggca  14940
cgacaggcag cggggactgg tgtgggacga tgaggattcc gccgacgaca gcagcgtgtt  15000
ggacttgggt gggagtggtg gtggtaaccc gttcgctcac ctgcgccccc gtatcgggcg  15060
cctgatgtaa gaatctgaaa aaataaaaga cggtactcac caaggccatg gcgaccagcg  15120
tgcgttcttc tctgttgttt gtagtagtat gatgaggcgc gtgtacccgg agggtcctcc  15180
tccctcgtac gagagcgtga tgcagcaggc ggtggcggcg gcgatgcagc ccccgctgga  15240
ggcgccttac gtgccccgc ggtacctggc gcctacggag gggcggaaca gcattcgtta  15300
ctcggagctg gcaccccttgt acgataccac ccggttgtac ctggtggaca caagtcggc  15360
ggacatcgcc tcgctgaact accagaacga ccacagcaac ttcctgacca ccgtggtgca  15420
gaacaacgat ttcaccccca cggaggccag cacccagacc atcaactttg acgagcgctc  15480
gcggtggggc ggcagctga aaccatcat gcacaccaac atgcccaacg tgaacgagtt  15540
catgtacagc aacaagttca aggcgcgggt gatggtctcg cgcaagaccc ccaacggggt  15600
cacggtaggg gatgattatg atggtagtca ggacgagctg acctacgagt gggtggagtt  15660
tgagctgccc gagggcaact tctcggtgac catgaccatc gatctgatga caacgccat  15720
catcgacaac tacttggcgg tggggcggca gaacggggtg ctggagagcg acatcggcgt  15780
gaagttcgac acgcgcaact tccggctggg ctgggacccc gtgaccgagc tggtgatgcc  15840
gggcgtgtac accaacgagg ccttccaccc cgacatcgtc ctgctgcccg gctgcggcgt  15900
ggacttcacc gagagccgcc tcagcaacct gctgggcatc cgcaagcggc agcccttcca  15960
ggagggcttc cagatcctgt acgaggacct ggaggggggg aacatccccg cgctcttgga  16020
tgtcgaagcc tatgaagaaa gtaaggaaaa agcagaggct gaggcaacta cagccgtggc  16080
taccgccgcg actgtggcag atgccactgt caccaggggc gatacattcg ccacccaggc  16140
ggaggaagca gccgccctag cggcgaccga tgatagtgaa agtaagatag tcatcaagcc  16200
ggtggagaag gacagcaaga acaggagcta caacgttcta ccggatggaa agaacaccgc  16260
ctaccgcagc tggtacctgg cctacaacta cggcgacccc gagaagggcg tgcgctcctg  16320
gacgctgctc accacctcgg acgtcacctg cggcgtggag caagtctact ggtcgctgcc  16380
```

```
cgacatgatg caagacccgg tcaccttccg ctccacgcga caagttagca actacccggt   16440
ggtgggcgcc gagctcctgc ccgtctactc caagagcttc ttcaacgagc aggccgtcta   16500
ctcgcagcag ctgcgtgcct tcacctcgct cacgcacgtc ttcaaccgct tccccgagaa   16560
ccagatcctc gtccgcccgc ccgcgcccac cattaccacc gtcagtgaaa cgttcctgc    16620 tctcacagat cacgggaccc tgccgctgcg cagcagtatc cggggagtcc agcgcgtgac   16680
cgtcactgac gccagacgcc gcacctgccc ctacgtctac aaggccctgg gcgtagtcgc   16740
gccgcgcgtc ctctcgagcc gcaccttcta aaaaatgtcc attctcatct cgcccagtaa   16800
taacaccggt tgggcctgc gcgcgcccag caagatgtac ggaggcgctc gccaacgctc    16860
cacgcaacac cccgtgcgcg tgcgcgggca cttccgcgct ccctgggcg ccctcaaggg    16920 ccgcgtgcgc tcgcgcacca ccgtcgacga cgtgatcgac caggtggtgg ccgacgcgcg   16980
caactacacg cccgccgccg cgcccgcctc caccgtggac gccgtcatcg acagcgtggt   17040
ggccgacgcg cgccggtacg cccgcgccaa gagccggcgg cggcgcatcg ccggcggca    17100 ccggagcacc cccgccatgc gcgcggcgcg agccttgctg cgcagggcca ggcgcacggg   17160
acgcagggcc atgctcaggg cggccagacg cgcggcctcc ggcagcagca gcgccggcag   17220
gacccgcaga cgcgcggcca cggcggcggc ggcggccatc gccagcatgt cccgcccgcg   17280
gcgcggcaac gtgtactggg tgcgcgacgc cgccaccggt gtgcgcgtgc ccgtgcgcac   17340
ccgcccccct cgcacttgaa gatgctgact tcgcgatgtt gatgtgtccc agcggcgagg   17400
aggatgtcca agcgcaaata caaggaagag atgctccagg tcatcgcgcc tgagatctac   17460
ggccccgcgg cggcggtgaa ggaggaaaga aagccccgca aactgaagcg ggtcaaaaag   17520
gacaaaaagg aggaggaaga tgacggactg gtggagtttg tgcgcgagtt cgccccccgg   17580
cggcgcgtgc agtggcgcgg gcggaaagtg aaaccggtgc tgcggccggg caccacggtg   17640
gtcttcacgc ccggcgagcg ttccggctcc gcctccaagc gctcctacga cgaggtgtac   17700
ggggacgagg acatcctcga gcaggcggtc gagcgtctgg gcgagtttgc ttacggcaag   17760
cgcagccgcc ccgcgccctt gaaagaggag gcggtgtcca tcccgctgga ccacggcaac   17820
cccacgccga gcctgaagcc ggtgaccctg cagcaggtgc tgccgagcgc ggcgccgcgc   17880
cggggcttca gcgcgagggg cggcgaggat ctgtacccga ccatgcagct gatggtgccc   17940
aagcgccaga agctggagga cgtgctggag cacatgaagg tggaccccga ggtgcagccc   18000
gaggtcaagg tgcggcccat caagcaggtg gccccgggcc tgggcgtgca gaccgtggac   18060
atcaagatcc ccacggagcc catggaaacg cagaccgagc ccgtgaagcc cagcaccagc   18120
accatggagg tgcagacgga tccctggatg ccagcggctt ccaccaccac cactcgccga   18180
agacgcaagt acggcgcggc cagcctgctg atgcccaact acgcgctgca tccttccatc   18240
atccccacgc cgggctaccg cggcacgcgc ttctaccgcg gctacaccag cagccgccgc   18300
cgcaagacca ccaccccgcc ccgtcgtcgc agccgccgca gcagccacgc gacttccgcc   18360
ttggtgcgga gagtgtatcg cagcgggcgc gagcctctga ccctgccgcg cgcgcgctac   18420 caccccgagca tcgccattta actaccgcct cctacttgca gatatggccc tcacatgccg   18480
cctccgcgtc cccattacgg gctaccgagg aagaaagccg cgccgtagaa ggctgacggg   18540
gaacgggctg cgtcgccatc accaccggcg gcggcgcgcc atcagcaagc ggttgggggg   18600
aggcttcctg cccgcgctga tccccatcat cgccgcggcg atcggggcga tccccggcat   18660
agcttccgtg gcggtgcagg cctctcagcg ccactgagac acaaaaaagc atggatttgt   18720
aataaaaaaa tggactgacg ctcctggtcc tgtgatgtgt gtttttagat ggaagacatc   18780
```

```
aattttttcgt ccctggcacc gcgacacggc acgcggccgt ttatgggcac ctggagcgac    18840
atcggcaaca gccaactgaa cgggggcgcc ttcaattgga gcagtctctg gagcgggctt    18900
aagaatttcg ggtccacgct caaaacctat ggcaacaagg cgtggaacag cagcacaggg    18960
caggcgctga gggaaaagct gaaagagcag aacttccagc agaaggtggt cgatggcctg    19020
gcctcgggca tcaacggggt ggtggacctg gccaaccagg ccgtgcagaa acagatcaac    19080
agccgcctgg acgcggtccc gcccgcgggg tccgtggaga tgccccaggt ggaggaggag    19140
ctgcctcccc tggacaagcg cggcgacaag cgaccgcgtc ccgacgcgga ggagacgctg    19200
ctgacgcaca cggacgagcc gcccccgtac gaggaggcgg tgaaactggg tctgcccacc    19260
acgcggcccg tggcgcctct ggccaccggg gtgctgaaac ccagcagcag cagccagccc    19320
gcgaccctgg acttgcctcc gcctgcttcc cgccccctcca cagtggctaa gcccctgccg    19380
ccggtggccg tcgcgtcgcg cgcccccga ggccgccccc aggcgaactg cagagcact     19440 ctgaacagca tcgtgggtct gggagtgcag agtgtgaagc gccgccgctg ctattaaaag    19500
acactgtagc gcttaacttg cttgtctgtg tgtgtatatg tatgtccgcc gaccagaagg    19560
aggaagaggc gcgtcgccga gttgcaagat ggccaccca tcgatgctgc cccagtgggc    19620
gtacatgcac atcgccggac aggacgcttc ggagtacctg agtccgggtc tggtgcagtt    19680
cgcccgcgcc acagacacct acttcagtct ggggaacaag tttaggaacc ccacggtggc    19740
gcccacgcac gatgtgacca ccgaccgcag ccagcggctg acgctgcgct tcgtgcccgt    19800
ggaccgcgag gacaacacct actcgtacaa agtgcgctac acgctggccg tgggcgacaa    19860
ccgcgtgctg gacatggcca gcacctactt tgacatccgc ggcgtgctgg atcggggccc    19920
cagcttcaaa ccctactccg gcaccgccta acagccta gctcccaagg gagcgcccaa    19980
cacctcacag tggaaggatt ccgacagcaa aatgcatact tttggagttg ctgccatgcc    20040
cggtgttgtt ggtaaaaaaa tagaagccga tggtctgcct attggaatag attcatcctc    20100
tggaactgac accataattt atgctgataa aactttccaa ccagagccac aggttggaag    20160
tgacagttgg gtcgacacca atggtgcaga ggaaaaatat ggaggtagag ctcttaagga    20220
cactacaaac atgaagccct gctacggttc ttttgccagg cctaccaaca aagaaggtgg    20280
acaggctaac ataaaagatt ctgaaactgc cagcactact cctaactatg atatagattt    20340
ggcattcttt gacagcaaaa atattgcagc taactacgat ccagatattg taatgtacac    20400
agaaaatgtt gagttgcaaa ctccagatac tcatattgtg tttaagccag gaacttcaga    20460
tgaaagttca gaagccaatt tgggccagca ggccatgccc aacagaccca actacatcgg    20520
gttcagagac aactttatcg ggctcatgta ctacaacagc actggcaata tgggtgtact    20580
ggctggtcag gcctcccagc taaatgctgt ggtggacttg caggacagaa acaccgaact    20640
gtcctaccag ctcttgcttg actctctggg tgacagaacc aggtatttca gtatgtggaa    20700
tcaggcggtg gacagctatg accccgatgt gcgcattatt gaaaatcacg gtgtggagga    20760
tgaactcccc aattattgct tccctttgaa tggtgtaggc tttacagata cttaccaggg    20820
tgttaaagtt aagacagata cagccgctac tggtaccaat ggaacgcagt gggacaaaga    20880
tgataccaca gtcagcactg ccaatgagat ccactcaggc aatcctttcg ccatgagat    20940 caacatccag gccaacctgt ggcggaactt cctctacgcg aacgtggcgc tgtacctgcc    21000
cgactcctac aagtacacgc cggccaacat cacgctgccg accaacacca cacacctacga    21060 ttacatgaac ggccgcgtgg tggcgccctc gctggtggac gcctacatca acatcggggc    21120
```

```
gcgctggtcg ctggacccca tggacaacgt caacccct tc aaccaccacc gcaacgcggg   21180
cctgcgctac cgctccatgc tcctgggcaa cgggcgctac gtgcccttcc acatccaggt   21240
gccccaaaag ttttcgcca tcaagagcct cctgctcctg cccgggtcct acacctacga   21300
gtggaacttc cgcaaggacg tcaacatgat cctgcagagc tccctcggca acgacctgcg   21360
cacggacggg gcctccatcg ccttcaccag catcaacctc tacgccacct tcttccccat   21420
ggcgcacaac accgcctcca cgctcgaggc catgctgcgc aacgacacca acgaccagtc   21480
cttcaacgac tacctctcgg cggccaacat gctctacccc atcccggcca acgccaccaa   21540
cgtgcccatc tccatcccct cgcgcaactg ggccgcctc cgcggatggt ccttcacgcg   21600
cctcaagacc cgcgagacgc cctcgctcgg ctccgggttc gaccctact cgtctactc   21660 gggctccatc ccctacctcg acggcacctt ctacctcaac cacaccttca gaaggtctc   21720 catcaccttc gactcctccg tcagctggcc cggcaacgac cgcctcctga cgcccaacga   21780
gttcgaaatc aagcgcaccg tcgacggaga gggatacaac gtggcccagt gcaacatgac   21840
caaggactgg ttcctggtcc agatgctggc ccactacaac atcggctacc agggcttcta   21900
cgtgcccgag ggctacaagg accgcatgta ctccttcttc cgcaacttcc agcccatgag   21960
ccgccaggtc gtggacgagg tcaactacaa ggactaccag gccgtcaccc tggcctacca   22020
gcacaacaac tcgggcttcg tcggctacct cgcgcccacc atgcgccagg gccagcccta   22080
ccccgccaac taccccctacc cgctcatcgg caagagcgcc gtcgcagcg tcacccagaa   22140 aaagttcctc tgcgaccggg tcatgtggcg catcccct tc tccagcaact tcatgtccat   22200
gggcgcgctc accgacctcg gccagaacat gctctacgcc aactccgccc acgcgctaga   22260
catgaatttc gaagtcgacc ccatggatga gtccaccctt ctctatgttg tcttcgaagt   22320
cttcgacgtc gtccgagtgc accagcccca ccgcggcgtc atcgaggccg tctacctgcg   22380
cacgcccttc tcggccggca acgccaccac ctaaagcccc gctcttgctt cttgcaagat   22440
gacggcctgt ggctccggcg agcaggagct cagggccatc ctccgcgacc tgggctgcgg   22500
gccctgcttc ctgggcacct tcgacaagcg cttcccggga ttcatggccc cgcacaagct   22560
ggcctgcgcc atcgtcaaca cggccggccg cgagaccggg ggcgagcact ggctggcctt   22620
cgcctggaac ccgcgctccc acacctgcta cctcttcgac ccctcgggt tctcggacga   22680 gcgcctcaag cagatctacc agttcgagta cgagggcctg ctgcgccgca gcgccctggc   22740
caccgaggac cgctgcatca ccctggaaaa gtccacccag accgtgcagg tccgcgctc   22800 ggccgcctgc gggctcttct gctgcatgtt cctgcacgcc ttcgtgcact ggcccgaccg   22860
ccccatggac aagaaccca ccatgaactt gctgacgggg gtgcccaacg gcatgctcca   22920
gtcgccccag gtggaaccca ccctgcgccg caaccaggag gcgctctacc gcttcctcaa   22980
cgcccactcc gcctactttc gctcccaccg cgcgcgcatc gagaaggcca ccgccttcga   23040
ccgcatgaat caagacatgt aaactgtgtg tatgtgaatg ctttattcat cataataaac   23100
agcacatgtt tatgccacct tctctgaggc tctgacttta tttagaaatc gaagggttc   23160 tgccggctct cggcgtgccc cgcgggcagg gatacgttgc ggaactggta cttgggcagc   23220
cacttgaact cggggatcag cagcttcggc acggggaggt cggggaacga gtcgctccac   23280
agcttgcgcg tgagttgcag ggcgcccagc aggtcgggcg cggagatctt gaaatcgcag   23340
ttgggacccg cgttctgcgc gcgagagttg cggtacacgg ggttgcagca ctggaacacc   23400
atcagggccg ggtgcttcac gctcgccagc accgtcgcgt cggtgatgcc ctccacgtcc   23460
agatcctcgg cgttggccat cccgaagggg gtcatcttgc aggtctgccg ccccatgctg   23520
```

```
ggcacgcagc cgggcttgtg gttgcaatcg cagtgcaggg ggatcagcat catctgagcc   23580
tgctcggagc tcatgcccgg gtacatggcc ttcatgaaag cctccagctg gcggaaggcc   23640
tgctgcgcct tgccgccctc ggtgaagaag accccacagg acttgctaga gaactggttg   23700
gtggcgcagc ccgcgtcgtg cacgcagcag cgcgcgtcgt tgttggccag ctgcaccacg   23760
ctgcgccccc agcggttctg ggtgatcttg gcccggtcgg ggttctcctt cagcgcgcgc   23820
tgcccgttct cgctcgccac atccatctcg atcgtgtgct ccttctggat catcacggtc   23880
ccgtgcaggc accgcagctt gccctcggcc tcggtgcacc cgtgcagcca cagcgcgcag   23940
ccggtgcact cccagttctt gtgggcgatc tgggagtgcg agtgcacgaa gccctgcagg   24000
aagcggccca tcatcgtggt cagggtcttg ttgctggtga aggtcagcgg gatgccgcgg   24060
tgctcctcgt tcacatacag gtggcagatg cggcggtaca cctcgccctg ctcgggcatc   24120
agctggaagg cggacttcag gtcgctctcc acgcggtacc gctccatcag cagcgtcatc   24180
acttccatgc cctctcccca ggccgaaacg atcggcaggc tcaggggatt cttcaccgtc   24240
atcttagtcg ccgccgccga agtcaggggg tcgttctcgt ccagggtctc aaacactcgc   24300
ttgccgtcct tctcggtgat gcgcacgggg ggaaagctga agcccacggc cgccagctcc   24360
tcctcggcct gccttcgtc ctcgctgtcc tggctgatgt cttgcaaagg cacatgcttg   24420
gtcttgcggg gtttcttttt gggcggcaga ggcggcggcg gagacgtgct gggcgagcgc   24480
gagttctcgc tcaccacgac tatttcttct tcttggccgt cgtccgagac cacgcggcgg   24540
taggcatgcc tcttctgggg cagaggcgga ggcgacgggc tctcgcggtt cggcgggcgg   24600
ctggcagagc cccttccgcg ttcggggtg cgctcctggc ggcgctgctc tgactgactt   24660
cctccgcggc cggccattgt gttctcctag ggagcaacaa gcatggagac tcagccatcg   24720
tcgccaacat cgccatctgc ccccgccgcc gacgagaacc agcagcagca gaatgaaagc   24780
ttaaccgccc cgccgcccag ccccacctcc gacgccgccg cggccccaga catgcaagag   24840
atggaggaat ccatcgagat tgacctgggc tacgtgacgc ccgcggagca cgaggaggag   24900
ctggcagcgc gcttttcagc cccggaagag aaccaccaag agcagccaga gcaggaagca   24960
gagagcgagc agcagcaggc tgggctcgag catggcgact acctgagcgg ggcagaggac   25020
gtgctcatca gcatctggcc ccgccaaagc atcatcgtca aggacgcgct gctcgaccgc   25080
gccgaggtgc ccctcagcgt ggcggagctc agccgcgcct acgagcgcaa cctcttctcg   25140
ccgcgcgtgc cccccaagcg ccagcccaac ggcacctgcg agcccaaccc gcgcctcaac   25200
ttctacccgg tcttcgcggt gcccgaggcc ctggccacct accacctctt tttcaagaac   25260
caaaggatcc ccgtctcctg ccgcgccaac cgcacccgcg ccgacgccct gctcaacctg   25320
ggtcccggcg cccgcctacc tgatatcacc tccttggaag aggttcccaa gatcttcgag   25380
ggtctgggca gcgacgagac tcgggccgcg aacgctctgc aaggaagcgg agaggagcat   25440
gagcaccaca cgcgccctgg tggagttggaa ggcgacaacg cgcgcctggc ggtgctcaag   25500
cgcacggtcg agctgaccca cttcgcctac ccggcgctca acctgccccc caaggtcatg   25560
agcgccgtca tggaccaggt gctcatcaag cgcgcctcgc ccctctcaga ggaggagatg   25620
caggaccccg agagctcgga cgagggcaag cccgtggtca cgcgacgagca gctggcgcgc   25680
tggctgggag cgagcagcac ccccagagc ctggaagagc ggcgcaagct catgatggcc   25740
gtggtcctgg tgaccgtgga gctggagtgt ctgcgccgct tcttcgccga cgcggagacc   25800
ctgcgcaagg tcgaggagaa cctgcactac ctcttcaggc acgggttcgt gcgccaggcc   25860
```

```
tgcaagatct ccaacgtgga gctgaccaac ctggtctcct acatgggcat cctgcacgag   25920
aaccgcctgg ggcagaacgt gctgcacacc accctgcgcg gggaggcccg ccgcgactac   25980
atccgcgact gcgtctacct gtacctctgc cacacctggc agacgggcat gggcgtgtgg   26040
cagcagtgcc tggaggagca gaacctgaaa gagctctgca agctcctgca gaagaacctc   26100
aaggccctgt ggaccgggtt cgacgagcgc accaccgcct cggacctggc cgacctcatc   26160
ttccccgagc gcctgcggct gacgctgcgc aacgggctgc ccgactttat gagccaaagc   26220
atgttgcaaa actttcgctc tttcatcctc gaacgctccg ggatcctgcc cgccacctgc   26280
tccgcactgc cctcggactt cgtgccgctg accttccgcg agtgcccccc gccgctctgg   26340
agccactgct acttgctgcg cctggccaac tacctggcct accactcgga cgtgatcgag   26400
gacgtcagca gcgagggtct gctcgagtgc cactgccgct gcaacctctg cacgccgcac   26460
cgctccttgg cctgcaaccc ccagctgctg agcgagaccc agatcatcgg caccttcgag   26520
ttgcaaggcc ccggcgaggg caagggggggt ctcaaactca ccccggggct gtggacctcg   26580
gcctacttgc gcaagttcgt gcccgaggac taccatccct tcgagatcag gttctacgag   26640
gaccaatccc agccgcccaa ggccgagctg tcggcctgcg tcatcaccca ggggggccatc   26700
ctggcccaat tgcaagccat ccagaaatcc cgccaagaat ttctgctgaa aaagggccac   26760
ggggtctact tggacccccca gaccggagag gagctcaacc ccagcttccc ccaggatgcc   26820
ccgaggaagc agcaagaagc tgaaagtgga gctgccgctg ccgccggagg atttggagga   26880
agactgggag agcagtcagg cagaggagat ggaagactgg gacagcactc aggcagagga   26940
ggacagcctg caagacagtc tggaggagga agacgaggtg gaggaggagg cagaggaaga   27000
agcagccgcc gccagaccgt cgtcctcggc ggaggagaaa gcaagcagca cggataccat   27060
ctccgctccg ggtcggggtc gcggcggccg ggcccacagt agatgggacg agaccggggcg   27120
cttcccgaac cccaccaccc agaccggtaa gaaggagcgg cagggataca agtcctggcg   27180
ggggcacaaa aacgccatcg tctcctgctt gcaagcctgc gggggcaaca tctccttcac   27240
ccggcgctac ctgctcttcc accgcggggt gaacttcccc cgcaacatct tgcattacta   27300
ccgtcacctc cacagcccct actactgttt ccaagaagag gcagaaaccc agcagcagca   27360
gcagaaaacc agcggcagca gcagcagcta gaaaatccac agcggcggca ggtggactga   27420
ggatcgcggc gaacgagccg gcgcagaccc gggagctgag gaaccggatc tttcccaccc   27480
tctatgccat cttccagcag agtcgggggc aggagcagga actgaaagtc aagaaccgtt   27540
ctctgcgctc gctcacccgc agttgtctgt atcacaagag cgaagaccaa cttcagcgca   27600
ctctcgagga cgccgaggct ctcttcaaca gtactgcgcg gctcactctt aaagagtagc   27660
ccgcgcccgc ccacacacgg aaaaaggcgg gaattacgtc accacctgcg cccttcgccc   27720
gaccatcatc atgagcaaag agattcccac gccttacatg tggagctacc agccccagat   27780
gggcctggcc gccggcgccg cccaggacta ctccacccgc atgaactggc tcagtgccgg   27840
gccccgcgatg atctcacggg tgaatgacat ccgcgcccac cgaaaccaga tactcctaga   27900
acagtcagcg atcaccgcca cgccccgcca tcaccttaat ccgcgtaatt ggcccgccgc   27960
cctggtgtac caggaaattc cccagcccac gaccgtacta cttccgcgag cgcccaggcc   28020
cgaagtccag ctgactaact caggtgtcca gctggccggc ggcgccgccc tgtgtcgtca   28080
ccgcccccgct cagggtataa agcggctggt gatccgagcc agaggcacac agctcaacga   28140
cgaggtggtg agctcttcgc tgggtctgcg acctgacgga gtcttccaac tcgccggatc   28200
ggggagatct tccttcacgc ctcgtcaggc cgtcctgact ttggagagtt cgtcctcgca   28260
```

```
gccccgctcg ggcggcatcg gcactctcca gttcgtggag gagttcactc cctcggtcta    28320 cttcaaccccc ttctccggct cccccggcca ctacccggac gagttcatcc cgaacttcga   28380
cgccatcagc gagtcggtgg acggctacga ttgaatgtcc catggtggcg cggctgacct    28440
agctcggctt cgacacctgg accactgtta attaatcgcc tctcctacga gctcctgcag    28500
cagcgccaga agttcacctg cctggtcgga gtcaacccca tcgtcatcac ccagcagtcg    28560
ggcgatacca agggtgcat ccactgctcc tgcgactccc ccgactgcgt ccacactctg     28620
atcaagaccc tctgcggcct ccgcgacctc ctccccatga actaatcacc cccttatcca    28680
gtgaaataaa gatcatattg atgatgattt tacagaaata aagatacaat catattgatg    28740
atttgagttt aataaaaaat aaagaatcac ttacttgaaa tctgatacca ggtctctgtc    28800
catgttttct gccaacacca cttcactccc ctcttcccag ctctggtact gcaggccccg    28860
gcgggctgca aacttcctcc acacgctgaa ggggatgtca aattcctcct gtccctcaat    28920
cttcatttta tcttctatca gatgtccaaa aagcgcgtcc gggtggatga tgacttcgac    28980
cccgtctacc cctacgatgc agacaacgca ccgaccgtgc ccttcatcaa ccccccccttc   29040 gtctcttcag atggattcca agagaagccc ctggggggtgc tgtccctgcg actggccgac   29100
cccgtcacca ccaagaacgg ggaaatcacc ctcaagctgg gagaggggggt ggacctcgac  29160 tcctcgggaa aactcatctc caacacggcc accaaggccg ccgcccctct cagttttttcc  29220 aacaacacca tttcccttaa catggatcac ccctttttaca ctaaagatgg aaaattatcc   29280
ttacaagttt ctccaccatt aaatatactg agaacaagca ttctaaacac actagcttta    29340
ggttttggat caggtttagg actccgtggc tctgccttgg cagtacagtt agtctctcca    29400
cttacatttg atactgatgg aaacataaag cttaccttag acagaggttt gcatgttaca    29460
acaggagatg caattgaaag caacataagc tgggctaaag gtttaaaatt tgaagatgga    29520
gccatagcaa ccaacattgg aaatgggtta gagtttggaa gcagtagtac agaaacaggt    29580
gttgatgatg cttacccaat ccaagttaaa cttggatctg gccttagctt tgacagtaca    29640
ggagccataa tggctggtaa caaagaagac gataaactca ctttgtggac aacacctgat    29700
ccatcgccaa actgtcaaat actcgcagaa aatgatgcaa aactaacact ttgcttgact    29760
aaatgtggta gtcaaatact ggccactgtg tcagtcttag ttgtaggaag tggaaaccta    29820 aacccccatta ctggcaccgt aagcagtgct caggtgtttc tacgttttga tgcaaacggt    29880
gttcttttaa cagaacattc tacactaaaa aaatactggg ggtataggca gggagatagc    29940
atagatggca ctccatatac caatgctgta ggattcatgc ccaattttaaa agcttatcca   30000 aagtcacaaa gttctactac taaaaataat atagtagggc aagtatacat gaatggagat    30060
gtttcaaaac ctatgcttct cactataacc ctcaatggta ctgatgacag caacagtaca    30120
tattcaatgt cattttcata cacctggact aatggaagct atgttggagc aacatttggg    30180
gctaactctt ataccttctc atacatcgcc caagaatgaa cactgtatcc caccctgcat    30240
gccaaccctt cccaccccac tctgtggaaa aaactctgaa acacaaaata aaataaagtt    30300 caagtgttttt attgattcaa cagttttaca ggattcgagc agttatttttt cctccaccct   30360 cccaggacat ggaatacacc acccctctccc cccgcacagc cttgaacatc tgaatgccat    30420
tggtgatgga catgcttttg gtctccacgt tccacacagt ttcagagcga gccagtctcg    30480
ggtcggtcag ggagatgaaa ccctccgggc acaattggga gaagtactcg cctacatggg    30540
ggtagagtca taatcgtgca tcaggatagg gcggtggtgc tgcagcagcg cgcgaataaa    30600
```

```
ctgctgccgc cgccgctccg tcctgcagga atacaacatg gcagtggtct cctcagcgat    30660
gattcgcacc gcccgcagca taaggcgcct tgtcctccgg gcacagcagc gcaccctgat    30720
ctcacttaaa tcagcacagt aactgcagca cagcaccaca atattgttca aaatcccaca    30780
gtgcaaggcg ctgtatccaa agctcatggc ggggaccaca gaacccacgt ggccatcata    30840
ccacaagcgc aggtagatta agtggcgacc cctcataaac acgctggaca taaacattac    30900
ctcttttggc atgttgtaat tcaccacctc ccggtaccat ataaacctct gattaaacat    30960
ggcgccatcc accaccatcc taaaccagct ggccaaaacc tgcccgccgg ctatacactg    31020
cagggaaccg ggactggaac aatgacagtg gagagcccag gactcgtaac catggatcat    31080
catgctcgtc atgatatcaa tgttggcaca acacaggcac acgtgcatac acttcctcag    31140
gattacaagc tcctcccgcg ttagaaccat atcccaggga acaacccatt cctgaatcag    31200
cgtaaatccc acactgcagg gaagacctcg cacgtaactc acgttgtgca ttgtcaaagt    31260
gttacattcg ggcagcagcg gatgatcctc cagtatggta gcgcgggttt ctgtctcaaa    31320
aggaggtaga cgatccctac tgtacggagt gcgccgagac aaccgagatc gtgttggtcg    31380
tagtgtcatg ccaaatggaa cgccggacgt agtcatattt cctgaagtct ggcgcgcca    31440 aagtctagaa gcggtccata gcttaccgag cggcagcagc agcggcacac aacaggcgca    31500
agagtcagag aaaagactga gctctaacct gtccgcccgc tctctgctca atatatagcc    31560
cagatctaca ctgacgtaaa ggccaaagtc taaaaatacc cgccaaatag tcacacacg     31620 ccagcacacg cccagaaacc ggtgacacac tcaaaaaaat acgcgcactt cctcaaacgc    31680
ccaaactgcc gtcatttccg ggttcccacg ctacgtcatc aaaacacgac tttcaaattc    31740
cgtcgaccgt taaaaacgtc acccgccccg ccctaacgg tcgcccgtct ctcagccaat     31800
cagcgccccg catccccaaa ttcaaacacc tcatttgcat attaacgcgc accaaaagtt    31860
tgaggtatat tattgatgat g                                              31881

<210> SEQ ID NO 5
<211> LENGTH: 31110
<212> TYPE: DNA
<213> ORGANISM: Artificial Sequence
<220> FEATURE:
<223> OTHER INFORMATION: synthetic chimpanzee adenovirus serotype ChAd63
      with Ebola virus Sudan/Gulu codon optimized
      transmembrane envelope glycoprotein (GP) insert
      (ChAd63 GP Ebola S/G (PB/6611))
<220> FEATURE:
<221> NAME/KEY: CDS
<222> LOCATION: (1630)...(3660)
<223> OTHER INFORMATION: Ebola virus Sudan/Gulu codon optimized
      transmembrane envelope glycoprotein (GP) insert in ChAd63 GP Ebola
      S/G (PB/6611)
<220> FEATURE:
<221> NAME/KEY: CDS
<222> LOCATION: (14372)...(16000)
<223> OTHER INFORMATION: chimpanzee adenovirus serotype ChAd63 penton
<220> FEATURE:
<221> NAME/KEY: CDS
<222> LOCATION: (18767)...(21643)
<223> OTHER INFORMATION: chimpanzee adenovirus serotype ChAd63 hexon
<220> FEATURE:
<221> NAME/KEY: CDS
<222> LOCATION: (28171)...(29448)
<223> OTHER INFORMATION: chimpanzee adenovirus serotype ChAd63 fiber

<400> SEQUENCE: 5
catcatcaat aatataccte aaacttttgg tgcgcgttaa tatgcaaatg aggtgtttga     60
atttggggat gcggggcgct gattggctga gagacgggcg accgttaggg gcggggcggg    120
```

```
tgacgttttg atgacgtggc cgtgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaattccg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacggatat ctccattgca tacgttgtat    480
ccatatcata atatgtacat ttatattggc tcatgtccaa cattaccgcc atgttgacat    540
tgattattga ctagttatta atagtaatca attacggggt cattagttca tagcccatat    600
atggagttcc gcgttacata acttacggta atggcccgc ctggctgacc gcccaacgac     660
ccccgcccat tgacgtcaat aatgacgtat gttcccatag taacgccaat agggactttc    720
cattgacgtc aatgggtgga gtatttacgg taaactgccc acttggcagt acatcaagtg    780
tatcatatgc caagtacgcc ccctattgac gtcaatgacg gtaaatggcc cgcctggcat    840
tatgcccagt acatgacctt atgggacttt cctacttggc agtacatcta cgtattagtc    900
atcgctatta ccatggtgat gcggttttgg cagtacatca atgggcgtgg atagcggttt    960
gactcacggg gatttccaag tctccacccc attgacgtca atgggagttt gttttggaac    1020
caaaatcaac gggactttcc aaaatgtcgt aacaactccg ccccattgac gcaaatgggc    1080
ggtaggcgtg tacggtggga ggtctatata agcagagctc tccctatcag tgatagagat    1140
ctccctatca gtgatagaga tcgtcgacga gctcgtttag tgaaccgtca gatcgcctgg    1200
agacgccatc cacgctgttt tgacctccat agaagacacc gggaccgatc cagcctccat    1260
cggctcgcat ctctccttca cgcgcccgcc gccctacctg aggccgccat ccacgccggt    1320
tgagtcgcgt tctgccgcct cccgcctgtg gtgcctcctg aactgcgtcc gccgtctagg    1380
taagtttaaa gctcaggtcg agaccgggcc tttgtccggc gctcccttgg agcctaccta    1440
gactcagccg gctctccacg ctttgcctga ccctgcttgc tcaactctag ttaacggtgg    1500
agggcagtgt agtctgagca gtactcgttg ctgccgcgcg cgccaccaga cataatagct    1560
gacagactaa cagactgttc cttttccatgg gtcttttctg cagtcaccgt cgtcgacgat    1620
atcgccgcca tggagggcct gagcctgctg cagctgccca gggacaagtt caggaagagc    1680
agcttcttcg tgtgggtgat catcctgttc cagaaggcct tcagcatgcc cctgggcgtg    1740
gtgaccaaca gcaccctgga ggtgaccgag atcgaccagc tggtgtgcaa ggaccacctg    1800
gccagcaccg accagctgaa gagcgtgggc ctgaacctgg agggcagcgg cgtgagcacc    1860
gacatcccca gcgccaccaa gaggtggggc ttcaggagcg gcgtgcctcc caaggtggtg    1920
agctacgagg ccggcgagtg ggccgagaac tgctacaacc tggagatcaa gaagcccgac    1980
ggcagcgagt gcctgcctcc tcctcctgac ggcgtgaggg gcttcccag gtgcaggtac     2040 gtgcacaagg cccagggcac cggccctgc cccggcgact acgccttcca aaggacggc      2100 gccttcttcc tgtacgacag gctggccagc accgtgatct acagggggcgt gaacttcgcc    2160 gagggcgtga tcgccttcct gatcctggcc aagcccaagg agaccttcct gcagagccct    2220
cccatcagga ggccgtgaa ctacaccgag aacaccagca gctactacgc caccagctat     2280
ctagagtacg agatcgagaa cttcggcgcc cagcacagca ccaccctgtt caagatcgac    2340
aacaacacct tcgtgaggct ggacaggccc acaccctc agttcctgtt ccagctgaac      2400
gacaccatcc acctgcacca gcagctgagc aacaccaccg gcaggctgat ctggaccctg    2460
gacgccaaca tcaacgccga catcggcgag tgggcttct gggagaacaa gaagaacctg    2520
```

```
agcgagcagc tgaggggcga ggagctgagc ttcgaggccc tgagcctgaa cgagaccgag    2580
gacgacgacg ccgccagcag caggatcacc aagggcagga tcagcgacag ggccaccagg    2640
aagtacagcg acctggtgcc caagaacagc cccggcatgg tgcccctgca catccccgag    2700
ggcgagacca ccctgcccag ccagaacagc accgagggca ggagggtggg cgtgaacacc    2760
caggagacca tcaccgagac cgccgccacc atcatcggca ccaacggcaa ccacatgcag    2820
atcagcacca tcggcatcag gcccagcagc agccagatcc ccagcagcag ccccaccacc    2880
gcccctagcc ccgaggccca gaccccccacc acccacacca gcggacccag cgtgatggcc    2940
accgaggagc ccaccacccc tcccggcagc agccccggac ccaccaccga ggcccctacc    3000
ctgaccaccc ctgagaacat caccaccgcc gtgaagaccg tgctgcccca ggagagcacc    3060
agcaacggcc tgatcaccag caccgtgacc ggcatcctgg gcagcctggg cctgaggaag    3120
aggagcagga ggcagaccaa caccaaggcc accggcaagt gcaaccccaa cctgcactac    3180
tggaccgccc aggagcagca caacgccgcc ggcatcgcct ggattcccta cttcggcccc    3240
ggcgccgagg gcatctacac cgagggcctg atgcacaacc agaacgccct ggtgtgcggc    3300
ctgaggcagc tggccaacga gaccacccag gccctgcagc tgttcctgag gccaccacc    3360 gagctgagga cctacaccat cctgaacagg aaggccatcg acttcctgct gaggaggtgg    3420
ggcggcacct gcaggattct gggccccgac tgctgcatcg agcccacgga ctggaccaag    3480
aacatcaccg acaagatcaa ccagatcatc cacgacttca tcgacaaccc tctgcccaac    3540
caggacaacg acgacaactg gtggaccggc tggcggcagt ggatacctgc cggcatcggc    3600
atcaccggca tcatcatcgc catcatcgct ctgctgtgcg tgtgcaagct gctgtgctga    3660
gaattcagat ctgctgtgcc ttctagttgc cagccatctg ttgtttgccc ctccccgtg    3720 ccttccttga ccctggaagg tgccactccc actgtccttt cctaataaaa tgaggaaatt    3780
gcatcgcatt gtctgagtag gtgtcattct attctggggg gtggggtggg caggacagc    3840 aagggggagg attgggaaga caatagcagg catgctgggg atgcggtggg ctctagatat    3900
cagcgatcgc gtgagtagtg tttggggtg ggtgggagcc tgcatgatgg gcagaatgac    3960
taaaatctgt gttttctgt gtgttgcagc agcatgagcg gaagcgcctc ctttgaggga    4020
ggggtattca gcccttatct gacggggcgt ctcccctcct gggcgggagt gcgtcagaat    4080
gtgatgggat ccacggtgga cggccggccc gtgcagcccg cgaactcttc aaccctgacc    4140
tacgcgaccc tgagctcctc gtccgtggac gcagctgccg ccgcagctgc tgcttccgcc    4200
gccagcgccg tgcgcggaat ggccctgggc gccggctact acagctctct ggtggccaac    4260
tcgagttcca ccaataatcc cgccagcctg aacgaggaga agctgttgct gctgatggcc    4320
cagctcgagg ccctgaccca gcgcctgggc gagctgaccc agcaggtggc tcagctgcag    4380
gcggagacgc gggccgcggt tgccacggtg aaaaccaaat aaaaatgaa tcaataaata    4440 aacggagacg gttgttgatt ttaacacaga gtcttgaatc tttatttgat ttttcgcgcg    4500
cggtaggccc tggaccaccg gtctcgatca ttgagcaccc ggtggatctt ttccaggacc    4560
cggtagaggt gggcttggat gttgaggtac atgggcatga gccgtcccg ggggtggagg    4620 tagctccatt gcagggcctc gtgctcgggg gtggtgttgt aaatcaccca gtcatagcag    4680
gggcgcaggg cgtggtgctg cacgatgtct tgaggagga gactgatggc cacgggcagc    4740
cccttggtgt aggtgttgac gaacctattg agctgggagg gatgcatgcg ggggagatg    4800 agatgcatct tggcctggat cttgagattg gcgatgttcc cgcccagatc ccgccggggg    4860
```

```
ttcatgttgt gcaggaccac cagcacggtg tatccggtgc acttggggaa tttgtcatgc    4920
aacttggaag ggaaggcgtg aaagaatttg gagacgccct tgtgaccgcc caggttttcc    4980
atgcactcat ccatgatgat ggcgatgggc ccgtgggcgg cggcctgggc aaagacgttt    5040
cgggggtcgg acacatcgta gttgtggtcc tgggtgagct cgtcataggc cattttaatg    5100
aatttggggc ggagggtacc cgactggggg acaaaggtgc cctcgatccc ggggcgtag     5160 ttcccctcgc agatctgcat ctcccaggcc ttgagctcgg agggggggat catgtccacc    5220
tgcggggcga tgaaaaaaac ggtttccggg gcggggagga tgagctgcgc cgaaagcagg    5280
ttccggagca gctgggactt gccgcagccg gtggggccgt agatgacccc gatgaccggc    5340
tgcaggtggt agttgaggga gagacagctg ccgtcctcgc ggaggagggg ggccacctcg    5400
ttcatcatct cgcgcacatg catgttctcg cgcacgagtt ccgccaggag gcgctcgccc    5460
cccagcgaga ggagctcttg cagcgaggcg aagtttttca gcggcttgag cccgtcggcc    5520
atgggcattt tggagagggt ctgttgcaag agttccagac ggtcccagag ctcggtgatg    5580
tgctctaggg catctcgatc cagcagacct cctcgtttcg cggttggggg cgactgcggg    5640
agtagggcac caggcgatgg gcgtccagcg aggccagggt ccggtccttc cagggtcgca    5700
gggtccgcgt cagcgtggtc tccgtcacgg tgaaggggtg cgcgccgggc tgggcgcttg    5760
cgagggtgcg cttcaggctc atccggctgg tcgagaaccg ctcccggtcg gcgccctgcg    5820
cgtcggccag gtagcaattg agcatgagtt cgtagttgag cgcctcggcc gcgtggccct    5880
tggcgcggag cttaccttg gaagtgtgtc cgcagacggg acagaggagg gacttgaggg     5940
cgtagagctt gggggcgagg aagacggact cggggggcgta ggcgtccgcg ccgcagctgg    6000
cgcagacggt ctcgcactcc acgagccagg tgaggtcggg gcggtcgggg tcaaaaacga    6060
ggtttcctcc gtgcttttg atgcgtttct tacctctggt ctccatgagc tcgtgtcccc     6120
gctgggtgac aaagaggctg tccgtgtccc cgtagaccga ctttatgggc cggtcctcga    6180
gcggggtgcc gcggtcctcg tcgtagagga accccgccca ctccgagacg aaggcccggg    6240
tccaggccag cacgaaggag gccacgtggg aggggtagcg gtcgttgtcc accagcgggt    6300
ccaccttctc cagggtatgc aagcacatgt ccccctcgtc cacatccagg aaggtgattg    6360
gcttgtaagt gtaggccacg tgaccggggg tcccggccgg gggggtataa aaggggggcgg    6420 gcccctgctc gtcctcactg tcttccggat cgctgtccag gagcgccagc tgttggggta    6480
ggtattccct ctcgaaggcg ggcatgacct cggcactcag gttgtcagtt tctagaaacg    6540
aggaggattt gatattgacg gtgccgttgg agacgccttt catgagcccc tcgtccatct    6600
ggtcagaaaa gacgatcttt tgttgtcga gcttggtggc gaaggagccg tagagggcgt      6660
tggagagcag cttggcgatg gagcgcatgg tctggttctt ttccttgtcg gcgcgctcct    6720
tggcggcgat gttgagctgc acgtactcgc gcgccacgca cttccattcg gggaagacgg    6780
tggtgagctc gtcgggcacg attctgaccc gccagccgcg gttgtgcagg gtgatgaggt    6840
ccacgctggt ggccacctcg ccgcgcaggg gctcgttggt ccagcagagg cgcccgccct    6900
tgcgcgagca aaggggggc agcgggtcca gcatgagctc gtcgggggg tcggcgtcca      6960 cggtgaagat gccgggcagg agctcggggt cgaagtagct gatgcaggtg cccagatcgt    7020
ccagacttgc ttgccagtcg cgcacggcca gcgcgcgctc gtagggggctg aggggcgtgc    7080 cccagggcat ggggtgcgtg agcgcggagg cgtacatgcc gcagatgtcg tagacgtaga    7140
ggggctcctg gaggacgccg atgtaggtgg ggtagcagcg ccccccgcgg atgctggcgc    7200
gcacgtagtc gtacagctcg tgcgagggcg cgaggagccc cgtgccgaga ttggagcgct    7260
```

```
gcggctttc     ggcgcggtag     acgatctggc     ggaagatggc     gtgggagttg     gaggagatgg       7320
tgggcctctg    gaagatgttg     aagtgggcat     ggggcagtcc     gaccgagtcc     ctgatgaagt       7380
gggcgtagga    gtcctgcagc     ttggcgacga     gctcggcggt     gacgaggacg     tccagggcgc       7440
agtagtcgag    ggtctcttgg     atgatgtcgt     acttgagctg     gcccttctgc     ttccacagct       7500
cgcggttgag    aaggaactct     tcgcggtcct     tccagtactc     ttcgagggg      aacccgtcct       7560 gatcggcacg    gtaagagccc     accatgtaga     actggttgac     ggccttgtag     gcgcagcagc       7620
ccttctccac    ggggagggcg     taagcttgcg     cggccttgcg     cagggaggtg     tgggtgaggg       7680
cgaaggtgtc    gcgcaccatg     actttgagga     actggtgctt     gaagtcgagg     tcgtcgcagc       7740
cgccctgctc    ccagagctgg     aagtccgtgc     gcttcttgta     ggcggggttg     ggcaaagcga       7800
aagtaacatc    gttgaagagg     atcttgcccg     cgcggggcat     gaagttgcga     gtgatgcgga       7860
aaggctgggg    cacctcggcc     cggttgttga     tgacctgggc     ggcgaggacg     atctcgtcga       7920
agccgttgat    gttgtgcccg     acgatgtaga     gttccacgaa     tcgcgggcgg     cccttgacgt       7980
ggggcagctt    cttgagctcg     tcgtaggtga     gctcggcggg     gtcgctgagc     ccgtgctgct       8040
cgagggccca    gtcggcgacg     tgggggttgg     cgctgaggaa     ggaagtccag     agatccacgg       8100
ccagggcggt    ctgcaagcgg     tcccggtact     gacggaactg     ctggcccacg     gccatttttt       8160 cggggggtgac   gcagtagaag     gtgcgggggt     cgccgtgcca     gcggtcccac     ttgagctgga       8220
gggcgaggtc    gtgggcgagc     tcgacgagcg     gcgggtcccc     ggagagtttc     atgaccagca       8280
tgaaggggac    gagctgcttg     ccgaaggacc     ccatccaggt     gtaggtttcc     acatcgtagg       8340
tgaggaagag    cctttcggtg     cgaggatgcg     agccgatggg     gaagaactgg     atctcctgcc       8400
accagttgga    ggaatggctg     ttgatgtgat     ggaagtagaa     atgccgacgg     cgcgccgagc       8460
actcgtgctt    gtgtttatac     aagcgtccgc     agtgctcgca     acgctgcacg     ggatgcacgt       8520
gctgcacgag    ctgtacctgg     gttcctttga     cgaggaattt     cagtgggcag     tggagcgctg       8580
gcggctgcat    ctggtgctgt     actacgtcct     ggccatcggc     gtggccatcg     tctgcctcga       8640
tggtggtcat    gctgacgagc     ccgcgcggga     ggcaggtcca     gacctcggct     cggacgggtc       8700
ggagagcgag    gacgagggcg     cgcaggccgg     agctgtccag     ggtcctgaga     cgctgcggag       8760
tcaggtcagt    gggcagcggc     ggcgcgcggt     tgacttgcag     gagcttttcc     agggcgcgcg       8820
ggaggtccag    atggtacttg     atctccacgg     cgccgttggt     ggcgacgtcc     acggcttgca       8880
gggtcccgtg    cccctggggc     gccaccaccg     tgccccgttt     cttcttgggc     ggcggcggct       8940
ccatgcttag    aagcggcggc     gaggacgcgc     gccgggcgc     aggggcggct     cggggcccgg       9000
aggcaggggc    ggcaggggca     cgtcggcgcc     gcgcgcgggc     aggttctggt     actgcgcccg       9060
gagaagactg    gcgtgagcga     cgacgcgacg     gttgacgtcc     tggatctgac     gcctctgggt       9120
gaaggccacg    ggacccgtga     gtttgaacct     gaaagagagt     tcgacagaat     caatctcggt       9180
atcgttgacg    gcgccctgcc     gcaggatctc     ttgcacgtcg     cccagttgt      cctggtaggc       9240 gatctcggtc    atgaactgct     cgatctcctc     ctcctgaagg     tctccgcggc     cggcgcgctc       9300
gacggtggcc    gcgaggtcgt     tggagatgcg     gcccatgagc     tgcagaagg      cgttcatgcc       9360 ggcctcgttc    cagacgcggc     tgtagaccac     ggctccgtcg     gggtcgcgcg     cgcgcatgac       9420
cacctgggcg    aggttgagct     cgacgtggcg     cgtgaagacc     gcgtagttgc     agaggcgctg       9480
gtagaggtag    ttgagcgtgg     tggcgatgtg     ctcggtgacg     aagaagtaca     tgatccagcg       9540
gcggagcggc    atctcgctga     cgtcgcccag     ggcttccaag     cgctccatgg     cctcgtagaa       9600
```

-continued

| | |
|---|---|
| gtccacggcg aagttgaaaa actgggagtt gcgcgccgag acggtcaact cctcctccag | 9660 |
| aagacggatg agctcggcga tggtggcgcg cacctcgcgc tcgaaggccc cgggggggctc | 9720 |
| ctcttccatt tcctcctctt cctcctccac taacatctct tctacttcct cctcaggagg | 9780 |
| cggcggcggg ggaggggccc tgcgtcgccg gcggcgcacg ggcagacggt cgatgaagcg | 9840 |
| ctcgatggtc tccccgcgcc ggcgacgcat ggtctcggtg acggcgcgcc cgtcctcgcg | 9900 |
| gggccgcagc gtgaagacgc cgccgcgcat ctccaggtgg ccgccggggg ggtctccgtt | 9960 |
| gggcagggag agggcgctga cgatgcatct tatcaattga cccgtaggga ctccgcgcaa | 10020 |
| ggacctgagc gtctcgagat ccacgggatc cgaaaaccgc tgaacgaagg cttcgagcca | 10080 |
| gtcgcagtcg caaggtaggc tgagcccggt ttcttgttct tcgggtattt ggtcgggagg | 10140 |
| cgggcgggcg atgctgctgg tgatgaagtt gaagtaggcg gtcctgagac ggcggatggt | 10200 |
| ggcgaggagc accaggtcct tgggcccggc ttgctggatg cgcagacggt cggccatgcc | 10260 |
| ccaggcgtgg tcctgacacc tggcgaggtc cttgtagtag tcctgcatga gccgctccac | 10320 |
| gggcacctcc tcctcgcccg cgcggccgtg catgcgcgtg agcccgaacc cgcgctgcgg | 10380 |
| ctggacgagc gccaggtcgg cgacgacgcg ctcggcgagg atggcctgct ggatctgggt | 10440 |
| gagggtggtc tggaagtcgt cgaagtcgac gaagcggtgg taggctccgg tgttgatggt | 10500 |
| gtaggagcag ttggccatga cggaccagtt gacggtctgg tggccggggc gcacgagctc | 10560 |
| gtggtacttg aggcgcgagt aggcgcgcgt gtcgaagatg tagtcgttgc aggtgcgcac | 10620 |
| gaggtactgg tatccgacga ggaagtgcgg cggcggctgg cggtagagcg gccatcgctc | 10680 |
| ggtggcgggg gcgccgggcg cgaggtcctc gagcatgagg cggtggtagc cgtagatgta | 10740 |
| cctggacatc caggtgatgc cggcggcggt ggtggaggcg cgcgggaact cgcggacgcg | 10800 |
| gttccagatg ttgcgcagcg gcaggaagta gttcatggtg gccgcggtct ggcccgtgag | 10860 |
| gcgcgcgcag tcgtggatgc tctagacata cgggcaaaaa cgaaagcggt cagcggctcg | 10920 |
| actccgtggc ctggaggcta agcgaacggg ttgggctgcg cgtgtacccc ggttcgaatc | 10980 |
| tcgaatcagg ctggagccgc agctaacgtg gtactggcac tcccgtctcg acccaagcct | 11040 |
| gctaacgaaa cctccaggat acggaggcgg gtcgtttttt ggccttggtc gctggtcatg | 11100 |
| aaaaactagt aagcgcggaa agcggccgcc cgcgatggct cgctgccgta gtctggagaa | 11160 |
| agaatcgcca gggttgcgtt gcggtgtgcc ccggttcgag cctcagcgct cggcgccggc | 11220 |
| cggattccgc ggctaacgtg ggcgtggctg ccccgtcgtt tccaagaccc cttagccagc | 11280 |
| cgacttctcc agttacggag cgagcccctc ttttttttctt gtgttttttgc cagatgcatc | 11340 |
| ccgtactgcg gcagatgcgc ccccacccctc caccacaacc gcccctaccg cagcagcagc | 11400 |
| aacagccggc gcttctgccc ccgccccagc agcagcagcc agccactacc gcggcggccg | 11460 |
| ccgtgagcgg agccggcgtt cagtatgacc tggccttgga gagggcgag gggctggcgc | 11520 |
| ggctgggggc gtcgtcgccg gagcggcacc cgcgcgtgca gatgaaaagg gacgctcgcg | 11580 |
| aggcctacgt gcccaagcag aacctgttca gagacaggag cggcgaggag cccgaggaga | 11640 |
| tgcgcgcctc ccgcttccac gcggggcggg agctgcggcg cggcctggac cgaaagcggg | 11700 |
| tgctgaggga cgaggatttc gaggcggacg agctgacggg gatcagcccc gcgcgcgcgc | 11760 |
| acgtggccgc ggccaacctg gtcacggcgt acagcagac cgtgaaggag gagagcaact | 11820 |
| tccaaaaatc cttcaacaac cacgtgcgca cgctgatcgc gcgcgaggag gtgaccctgg | 11880 |
| gcctgatgca cctgtgggac ctgctggagg ccatcgtgca gaaccccacg agcaagccgc | 11940 |
| tgacggcgca gctgtttctg gtggtgcagc acagtcggga caacgagacg ttcagggagg | 12000 |

```
cgctgctgaa tatcaccgag cccgagggcc gctggctcct ggacctggtg aacattctgc   12060
agagcatcgt ggtgcaggag cgcgggctgc cgctgtccga gaagctggcg gccatcaact   12120
tctcggtgct gagcctgggc aagtactacg ctaggaagat ctacaagacc ccgtacgtgc   12180
ccatagacaa ggaggtgaag atcgatgggt tttacatgcg catgaccctg aaagtgctga   12240
ccctgagcga cgatctgggg gtgtaccgca acgacaggat gcaccgcgcg gtgagcgcca   12300
gccgccggcg cgagctgagc gaccaggagc tgatgcacag cctgcagcgg gccctgaccg   12360
gggccgggac cgaggcggag agctactttg acatgggcgc ggacctgcgc tggcagccca   12420
gccgccggcc cttggaagct gccggcggcg tgccctacgt ggaggaggtg gacgatgagg   12480
aggaggaggg cgagtacctg aagactgat ggcgcgaccg tattttttgct agatgcagca   12540 acagccaccg ccgccgcctc ctgatcccgc gatgcgggcg gcgctgcaga gccagccgtc   12600
cggcattaac tcctcggacg attggaccca ggccatgcaa cgcatcatgg cgctgacgac   12660
ccgcaatccc gaagcctttta gacagcagcc tcaggccaac cggctctcgg ccatcctgga   12720
ggccgtggtg ccctcgcgct cgaaccccac gcacgagaag gtgctggcca tcgtgaacgc   12780
gctggtggag aacaaggcca tccgcggcga cgaggccggg ctggtgtaca acgcgctgct   12840
ggagcgcgtg gcccgctaca acagcaccaa cgtgcagacg aacctggacc gcatggtgac   12900
cgacgtgcgc gaggcggtgt cgcagcgcga gcggttccac cgcgagtcga acctgggctc   12960
catggtggcg ctgaacgcct tcctgagcac gcagcccgcc aacgtgcccc ggggccagga   13020
ggactacacc aacttcatca gcgcgctgcg gctgatggtg gccgaggtgc cccagagcga   13080
ggtgtaccag tcggggccgg actacttctt ccagaccagt cgccagggct tgcagaccgt   13140
gaacctgagc caggctttca agaacttgca gggactgtgg ggcgtgcagg ccccggtcgg   13200
ggaccgcgcg acggtgtcga gcctgctgac gccgaactcg cgcctgctgc tgctgctggt   13260 ggcgccctte acggacagcg gcagcgtgag ccgcgactcg tacctgggct acctgcttaa   13320
cctgtaccgc gaggccatcg ggcaggcgca cgtggacgag cagacctacc aggagatcac   13380
ccacgtgagc cgcgcgctgg gccaggagga cccgggcaac ctggaggcca ccctgaactt   13440
cctgctgacc aaccggtcgc agaagatccc gccccagtac gcgctgagca ccgaggagga   13500
gcgcatcctg cgctacgtgc agcagagcgt ggggctgttc ttgatgcagg aggggggccac   13560 gcccagcgcc gcgctcgaca tgaccgcgcg caacatggag cccagcatgt acgcccgcaa   13620
ccgcccgttc atcaataagc tgatggacta cttgcatcgg gcggccgcca tgaactcgga   13680
ctactttacc aacgccatct tgaacccgca ctggctcccg ccgcccgggt tctacacggg   13740
cgagtacgac atgcccgacc ccaacgacgg gttcctgtgg gacgacgtgg acagcagcgt   13800
gttctcgccg cggcccacca ccaccaccgt gtggaagaaa gagggcgggg accggcggcc   13860
gtcctcggcg ctgtccggtc gcgcgggtgc tgccgcggcg gtgcccgagg ctgccagccc   13920
cttcccgagc ctgccctttt cgctgaacag cgtgcgcagc agcgagctgg tcggctgac   13980 gcggccgcgc ctgctgggcg aggaggagta cctgaacgac tccttgttga agcccgagcg   14040
cgagaagaac ttccccaata acgggataga gagcctggtg gacaagatga gccgctggaa   14100
gacgtacgcg cacgagcaca gggacgagcc ccgagctagc agcgcaggca cccgtagacg   14160
ccagcggcac gacaggcagc gggactggt gtgggacgat gaggattccg ccgacgacag   14220
cagcgtgttg gacttgggtg ggagtggtgg tggtaacccg ttcgctcacc tgcgcccccg   14280
tatcgggcgc ctgatgtaag aatctgaaaa aataaaagac ggtactcacc aaggccatgg   14340
```

```
cgaccagcgt gcgttcttct ctgttgtttg tagtagtatg atgaggcgcg tgtacccgga   14400
gggtcctcct ccctcgtacg agagcgtgat gcagcaggcg gtggcggcgg cgatgcagcc   14460
cccgctggag gcgccttacg tgcccccgcg gtacctggcg cctacggagg ggcggaacag   14520
cattcgttac tcggagctgg cacccttgta cgataccacc cggttgtacc tggtggacaa   14580
caagtcggcg gacatcgcct cgctgaacta ccagaacgac cacagcaact tcctgaccac   14640
cgtggtgcag aacaacgatt tcacccccac ggaggccagc acccagacca tcaactttga   14700
cgagcgctcg cggtggggcg gccagctgaa aaccatcatg cacaccaaca tgcccaacgt   14760
gaacgagttc atgtacagca acaagttcaa ggcgcgggtg atggtctcgc gcaagacccc   14820 caacgggtc acggtagggg atgattatga tggtagtcag gacgagctga cctacgagtg   14880
ggtggagttt gagctgcccg agggcaactt ctcggtgacc atgaccatcg atctgatgaa   14940
caacgccatc atcgacaact acttggcggt ggggcggcag aacggggtgc tggagagcga   15000
catcggcgtg aagttcgaca cgcgcaactt ccggctgggc tgggaccccg tgaccgagct   15060
ggtgatgccg ggcgtgtaca ccaacgaggc cttccacccc gacatcgtcc tgctgcccgg   15120
ctgcggcgtg gacttcaccg agagccgcct cagcaacctg ctgggcatcc gcaagcggca   15180
gcccttccag gagggcttcc agatcctgta cgaggacctg gagggggggca acatccccgc   15240 gctcttggat gtcgaagcct atgaagaaag taaggaaaaa gcagaggctg aggcaactac   15300
agccgtggct accgccgcga ctgtggcaga tgccactgtc accaggggcg atacattcgc   15360
cacccaggcg gaggaagcag ccgccctagc ggcgaccgat gatagtgaaa gtaagatagt   15420
catcaagccg gtggagaagg acagcaagaa caggagctac aacgttctac cggatggaaa   15480
gaacaccgcc taccgcagct ggtacctggc ctacaactac ggcgaccccg agaagggcgt   15540
gcgctcctgg acgctgctca ccacctcgga cgtcacctgc ggcgtggagc aagtctactg   15600
gtcgctgccc gacatgatgc aagacccggt caccttccgc tccacgcgac aagttagcaa   15660
ctacccggtg gtgggcgccg agctcctgcc cgtctactcc aagagcttct tcaacgagca   15720
ggccgtctac tcgcagcagc tgcgtgcctt cacctcgctc acgcacgtct tcaaccgctt   15780
ccccgagaac cagatcctcg tccgcccgcc cgcgcccacc attaccaccg tcagtgaaaa   15840
cgttcctgct ctcacagatc acgggaccct gccgctgcgc agcagtatcc ggggagtcca   15900
gcgcgtgacc gtcactgacg ccagacgccg cacctgcccc tacgtctaca aggccctggg   15960
cgtagtcgcg ccgcgcgtcc tctcgagccg caccttctaa aaaatgtcca ttctcatctc   16020
gcccagtaat aacaccggtt ggggcctgcg cgcgcccagc aagatgtacg gaggcgctcg   16080
ccaacgctcc acgcaacacc ccgtgcgcgt gcgcgggcac ttccgcgctc cctggggcgc   16140
cctcaagggc cgcgtgcgct cgcgcaccac cgtcgacgac gtgatcgacc aggtggtggc   16200
cgacgcgcgc aactacacgc ccgccgccgc gcccgcctcc accgtggacg ccgtcatcga   16260
cagcgtggtg gccgacgcgc gccggtacgc ccgcgcaaag agccggcggc ggcgcatcgc   16320
ccggcggcac cggagcaccc ccgccatgcg cgcggcgcga gccttgctgc gcagggccag   16380
gcgcacggga cgcagggcca tgctcagggc ggccagacgc gcggcctccg gcagcagcag   16440
cgccggcagg acccgcagac gcgcggccac ggcggcggcg gcggccatcg ccagcatgtc   16500
ccgcccgcgg cgcggcaacg tgtactgggt gcgcgacgcc gccaccggtg tgcgcgtgcc   16560
cgtgcgcacc cgcccccctc gcacttgaag atgctgactt cgcgatgttg atgtgtccca   16620
gcggcgagga ggatgtccaa gcgcaaatac aaggaagaga tgctccaggt catcgcgcct   16680
gagatctacg gccccgcggc ggcggtgaag gaggaaagaa agccccgcaa actgaagcgg   16740
```

```
gtcaaaaagg acaaaaagga ggaggaagat gacggactgg tggagtttgt gcgcgagttc   16800 gcccccggc ggcgcgtgca gtggcgcggg cggaaagtga aaccggtgct gcggcccggc   16860
accacggtgg tcttcacgcc cggcgagcgt tccggctccg cctccaagcg ctcctacgac   16920
gaggtgtacg gggacgagga catcctcgag caggcggtcg agcgtctggg cgagtttgct   16980
tacggcaagc gcagccgccc cgcgcccttg aaagaggagg cggtgtccat cccgctggac   17040
cacggcaacc ccacgccgag cctgaagccg gtgaccctgc agcaggtgct gccgagcgcg   17100
gcgccgcgcc ggggcttcaa gcgcgagggc ggcgaggatc tgtacccgac catgcagctg   17160
atggtgccca agcgccagaa gctggaggac gtgctggagc acatgaaggt ggaccccgag   17220
gtgcagcccg aggtcaaggt gcggcccatc aagcaggtgg ccccgggcct gggcgtgcag   17280
accgtggaca tcaagatccc cacggagccc atggaaacgc agaccgagcc cgtgaagccc   17340
agcaccagca ccatggaggt gcagacggat ccctggatgc cagcggcttc caccaccacc   17400
actcgccgaa gacgcaagta cggcgcgcc agcctgctga tgcccaacta cgcgctgcat   17460
ccttccatca tccccacgcc gggctaccgc ggcacgcgct tctaccgcgg ctacaccagc   17520
agccgccgcc gcaagaccac cacccgccgc cgtcgtcgca gccgccgcag cagcaccgcg   17580
acttccgcct tggtgcggag agtgtatcgc agcgggcgcg agcctctgac cctgccgcgc   17640
gcgcgctacc acccgagcat cgccatttaa ctaccgcctc ctacttgcag atatggccct   17700
cacatgccgc ctccgcgtcc ccattacggg ctaccgagga agaaagccgc gccgtagaag   17760
gctgacgggg aacgggctgc gtcgccatca ccaccggcgg cggcgcgcca tcagcaagcg   17820
gttgggggga ggcttcctgc ccgcgctgat ccccatcatc gccgcggcga tcggggcgat   17880
ccccggcata gcttccgtgg cggtgcaggc ctctcagcgc cactgagaca caaaaaagca   17940
tggatttgta ataaaaaaat ggactgacgc tcctggtcct gtgatgtgtg tttttagatg   18000
gaagacatca atttttcgtc cctggcaccg cgacacggca cgcggccgtt tatgggcacc   18060
tggagcgaca tcggcaacag ccaactgaac gggggcgcct tcaattggag cagtctctgg   18120
agcgggctta agaatttcgg gtccacgctc aaaacctatg caacaaggc gtggaacagc   18180 agcacagggc aggcgctgag ggaaaagctg aaagagcaga acttccagca gaaggtggtc   18240
gatggcctgg cctcgggcat caacgggtg gtggacctgg ccaaccaggc cgtgcagaaa   18300
cagatcaaca gccgcctgga cgcggtcccg cccgcggggt ccgtggagat gccccaggtg   18360
gaggaggagc tgcctcccct ggacaagcgc ggcgacaagc gaccgcgtcc gacgcggag   18420 gagacgctgc tgacgcacac ggacgagccg ccccccgtacg aggaggcggt gaaactgggt   18480
ctgcccacca cgcggccgt ggcgcctctg gccaccgggg tgctgaaacc cagcagcagc   18540
agccagcccg cgaccctgga cttgcctccg cctgcttccc gccctccac agtggctaag   18600 cccctgccgc cggtggccgt cgcgtcgcgc gccccccgag gccgccccca ggcgaactgg   18660
cagagcactc tgaacagcat cgtgggtctg ggagtgcaga gtgtgaagcg ccgccgctgc   18720
tattaaaaga cactgtagcg cttaacttgc ttgtctgtgt gtgtatatgt atgtccgccg   18780
accagaagga ggaagaggcg cgtcgccgag ttgcaagatg gccacccat cgatgctgcc   18840 ccagtgggcg tacatgcaca tcgccggaca ggacgcttcg gagtacctga gtccgggtct   18900
ggtgcagttc gcccgcgcca cagacaccta cttcagtctg ggaacaagt ttaggaaccc   18960 cacggtggcg cccacgcacg atgtgaccac cgaccgcagc cagcggctga cgctgcgctt   19020
cgtgcccgtg gaccgcgagg acaacaccta ctcgtacaaa gtgcgctaca cgctggccgt   19080
```

```
gggcgacaac cgcgtgctgg acatggccag cacctacttt gacatccgcg gcgtgctgga   19140
tcggggcccc agcttcaaac cctactccgg caccgcctac aacagcctag ctcccaaggg   19200
agcgcccaac acctcacagt ggaaggattc cgacagcaaa atgcatactt ttggagttgc   19260
tgccatgccc ggtgttgttg gtaaaaaaat agaagccgat ggtctgccta ttggaataga   19320
ttcatcctct ggaactgaca ccataattta tgctgataaa actttccaac cagagccaca   19380
ggttggaagt gacagttggg tcgacaccaa tggtgcagag gaaaaatatg gaggtagagc   19440
tcttaaggac actacaaaca tgaagccctg ctacggttct tttgccaggc ctaccaacaa   19500
agaaggtgga caggctaaca taaaagattc tgaaactgcc agcactactc ctaactatga   19560
tatagatttg gcattctttg acagcaaaaa tattgcagct aactacgatc cagatattgt   19620
aatgtacaca gaaaatgttg agttgcaaac tccagatact catattgtgt ttaagccagg   19680
aacttcagat gaaagttcag aagccaattt gggccagcag gccatgccca acagacccaa   19740
ctacatcggg ttcagagaca actttatcgg gctcatgtac tacaacagca ctggcaatat   19800
gggtgtactg gctggtcagg cctcccagct aaatgctgtg gtggacttgc aggacagaaa   19860
caccgaactg tcctaccagc tcttgcttga ctctctgggt gacagaacca ggtatttcag   19920
tatgtggaat caggcggtgg acagctatga ccccgatgtg cgcattattg aaaatcacgg   19980
tgtggaggat gaactcccca attattgctt ccctttgaat ggtgtaggct ttacagatac   20040
ttaccagggt gttaaagtta agacagatac agccgctact ggtaccaatg gaacgcagtg   20100
ggacaaagat gataccacag tcagcactgc caatgagatc cactcaggca atcctttcgc   20160
catggagatc aacatccagg ccaacctgtg gcggaacttc ctctacgcga acgtggcgct   20220
gtacctgccc gactcctaca gtacacgcc ggccaacatc acgctgccga ccaacaccaa   20280
cacctacgat tacatgaacg gccgcgtggt ggcgccctcg ctggtggacg cctacatcaa   20340
catcggggcg cgctggtcgc tggaccccat ggacaacgtc aacccccttca accaccaccg   20400 caacgcgggc ctgcgctacc gctccatgct cctgggcaac gggcgctacg tgcccttcca   20460
catccaggtg ccccaaaagt ttttcgccat caagagcctc ctgctcctgc ccgggtccta   20520
cacctacgag tggaacttcc gcaaggacgt caacatgatc ctgcagagct ccctcggcaa   20580
cgacctgcgc acggacgggg cctccatcgc cttcaccagc atcaacctct acgccacctt   20640
cttccccatg gcgcacaaca ccgcctccac gctcgaggcc atgctgcgca acgacaccaa   20700
cgaccagtcc ttcaacgact acctctcggc ggccaacatg ctctaccccca tcccggccaa   20760 cgccaccaac gtgcccatct ccatccccctc gcgcaactgg gccgccttcc gcggatggtc   20820
cttcacgcgc ctcaagaccc gcgagacgcc ctcgctcggc tccgggttcg accccctactt   20880 cgtctactcg ggctccatcc cctacctcga cggcaccttc tacctcaacc acaccttcaa   20940
gaaggtctcc atcaccttcg actcctccgt cagctggccc ggcaacgacc gcctcctgac   21000
gcccaacgag ttcgaaatca agcgcaccgt cgacggagag ggatacaacg tggcccagtg   21060
caacatgacc aaggactggt tcctggtcca gatgctggcc cactacaaca tcggctacca   21120
gggcttctac gtgcccgagg ctacaagga ccgcatgtac tccttcttcc gcaacttcca   21180
gcccatgagc cgccaggtcg tggacgaggt caactacaag gactaccagg ccgtcacctt   21240
ggcctaccag cacaacaact cgggcttcgt cggctacctc gcgccaccca tgcgccaggg   21300 ccagcccctac cccgccaact accccctaccc gctcatcggc aagagcgccg tcgccagcgt   21360
cacccagaaa aagttcctct gcgaccgggt catgtgcgcc atccccttct ccagcaactt   21420
catgtccatg ggcgcgctca ccgacctcgg ccagaacatg ctctacgcca actccgccca   21480
```

```
cgcgctagac atgaatttcg aagtcgaccc catggatgag tccacccttc tctatgttgt    21540
cttcgaagtc ttcgacgtcg tccgagtgca ccagccccac cgcggcgtca tcgaggccgt    21600
ctacctgcgc acgcccttct cggccggcaa cgccaccacc taaagcccg ctcttgcttc     21660 ttgcaagatg acggcctgtg gctccggcga gcaggagctc agggccatcc tccgcgacct    21720
gggctgcggg ccctgcttcc tgggcacctt cgacaagcgc ttcccgggat tcatggcccc    21780
gcacaagctg gcctgcgcca tcgtcaacac ggccggccgc gagaccgggg gcgagcactg    21840
gctggccttc gcctggaacc gcgctcccca cacctgctac ctcttcgacc ccttcgggtt    21900
ctcggacgag cgcctcaagc agatctacca gttcgagtac gagggcctgc tgcgccgcag    21960
cgccctggcc accgaggacc gctgcatcac cctggaaaag tccacccaga ccgtgcaggg    22020
tccgcgctcg gccgcctgcg ggctcttctg ctgcatgttc ctgcacgcct tcgtgcactg    22080
gcccgaccgc cccatggaca agaaccccac catgaacttg ctgacggggg tgcccaacgg    22140
catgctccag tcgccccagg tggaacccac cctgcgccgc aaccaggagg cgctctaccg    22200
cttcctcaac gcccactccg cctactttcg ctcccaccgc gcgcgcatcg agaaggccac    22260
cgccttcgac cgcatgaatc aagacatgta aactgtgtgt atgtgaatgc tttattcatc    22320
ataataaaca gcacatgttt atgccacctt ctctgaggct ctgactttat ttagaaatcg    22380
aaggggttct gccggctctc ggcgtgcccc gcgggcaggg atacgttgcg gaactggtac    22440
ttgggcagcc acttgaactc ggggatcagc agcttcggca cggggaggtc ggggaacgag    22500
tcgctccaca gcttgcgcgt gagttgcagg gcgcccagca ggtcgggcgc ggagatcttg    22560
aaatcgcagt tgggacccgc gttctgcgcg cgagagttgc ggtacacggg gttgcagcac    22620
tggaacacca tcagggccgg gtgcttcacg ctcgccagca ccgtcgcgtc ggtgatgccc    22680
tccacgtcca gatcctcggc gttggccatc ccgaaggggg tcatcttgca ggtctgccgc    22740
cccatgctgg gcacgcagcc gggcttgtgg ttgcaatcgc agtgcagggg gatcagcatc    22800
atctgagcct gctcggagct catgcccggg tacatggcct tcatgaaagc ctccagctgg    22860
cggaaggcct gctgcgcctt gccgcccctcg gtgaagaaga ccccacagga cttgctagag    22920
aactggttgg tggcgcagcc cgcgtcgtgc acgcagcagc gcgcgtcgtt gttggccagc    22980
tgcaccacgc tgcgccccca gcggttctgg gtgatcttgg cccggtcggg gttctccttc    23040
agcgcgcgct gcccgttctc gctcgccaca tccatctcga tcgtgtgctc cttctggatc    23100
atcacggtcc cgtgcaggca ccgcagcttg ccctcggcct cggtgcaccc gtgcagccac    23160
agcgcgcagc cggtgcactc ccagttcttg tgggcgatct gggagtgcga gtgcacgaag    23220
ccctgcagga agcggcccat catcgtggtc agggtcttgt tgctggtgaa ggtcagcggg    23280
atgccgcggt gctcctcgtt cacatacagg tggcagatgc ggcggtacac ctcgccctgc    23340
tcgggcatca gctggaaggc ggacttcagg tcgctctcca cgcggtaccg ctccatcagc    23400
agcgtcatca cttccatgcc cttctcccag gccgaaacga tcggcaggct caggggttc     23460 ttcaccgtca tcttagtcgc cgccgccgaa gtcagggggt cgttctcgtc cagggtctca    23520
aacactcgct tgccgtcctt ctcggtgatg cgcacggggg gaaagctgaa gcccacggcc    23580
gccagctcct cctcggcctg cctttcgtcc tcgctgtcct ggctgatgtc ttgcaaaggc    23640
acatgcttgg tcttgcgggg tttcttttg ggcggcagag gcggcggcgg agacgtgctg     23700
ggcgagcgcg agttctcgct caccacgact atttcttctt cttggccgtc gtccgagacc    23760
acgcggcggt aggcatgcct cttctggggc agaggcggag gcgacgggct ctcgcggttc    23820
```

-continued

```
ggcgggcggc tggcagagcc ccttccgcgt tcggggtgc gctcctggcg gcgctgctct    23880
gactgacttc ctccgcggcc ggccattgtg ttctcctagg gagcaacaag catggagact    23940
cagccatcgt cgccaacatc gccatctgcc cccgccgccg acgagaacca gcagcagcag    24000
aatgaaagct taaccgcccc gccgcccagc cccacctccg acgccgccgc ggccccagac    24060
atgcaagaga tggaggaatc catcgagatt gacctgggct acgtgacgcc cgcggagcac    24120
gaggaggagc tggcagcgcg cttttcagcc ccggaagaga accaccaaga gcagccagag    24180
caggaagcag agagcgagca gcagcaggct gggctcgagc atggcgacta cctgagcggg    24240
gcagaggacg tgctcatcaa gcatctggcc cgccaaagca tcatcgtcaa ggacgcgctg    24300
ctcgaccgcg ccgaggtgcc cctcagcgtg gcggagctca gccgcgccta cgagcgcaac    24360
ctcttctcgc cgcgcgtgcc ccccaagcgc cagcccaacg gcacctgcga gcccaacccg    24420
cgcctcaact tctacccggt cttcgcggtg cccgaggccc tggccaccta ccacctctttt   24480
ttcaagaacc aaaggatccc cgtctcctgc cgcgccaacc gcacccgcgc cgacgccctg    24540
ctcaacctgg gtcccggcgc ccgcctacct gatatcacct ccttggaaga ggttcccaag    24600
atcttcgagg gtctgggcag cgacgagact cgggccgcga acgctctgca aggaagcgga    24660
gaggagcatg agcaccacag cgccctggtg gagttggaag gcgacaacgc gcgcctggcg    24720
gtgctcaagc gcacggtcga gctgacccac ttcgcctacc ggcgctcaa cctgcccccc    24780
aaggtcatga gcgccgtcat ggaccaggtg ctcatcaagc gcgcctcgcc cctctcagag    24840
gaggagatgc aggaccccga gagctcggac gagggcaagc ccgtggtcag cgacgagcag    24900
ctggcgcgct ggctgggagc gagcagcacc ccccagagcc tggaagagcg gcgcaagctc    24960
atgatggccg tggtcctggt gaccgtggag ctggagtgtc tgcgccgctt cttcgccgac    25020
gcggagaccc tgcgcaaggt cgaggagaac ctgcactacc tcttcaggca cgggttcgtg    25080
cgccaggcct gcaagatctc caacgtggag ctgaccaacc tggtctccta catgggcatc    25140
ctgcacgaga accgcctggg gcagaacgtg ctgcacacca ccctgcgcgg ggaggcccgc    25200
cgcgactaca tccgcgactg cgtctacctg tacctctgcc acacctggca gacgggcatg    25260
ggcgtgtggc agcagtgcct ggaggagcag aacctgaaag agctctgcaa gctcctgcag    25320
aagaacctca aggccctgtg gaccgggttc gacgagcgca ccaccgcctc ggacctggcc    25380
gacctcatct tccccgagcg cctgcggctg acgctgcgca cgggctgccc cgactttatg    25440
agccaaagca tgttgcaaaa cttttcgctct ttcatcctcg aacgctccgg gatcctgccc    25500
gccacctgct ccgcactgcc ctcggacttc gtgccgctga ccttccgcga gtgcccccccg    25560
ccgctctgga gccactgcta cttgctgcgc ctggccaact acctggccta ccactcggac    25620
gtgatcgagg acgtcagcag cgagggtctg ctcgagtgcc actgccgctg caacctctgc    25680
acgccgcacc gctccttggc ctgcaacccc cagctgctga gcgagaccca gatcatcggc    25740
accttcgagt tgcaaggccc cggcgagggc aaggggggtc tcaaactcac ccccggggctg   25800
tggacctcgg cctacttgcg caagttcgtg cccgaggact accatccctt cgagatcagg    25860
ttctacgagg accaatccca gccgcccaag gccgagctgt cggcctgcgt catcacccag    25920
ggggccatcc tggcccaatt gcaagccatc cagaaatccc gccaagaatt tctgctgaaa    25980
aagggccacg gggtctactt ggaccccag accggagagg agctcaaccc cagcttcccc    26040
caggatgccc cgaggaagca gcaagaagct gaaagtggag ctgccgctgc cgccggagga    26100
tttggaggaa gactggggaga gcagtcaggc agaggagatg gaagactggg acagcactca    26160
ggcagaggag gacagcctgc aagacagtct ggaggaggaa gacgaggtgg aggaggaggc    26220
```

```
agaggaagaa gcagccgccg ccagaccgtc gtcctcggcg gaggagaaag caagcagcac  26280
ggataccatc tccgctccgg gtcggggtcg cggcggccgg gcccacagta gatgggacga  26340
gaccgggcgc ttcccgaacc ccaccaccca gaccggtaag aaggagcggc agggatacaa  26400
gtcctggcgg gggcacaaaa acgccatcgt ctcctgcttg caagcctgcg ggggcaacat  26460
ctccttcacc cggcgctacc tgctcttcca ccgcggggtg aacttccccc gcaacatctt  26520
gcattactac cgtcacctcc acagcccta ctactgtttc caagaagagg cagaaaccca   26580
gcagcagcag cagaaaacca gcggcagcag cagcagctag aaaatccaca gcggcggcag  26640
gtggactgag gatcgcggcg aacgagccgg cgcagacccg ggagctgagg aaccggatct  26700
ttcccaccct ctatgccatc ttccagcaga gtcgggggca ggagcaggaa ctgaaagtca  26760
agaaccgttc tctgcgctcg ctcacccgca gttgtctgta tcacaagagc gaagaccaac  26820
ttcagcgcac tctcgaggac gccgaggctc tcttcaacaa gtactgcgcg ctcactctta  26880
aagagtagcc cgcgcccgcc cacacacgga aaaaggcggg aattacgtca ccacctgcgc  26940
ccttcgcccg accatcatca tgagcaaaga gattcccacg ccttacatgt ggagctacca  27000
gccccagatg ggcctggccg ccggcgccgc ccaggactac tccacccgca tgaactggct  27060
cagtgccggg cccgcgatga tctcacgggt gaatgacatc cgcgcccacc gaaaccagat  27120
actcctagaa cagtcagcga tcaccgccac gccccgccat caccttaatc cgcgtaattg  27180
gcccgccgcc ctggtgtacc aggaaattcc ccagcccacg accgtactac ttccgcgaga  27240 cgccaggcc gaagtccagc tgactaactc aggtgtccag ctggccggcg gcgccgccct   27300
gtgtcgtcac cgcccccgctc agggtataaa gcggctggtg atccgaggca gaggcacaca  27360
gctcaacgac gaggtggtga gctcttcgct gggtctgcga cctgacggag tcttccaact  27420
cgccggatcg gggagatctt ccttcacgcc tcgtcaggcc gtcctgactt tggagagttc  27480
gtcctcgcag ccccgctcgg gcggcatcgg cactctccag ttcgtggagg agttcactcc  27540
ctcggtctac ttcaaccccct ctccggctc ccccggccac tacccggacg agttcatccc  27600
gaacttcgac gccatcagcg agtcggtgga cggctacgat tgaatgtccc atggtggcgc  27660
ggctgaccta gctcggcttc gacacctgga ccactgttaa ttaatcgcct ctcctacgag  27720
ctcctgcagc agcgccagaa gttcacctgc ctggtcggag tcaacccccat cgtcatcacc  27780 cagcagtcgg gcgataccaa ggggtgcatc cactgctcct gcgactcccc cgactgcgtc  27840
cacactctga tcaagaccct ctgcggcctc cgcgacctcc tccccatgaa ctaatcaccc  27900
ccttatccag tgaaataaag atcatattga tgatgatttt acagaaataa agatacaatc  27960
atattgatga tttgagttta ataaaaaata aagaatcact tacttgaaat ctgataccag  28020
gtctctgtcc atgttttctg ccaacaccac ttcactcccc tcttcccagc tctggtactg  28080
caggccccgg cgggctgcaa acttcctcca cacgctgaag gggatgtcaa attcctcctg  28140
tccctcaatc ttcattttat cttctatcag atgtccaaaa agcgcgtccg ggtggatgat  28200
gacttcgacc ccgtctaccc ctacgatgca gacaacgcac cgaccgtgcc cttcatcaac  28260 cccccccttcg tctcttcaga tggattccaa gagaagcccc tgggggtgct gtccctgcga  28320
ctggccgacc ccgtcaccac caagaacggg gaaatcaccc tcaagctggg agaggggtg   28380 gacctcgact cctcgggaaa actcatctcc aacacggcca ccaaggccgc cgcccctctc  28440 agttttttcca acaacaccat ttcccttaac atggatcacc ccttttacac taaagatgga  28500
aaattatcct tacaagtttc tccaccatta aatatactga gaacaagcat tctaaacaca  28560
```

```
ctagctttag gttttggatc aggtttagga ctccgtggct ctgccttggc agtacagtta  28620
gtctctccac ttacatttga tactgatgga aacataaagc ttaccttaga cagaggtttg  28680
catgttacaa caggagatgc aattgaaagc aacataagct gggctaaagg tttaaaattt  28740
gaagatggag ccatagcaac caacattgga aatgggttag agtttggaag cagtagtaca  28800
gaaacaggtg ttgatgatgc ttacccaatc caagttaaac ttggatctgg ccttagcttt  28860
gacagtacag gagccataat ggctggtaac aaagaagacg ataaactcac tttgtggaca  28920
acacctgatc catcgccaaa ctgtcaaata ctcgcagaaa atgatgcaaa actaacactt  28980
tgcttgacta aatgtggtag tcaaatactg gccactgtgt cagtcttagt tgtaggaagt  29040
ggaaacctaa accccattac tggcaccgta agcagtgctc aggtgtttct acgttttgat  29100
gcaaacggtg ttcttttaac agaacattct acactaaaaa atactgggg gtataggcag  29160 ggagatagca tagatggcac tccatatacc aatgctgtag gattcatgcc caatttaaaa  29220
gcttatccaa agtcacaaag ttctactact aaaaataata tagtagggca agtatacatg  29280
aatggagatg tttcaaaacc tatgcttctc actataaccc tcaatggtac tgatgacagc  29340
aacagtacat attcaatgtc attttcatac acctggacta atggaagcta tgttggagca  29400
acatttgggg ctaactctta taccttctca tacatcgccc aagaatgaac actgtatccc  29460
accctgcatg ccaacccttc ccaccccact ctgtggaaaa aactctgaaa cacaaaataa  29520
aataaagttc aagtgtttta ttgattcaac agttttacag gattcgagca gttattttc  29580 ctccaccctc ccaggacatg aatacacca ccctctcccc ccgcacagcc ttgaacatct  29640
gaatgccatt ggtgatggac atgcttttgg tctccacgtt ccacacagtt tcagagcgag  29700
ccagtctcgg gtcggtcagg gagatgaaac cctccgggca caattgggag aagtactcgc  29760
ctacatgggg gtagagtcat aatcgtgcat caggataggg cggtggtgct gcagcagcgc  29820
gcgaataaac tgctgccgcc gccgctccgt cctgcaggaa tacaacatgg cagtggtctc  29880
ctcagcgatg attcgcaccg cccgcagcat aaggcgcctt gtcctccggg cacagcagcg  29940
caccctgatc tcacttaaat cagcacagta actgcagcac agcaccacaa tattgttcaa  30000
aatcccacag tgcaaggcgc tgtatccaaa gctcatggcg gggaccacag aacccacgtg  30060
gccatcatac cacaagcgca ggtagattaa gtggcgaccc ctcataaaca cgctggacat  30120
aaacattacc tcttttggca tgttgtaatt caccacctcc cggtaccata taaacctctg  30180
attaaacatg gcgccatcca ccaccatcct aaaccagctg gccaaaacct gcccgccggc  30240
tatacactgc agggaaccgg gactggaaca atgacagtgg agagcccagg actcgtaacc  30300
atggatcatc atgctcgtca tgatatcaat gttggcacaa cacaggcaca cgtgcataca  30360
cttcctcagg attacaagct cctcccgcgt tagaaccata tcccagggaa caacccattc  30420
ctgaatcagc gtaaatccca cactgcaggg aagacctcgc acgtaactca cgttgtgcat  30480
tgtcaaagtg ttcacattcgg gcagcagcgg atgatcctcc agtatggtag cgcgggtttc  30540
tgtctcaaaa ggaggtagac gatccctact gtacggagtg cgccgagaca accgagatcg  30600
tgttggtcgt agtgtcatgc caaatggaac gccggacgta gtcatatttc ctgaagtctt  30660
ggcgcgccaa agtctagaag cggtccatag cttaccgagc ggcagcagca gcggcacaca  30720
acaggcgcaa gagtcagaga aaagactgag ctctaacctg tccgcccgct ctctgctcaa  30780
tatatagccc agatctacac tgacgtaaag gccaaagtct aaaataccc gccaaatagt  30840 cacacacgcc cagcacacgc ccagaaaccg gtgcacacact caaaaaaata cgcgcacttc  30900
ctcaaacgcc caaactgccg tcatttccgg gttcccacgc tacgtcatca aaacacgact  30960
```

-continued

```
ttcaaattcc gtcgaccgtt aaaaacgtca cccgccccgc ccctaacggt cgcccgtctc    31020
tcagccaatc agcgcccccgc atccccaaat tcaaacacct catttgcata ttaacgcgca   31080
ccaaaagttt gaggtatatt attgatgatg                                     31110
```

<210> SEQ ID NO 6
<211> LENGTH: 31158
<212> TYPE: DNA
<213> ORGANISM: Artificial Sequence
<220> FEATURE:
<223> OTHER INFORMATION: synthetic chimpanzee adenovirus serotype ChAd63 with Marburg virus Angola codon optimized transmembrane envelope glycoprotein (GP) insert (ChAd63 GP Marburg (PB/6712))
<220> FEATURE:
<221> NAME/KEY: CDS
<222> LOCATION: (1662)...(3704)
<223> OTHER INFORMATION: Marburg virus Angola codon optimized transmembrane envelope glycoprotein (GP) insert in ChAd63 GP Marburg (PB/6712)
<220> FEATURE:
<221> NAME/KEY: CDS
<222> LOCATION: (14420)...(16048)
<223> OTHER INFORMATION: chimpanzee adenovirus serotype ChAd63 penton
<220> FEATURE:
<221> NAME/KEY: CDS
<222> LOCATION: (18815)...(21691)
<223> OTHER INFORMATION: chimpanzee adenovirus serotype ChAd63 hexon
<220> FEATURE:
<221> NAME/KEY: CDS
<222> LOCATION: (28219)...(29496)
<223> OTHER INFORMATION: chimpanzee adenovirus serotype ChAd63 fiber

<400> SEQUENCE: 6

```
catcatcaat aatatacctc aaacttttgg tgcgcgttaa tatgcaaatg aggtgtttga      60
atttggggat gcggggcgct gattggctga gagacgggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaattccg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt tacggatat ctccattgca tacgttgtat     480
ccatatcata atatgtacat ttatattggc tcatgtccaa cattaccgcc atgttgacat     540
tgattattga ctagttatta atagtaatca attacgggt cattagttca tagcccatat     600
atggagttcc gcgttacata acttacggta aatggcccgc ctggctgacc gcccaacgac     660
ccccgcccat tgacgtcaat aatgacgtat gttcccatag taacgccaat agggactttc     720
cattgacgtc aatgggtgga gtatttacgg taaactgccc acttggcagt acatcaagtg     780
tatcatatgc caagtacgcc ccctattgac gtcaatgacg gtaaatggcc cgcctggcat     840
tatgcccagt acatgacctt atgggacttt cctacttggc agtacatcta cgtattagtc     900
atcgctatta ccatggtgat gcggttttgg cagtacatca atgggcgtgg atagcggttt     960
gactcacggg gatttccaag tctccacccc attgacgtca atgggagttt gttttggaac    1020
caaaatcaac gggactttcc aaaatgtcgt aacaactccg ccccattgac gcaaatgggc    1080
ggtaggcgtg tacggtggga ggtctatata agcagagctc tccctatcag tgatagagat    1140
ctccctatca gtgatagaga tcgtcgacga gctcgtttag tgaaccgtca gatcgcctgg    1200
agacgccatc cacgctgttt tgacctccat agaagacacc gggaccgatc cagcctccat    1260
```

```
cggctcgcat ctctccttca cgcgcccgcc gccctacctg aggccgccat ccacgccggt    1320
tgagtcgcgt tctgccgcct cccgcctgtg gtgcctcctg aactgcgtcc gccgtctagg    1380
taagtttaaa gctcaggtcg agaccgggcc tttgtccggc gctcccttgg agcctaccta    1440
gactcagccg gctctccacg ctttgcctga ccctgcttgc tcaactctag ttaacggtgg    1500
agggcagtgt agtctgagca gtactcgttg ctgccgcgcg cgccaccaga cataatagct    1560
gacagactaa cagactgttc cttccatgg gtcttttctg cagtcaccgt cgtcgacacg     1620
tgtgatcaga tatcgcggcc gctctagaga tatcggccgc catgaagacc acctgcctgc    1680
tgatcagcct gatcctgatc cagggcgtga agacccctgcc catcctggag atcgccagca   1740
acatccagcc ccagaacgtg gacagcgtgt gcagcggcac cctgcagaag accgaggacg    1800
tgcacctgat gggcttcacc ctgagcggcc agaaggtggc cgacagccct ctggaggcca    1860
gcaagaggtg ggccttcagg gccggcgtgc cccccaagaa cgtggagtac accgagggcg    1920
aggaggccaa gacctgctac aacatcagcg tgaccgaccc cagcggcaag agcctgctgc    1980
tggaccctcc caccaacatc agggactacc ctaagtgcaa gaccatccac cacatccagg    2040
gccagaaccc tcacgcccag ggcatcgccc tgcacctgtg gggcgccttc ttcctgtacg    2100
acaggatcgc cagcaccacc atgtacagag gaaaagtgtt cacagaggga aacatcgctg    2160
ctatgatcgt gaacaagacc gtgcataaga tgatcttcag cagacaggga cagggatata    2220
gacatatgaa cctgacatcc acaaacaagt actggacaag cagcaacgga acacagacaa    2280
acgatacagg atgttttgga acactgcagg aatacaactc caccaagaac cagacatgtg    2340
cccctagcaa gaagcctctg cctctgccta cagctcatcc tgaagtgaag ctgacatcca    2400
caagcacaga tgccacaaag ctgaacacaa cagatcctaa tagcgacgac gaggatctga    2460
caacaagcgg atccggatcc ggagaacagg aaccttatac aacaagcgac gctgctacaa    2520
aacagggact gtcctccaca atgcctccta cacctagccc tcagcctagc cacctcagc     2580 agggaggcaa caacacaaac cattcccagg gagtggtgac agaacctgga aagacaaaca    2640
caacagccca gcctagcatg cctcctcata acacaacaac aatcagcaca acaacaccct    2700
ccaagcacaa tctgagcaca cctagcgtgc ctattcagaa tgccaccaac tacaacacac    2760
agtccacagc ccctgaaaac gaacagacct ccgccccttc caaaacaacc ctgctgccta    2820
cagaaaaccc tacaacagcc aagagcacaa acagcacaaa gagccctaca caacagtgc    2880 ctaacacaac aaacaagtat agcacaagcc ctagccctac acctaattcc acagctcagc    2940
atctggtgta tttagaaga aagagaaaca tcctgtggag agaaggagat atgttccctt    3000
ttctggatgg actgatcaac gctcctatcg attttgatcc tgtgcctaac acaaagacaa    3060
tctttgatga agcagcagc agcggagcct ccgccgaaga agatcagcat gcctccccta    3120
acatcagcct gacactgagc tattttccta aggtgaacga aaacacagcc cattccggag    3180
aaaacgaaaa cgattgtgat gccgaactga gaatctggag cgtgcaggaa gatgatctgg    3240
ccgccggact gagctggatc cctttttttg gcccggaat tgaaggactg tacaccgccg    3300
gcctgatcaa gaaccagaac aacctggtgt gcaggctgag gaggctggcc aaccagaccg    3360
ccaagagcct ggagctgctg ctgagggtga ccaccgagga ggaccttc agcctgatca     3420 acaggcacgc catcgacttc ctgctggcta ggtggggcgg cacctgcaag gtgctgggcc    3480
ccgactgctg catcggcatc gaggacctga gcaggaacat cagcgagcag atcgaccaga    3540
tcaagaagga cgagcagaag gagggcaccg gctggggcct gggcggcaag tggtggacca    3600
```

-continued

```
gcgactgggg agtgctgaca aacctgggaa tcctgctgct gctgagcatt gccgtgctca    3660
ttgctctgtc ctgtatctgt agaatcttta ccaagtacat cggatgatag atccagatct    3720
gctgtgcctt ctagttgcca gccatctgtt gtttgcccct cccccgtgcc ttccttgacc    3780
ctggaaggtg ccactcccac tgtcctttcc taataaaatg aggaaattgc atcgcattgt    3840
ctgagtaggt gtcattctat tctgggggt ggggtggggc aggacagcaa gggggaggat     3900
tgggaagaca atagcaggca tgctggggat gcggtgggct ctagatatca gcgatcgcgt    3960
gagtagtgtt tgggggtggg tgggagcctg catgatgggc agaatgacta aaatctgtgt    4020
ttttctgtgt gttgcagcag catgagcgga agcgcctcct ttgagggagg gtattcagc    4080 ccttatctga cggggcgtct cccctcctgg gcgggagtgc gtcagaatgt gatgggatcc    4140
acggtggacg gccggcccgt gcagcccgcg aactcttcaa ccctgaccta cgcgaccctg    4200
agctcctcgt ccgtggacgc agctgccgcc gcagctgctg cttccgccgc cagcgccgtg    4260
cgcggaatgg ccctgggcgc cggctactac agctctctgg tggccaactc gagttccacc    4320
aataatcccg ccagcctgaa cgaggagaag ctgttgctgc tgatggccca gctcgaggcc    4380
ctgacccagc gcctgggcga gctgacccag caggtggctc agctgcaggc ggagacgcgg    4440
gccgcggttg ccacggtgaa aaccaaataa aaatgaatc aataaataaa cggagacggt     4500
tgttgatttt aacacagagt cttgaatctt tatttgattt ttcgcgcgcg gtaggccctg    4560
gaccaccggt ctcgatcatt gagcaccggg tggatctttt ccaggaccccg gtagaggtgg   4620 gcttggatgt tgaggtacat gggcatgagc ccgtcccggg ggtggaggta gctccattgc    4680
agggcctcgt gctcggggt ggtgttgtaa atcacccagt catagcaggg gcgcagggcg     4740
tggtgctgca cgatgtcttt gaggaggaga ctgatggcca cgggcagccc cttggtgtag    4800
gtgttgacga acctattgag ctgggaggga tgcatgcggg gggagatgag atgcatcttg    4860
gcctggatct tgagattggc gatgttcccg cccagatccc gccgggggtt catgttgtgc    4920
aggaccacca gcacggtgta tccggtgcac ttggggaatt tgtcatgcaa cttggaaggg    4980
aaggcgtgaa agaatttgga gacgcccttg tgaccgccca ggttttccat gcactcatcc    5040
atgatgatgg cgatgggccc gtgggcggcg gcctgggcaa agacgtttcg ggggtcggac    5100
acatcgtagt tgtggtcctg ggtgagctcg tcataggcca ttttaatgaa tttggggcgg    5160
agggtacccg actgggggac aaaggtgccc tcgatcccgg gggcgtagtt cccctcgcag    5220
atctgcatct cccaggcctt gagctcggag ggggggatca tgtccacctg cggggcgatg    5280
aaaaaaacgg tttccggggc gggggagatg agctgcgccg aaagcaggtt ccggagcagc    5340
tgggacttgc cgcagccggt ggggccgtag atgaccccga tgaccggctg caggtggtag    5400
ttgagggaga gacagctgcc gtcctcgcgg aggagggggg ccacctcgtt catcatctcg    5460
cgcacatgca tgttctcgcg cacgagttcc gccaggaggc gctcgccccc cagcgagagg    5520
agctcttgca gcgaggcgaa gttttttcagc ggcttgagcc cgtcggccat ggcattttg    5580 gagagggtct gttgcaagag ttccagacgg tcccagagct cggtgatgtg ctctagggca    5640
tctcgatcca gcagacctcc tcgtttcgcg ggttggggcg actgcgggag tagggcacca    5700
ggcgatgggc gtccagcgag gccagggtcc ggtccttcca gggtcgcagg gtccgcgtca    5760
gcgtggtctc cgtcacggtg aagggggtgcg cgccgggctg ggcgcttgcg agggtgcgct    5820
tcaggctcat ccggctggtc gagaaccgct cccggtcggc gccctgcgcg tcggccaggt    5880
agcaattgag catgagttcg tagttgagcg cctcggccgc gtggcccttg gcgcggagct    5940
tacctttgga agtgtgtccg cagacgggac agaggaggga cttgagggcg tagagcttgg    6000
```

```
gggcgaggaa gacggactcg ggggcgtagg cgtccgcgcc gcagctggcg cagacggtct    6060
cgcactccac gagccaggtg aggtcggggc ggtcggggtc aaaaacgagg tttcctccgt    6120
gcttttgat gcgtttctta cctctggtct ccatgagctc gtgtcccgc tgggtgacaa     6180
agaggctgtc cgtgtccccg tagaccgact ttatgggccg gtcctcgagc ggggtgccgc    6240
ggtcctcgtc gtagaggaac cccgcccact ccgagacgaa ggcccgggtc caggccagca    6300
cgaaggaggc cacgtgggag gggtagcggt cgttgtccac cagcgggtcc accttctcca    6360
gggtatgcaa gcacatgtcc ccctcgtcca catccaggaa ggtgattggc ttgtaagtgt    6420
aggccacgtg accggggtc ccggccgggg gggtataaaa gggggcgggc ccctgctcgt     6480
cctcactgtc ttccggatcg ctgtccagga gcgccagctg ttggggtagg tattccctct    6540
cgaaggcggg catgacctcg gcactcaggt tgtcagtttc tagaaacgag gaggatttga    6600
tattgacggt gccgttggag acgcctttca tgagcccctc gtccatctgg tcagaaaaga    6660
cgatcttttt gttgtcgagc ttggtggcga aggagccgta gagggcgttg gagagcagct    6720
tggcgatgga gcgcatggtc tggttctttt ccttgtcggc gcgctccttg gcggcgatgt    6780
tgagctgcac gtactcgcgc gccacggcact tccattcggg gaagacggtg gtgagctcgt    6840
cgggcacgat tctgacccgc cagccgcggt tgtgcagggt gatgaggtcc acgctggtgg    6900
ccacctcgcc gcgcagggc tcgttggtcc agcagaggcg cccgcccttg cgcgagcaga     6960
agggggcag cgggtccagc atgagctcgt cgggggggtc ggcgtccacg gtgaagatgc      7020
cgggcaggag ctcggggtcg aagtagctga tgcaggtgcc cagatcgtcc agacttgctt    7080
gccagtcgcg cacggccagc gcgcgctcgt aggggctgag gggcgtgccc cagggcatgg    7140
ggtgcgtgag cgcggaggcg tacatgccgc agatgtcgta gacgtagagg ggctcctgga    7200
ggacgccgat gtaggtgggg tagcagcgcc ccccgcggat gctggcgcgc acgtagtcgt    7260
acagctcgtg cgagggcgcg aggagccccg tgccgagatt ggagcgctgc ggcttttcgg    7320
cgcggtagac gatctggcgg aagatggcgt gggagttgga ggagatggtg ggcctctgga    7380
agatgttgaa gtgggcatgg ggcagtccga ccgagtccct gatgaagtgg gcgtaggagt    7440
cctgcagctt ggcgacgagc tcggcggtga cgaggacgtc cagggcgcag tagtcgaggg    7500
tctcttggat gatgtcgtac ttgagctggc ccttctgctt ccacagctcg cggttgagaa    7560
ggaactcttc gcgtccttc cagtactctt cgagggggaa cccgtcctga tcggcacggt     7620
aagagcccac catgtagaac tggttgacgg ccttgtaggc gcagcagccc ttctccacgg    7680
ggagggcgta agcttgcgcg gccttgcgca ggaggtgtg ggtgagggcg aaggtgtcgc     7740
gcaccatgac tttgaggaac tggtgcttga agtcgaggtc gtcgcagccg ccctgctccc    7800
agagctggaa gtccgtgcgc ttcttgtagg cggggttggg caaagcgaaa gtaacatcgt    7860
tgaagaggat cttgcccgcg cggggcatga agttgcgagt gatgcggaaa ggctggggca    7920
cctcggcccg gttgttgatg acctgggcgg cgaggacgat ctcgtcgaag ccgttgatgt    7980
tgtgcccgac gatgtagagt tccacgaatc gcggcggcc cttgacgtgg gcagcttct      8040
tgagctcgtc gtaggtgagc tcggcggggt cgctgagccc gtgctgctcg agggcccagt    8100
cggcgacgtg ggggttggcg ctgaggaagg aagtccagag atccacggcc agggcggtct    8160
gcaagcggtc ccggtactga cggaactgct ggcccacggc cattttttcg ggggtgacgc    8220
agtagaaggt gcggggtcg ccgtgccagc ggtcccactt gagctggagg gcgaggtcgt     8280
gggcgagctc gacgagcggc gggtcccgg agagtttcat gaccagcatg aaggggacga     8340
```

```
gctgcttgcc gaaggacccc atccaggtgt aggtttccac atcgtaggtg aggaagagcc   8400
tttcggtgcg aggatgcgag ccgatgggga agaactggat ctcctgccac cagttggagg   8460
aatggctgtt gatgtgatgg aagtagaaat gccgacggcg cgccgagcac tcgtgcttgt   8520
gtttatacaa gcgtccgcag tgctcgcaac gctgcacggg atgcacgtgc tgcacgagct   8580
gtacctgggt tcctttgacg aggaatttca gtgggcagtg gagcgctggc ggctgcatct   8640
ggtgctgtac tacgtcctgg ccatcggcgt ggccatcgtc tgcctcgatg gtggtcatgc   8700
tgacgagccc gcgcgggagg caggtccaga cctcggctcg gacgggtcgg agagcgagga   8760
cgagggcgcg caggccggag ctgtccaggg tcctgagacg ctgcggagtc aggtcagtgg   8820
gcagcggcgg cgcgcggttg acttgcagga gcttttccag ggcgcgcggg aggtccagat   8880
ggtacttgat ctccacgcg ccgttggtgg cgacgtccac ggcttgcagg gtcccgtgcc   8940
cctggggcgc caccaccgtg cccgtttct tcttgggcgg cggcggctcc atgcttagaa   9000
gcggcggcga ggacgcgcgc cgggcggcag gggcggctcg gggcccggag gcaggggcgg   9060
caggggcacg tcggcgccgc gcgcgggcag gttctggtac tgcgcccgga gaagactggc   9120
gtgagcgacg acgcgacggt tgacgtcctg gatctgacgc ctctgggtga aggccacggg   9180
acccgtgagt ttgaacctga aagagagttc gacagaatca atctcggtat cgttgacggc   9240
ggcctgccgc aggatctctt gcacgtcgcc cgagttgtcc tggtaggcga tctcggtcat   9300
gaactgctcg atctcctcct cctgaaggtc tccgcgccg gcgcgctcga cggtggccgc   9360
gaggtcgttg gagatgcggc ccatgagctg cgagaaggcg ttcatgccgg cctcgttcca   9420
gacgcggctg tagaccacgg ctccgtcggg gtcgcgcgcg cgcatgacca cctgggcgag   9480
gttgagctcg acgtggcgcg tgaagaccgc gtagttgcag aggcgctggt agaggtagtt   9540
gagcgtggtg gcgatgtgct cggtgacgaa gaagtacatg atccagcggc ggagcggcat   9600
ctcgctgacg tcgcccaggg cttccaagcg ctccatggcc tcgtagaagt ccacggcgaa   9660
gttgaaaaac tgggagttgc gcgccagac ggtcaactcc tcctccagaa gacggatgag   9720
ctcggcgatg gtggcgcgca cctcgcgctc gaaggccccg gggggctcct cttccatttc   9780
ctcctcttcc tcctccacta acatctcttc tacttcctcc tcaggaggcg gcggcggggg   9840
aggggccctg cgtcgccggc ggcgcacggg cagacggtcg atgaagcgct cgatggtctc   9900
cccgcgccgg cgacgcatgg tctcggtgac ggcgcgcccg tcctcgcggg gccgcagcgt   9960
gaagacgccg ccgcgcatct ccaggtggcc gccggggggg tctccgttgg gcagggagag  10020
ggcgctgacg atgcatctta tcaattgacc cgtagggact ccgcgcaagg acctgagcgt  10080
ctcgagatcc acgggatccg aaaaccgctg aacgaaggct tcgagccagt cgcagtcgca  10140
aggtaggctg agcccggttt cttgttcttc gggtatttgg tcgggaggcg ggcgggcgat  10200
gctgctggtg atgaagttga agtaggcggt cctgagacgg cggatggtgg cgaggagcac  10260
caggtccttg ggcccggctt gctggatgcg cagacggtcg gccatgcccc aggcgtggtc  10320
ctgacacctg gcgaggtcct tgtagtagtc ctgcatgagc cgctccacgg gcacctcctc  10380
ctcgcccgcg cggccgtgca tgcgcgtgag cccgaacccg cgctgcggct ggacgagcgc  10440
caggtcggcg acgacgcgct cggcgaggat ggcctgctgg atctgggtga gggtggtctg  10500
gaagtcgtcg aagtcgacga agcggtggta ggctccggtg ttgatggtgt aggagcagtt  10560
ggccatgacg gaccagttga cggtctggtg gccggggcgc acgagctcgt ggtacttgag  10620
gcgcgagtag gcgcgcgtgt cgaagatgta gtcgttgcag gtgcgcacga ggtactggta  10680
tccgacgagg aagtgcggcg gcggctggcg gtagagcggc catcgctcgg tggcgggggc  10740
```

```
gccgggcgcg aggtcctcga gcatgaggcg gtggtagccg tagatgtacc tggacatcca   10800
ggtgatgccg gcggcggtgg tggaggcgcg cgggaactcg cggacgcggt tccagatgtt   10860
gcgcagcggc aggaagtagt tcatggtggc cgcggtctgg cccgtgaggc gcgcgcagtc   10920
gtggatgctc tagacatacg ggcaaaaacg aaagcggtca gcggctcgac tccgtggcct   10980
ggaggctaag cgaacgggtt gggctgcgcg tgtaccccgg ttcgaatctc gaatcaggct   11040
ggagccgcag ctaacgtggt actggcactc ccgtctcgac ccaagcctgc taacgaaacc   11100
tccaggatac ggaggcgggt cgttttttgg ccttggtcgc tggtcatgaa aaactagtaa   11160
gcgcggaaag cggccgcccg cgatggctcg ctgccgtagt ctggagaaag aatcgccagg   11220
gttgcgttgc ggtgtgcccc ggttcgagcc tcagcgctcg gcgccggccg gattccgcgg   11280
ctaacgtggg cgtggctgcc ccgtcgtttc caagacccct tagccagccg acttctccag   11340
ttacggagcg agcccctctt tttttcttgt gttttttgcca gatgcatccc gtactgcggc   11400
agatgcgccc ccaccctcca ccacaaccgc ccctaccgca gcagcagcaa cagccggcgc   11460
ttctgccccc gccccagcag cagcagccag ccactaccgc ggcggccgcc gtgagcggag   11520
ccggcgttca gtatgacctg gccttggaag agggcgaggg gctggcgcgg ctgggggcgt   11580
cgtcgccgga gcggcacccg cgcgtgcaga tgaaaaggga cgctcgcgag gcctacgtgc   11640
ccaagcagaa cctgttcaga gacaggagcg gcgaggagcc cgaggagatg cgcgcctccc   11700
gcttccacgc ggggcgggag ctgcggcgcg gcctggaccg aaagcgggtg ctgagggacg   11760
aggatttcga ggcggacgag ctgacgggga tcagccccgc gcgcgcgcac gtggccgcgg   11820
ccaacctggt cacggcgtac gagcagaccg tgaaggagga gagcaacttc caaaaatcct   11880
tcaacaacca cgtgcgcacg ctgatcgcgc gcgaggaggt gaccctgggc ctgatgcacc   11940
tgtgggacct gctggaggcc atcgtgcaga accccacgag caagccgctg acggcgcagc   12000
tgtttctggt ggtgcagcac agtcgggaca acgagacgtt cagggaggcg ctgctgaata   12060
tcaccgagcc cgagggccgc tggctcctgg acctggtgaa cattctgcag agcatcgtgg   12120
tgcaggagcg cgggctgccg ctgtccgaga gctggcggc catcaacttc tcggtgctga   12180
gcctgggcaa gtactacgct aggaagatct acaagacccc gtacgtgccc atagacaagg   12240
aggtgaagat cgatgggttt tacatgcgca tgaccctgaa agtgctgacc ctgagcgacg   12300
atctgggggt gtaccgcaac gacaggatgc accgcgcggt gagcgccagc cgccggcgcg   12360
agctgagcga ccaggagctg atgcacagcc tgcagcgggc cctgaccggg gccgggaccg   12420 aggggggagag ctactttgac atgggcgcgg acctgcgctg gcagcccagc cgccgggcct   12480
tggaagctgc cggcggcgtg ccctacgtgg aggaggtgga cgatgaggag gaggagggcg   12540
agtacctgga agactgatgg cgcgaccgta ttttttgctag atgcagcaac agccaccgcc   12600
gccgcctcct gatcccgcga tgcgggcggc gctgcagagc cagccgtccg gcattaactc   12660
ctcggacgat tggacccagg ccatgcaacg catcatggcg ctgacgaccc gcaatcccga   12720
agcctttaga cagcagcctc aggccaaccg gctctcggcc atcctggagg ccgtggtgcc   12780
ctcgcgctcg aacccccacgc acgagaaggt gctggccatc gtgaacgcgc tggtggagaa   12840
caaggccatc gcggcgacg aggccgggct ggtgtacaac gcgctgctgg agcgcgtggc   12900
ccgctacaac agcaccaacg tgcagacgaa cctggaccgc atggtgaccg acgtgcgcga   12960
ggcggtgtcg cagcgcgagc ggttccaccg cgagtcgaac ctgggctcca tggtggcgct   13020
gaacgccttc ctgagcacgc agcccgccaa cgtgccccgg ggccaggagg actacaccaa   13080
```

```
cttcatcagc gcgctgcggc tgatggtggc cgaggtgccc cagagcgagg tgtaccagtc    13140
ggggccggac tacttcttcc agaccagtcg ccagggcttg cagaccgtga acctgagcca    13200
ggctttcaag aacttgcagg gactgtgggg cgtgcaggcc ccggtcgggg accgcgcgac    13260
ggtgtcgagc ctgctgacgc cgaactcgcg cctgctgctg ctgctggtgg cgcccttcac    13320
ggacagcggc agcgtgagcc gcgactcgta cctgggctac ctgcttaacc tgtaccgcga    13380
ggccatcggg caggcgcacg tggacgagca gacctaccag gagatcaccc acgtgagccg    13440
cgcgctgggc caggaggacc cgggcaacct ggaggccacc ctgaacttcc tgctgaccaa    13500
ccggtcgcag aagatcccgc cccagtacgc gctgagcacc gaggaggagc gcatcctgcg    13560
ctacgtgcag cagagcgtgg ggctgttctt gatgcaggag ggggccacgc ccagcgccgc    13620
gctcgacatg accgcgcgca acatggagcc cagcatgtac gcccgcaacc gcccgttcat    13680
caataagctg atggactact tgcatcgggc ggccgccatg aactcggact actttaccaa    13740
cgccatcttg aacccgcact ggctcccgcc gcccgggttc tacacgggcg agtacgacat    13800
gccccgacccc aacgacgggt tcctgtggga cgacgtggac agcagcgtgt tctcgccgcg    13860
gcccaccacc accaccgtgt ggaagaaaga gggcggggac cggcggccgt cctcggcgct    13920
gtccggtcgc gcgggtgctg ccgcggcggt gcccgaggct gccagcccct tcccgagcct    13980
gcccttttcg ctgaacagcg tgcgcagcag cgagctgggt cggctgacgc ggccgcgcct    14040
gctgggcgag gaggagtacc tgaacgactc cttgttgaag cccagcgcgc agaagaactt    14100
ccccaataac gggatagaga gcctggtgga caagatgagc cgctggaaga cgtacgcgca    14160
cgagcacagg gacgagcccc gagctagcag cgcaggcacc cgtagacgcc agcggcacga    14220
caggcagcgg ggactggtgt gggacgatga ggattccgcc gacgacagca gcgtgttgga    14280
cttgggtggg agtggtggtg gtaacccgtt cgctcacctg cgcccccgta tcgggcgcct    14340
gatgtaagaa tctgaaaaaa taaaagacgg tactcaccaa ggccatggcg accagcgtgc    14400
gttcttctct gttgtttgta gtagtatgat gaggcgcgtg tacccggagg gtcctcctcc    14460
ctcgtacgag agcgtgatgc agcaggcggt ggcggcggcg atgcagcccc gctggaggc    14520
gccttacgtg cccccgcggt acctggcgcc tacgaggggg cggaacagca ttcgttactc    14580
ggagctggca cccttgtacg ataccaccccg gttgtacctg gtggacaaca gtcggcgga    14640
catcgcctcg ctgaactacc agaacgacca cagcaacttc ctgaccaccg tggtgcagaa    14700
caacgatttc acccccacgg aggccagcac ccagaccatc aactttgacg agcgctcgcg    14760
gtgggcggc cagctgaaaa ccatcatgca caccaacatg cccaacgtga acagttcat    14820
gtacagcaac aagttcaagg cgcgggtgat ggtctcgcgc aagaccccca cggggtcac    14880
ggtaggggat gattatgatg gtagtcagga cgagctgacc tacgagtggg tggagtttga    14940
gctgcccgag ggcaacttct cggtgaccat gaccatcgat ctgatgaaca cgccatcat    15000
cgacaactac ttggcggtgg ggcggcagaa cggggtgctg gagagcgaca tcggcgtgaa    15060
gttcgacacg cgcaacttcc ggctgggctg ggacccgtg accgagctgg tgatgccggg    15120
cgtgtacacc aacgaggcct tccaccccga catcgtcctg ctgccgggct gcggcgtgga    15180
cttcaccgag agccgcctca gcaacctgct gggcatccgc aagcggcagc cttccagga    15240
gggcttccag atcctgtacg aggacctgga gggggcaac atccccgcgc tcttggatgt    15300
cgaagcctat gaagaaagta aggaaaaagc agaggctgag gcaactacag ccgtggctac    15360
cgccgcgact gtggcagatg ccactgtcac caggggcgat acattcgcca cccaggcgga    15420
ggaagcagcc gccctagcgg cgaccgatga tagtgaaagt aagatagtca tcaagccggt    15480
```

```
ggagaaggac agcaagaaca ggagctacaa cgttctaccg gatggaaaga acaccgccta   15540
ccgcagctgg tacctggcct acaactacgg cgaccccgag aagggcgtgc gctcctggac   15600
gctgctcacc acctcggacg tcacctgcgg cgtggagcaa gtctactggt cgctgcccga   15660
catgatgcaa gacccggtca ccttccgctc cacgcgacaa gttagcaact acccggtggt   15720
gggcgccgag ctcctgcccg tctactccaa gagcttcttc aacgagcagg ccgtctactc   15780
gcagcagctg cgtgccttca cctcgctcac gcacgtcttc aaccgcttcc ccgagaacca   15840
gatcctcgtc cgcccgcccg cgcccaccat taccaccgtc agtgaaaacg ttcctgctct   15900
cacagatcac gggaccctgc cgctgcgcag cagtatccgg ggagtccagc gcgtgaccgt   15960
cactgacgcc agacgccgca cctgccccta cgtctacaag gccctgggcg tagtcgcgcc   16020
gcgcgtcctc tcgagccgca ccttctaaaa aatgtccatt ctcatctcgc ccagtaataa   16080
caccggttgg ggcctgcgcg cgcccagcaa gatgtacgga ggcgctcgcc aacgctccac   16140
gcaacacccc gtgcgcgtgc gcgggcactt ccgcgctccc tggggcgccc tcaagggccg   16200
cgtgcgctcg cgcaccaccg tcgacgacgt gatcgaccag gtggtggccg acgcgcgcaa   16260
ctacacgccc gccgccgcgc ccgcctccac cgtggacgcc gtcatcgaca gcgtggtggc   16320
cgacgcgcgc cggtacgccc gcgccaagag ccggcggcgg cgcatcgccc ggcggcaccg   16380
gagcaccccc gccatgcgcg cggcgcgagc cttgctgcgc agggccaggc gcacgggacg   16440
cagggccatg ctcagggcgg ccagacgcgc ggcctccggc agcagcagcg ccggcaggac   16500
ccgcagacgc gcggccacgg cggcggcggc ggccatcgcc agcatgtccc gcccgcggcg   16560
cggcaacgtg tactgggtgc gcgacgccgc caccggtgtg cgcgtgcccg tgcgcacccg   16620
cccccctcgc acttgaagat gctgacttcg cgatgttgat gtgtcccagc ggcgaggagg   16680
atgtccaagc gcaaatacaa ggaagagatg ctccaggtca tcgcgcctga gatctacggc   16740
cccgcggcgg cggtgaagga ggaaagaaag ccccgcaaac tgaagcgggt caaaaaggac   16800
aaaaaggagg aggaagatga cggactggtg gagtttgtgc gcgagttcgc ccccggcgg   16860
cgcgtgcagt ggcgcgggcg gaaagtgaaa ccggtgctgc ggcccggcac cacggtggtc   16920
ttcacgcccg gcgagcgttc cggctccgcc tccaagcgct cctacgacga ggtgtacggg   16980
gacgaggaca tcctcgagca ggcggtcgag cgtctgggcg agtttgctta cggcaagcgc   17040
agccgccccg cgcccttgaa agaggaggcg gtgtccatcc cgctggacca cggcaacccc   17100
acgccgagcc tgaagccggt gaccctgcag caggtgctgc cgagcgcggc gccgcgccgg   17160
ggcttcaagc gcgagggcgg cgaggatctg tacccgacca tgcagctgat ggtgcccaag   17220
cgccagaagc tggaggacgt gctggagcac atgaaggtgg accccgaggt gcagcccgag   17280
gtcaaggtgc ggcccatcaa gcaggtggcc ccgggcctgg gcgtgcagac cgtggacatc   17340
aagatcccca cggagcccat ggaaacgcag accgagcccg tgaagcccag caccagcacc   17400
atggaggtgc agacggatcc ctggatgcca gcggcttcca ccaccaccac tcgccgaaga   17460
cgcaagtacg gcgcggccag cctgctgatg cccaactacg cgctgcatcc ttccatcatc   17520
cccacgccgg gctaccgcgg cacgcgcttc taccgcggct acaccagcag ccgccgccgc   17580
aagaccacca cccgccgccg tcgtcgcagc cgccgcagca gcaccgcgac ttccgccttg   17640
gtgcggagag tgtatcgcag cgggcgcgag cctctgaccc tgccgcgcgc gcgctaccac   17700
ccgagcatcg ccatttaact accgcctcct acttgcagat atggccctca catgccgcct   17760
ccgcgtcccc attacgggct accgaggaag aaagccgcgc cgtagaaggc tgacggggaa   17820
```

```
cgggctgcgt cgccatcacc accggcggcg gcgcgccatc agcaagcggt tggggggagg    17880
cttcctgccc gcgctgatcc ccatcatcgc cgcggcgatc ggggcgatcc ccggcatagc    17940
ttccgtggcg gtgcaggcct ctcagcgcca ctgagacaca aaaaagcatg gatttgtaat    18000
aaaaaaatgg actgacgctc ctggtcctgt gatgtgtgtt tttagatgga agacatcaat    18060
ttttcgtccc tggcaccgcg acacggcacg cggccgttta tgggcacctg gagcgacatc    18120
ggcaacagcc aactgaacgg gggcgccttc aattggagca gtctctggag cgggcttaag    18180
aatttcgggt ccacgctcaa aacctatggc aacaaggcgt ggaacagcag cacagggcag    18240
gcgctgaggg aaaagctgaa agagcagaac ttccagcaga aggtggtcga tggcctggcc    18300
tcgggcatca acggggtggt ggacctggcc aaccaggccg tgcagaaaca gatcaacagc    18360
cgcctggacg cggtcccgcc cgcggggtcc gtggagatgc cccaggtgga ggaggagctg    18420
cctcccctgg acaagcgcgg cgacaagcga ccgcgtcccg acgcggagga gacgctgctg    18480
acgcacacgg acgagccgcc cccgtacgag gaggcggtga aactgggtct gcccaccacg    18540
cggcccgtgg cgcctctggc caccggggtg ctgaaaccca gcagcagcag ccagcccgcg    18600
accctggact tgcctccgcc tgcttcccgc ccctccacag tggctaagcc cctgccgccg    18660
gtggccgtcg cgtcgcgcgc ccccccgagg cgccccccagg cgaactggca gagcactctg    18720
aacagcatcg tgggtctggg agtgcagagt gtgaagcgcc gccgctgcta ttaaaagaca    18780
ctgtagcgct taacttgctt gtctgtgtgt gtatatgtat gtccgccgac cagaaggagg    18840
aagaggcgcg tcgccgagtt gcaagatggc cacccccatcg atgctgcccc agtgggcgta    18900
catgcacatc gccggacagg acgcttcgga gtacctgagt ccgggtctgg tgcagttcgc    18960
ccgcgccaca gacacctact tcagtctggg gaacaagttt aggaacccca cggtggcgcc    19020
cacgcacgat gtgaccaccg accgcagcca gcggctgacg ctgcgcttcg tgcccgtgga    19080
ccgcgaggac aacacctact cgtacaaagt gcgctacacg ctggccgtgg gcgacaaccg    19140
cgtgctggac atggccagca cctactttga catccgcggc gtgctggatc ggggccccag    19200
cttcaaaccc tactccggca ccgcctacaa cagcctagct cccaagggag cgcccaacac    19260
ctcacagtgg aaggattccg acagcaaaat gcatactttt ggagttgctg ccatgccggg    19320
tgttgttggt aaaaaaatag aagccgatgg tctgcctatt ggaatagatt catcctctgg    19380
aactgacacc ataatttatg ctgataaaac tttccaacca gagccacagg ttggaagtga    19440
cagttgggtc gacaccaatg gtgcagagga aaaatatgga ggtagagctc ttaaggacac    19500
tacaaacatg aagccctgct acggttcttt tgccaggcct accaacaaag aaggtggaca    19560
ggctaacata aaagattctg aaactgccag cactactcct aactatgata tagatttggc    19620
attctttgac agcaaaaata ttgcagctaa ctacgatcca gatattgtaa tgtacacaga    19680
aaatgttgag ttgcaaactc cagatactca tattgtgttt aagccaggaa cttcagatga    19740
aagttcagaa gccaatttgg gccagcaggc catgcccaac agacccaact acatcgggtt    19800
cagagacaac tttatcgggc tcatgtacta caacagcact ggcaatatgg gtgtactggc    19860
tggtcaggcc tcccagctaa atgctgtggt ggacttgcag gacagaaaca ccgaactgtc    19920
ctaccagctc ttgcttgact ctctgggtga cagaaccagg tatttcagta tgtgaatca    19980
ggcggtggac agctatgacc ccgatgtgcg cattattgaa aatcacggtg tggaggatga    20040
actccccaat tattgcttcc ctttgaatgg tgtaggcttt acagatactt accagggtgt    20100
taaagttaag acagatacag ccgctactgg taccaatgga acgcagtggg acaaagatga    20160
taccacagtc agcactgcca atgagatcca ctcaggcaat cctttcgcca tggagatcaa    20220
```

```
catccaggcc aacctgtggc ggaacttcct ctacgcgaac gtggcgctgt acctgcccga    20280
ctcctacaag tacacgccgg ccaacatcac gctgccgacc aacaccaaca cctacgatta    20340
catgaacggc cgcgtggtgg cgccctcgct ggtggacgcc tacatcaaca tcggggcgcg    20400
ctggtcgctg gaccccatgg acaacgtcaa ccccttcaac caccaccgca acgcgggcct    20460
gcgctaccgc tccatgctcc tgggcaacgg cgctacgtg cccttccaca tccaggtgcc    20520
ccaaaagttt ttcgccatca agagcctcct gctcctgccc gggtcctaca cctacgagtg    20580
gaacttccgc aaggacgtca acatgatcct gcagagctcc ctcggcaacg acctgcgcac    20640
ggacggggcc tccatcgcct tcaccagcat caacctctac gccaccttct tccccatggc    20700
gcacaacacc gcctccacgc tcgaggccat gctgcgcaac gacaccaacg accagtcctt    20760
caacgactac ctctcggcgg ccaacatgct ctaccccatc ccggccaacg ccaccaacgt    20820
gcccatctcc atccctcgc gcaactgggc cgccttccgc ggatggtcct tcacgcgcct    20880
caagacccgc gagacgccct cgctcggctc cgggttcgac ccctacttcg tctactcggg    20940
ctccatcccc tacctcgacg gcaccttcta cctcaaccac accttcaaga aggtctccat    21000
caccttcgac tcctccgtca gctggcccgg caacgaccgc ctcctgacgc ccaacgagtt    21060
cgaaatcaag cgcaccgtcg acggagaggg atacaacgtg gcccagtgca acatgaccaa    21120
ggactggttc ctggtccaga tgctggccca ctacaacatc ggctaccagg gcttctacgt    21180
gcccgagggc tacaaggacc gcatgtactc cttcttccgc aacttccagc ccatgagccg    21240
ccaggtcgtg gacgaggtca actacaagga ctaccaggcc gtcaccctgg cctaccagca    21300
caacaactcg ggcttcgtcg gctacctcgc gcccaccatg cgccagggcc agccctaccc    21360
cgccaactac ccctacccgc tcatcggcaa gagcgccgtc gccagcgtca cccagaaaaa    21420
gttcctctgc gaccgggtca tgtggcgcat ccccttctcc agcaacttca tgtccatggg    21480
cgcgctcacc gacctcggcc agaacatgct ctacgccaac tccgcccacg cgctagacat    21540
gaatttcgaa gtcgaccccsa tggatgagtc caccttctc tatgttgtct tcgaagtctt    21600
cgacgtcgtc cgagtgcacc agccccaccg cggcgtcatc gaggccgtct acctgcgcac    21660
gcccttctcg gccggcaacg ccaccaccta aagcccgct cttgcttctt gcaagatgac    21720
ggcctgtggc tccggcgagc aggagctcag ggccatcctc cgcgacctgg gctgcgggcc    21780
ctgcttcctg ggcaccttcg acaagcgctt cccgggattc atggccccgc acaagctggc    21840
ctgcgccatc gtcaacacgg ccggccgcga daccgggggc gagcactggc tggccttcgc    21900
ctggaacccg cgctccccaca cctgctacct cttcgacccc ttcgggttct cggacgagcg    21960
cctcaagcag atctaccagt tcgagtacga gggcctgctg cgccgcagcg ccctggccac    22020
cgaggaccgc tgcatcaccc tggaaaagtc caccccagacc gtgcagggtc cgcgctcggc    22080
cgcctgcggg ctcttctgct gcatgttcct gcacgccttc gtgcactggc ccgaccgccc    22140
catggacaag aaccccacca tgaacttgct gacgggggtg cccaacgcga tgctccagtc    22200
gccccaggtg gaacccaccc tgcgccgcaa ccaggaggcg ctctaccgct tcctcaacgc    22260
ccactccgcc tactttcgct cccaccgcgc gcgcatcgag aaggccaccg ccttcgaccg    22320
catgaatcaa acatgtaaa ctgtgtgtat gtgaatgctt tattcatcat aataacagc    22380
acatgtttat gccaccttct ctgaggctct gactttattt agaaatcgaa ggggttctgc    22440
cggctctcgg cgtgccccgc gggcagggat acgttgcgga actggtactt gggcagccac    22500
ttgaactcgg ggatcagcag cttcggcacg gggaggtcgg ggaacgagtc gctccacagc    22560
```

```
ttgcgcgtga gttgcagggc gcccagcagg tcgggcgcgg agatcttgaa atcgcagttg    22620
ggacccgcgt tctgcgcgcg agagttgcgg tacacggggt tgcagcactg gaacaccatc    22680
agggccgggt gcttcacgct cgccagcacc gtcgcgtcgg tgatgccctc cacgtccaga    22740
tcctcggcgt tggccatccc gaaggggggtc atcttgcagg tctgccgccc catgctgggc    22800
acgcagccgg gcttgtggtt gcaatcgcag tgcaggggga tcagcatcat ctgagcctgc    22860
tcggagctca tgcccgggta catggccttc atgaaagcct ccagctggcg gaaggcctgc    22920
tgcgccttgc cgccctcggt gaagaagacc ccacaggact tgctagagaa ctggttggtg    22980
gcgcagcccg cgtcgtgcac gcagcagcgc gcgtcgttgt tggccagctg caccacgctg    23040
cgcccccagc ggttctgggt gatcttggcc cggtcggggt tctccttcag cgcgcgctgc    23100
ccgttctcgc tcgccacatc catctcgatc gtgtgctcct tctggatcat cacggtcccg    23160
tgcaggcacc gcagcttgcc ctcggcctcg gtgcacccgt gcagccacag cgcgcagccg    23220
gtgcactccc agttcttgtg ggcgatctgg gagtgcgagt gcacgaagcc ctgcaggaag    23280
cggcccatca tcgtggtcag ggtcttgttg ctggtgaagg tcagcgggat gccgcggtgc    23340
tcctcgttca catacaggtg gcagatgcgg cggtacacct cgccctgctc gggcatcagc    23400
tggaaggcgg acttcaggtc gctctccacg cggtaccgct ccatcagcag cgtcatcact    23460
tccatgccct tctcccaggc cgaaacgatc ggcaggctca gggggttctt caccgtcatc    23520
ttagtcgccg ccgccgaagt caggggggtcg ttctcgtcca gggtctcaaa cactcgcttg    23580
ccgtccttct cggtgatgcg cacgggggga aagctgaagc ccacggccgc cagctcctcc    23640
tcggcctgcc tttcgtcctc gctgtcctgg ctgatgtctt gcaaaggcac atgcttggtc    23700
ttgcggggtt tcttttttggg cggcagaggc ggcggcggag acgtgctggg cgagcgcgag    23760
ttctcgctca ccacgactat ttcttcttct tggccgtcgt ccgagaccac gcggcggtag    23820
gcatgcctct tctggggcag aggcggaggc gacgggctct cgcggttcgg cgggcggctg    23880
gcagagcccc ttccgcgttc gggggtgcgc tcctggcggc gctgctctga ctgacttcct    23940
ccgcggccgg ccattgtgtt ctcctaggga gcaacaagca tggagactca gccatcgtcg    24000
ccaacatcgc catctgcccc cgccgccgac gagaaccagc agcagcagaa tgaaagctta    24060
accgccccgc cgcccagccc cacctccgac gccgccgcgg ccccagacat gcaagagatg    24120
gaggaatcca tcgagattga cctgggctac gtgacgcccg cggagcacga ggaggagctg    24180
gcagcgcgct tttcagcccc ggaagagaac caccaagagc agccagagca ggaagcagag    24240
agcgagcagc agcaggctgg gctcgagcat ggcgactacc tgagcggggc agaggacgtg    24300
ctcatcaagc atctggcccg ccaaaagcatc atcgtcaagg acgcgctgct cgaccgcgcc    24360
gaggtgcccc tcagcgtggc ggagctcagc cgcgcctacg agcgcaacct cttctcgccg    24420
cgcgtgcccc caagcgcca gcccaacggc acctgcgagc ccaacccgcg cctcaacttc    24480
taccgggtct tcgcggtgcc cgaggccctg gccacctacc acctcttttt caagaaccaa    24540
aggatccccg tctcctgccg cgccaaccgc acccgcgccg acgccctgct caacctgggt    24600
cccggcgccc gcctacctga tatcacctcc ttggaagagg ttcccaagat cttcgagggt    24660
ctgggcagcg acgagactcg ggccgcgaac gctctgcaag gaagcggaga ggagcatgag    24720
caccacagcg ccctggtgga gttggaaggc gacaacgcgc gcctggcggt gctcaagcgc    24780
acggtcgagc tgacccactt cgcctacccg gcgctcaacc tgcccccaa ggtcatgagc    24840 gccgtcatgg accaggtgct catcaagcgc gcctcgcccc tctcagagga ggagatgcag    24900
gaccccgaga gctcggacga gggcaagccc gtggtcagcg acgagcagct ggcgcgctgg    24960
```

```
ctgggagcga gcagcacccc ccagagcctg gaagagcggc gcaagctcat gatggccgtg   25020
gtcctggtga ccgtggagct ggagtgtctg cgccgcttct tcgccgacgc ggagaccctg   25080
cgcaaggtcg aggagaacct gcactacctc ttcaggcacg ggttcgtgcg ccaggcctgc   25140
aagatctcca acgtggagct gaccaacctg gtctcctaca tgggcatcct gcacgagaac   25200
cgcctggggc agaacgtgct gcacaccacc ctgcgcgggg aggcccgccg cgactacatc   25260
cgcgactgcg tctacctgta cctctgccac acctggcaga cgggcatggg cgtgtggcag   25320
cagtgcctgg aggagcagaa cctgaaagag ctctgcaagc tcctgcagaa gaacctcaag   25380
gccctgtgga ccgggttcga cgagcgcacc accgcctcgg acctggccga cctcatcttc   25440
cccgagcgcc tgcggctgac gctgcgcaac gggctgcccg actttatgag ccaaagcatg   25500
ttgcaaaact ttcgctcttt catcctcgaa cgctccggga tcctgcccgc cacctgctcc   25560
gcactgccct cggacttcgt gccgctgacc ttccgcgagt gccccccgcc gctctggagc   25620
cactgctact tgctgcgcct ggccaactac ctggcctacc actcggacgt gatcgaggac   25680
gtcagcagcg agggtctgct cgagtgccac tgccgctgca acctctgcac gccgcaccgc   25740
tccttggcct gcaaccccca gctgctgagc gagacccaga tcatcggcac cttcgagttg   25800
caaggccccg gcgagggcaa gggggtctc aaactcaccc cggggctgtg gacctcggcc   25860
tacttgcgca gttcgtgcc cgaggactac catcccttcg agatcaggtt ctacgaggac   25920
caatcccagc cgcccaaggc cgagctgtcg gcctgcgtca tcacccaggg ggccatcctg   25980
gcccaattgc aagccatcca gaatcccgc caagaatttc tgctgaaaaa gggccacggg   26040
gtctacttgg accccagac cggagaggag ctcaacccca gcttccccca ggatgccccg   26100
aggaagcaga aagaagctga aagtggagct gccgctgccg ccggaggatt tggaggaaga   26160
ctgggagagc agtcaggcag aggagatgga agactgggac agcactcagg cagaggagga   26220
cagcctgcaa gacagtctgg aggaggaaga cgaggtggag gaggaggcag aggaagaagc   26280
agccgccgcc agaccgtcgt cctcggcgga ggagaaagca agcagcacgg ataccatctc   26340
cgctccgggt cggggtcgcg gcggccggcc ccacagtaga tgggacgaga ccgggcgctt   26400
cccgaacccc accacccaga ccggtaagaa ggagcggcag ggatacaagt cctggcgggg   26460
gcacaaaaac gccatcgtct cctgcttgca agcctgcggg ggcaacatct ccttcacccg   26520
gcgctacctg ctcttccacc gcggggtgaa cttccccgc aacatcttgc attactaccg   26580
tcacctccac agccctact actgtttcca agaagaggca gaaacccagc agcagcagca   26640
gaaaaccagc ggcagcagca gcagctagaa atccacagc ggcggcaggt ggactgagga   26700
tcgcggcgaa cgagccggcg cagacccggg agctgaggaa ccggatcttt cccacctct   26760 atgccatctt ccagcagagt cggggcagg agcaggaact gaaagtcaag aaccgttctc   26820
tgcgctcgct caccegcagt tgtctgtatc acaagagcga agaccaactt cagcgcactc   26880
tcgaggacgc cgaggctctc ttcaacaagt actgcgcgct cactcttaaa gagtagcccg   26940
cgcccgccca cacacggaaa aaggcgggaa ttacgtcacc acctgcgccc ttcgcccgac   27000
catcatcatg agcaaagaga ttcccacgcc ttacatgtgg agctaccagc cccagatggg   27060
cctggccgcc ggcgccgccc aggactactc cacccgcatg aactggctca gtgccgggcc   27120
cgcgatgatc tcacgggtga atgacatccg cgcccaccga aaccagatac tcctagaaca   27180
gtcagcgatc accgccacgc cccgccatca ccttaatccg cgtaattggc ccgccgccct   27240
ggtgtaccag gaaattcccc agcccacgac cgtactactt ccgcgagacg cccaggccga   27300
```

```
agtccagctg actaactcag gtgtccagct ggccggcggc gccgccctgt gtcgtcaccg    27360 cccccgctcag ggtataaagc ggctggtgat ccgaggcaga ggcacacagc tcaacgacga   27420
ggtggtgagc tcttcgctgg gtctgcgacc tgacggagtc ttccaactcg ccggatcggg    27480
gagatcttcc ttcacgcctc gtcaggccgt cctgactttg gagagttcgt cctcgcagcc    27540
ccgctcgggc ggcatcggca ctctccagtt cgtggaggag ttcactccct cggtctactt    27600 caacccttc tccggctccc ccggccacta cccggacgag ttcatcccga acttcgacgc     27660
catcagcgag tcggtggacg gctacgattg aatgtcccat ggtggcgcgg ctgacctagc    27720
tcggcttcga cacctggacc actgttaatt aatcgcctct cctacgagct cctgcagcag    27780
cgccagaagt tcacctgcct ggtcggagtc aaccccatcg tcatcaccca gcagtcgggc    27840
gataccaagg ggtgcatcca ctgctcctgc gactcccccg actgcgtcca cactctgatc    27900
aagaccctct gcggcctccg cgacctcctc cccatgaact aatcacccc ttatccagtg     27960 aaataaagat catattgatg atgattttac agaaataaag atacaatcat attgatgatt    28020
tgagtttaat aaaaaataaa gaatcactta cttgaaatct gataccaggt ctctgtccat    28080
gttttctgcc aacaccactt cactcccctc ttcccagctc tggtactgca ggccccggcg    28140
ggctgcaaac ttcctccaca cgctgaaggg gatgtcaaat tcctcctgtc cctcaatctt    28200
cattttatct tctatcagat gtccaaaaag cgcgtccggg tggatgatga cttcgacccc    28260
gtctacccct acgatgcaga caacgcaccg accgtgccct tcatcaaccc cccttcgtc    28320 tcttcagatg gattccaaga gaagcccctg ggggtgctgt ccctgcgact ggccgacccc    28380
gtcaccacca gaacggggga aatcaccctc aagctgggag aggggtgga cctcgactcc     28440 tcgggaaaac tcatctccaa cacggccacc aaggccgccg cccctctcag tttttccaac    28500
aacaccattt cccttaacat ggatcacccc ttttacacta aagatggaaa attatcctta    28560
caagtttctc caccattaaa tatactgaga acaagcattc taaacacact agctttaggt    28620
tttggatcag gttaggact ccgtggctct gccttggcag tacagttagt ctctccactt     28680
acatttgata ctgatggaaa cataaagctt accttagaca gaggtttgca tgttacaaca    28740
ggagatgcaa ttgaaagcaa cataagctgg gctaaaggtt taaaatttga agatggagcc    28800
atagcaacca acattggaaa tgggttagag tttggaagca gtagtacaga aacaggtgtt    28860
gatgatgctt acccaatcca agttaaactt ggatctggcc ttagctttga cagtacagga    28920
gccataatgg ctggtaacaa agaagacgat aaactcactt tgtggacaac acctgatcca    28980
tcgccaaact gtcaaatact cgcagaaaat gatgcaaaac taacactttg cttgactaaa    29040
tgtggtagtc aaatactggc cactgtgtca gtcttagttg taggaagtgg aaacctaaac    29100
cccattactg gcaccgtaag cagtgctcag gtgtttctac gttttgatgc aaacggtgtt    29160
cttttaacag aacattctac actaaaaaaa tactgggggt ataggcaggg agatagcata    29220
gatggcactc catataccaa tgctgtagga ttcatgccca atttaaaagc ttatccaaag    29280
tcacaaagtt ctactactaa aaataatata gtagggcaag tatacatgaa tggagatgtt    29340
tcaaaaccta tgcttctcac tataaccctc aatggtactg atgacagcaa cagtacatat    29400
tcaatgtcat tttcatacac ctggactaat ggaagctatg ttggagcaac atttgggggct   29460 aactcttata ccttctcata catcgcccaa gaatgaacac tgtatcccac cctgcatgcc    29520
aacccttccc accccactct gtggaaaaaa ctctgaaaca caaaataaaa taaagttcaa    29580 gtgtttatt gattcaacag ttttacagga ttcgagcagt tattttttcct ccaccctccc    29640 aggacatgga atacaccacc ctctccccc gcacagcctt gaacatctga atgccattgg    29700
```

```
tgatggacat gcttttggtc tccacgttcc acacagtttc agagcgagcc agtctcgggt    29760
cggtcaggga gatgaaaccc tccgggcaca attgggagaa gtactcgcct acatgggggt    29820
agagtcataa tcgtgcatca ggataggcg gtggtgctgc agcagcgcgc gaataaactg     29880
ctgccgccgc cgctccgtcc tgcaggaata caacatggca gtggtctcct cagcgatgat    29940
tcgcaccgcc cgcagcataa ggcgccttgt cctccgggca cagcagcgca ccctgatctc    30000
acttaaatca gcacagtaac tgcagcacag caccacaata ttgttcaaaa tcccacagtg    30060
caaggcgctg tatccaaagc tcatggcggg gaccacagaa cccacgtggc catcatacca    30120
caagcgcagg tagattaagt ggcgaccct cataaacacg ctggacataa acattacctc     30180
ttttggcatg ttgtaattca ccacctcccg gtaccatata aacctctgat taaacatggc    30240
gccatccacc accatcctaa accagctggc caaaacctgc ccgccggcta tacactgcag    30300
ggaaccggga ctgaacaat gacagtggag agcccaggac tcgtaaccat ggatcatcat     30360
gctcgtcatg atatcaatgt tggcacaaca caggcacacg tgcatacact tcctcaggat    30420
tacaagctcc tcccgcgtta gaaccatatc ccagggaaca acccattcct gaatcagcgt    30480
aaatcccaca ctgcagggaa gacctcgcac gtaactcacg ttgtgcattg tcaaagtgtt    30540
acattcgggc agcagcggat gatcctccag tatggtagcg cgggtttctg tctcaaaagg    30600
aggtagacga tccctactgt acggagtgcg ccgagacaac cgagatcgtg ttggtcgtag    30660
tgtcatgcca aatggaacgc cggacgtagt catatttcct gaagtcttgg cgcgccaaag    30720
tctagaagcg gtccatagct taccgagcgg cagcagcagc ggcacacaac aggcgcaaga    30780
gtcagagaaa agactgagct ctaacctgtc cgcccgctct ctgctcaata tatagcccag    30840
atctacactg acgtaaaggc caaagtctaa aaatacccgc caaatagtca cacacgccca    30900
gcacacgccc agaaaccggt gacacactca aaaaaatacg cgcacttcct caaacgccca    30960
aactgccgtc atttccgggt tcccacgcta cgtcatcaaa acacgacttt caaattccgt    31020
cgaccgttaa aaacgtcacc cgccccgccc ctaacggtcg cccgtctctc agccaatcag    31080
cgccccgcat ccccaaattc aaacacctca tttgcatatt aacgcgcacc aaaagtttga    31140
ggtatattat tgatgatg                                                 31158
```

<210> SEQ ID NO 7
<211> LENGTH: 37168
<212> TYPE: DNA
<213> ORGANISM: Artificial Sequence
<220> FEATURE:
<223> OTHER INFORMATION: synthetic chimpanzee adenovirus serotype PanAd3
      with Ebola virus Zaire wild type transmembrane
      envelope glycoprotein (GP) insert (PanAd3 Ebola
      Zaire (PB/6001))
<220> FEATURE:
<221> NAME/KEY: CDS
<222> LOCATION: (2133)...(4434)
<223> OTHER INFORMATION: Ebola virus Zaire wild type transmembrane
      envelope glycoprotein (GP) insert in PanAd3 Ebola Zaire
      (PB/6001)
<220> FEATURE:
<221> NAME/KEY: CDS
<222> LOCATION: (15442)...(17196)
<223> OTHER INFORMATION: chimpanzee adenovirus serotype ChAd63 penton
<220> FEATURE:
<221> NAME/KEY: CDS
<222> LOCATION: (20287)...(23181)
<223> OTHER INFORMATION: chimpanzee adenovirus serotype ChAd63 hexon
<220> FEATURE:
<221> NAME/KEY: CDS
<222> LOCATION: (34065)...(35693)
<223> OTHER INFORMATION: chimpanzee adenovirus serotype ChAd63 fiber

<400> SEQUENCE: 7

```
catcatcaat aatatacctt attttggatt gaagccaata tgataatgag gtgggcggag      60
cggggcgggg cggggaggag cggcggcgcg gggcgggccg ggaggtgtgg cggaagttga     120
gtttgtaagt gtggcggatg tgacttgcta gcgccggatg tggtaaaagt gacgtttttt     180
ggagtgcgac aacgcccacg ggaagtgaca ttttccccgc ggttttttacc ggatgtcgta     240
gtgaatttgg gcgttaccaa gtaagatttg gccattttcg cgggaaaact gaaatgggga     300
agtgaaatct gattaatttc gcgttagtca taccgcgtaa tatttgccga gggccgaggg     360
actttgaccg attacgtgga ggaatcgccc aggtgttttt tgaggtgaat ttccgcgttc     420
cgggtcaaag tctccgtttt attattatag gtatacccat tgcatacgtt gtatccatat     480
cataatatgt acatttatat tggctcatgt ccaacattac cgccatgttg acattgatta     540
ttgactagtt attaatagta atcaattacg gggtcattag ttcatagccc atatatggag     600
ttccgcgtta cataacttac ggtaaatggc ccgcctggct gaccgcccaa cgaccccgc      660
ccattgacgt caataatgac gtatgttccc atagtaacgc caatagggac tttccattga     720
cgtcaatggg tggagtattt acggtaaact gcccacttgg cagtacatca agtgtatcat     780
atgccaagta cgccccctat tgacgtcaat gacggtaaat ggcccgcctg gcattatgcc     840
cagtacatga ccttatggga ctttcctact tggcagtaca tctacgtatt agtcatcgct     900
attaccatgg tgatgcggtt ttggcagtac atcaatgggc gtggatagcg gtttgactca     960
cggggatttc caagtctcca ccccattgac gtcaatggga gtttgttttg gaaccaaaat    1020
caacgggact ttccaaaatg tcgtaacaac tccgccccat tgacgcaaat gggcggtagg    1080
cgtgtacggt gggaggtcta tataagcaga gctctcccta tcagtgatag agatctccct    1140
atcagtgata gagatcgtcg acgagctcgt ttagtgaacc gtcagatcgc ctggagacgc    1200
catccacgct gttttgacct ccatagaaga caccgggacc gatccagcct ccgcggccgg    1260
gaacggtgca ttggaacgcg gattccccgt gccaagagtg acgtaagtac cgcctataga    1320
ctctataggc acaccccttt ggctcttatg catgctatac tgttttggc ttggggccta    1380
tacaccccg cttccttatg ctataggtga tggtatagct tagcctatag gtgtgggtta    1440
ttgaccatta ttgaccactc ccctattggt gacgatactt tccattacta atccataaca    1500
tggctctttg ccacaactat ctctattggc tatatgccaa tactctgtcc ttcagagact    1560
gacacggact ctgtattttt acaggatggg gtcccattta ttatttacaa attcacatat    1620
acaacaacgc cgtcccccgt gcccgcagtt tttattaaac atagcgtggg atctccacgc    1680
gaatctcggg tacgtgttcc ggacatgggc tcttctccgg tagcggcgga gcttccacat    1740
ccgagccctg gtcccatgcc tccagcggct catggtcgct cggcagctcc ttgctcctaa    1800
cagtggaggc cagacttagg cacagcacaa tgcccaccac caccagtgtg ccgcacaagg    1860
ccgtggcggt agggtatgtg tctgaaaatg agcgtggaga ttgggctcgc acggctgacg    1920
cagatggaag acttaaggca gcggcagaag aagatgcagg cagctgagtt gttgtattct    1980
gataagagtc agaggtaact cccgttgcgg tgctgttaac ggtggagggc agtgtagtct    2040
gagcagtact cgttgctgcc gcgcgcgcca ccagacataa tagctgacag actaacagac    2100
tgttcctttc catgggtctt ttctgcagtc accgtcgtcg acacgtgtga tcagatatcg    2160
cggccgctct agaccaggcc ctggatcgat ccaacaacac aatgggcgtt acaggaatat    2220
tgcagttacc tcgtgatcga ttcaagagga catcattctt tctttgggta attatccttt    2280
```

```
tccaaagaac attttccatc ccacttggag tcatccacaa tagcacatta caggttagtg    2340
atgtcgacaa actagtttgt cgtgacaaac tgtcatccac aaatcaattg agatcagttg    2400
gactgaatct cgaagggaat ggagtggcaa ctgacgtgcc atctgcaact aaaagatggg    2460
gcttcaggtc cggtgtccca ccaaaggtgg tcaattatga agctggtgaa tgggctgaaa    2520
actgctacaa tcttgaaatc aaaaaacctg acgggagtga gtgtctacca gcagcgccag    2580
acgggattcg gggcttcccc cggtgccggt atgtgcacaa agtatcagga acgggaccgt    2640
gtgccggaga ctttgccttc cataaagagg gtgctttctt cctgtatgat cgacttgctt    2700
ccacagttat ctaccgagga acgactttcg ctgaaggtgt cgttgcattt ctgatactgc    2760
cccaagctaa gaaggacttc ttcagctcac accccttgag agagccggtc aatgcaacgg    2820
aggacccgtc tagtggctac tattctacca caattagata tcaggctacc ggttttggaa    2880
ccaatgagac agagtacttg ttcgaggttg acaatttgac ctacgtccaa cttgaatcaa    2940
gattcacacc acagtttctg ctccagctga atgagacaat atatacaagt gggaaaagga    3000
gcaataccac gggaaaacta atttggaagg tcaaccccga aattgataca acaatcgggg    3060
agtgggcctt ctgggaaact aaaaaaaacc tcactagaaa aattcgcagt gaagagttgt    3120
cttttcacagt tgtatcaaac ggagccaaaa acatcagtgg tcagagtccg gcgcgaactt    3180
cttccgaccc agggaccaac acaacaactg aagaccacaa aatcatggct tcagaaaatt    3240
cctctgcaat ggttcaagtg cacagtcaag gaagggaagc tgcagtgtcg catctaacaa    3300
cccttgccac aatctccacg agtccccaat ccctcacaac caaaccaggt ccggacaaca    3360
gcacccataa tacacccgtg tataaacttg acatctctga ggcaactcaa gttgaacaac    3420
atcaccgcag aacagacaac gacagcacag cctccgacac tccctctgcc acgaccgcag    3480
ccggacccccc aaaagcagag aacaccaaca cgagcaagag cactgacttc ctggaccccg    3540
ccaccacaac aagtccccaa accacagcg agaccgctgg caacaacaac actcatcacc    3600
aagataccgg agaagagagt gccagcagcg ggaagctagg cttaattacc aatactattg    3660
ctggagtcgc aggactgatc acaggcggga aagaactcg aagagaagca attgtcaatg    3720
ctcaaccccaa atgcaaccct aatttacatt actggactac tcaggatgaa ggtgctgcaa    3780
tcggactggc ctggatacca tatttcgggc cagcagccga gggaatttac atagaggggc    3840
taatgcacaa tcaagatggt ttaatctgtg ggttgagaca gctggccaac gagacgactc    3900
aagctcttca actgttcctg agagccacaa ctgagctacg caccttttca atcctcaacc    3960
gtaaggcaat tgatttcttg ctgcagcgat ggggcggcac atgccacatt ctgggaccgg    4020
actgctgtat cgaaccacat gattggacca agaacataac agacaaaatt gatcagatta    4080
ttcatgattt tgttgataaa acccttccgg accaggggga caatgacaat tggtggacag    4140
gatggagaca atggataccg gcaggtattg gagttacagg cgttgtaatt gcagttatcg    4200
ctttattctg tatatgcaaa tttgtctttt agttttcctt cagattgctt catggaaaag    4260
ctcagcctca aatcaatgaa accaggattt aattatatgg attacttgaa tctaagatta    4320
cttgacaaat gataatataa tacactggag ctttaaacat agccaatgtg attctaactc    4380
ctttaaactc acagttaatc ataaacaagg tttgaggtac cgagctcgaa ttgatctgct    4440
gtgccttcta gttgccagcc atctgttgtt tgccctccc ccgtgccttc cttgaccctg    4500
gaaggtgcca ctcccactgt cctttcctaa taaaatgagg aaattgcatc gcattgtctg    4560
agtaggtgtc attctattct ggggggtggg gtggggcagg acagcaaggg ggaggattgg    4620
gaagacaata gcaggcatgc tggggatgcg gtgggctcta gatatcagcg atcgctgagg    4680
```

```
tgggtgagtg ggcgtggtct gggggtggga agcaatatat aagttggggg tcttagggtc    4740
tctgtgtctg ttttgcagag ggaccgccgg cgccatgagc gggagcagta gcagcaacgc    4800
cttggatggc agcatcgtga gcccttattt gacgacgcgc atgccccact gggccggggt    4860
gcgtcagaat gtgatgggct ccagcatcga cggacgaccc gtgctgcccg caaattccgc    4920
cacgctgacc tacgcgaccg tcgcggggac cccgttggac gccaccgccg ccgccgccgc    4980
caccgccgcc gcctcggccg tgcgcagcct ggccacggac tttgcattct tgggacccct    5040
ggccaccggg gcggccgccc gtgccgccgt tcgcgatgac aagctgaccg ccctgctggc    5100
gcagttggat gcgcttaccc gggaactggg tgaccttgcg cagcaggtcg tggccctgcg    5160
ccagcaggtc tccgccctgc aggctagcgg gaatgcttct cctgcaaatg ccgtttaaga    5220
taaataaaac cagactctgt tgataaataa aaccagactc tgtttggatt aaagaaaagt    5280
agcaagtgca ttgctctctt tatttcataa ttttccgcgc gcgataggcc cgagtccagc    5340
gttctcggtc gttgagggtg cggtgtatct tctccaggac gtggtagagg tggctctgga    5400
cgttgagata catgggcatg agcccgtccc gggggtggag gtagcaccac tgcagagctt    5460
catgctccgg ggtggtgttg tagatgatcc agtcgtagca ggagcgctgg gcatggtgcc    5520
taaaaatgtc cttaagcagc aggccgatgg ccaggggag gcccttggtg taagtgttta    5580
caaaacggtt gagttgggaa gggtgcatgc ggggtgagat gatgtgcatc ttagattgta    5640
tttttagatt ggcgatgttt cctcccagat cccttctggg attcatgttg tggaggacca    5700
ccagcacagt atatccggtg cacttgggaa atttgtcatg cagcttagag ggaaatgcgt    5760
ggaagaactt ggagacgccc ttgtggcctc ccagattctc catgcattcg tccatgatga    5820
tggcaatggg cccgcgggag gcggcctggg caaagatgtt tctggggtca ctgacatcgt    5880
agttgtgttc cagggtgaga tcgtcatagg ccatttttat aaagcgcggg cggagggtgc    5940
ccgactgggg gatgatggtt ccctcggggc ccggggcgta gttgccttcg cagatctgca    6000
tttcccaggc cttaatctct gaggggggaa tcatatccac ttgcggggcg atgaagaaaa    6060
cggtttccgg agccggggag attaactggg atgagagcag gtttctcagc agctgtgact    6120
ttccacagcc ggtgggtcca taaataacac ctataaccgg ctgcagctgg tagttgagcg    6180
agctgcagct gccgtcgtcc cggaggaggg gggccacctc attgagcatg tcccggacgc    6240
gcttgttctc ctcgaccagg tccgccagaa ggcgctcgcc gcccagggac agcagctctt    6300
gcaaggaagc aaagtttttc agcggtttga ggccgtccgc cgtgggcatg ttttcaggg    6360 tctggccgag cagctccagg cggtcccaga gctcggtgac gtgctctacg gcatctctat    6420
ccagcatatc tcctcgtttc gcgggttggg gcggctttcg ctgtagggca ccaggcgatg    6480
gtcgtccagc gcggccagag tcatgtcctt ccatgggcgc agggtcctcg tcaggtggt    6540 ctgggtcacg gtgaaggggt gcgccccggg ctgggcgctg gccagggtgc gcttgagact    6600
ggtcctgctg gtgctgaagc gctgccggtc ttcgccctgc gcgtcggcca ggtagcattt    6660
gaccatggtg tcgtagtcca gcccctccgc ggcgtgtccc ttggcgcgca gcttgccctt    6720
ggaggtggcg ccgcacgcgg ggcactgcag gctcttgagc gcgtagagct tgggggcgag    6780
gaagaccgat tcggggagt aggcgtccgc gccgcaggcc ccgcacacgg tctcgcactc    6840
caccagccag gtgagctcgg ggcgctcggg gtcaaaaacc aggtttcccc catgcttttt    6900
gatgcgtttc ttacctcggg tctccatgag gcggtgtccc cgttcggtga cgaagaggct    6960
gtccgtgtct ccgtagaccg acttgagggg tctgtcctcc agggggtcc ctcggtcctc    7020
```

```
ttcgtagaga aactcggacc actctgagac aaaggcccgc gtccaggcca ggacgaagga   7080
ggccaggtgg gaggggtacc ggtcgttgtc cactagggggg tccaccttct ccaaggtgtg  7140
aagacacatg tcgccctcct cggcgtccag gaaggtgatt ggcttgtagg tgtaggccac   7200
gtgacccggg gttccggacg gggggtata aaaggggtg ggggcgcgct cgtcctcact    7260
ctcttccgca tcgctgtctg cgagggccag ctgctggggt gagtattccc tctcgaaggc  7320
gggcatgacc tcagcgctga ggctgtcagt ttctaaaaac gaggaggatt tgatgttcac   7380
ctgtcccgag ctgatgcctt tgagggtgcc cgcgtccatc tggtcagaaa acacgatctt  7440
tttattgtcc agcttggtgg cgaacgaccc gtagagggcg ttggagagca gcttggcgat   7500
ggagcgcagg gtctgattct tgtcccggtc ggcgcgctcc ttggccgcga tgttgagctg  7560
cacgtactcg cgcgcgacgc agcgccactc ggggaagacg gtggtgcgct cgtcgggcac   7620
caggcgcacg cgccagccgc ggttgtgcag ggtgacgagg tccacgctgg tggcgacctc  7680
gccgcgcagg cgctcgttgg tccagcagag gcgcccgccc ttgcgcgagc agaagggggg   7740
caggggggtcg agttgggttt cgtccggggg gtccgcgtcc accgtgaaga ccccgggggcg 7800
caggcgcgcg tcgaagtagt cgatcttgca tccttgcaag tccagcgccc gctgccagtc   7860
gcgggcggc agcgcgcgct cgtaggggtt gagcggcggg ccccagggca tggggtgggt   7920
gagcgcggag gcgtacatgc cgcagatgtc atagacgtag aggggctccc ggaggatgcc   7980
caggtaggtg gggtagcagc ggccgccgcg gatgctggcg cgcacgtagt cgtagagctc   8040
gtgcgagggg gcgaggaggt cggggcccag gttggtgcgg gcggggcgct ccgcgcggaa   8100
gacgatctgc ctgaagatgg catgcgagtt ggaagagatg gtgggggcgct ggaagacgtt  8160
gaagctggcg tcctgcaggc cgacggcgtc gcgcacgaag gaggcgtagg actcgcgcag   8220
cttgtgcacc agctcggcgg tgacctgcac gtcgagcgcg cagtagtcga gggtctcgcg   8280
gatgatgtca tacttagcct gcccctttctt ttttccacagc tcgcggttga ggacgaactc 8340
ttcgcggtct tttccagtact cttggatcgg gaaaccgtcc ggctccgaac ggtaagagcc  8400
cagcatgtag aactggttga cggcctggta ggcgcagcag cccttctcca cgggcagggc   8460
gtaggcctgc gcggccttgc ggagcgaggt gtgggtcagg gcgaaggtgt ccctgaccat   8520
gaccttgagg tactggtgtt tgaagtcgga gtcgtcgcag ccgccccgct cccagagcga   8580
gaagtcggtg cgcttttttgg agcgggggggtt gggcagcgcg aaggtgacat cgttgtagag 8640
gatcttgccc gcgcgaggca tgaagttgcg ggtgatgcgg aagggccccg gcacttccga   8700
gcggttgttg atgacctggg cggcgagcac gatctcgtcg aagccgttga tgttgtggcc   8760
cacgatgtag agttccagga agcggggccg gcccttgacg ctgggcagct tctttagctc   8820
ttcgtaggtg agctcctcgg gcgaggcgag gccgtgctcg gccagggccc agtccgccag   8880
gtgcgggttg tccgcgagga aggaccgcca gaggtcgcgg gccaggaggg tctgcaggcg   8940
gtccctgaag gtcctgaact ggcggcctac ggccatcttt tcggggggtga cgcagtagaa  9000
ggtgaggggg tcttgctgcc aggggtccca gtcgagctcc agggcgaggt cgcgcgcggc   9060
ggcgaccagg cgctcgtcgc ccccgaattt catgaccagc atgaagggca cgagctgctt   9120
tccgaaggcg cccatccaag tgtaggtctc tacatcgtag gtgacaaaga gacgttccgt   9180
gcgaggatgc gagccgatcg ggaagaactg gatctcccgc caccagttgg aggagtggct   9240
gttgatgtgg tgaaagtaga agtcccgtcg gcgggccgag cactcgtgct ggcttttgta   9300
aaagcgagcg cagtactggc agcgctgcac gggctgtacc tcttgcacga gatgcacctg   9360
ccgaccgcgg acgaggaagc tgagtgggaa tctgagcccc ccgcatggct cgcggcctgg   9420
```

```
ctggtgctct tctactttgg atgcgtggcc gtcaccgtct ggctcctcga ggggtgttac    9480
ggtggagcgg atcaccacgc cgcgcgagcc gcaggtccag atatcggcgc gcggcggtcg    9540
gagtttgatg acgacatcgc gcagctggga gctgtccatg gtctggagct cccgcggcgg    9600
cggcaggtca gccgggagtt cttgcaggtt tacctcgcag agacgggcca gggcgcgggg    9660
caggtccagg tggtacttga attcgagagg cgtgttggtg gcggcgtcga tggcttgcag    9720
tatgccgcag ccccgggggcg cgacgacggt gccccgcggg gcggtgaagc tcccgccgcc    9780
gctcctgctg tcgccgccgg tggcggggct tagaagcggt gccgcggtcg gcccccgga    9840
ggtaggggggg gctccggtcc cgcgggcagg ggcggcagcg gcacgtcggc gccgcgcgcg    9900
ggcaggagct ggtgctgcgc ccggaggttg ctggcgaagg cgacgacgcg gcggttgatc    9960
tcctggatct ggcgcctctg cgtgaagacg acgggtccgg tgagcttgaa cctgaaagag   10020
agttcgacag aatcaatctc ggtgtcattg accgcgacct ggcgcaggat ctcctgcacg   10080
tcgcccgagt tgtcttggta ggcgatctcg gccatgaact gttcaatctc ttcctcctgg   10140
aggtctccgc gtccggcgcg ctccacggtg gccgccaggt cgttggagat gcgcgccatg   10200
agctgcgaga aggcgttgag tccgccctcg ttccacactc ggctgtagac cacgccgccc   10260
tggtcgtcgc gggcgcgcat gaccacctgc gcgaggttga gttccacgtg gcgcgcaaag   10320
acggcgtagt tgcgcaggcg ctggaagagg tagttgaggg tggtggcggt gtgctcggcc   10380
acaaagaagt acatgaccca gcggcgcaac gtggattcgt tgatgtcccc caaggcctcc   10440
agtcgctcca tggcctcgta gaagtccacg gcgaagttga aaaactggga gttgcgcgcc   10500
gacacggtca actcctcctc cagaagacgg atgagctcgg cgacggtgtc gcgcacctcg   10560
cgctcgaagg ctatgggaat ctcttcctcc gccagcatca ccacctcttc ctcttcttcc   10620
tcctctggca cttccatgat ggcttcctcc tcttcggggg gtggcggcgg gggaggggggc   10680
gctcggcgcc ggcggcggcg caccgggagg cggtccacga agcgctcgat catctccccg   10740
cggcggcgac gcatggtctc ggtgacggcg cggccgttct ctcggggacg cagctggaag   10800
acgccgccgg tcatctggtg ctggggcggg tggccgtggg gcagcgagac cgcgctgacg   10860
atgcatctta acaattgctg cgtaggtacg ccgccgaggg acctgaggga gtccagatcc   10920
accggatccg aaaaccttc gaggaaggca tctaaccagt cgcagtcgca aggtaggctg   10980
agcaccgtgg cgggcggcgg ggggtggggg gagtgtctgg cggaggtgct gctgatgatg   11040
taattgaagt aggcggtctt gacacggcgg atggtcgaca ggagcaccat gtctttgggc   11100
ccggcctgct ggatgcggag gcggtcggcc atgcccagg cttcgttctg gcatctgcgc   11160
aggtctttgt agtagtcttg catgagcctt tccaccggca cctcttctcc ttcttcttct   11220
gacatctctg ctgcatctgc ggccctgggg cgacggcgcg cgccctgcc ccccatgcgc   11280
gtcaccccga accccctgag cggctggagc agggccaggt cggcgacgac gcgctcggcc   11340
aggatgcct gctggacctg cgtgagggtg gtttggaagt catccaagtc cacgaagcgg   11400
tggtaggcgc ccgtgttgat ggtgtaggtg cagttggcca tgacggacca gttgacggtc   11460
tggtggcccg gttgcgtcat ctcggtgtac ctgaggcgcg agtaggcgcg cgagtcgaag   11520
atgtagtcgt tgcaagtccg caccaggtac tggtagccca ccaggaagtg cggcggcggc   11580
tggcggtaga ggggccagcg gagggtggcg ggggctccgg gggccaggtc ttccagcatg   11640
aggcggtggt attcgtagat gtacctggac atccaggtga tgcccgcggc ggtggtggag   11700
gcgcgcggga agtcgcgcac ccggttccag atgttgcgca gcggcagaaa gtgctccatg   11760
```

```
gtaggcgtgc tctggccggt caggcgcgcg cagtcgttga tactctagac cagggaaaac    11820
gaaagccggt cagcgggcac tcttccgtgg tctggtggat aaattcgcaa gggtatcatg    11880
gcggagggcc tcggttcgag ccccgggccc gggccggacg gtccgccatg atccacgcgg    11940
ttaccgcccg cgtgtcgaac ccaggtggcg acgtcagaca acggtggagt gttccttttg    12000 ggttttttc  caaatttttc tggccgggcg ccgacgccgc cgcgtaagag actagagtgc    12060
aaaagcgaaa gcagtaagtg gctcgctccc tgtagcccgg aggatccttg ctaagggttg    12120
cgttgcggcg aaccccggtt cgagtctggc tctcgctggg ccgctcggt  cggccggaac    12180 cgcggctaag gcgggattgg cctcccctc  attaaagacc ccgcttgcgg attcctccgg    12240
acacagggga cgagcccctt tttacttttg cttttctcag atgcatccgg tgctgcggca    12300
gatgcgcccc ccgccccagc agcagcagca gcaacatcag caagagcggc accagcagca    12360
gcgggagtca tgcagggccc cctcgcccac gctcggcggt ccggcgacct cggcgtccgc    12420
ggccgtgtct ggagccggcg gcggtgggct ggcggacgac ccggaggagc ccccgcggcg    12480
cagggccaga cagtacctgg acctggagga gggcgagggc ctggcgcgac tggggcgcc    12540 gtcccccgag cgccacccgc gggtgcagct gaagcgcgac tcgcgcgagg cgtacgtgcc    12600
tcggcagaac ctgttcagag accgcgcggg cgaggagccc gaggagatgc gggaccgcag    12660
gttcgccgcg gggcgggagc tgcggcaggg gctgaaccgg gagcggctgc tgcgcgagga    12720
ggactttgag cccgacgcgc ggacggggat cagccccgcg cgcgcgcacg tggcggccgc    12780
cgacctggtg acggcgtacg agcagacggt gaaccaggag atcaacttcc aaaaaagctt    12840
caacaaccac gtgcgcacgc tggtggcgcg cgaggaggtg accatcggcc tgatgcacct    12900
gtgggacttt gtgagcgcgc tggagcagaa ccccaacagc aagcctctga cggcgcagct    12960
gttcctgata gtgcagcaca gcaggggcaa cgaggcgttc agggacgcgc tgctgaacat    13020
caccgagccc gagggtcggt ggctgctgga cctgattaac atcttgcaga gcatagtggt    13080
gcaggagcgc agcctgagcc tggccgacaa ggtggcggcc atcaattact cgatgctcag    13140
tctgggcaag ttttacgcgc gcaagatcta ccagacgccg tacgtgccca tagacaagga    13200
ggtgaagatc gacggcttct acatgcgcat ggcgctgaag gtgctgaccc tgagcgacga    13260
cctgggcgtg taccgcaacg agcgcatcca caaggccgtg agcgtgagcc ggcggcgcga    13320
gctgagcgac cgcgagctga tgcacagcct gcagcgggcg ctggcggggg ccggcagcgg    13380
cgacagggag gccgagtcct acttcgaggc gggggcggac ctgcgctggg tgcccagccg    13440
gagggccctg gaggccgcgg gggcccgccg cgaggactat gcagacgagg aggaggagga    13500
tgacgaggag tacgagctag aggagggcga gtacctggac taaaccgcag gtggtgtttt    13560
tggtagatgc aagacccgaa cgtggtggac ccggcgctgc gggcggctct gcagagccag    13620
ccgtccggcc ttaactctac agacgactgg cgacaggtca tggaccgcat catgtcgctg    13680
acggcgcgca atccggacgc gttccggcag cagccgcagg ccaacaggct ctccgccatc    13740
ttggaggcgg tggtgcctgc gcgcgcgaac cccacgcacg agaaggtgct ggccatagtg    13800
aacgcgctgg ccgagaacag ggccatccgc ccggacgagg ccgggctggt gtacgacgcg    13860
ctgctgcagc gcgtggcccg ctacaacagc ggcaacgtgc agaccaacct ggaccggctg    13920
gtgggggacg tgcgcgaggc ggtggcgcag cgggagcgcg cggagcggca gggaaacctg    13980
ggctccatgg tggcgctgaa cgccttcctg agcacgcagc cggccaacgt gccgcggggg    14040
caggaggact acaccaactt tgtgagcgcg ctgcggctga tggtgaccga cccccccag   14100 agcgaggtgt accagtcggg gccggactac ttttttccaga ccagcagaca gggcctgcag    14160
```

```
acggtgaacc tgagccaggc tttcaagaac ctgcggggc tgtgggcgt gaaggcgccc    14220 accgggacc  gggcgacggt gtccagcctg ctgacgccca actcgcgcct gctgctgctg    14280
ctgatcgcgc cgttcacgga cagcggcagc gtgtcccggg agacctacct cgggcacctg    14340
ctgacgctgt accgcgaggc catcgggcag acccaggtgg acgagcacac cttccaggag    14400
atcaccagcg tgagccgcgc gctggggcag gaggacacgg gcagcctgga ggcgaccctg    14460
aactacctgc tgaccaaccg gcggcagaag atccctcgc tgcatagttt gaccaccgag    14520
gaggagcgca tcctgcgcta cgtgcagcag agcgtgagcc tgaacctgat gcgcgacggg    14580
gtgacgccca gcgtggcgct ggacatgacc gcgcgcaaca tggaacgggg catgtacgcc    14640
gcgcatcggc cttacatcaa ccgcctgatg gactacttgc atcgcgcggc ggccgtgaac    14700
cccgagtact tcaccaacgc catcctgaac ccgcactggc tcccgccgcc cgggttctac    14760 agccgggggct tcgaggtccc cgaggccaac gacggcttcc tgtgggacga catggacgac    14820
agcgtgttct ccccgcggcc gcaggcgctg cggaggcgt cgctgctccg cctccccaag    14880
aaagaagaga gccgccggcc cagcagcgcg gcggcctctc tgtccgagct ggggggcggcg    14940 gccgcgcggc ccgggtccct gggggggcagc cccttttccca gtctggtggg gtctctgcag    15000
agcgggcgca ccacccggcc ccggctgctg ggcgaggacg agtacctgaa caactccctg    15060
atgcagccgg tgcgggagaa aaacctgccc ccgccttcc ccaacaacgg gatagagagc    15120
ctggtagaca agatgagcag atggaagacc tatgcgcagg agcacaggga ctcgcccgtg    15180
ctccgtccgc ccacgcggcg ccagcgccac gaccggcagc gggggctggt atgggatgac    15240
gaggactccg cggacgatag cagcgtgctg gacctgggg gagcggcgg taacccgttc    15300 gcgcacctgc gcccccgcct gggggaggatg tttcaataag aaaaatcaag catgatgcaa    15360 ggtttttttaa gcggataaat aaaaaactca ccaaggccat ggcgaccgag cgttgttggt    15420
ttcttgttgt gttcccttag tatgcggcgc gcggcgatgt accacgaggg acctcctccc    15480
tcttatgaga gcgtggtggg gcggcggcg gcctctccct ttgcgtcgca gctggagccg    15540
ccgtacgtgc ctccgcggta cctgcggcct acgggggaa gaaacagcat ccgttactcg    15600
gagctggcgc cctgtacga caccaccgg gtgtacctgg tggacaacaa gtcggcggac    15660
gtggcctccc tgaactacca gaacgaccac agcaattttt tgaccacggt catccagaac    15720
aatgactaca ccccgagcga ggccagcacc cagaccatca atctggatga ccggtcgcac    15780
tggggcggcg acctgaaaac catcctgcac accaacatgc caacgtgaa cgagttcatg    15840 ttcaccaata agttcaaggc gcgggtgatg gtgtcgcgtt cgcacaccaa ggacgaccgg    15900
gtggagctga agtacgagtg ggtagagttc gagctgcccg agggcaacta ctcggagacc    15960
atgaccatag acctgatgaa caacgcgatc gtggagcact atctgaaagt gggcaggcag    16020 aacgggcgtcc tggagagcga catcggggtc aagttcgaca ccaggaactt ccgcctgggg    16080
ctggaccccg tcaccgggct ggtcatgccc gggggtctaca ccaacgaggc cttccacccc    16140
gacatcatcc tgctgcccgg ctgcggggtg gacttcacct acagccgcct gagcaacctg    16200
ctgggcatcc gcaagcggca gcccttccag gagggctttta ggatcaccta cgaggacctg    16260
gaggggggca acatccccgc gctcctggat gtggaggcct accaggatag cttgaaggaa    16320
gaagaggcgg gagagggcag cggcggcggc ggcggcgccg gtcaggagga gggcggggcc    16380
tcctctgagg cctctgcgga cgccgccgct gccgccgagg cggaggcggc cgaccccgcg    16440
atggtggtag aggaagagaa ggatatgaat gacgaggcgg tgcgcggcga caccttttgcc    16500
```

```
acccgggggg aggagaagaa agcggaggcc gaggccgcgg cagaggaggc ggcagcggcg    16560
gcggcggcgc cagtagaggc ggcggccgag gcggagaagc ccccaagga gcccgtgatt    16620 aaggccctga ccgaagatag caagaagcgc agttacaacg tgctcaagga cagcaccaac    16680
accgcgtacc gcagctggta cctggcctac aactacggcg acccggcgac gggggtgcgc    16740
tcctggaccc tgctgtgtac gccggacgtg acctgcggct cggagcaggt gtactggtcg    16800
ctgcccgaca tgatgcaaga ccccgtgacc ttccgctcca cgcggcaggt cagcaacttc    16860
ccggtggtgg gcgccgagct gctgcccgtg cactccaaga gcttctacaa cgaccaggcc    16920
gtctactccc agctcatccg ccagttcacc tctctgaccc acgtgttcaa tcgctttcct    16980
gagaaccaga ttctggcgcg cccgcccgcc cccaccatca ccaccgtcag tgaaaacgtt    17040
cctgctctca cagatcacgg gacgctaccg ctgcgcaaca gcatcggagg agtccagcga    17100
gtgaccgtaa ctgacgccag acgccgcacc tgtccctacg tttacaaggc cctgggcata    17160
gtctcgccgc gcgtcctttc cagccgcact ttttaagcat gtccatcctc atctcgccca    17220
gcaataacac cggctggggc ctgctgcgcg cgcccagcaa gatgtttgga ggggcgagga    17280
agcgctccga ccagcacccc gtgcgcgtgc gcgggcacta ccgcgccccc tggggcgcgc    17340
acaaacgcgg gcgcaccggc accgcggggc gcaccaccgt ggacgaagcc atcgactcgg    17400
tggtggagca ggcgcgcaac tacacgcccg cggtctccac cgtggacgcg gctatcgaga    17460
gcgtggtgcg aggcgcgcgg cggtacgcca aggcgaagag ccgccggagg cgcgtggccc    17520
gccgccaccg ccgtcgaccc ggaagcgccg ccaagcgcgc cgccgccgcc ttgcttcgtc    17580
gggccagacg cacgggccgc cgcgccgcca tgagggccgc gcgccgcctg ccgccggca    17640 tcaccaccgt ggccccccgc gccagaagac gcgcggccgc tgccgccgcc gcggccatca    17700
gcgacctggc caccaggcgc cggggcaacg tgtactgggt gcgcgactcg gtgagcggca    17760
cgcgcgtgcc cgtgcgcttc cgccccccgc ggacttgaga ggagaggaca ggaaaaaagc    17820
atcaacaaca ccaccactga gtctcctgct gttgtgtgta tcccagcggc gcgcgcgcac    17880
acggcgacat gtccaagcgc aaaatcaaag aagagatgct ccaggtcgtc gcgccggaaa    17940
tctatgggcc cccgaagaag gaagagcagg atttcaagcc ccgcaagata aagcgggtca    18000
aaaagaaaaa gaaagatgac gatgatggcg aggtggagtt tctgcgcgcc acggcgccca    18060
ggcgcccgct gcagtggaag ggtcggcgcg taaagcgcgt tctgcgcccc ggcaccgcgg    18120
tggtcttcac gcccggcgag cgctccaccc gcactttcaa gcgcgtctat gacgaggtgt    18180
acggcgacga agacctgctg gagcaggcca acgatcgctc cggagagttt gcttacggaa    18240
agcggcaccg ggcgatggag aaggacgagg tgctggcgct gccgctggac cggggcaacc    18300
ccacccccag cctgaagccc gtgacccctgc agcaggtgct gccggccagc gcgccctccg    18360
agatgaagcg gggcctgaag cgcgagggcg gcgacctggc gccaccgtg cagctgatgg    18420 tgccaagcg gcagaggctg gaggacgtgc tggagaaaat gaaagtagac cccggcctgc    18480
agccggacat cagggtccgc cccatcaagc aggtggcgcc gggcctcggc gtgcagaccg    18540
tggacgtggt catccccacc ggcgcctcct cttccagcgc cgccgccgcc actagcaccg    18600
cggacatgga gacgcagact agctccgccc tcgccgcccc gcggccgcc gccgccgcca    18660 cctcctcggc ggaggtacag acggacccct ggatgccgcc gccggcggcc gccccctcgc    18720
gcgcacgccg cgggcgcagg aagtacggcg ccgccagccg gctcatgccc gagtacgcct    18780
tgcatccttc catcgcgccc accccgggct accgaggcta cagctaccgc ccgcgaagag    18840
ccaagggctc cacccgccgc agccgccgcg ccgccacctc tacccgccgc cgcagtcgcc    18900
```

```
gccgccgccg gcagcccgcg ctggctccga tctccgtgag gagagtggcg cgcaacgggg   18960
acaccttggt gctgcccagg gcgcgctacc accccagcat cgtttaaaag cctgttgtgg   19020
ttcttgcaga tatggccctc acttgccgcc tccgtttccc ggtgccggga taccgaggaa   19080
gatcgcgccg tagaagdggt atggccggac gcggcctgag cggaggcagc cgccgtgcgc   19140
accggcggcg acgcgccacc agccgacgca tgcgcggcgg ggtgctgcct ctgctgatcc   19200
ccctgatcgc cgcggcgatc ggcgccgtgc ccgggatcgc ctccgtggcc ttgcaggcgt   19260
cccagaggcg ttgacacaga cttcttgcaa gcttgcaaaa atatggaaaa aatcccccca   19320
ataaaaaagt ctagactctc acgctcgctt ggtcctgtga ctattttgta gaaaaaaaga   19380
tggaagacat caactttgcg tcgctggccc cgcgtcacgg ctcgcgcccg ttcctgggac   19440
actgaaacga tatcggcacc agcaacatga gcggtggcgc cttcagttgg ggctctctgt   19500
ggagcggcat taaaaatatc ggttctgccg ttaagaatta cggctccaag gcctggaaca   19560
gcagcacggg ccagatgttg agagacaagt tgaaagagca gaacttccag cagaaggtgg   19620
tggagggcct ggcctccggc atcaacgggg tggtggacct ggccaatcag gccgtgcaaa   19680
ataagatcaa cagcagactg gacccccggc cgccggtgga agagctgccg ccggcgctgg   19740
agacggtgtc ccccgatggg cggggcgaaa agcgcccgcg gcccgacagg aagagacca   19800 ctctggtcac gcacaccgat gagccgcccc cctacgagga agctctgaag caaggcttgc   19860
ccaccactcg gcccatcgcg cccatggcca ccggggtggt gggccgccac accccgcca   19920 ggctggacct gcctcctcct cctgtttctt cttcggccgc cgatgcgcag cagcagaagg   19980
cggcgctgcc cggtccgccc gcggccgccc cccgtcccac cgccagtcga gcgcccctgc   20040
gtcgcgcggc cagcggcccc cgcggggtcg cgaggcacag cagcggcaac tgcagaacca   20100
cgctgaacag catcgtgggt ctggggtgc agtccgtgaa gcgccgccga tgctactgaa   20160
tagcttagct aacggtgttg tatgtgtgta tgcgtcctat gtcaccgcca gaggagctgc   20220
tgagtcgccg ccgttcgcgc gcccaccgcc actaccaccg ccggtaccac tccagcgccc   20280
ctcaagatgg cgaccccatc gatgatgccg cagtggtcgt acatgcacat ctcgggccag   20340
gacgcctcgg agtacctgag ccccgggctg gtgcagttcg cccgcgccac cgacagctac   20400
ttcagcctga gtaacaagtt taggaacccc acggtggcgc ccacgcacga tgtgaccacc   20460
gaccggtccc agcgcctgac gctgcggttc atccccgtgg accgcgagga caccgcgtac   20520
tcttacaagg cgcggttcac cctggccgtg ggcgacaacc gcgtgctgga catggcctcc   20580
acctactttg acatccgcgg cgtgctggac aggggcccca ccttcaagcc ctactccggc   20640
accgcctaca actccctggc ccccaagggc gcccccaact cctgcgagtg ggagcaagag   20700
gagactcaga cagctgaaga ggcacaagac gaagaagaag atgaagctga agctgaggag   20760
gaaatgcctc aggaagagca agcacctgtc aaaaagactc atgtatatgc tcaggctccc   20820
ctttctggcg aaaaattac taaagacggt ctgcagatag aacgdacgc tacagctacc   20880 gaacaaaaac ctatttatgc agatcccaca ttccagccag aaccccaaat tggtgaatct   20940
cagtggaatg aggcagatgc ttcagttgcc ggcggtagag tgctgaagaa aactactccc   21000
atgaaaccct gttatggttc ctatgccagg cccacaaatg ccaatggagg tcagggtgta   21060
ttggtggaga aagacggtgg aaagatggaa agccaagtag atatgcaatt cttttcgact   21120
tctgaaaacg cccgtaacga ggctaacaac attcagccca aattggtgct gtacagcgag   21180
gatgtgcata tggagacccc agacacacac atttcttaca agcctgcaaa aagcgatgat   21240
```

```
aattcgaaag tcatgctggg tcagcagtcc atgcccaaca ggccaaatta catcggcttc   21300
agagacaact ttatcgggct catgtattac aacagcactg gcaacatggg ggtgctggca   21360
ggtcaggcct cacagttgaa tgcggtggtg gacttgcaag acagaaacac agaactgtcc   21420
taccagctct tgcttgattc catgggagac agaaccagat acttttccat gtggaatcag   21480
gcggtggaca gttatgatcc agatgtcaga attattgaaa atcatggaac tgaagatgag   21540
ctgcccaact attgtttccc tctgggaggc atagggggtaa ctgacactta ccaggccatt   21600
aagactaatg gcaatggcaa cggcggggc aataccactt ggaccaagga tgaaactttt   21660
gcagaccgca acgagatagg ggtgggaaac aatttcgcca tggagatcaa cctcagtgcc   21720
aacctgtgga ggaacttcct ctactccaac gtggccctgt acctgccaga caagcttaag   21780 tacaaccccct ccaacgtgga aatctctgac aaccccaaca cctacgacta catgaacaag   21840
cgagtggtgg ccccggggct ggtggactgc tacatcaacc tgggcgcgcg ctggtccctg   21900
gactacatgg acaacgtcaa ccccttcaac caccaccgca acgcgggcct gcgctaccgc   21960
tccatgcttc tgggcaacgg gcgctacgtg cccttccaca tccaggtgcc ccagaagttc   22020
tttgccatca agaacctcct cctcctgccg ggctcctaca cctacgagtg gaacttcagg   22080
aaggatgtca acatggtcct ccagagctct ctgggtaacg acctcagggt cgacggggcc   22140
agcatcaagt tcgagagcat ctgcctctac gccaccttct tccccatggc ccacaacacg   22200
gcctccacgc tcgaggccat gctcaggaac gacaccaacg accagtcctt caacgactac   22260
ctctccgccg ccaacatgct ctaccccatc cccgccaacg ccaccaacgt tcccatctcc   22320 atccctcgc gcaactgggc ggccttccgc ggctgggcct tcacccgcct caagaccaag   22380 gagacccct ccctgggctc gggtttcgac ccctactaca cctactcggg ctccataccc   22440
tacctggacg gaaccttcta cctcaaccac actttcaaga aggtctcggt cacccttcgac   22500 tcctcggtca gctggccggg caacgatcgc ctgctcaccc ccaacgagtt cgagatcaag   22560
cgctcggtcg acggggaggg ctacaacgtg gcccagtgca acatgaccaa ggactggttc   22620
ctcatccaaa tgctggccaa ctacaacatc ggctatcagg gcttctacat cccagagagc   22680
tacaaggaca ggatgtactc cttctttagg aacttccagc ccatgagccg gcaggtggtg   22740
gacgaaacca agtacaagga ctaccagcag gtgggcatca tccaccagca caacaactcg   22800
ggcttcgtgg gctacctcgc ccccaccatg cgcgagggac aggcctaccc cgccaacttc   22860
ccctacccgc tcattggcaa gaccgcggtc gacagcgtca cccagaaaaa gttcctctgc   22920
gaccgcaccc tctggcgcat ccccttctcc agcaacttca tgtccatggg tgcgctcacg   22980
gacctgggcc agaacctgct ctatgccaac tccgcccacg cgctcgacat gaccttcgag   23040 gtcgaccca tggacgagcc cacccttctc tatgttctgt tcgaagtctt tgacgtggtc   23100
cgggtccacc agccgcaccg cggcgtcatc gagaccgtgt acctgcgcac gcccttctcg   23160
gccggcaacg ccaccaccta agaagcaag ccgccaccgc caccacctgc atgtcgtcgg   23220
gttccaccga gcaggagctc aaggccatcg tcagagacct gggatgcggg ccctattttt   23280
tgggcacctt cgacaaacgc ttcccggggct tcgtcgcccc gcacaagctg gcctgcgcca   23340
tcgtcaacac ggccggccgc gagaccgggg gcgtgcactg gctggccttc gcctggaacc   23400
cgcgctccaa aacatgctac ctctttgacc ccttcggatt ctcggaccag cggctcaagc   23460
agatctacca gttcgagtac gagggcctgc tgcgccgcag cgccatcgcc tcctcgcccg   23520
accgctgcgt cacccctcgag aagtccacc agacgtgca ggggccccgac tcggccgcct   23580 gcggtctctt ctgctgcatg ttcctgcatg ccttttgtgca ctggccccag agtcccatgg   23640
```

```
accgcaaccc caccatgaac ttgctgacgg ggatccccaa ctccatgctc cagagccccc   23700
aggtcgcgcc caccctgcgc cgcaaccagg agcggctcta cagcttcctg gaacgccact   23760
cgccctactt ccgccgccac agcgcgcaga tcagggggc cacctctttc tgccgcatgc    23820
aagagatgca agggaaaatg caatgatgta cacagacact ttttcttttc tcaataaatg   23880
gcaactttat ttatacatgc tctctctcgg gtattcattt ccccaccacc caccacccgc   23940
cgccgccgta accatctgct gctggctttt tttttttttt ttaaaaatcg aaagggttct   24000
gccgggaatc gccgtgcgcc acgggcaggg acacgttgcg gaactggtag cgggtgcccc   24060
acttgaactc gggcaccacc atgcggggca agtcggggaa gttgtcggcc cacaggctgc   24120
gggtcagcac cagcgcgttc attaggtcgg gcgccgagat cttgaagtcg cagttggggc   24180
cgccgccctg cgcgcgcgag ttgcggtaca ccggggttgca acactggaac accagcagcg   24240
ccggataatt cacactggcc agcacgctcc ggtcggagat cagctcggcg tccaggtcct   24300
ccgcgttgct cagcgcgaac ggggtcagct tgggcacctg ccgccccagg aagggagcgt   24360
gccccggctt cgagttgcag tcgcagcgca gcgggatcag caggtgcccg cggccggact   24420
cggcgttggg gtacagcgcg cgcatgaagg cctccatctg gcggaaggcc atctgggcct   24480
tggcgccctc cgagaagaac atgccgcagg acttgcccga gaactggttc gcggggcagc   24540
tagcgtcgtg caggcagcag cgccgcgtcgg tgttggcgat ctgcaccacg ttgcgccccc   24600
accggttctt cacgattttg gccttggaag cctgctcctt cagcgcgcgc tgcccgttct   24660
cgctggtcac atccatctcg atcacgtgct ccttgttcac catgctgctg ccgtgcagac   24720
acttcagctc gccctccacc tcggtgcagc ggtgctgcca tagcgcgcag cccgtgggct   24780
cgaaatgctt gtaggtcacc tccgcgtagg actgcaggta ggcctgcagg aagcgccccca  24840 tcatggtcac gaaggtcttg ttgctgctga aggtcagctg cagcccgcgg tgctcctcgt   24900
tcagccaggc cttgcacacg gccgccagcc cctccacctg gtcgggcagc atcttgaagt   24960
tcagcttcag ctcattctcc acatggtact tgtccatcag cgcgcgcgca gcctccatgc   25020
ccttctccca ggccgacacc agcggcaggc tcaagggggtt caccaccgtc gcagccgccg   25080 ctgcgcttc gctttccgct ccgctgttct cttcttcctc ctcctcttct tcctcgccgc    25140
ccgcgcgcag cccccgcacc acgggtcgt cttcctgcag gcgccgcacc gagcgcttgc    25200
cgctcctgcc ctgcttgata cgcacggcg ggttgctgaa gcctaccatc accagcgcgg    25260
cctcttcttg ctcgtcctcg ctgtccacta tgacctcggg ggagggcgac ctcagaaccg   25320
tggcgcgctg cctcttcttt ttcctggggg cgtttgccag ctccgcggcc gcggccgccg   25380
ccgaggtcga aggccgaggg ctgggcgtgc gcggcaccag cgcgtcctgc gagccgtcct   25440
cgtcctcgga ctcgaggcgg cagcgagccc gcttcttcgg gggcgcgcgg ggcggcggcg   25500 gcggggcgg cggcgacgga gacggggacg agacatcgtc cagggtggga ggacggcggg    25560
ccgcgccgcg tccgcgctcg ggggtggttt cgcgctggtc ctcttcccga ctggccatct   25620
cccactgctc cttctcctat aggcagaaag agatcatgga gtctctcatg caagtcgaga   25680
aggaggagga cagcctaacc accaccgccc cctctgagcc ctccgccgcc gccgcggacg   25740
acgcgcccac caccaccgcc gccgccacca ccaccattac caccctaccc ggcgacgcag   25800
ccccgatcga gaaggaagtg ttgatcgagc aggacccggg ttttgtgagc gaagaggagg   25860
atgaggagga tgaaaaggag aaggataccc ccgcctcagt gccaaaagag gataaaaagc   25920
aagaccagga cgacgcagag acagatgagg cagcagtcgg gcgggggac ggaaggcatg     25980
```

```
atgatgatga cggctaccta gacgtgggag acgacgtgct gcttaagcac ctgcaccgcc   26040
agtgcgtcat cgtctgcgac gcgctgcagg agcgctgcga agtgcccctg acgtggcgg    26100
aggtcagccg cgcctacgag cggcacctct tcgcgccaca cgtgcccccc aagcgccggg   26160
agaacggcac ctgcgagccc aacccgcgcc tcaacttcta cccggtcttc gcggtacccg   26220
aggtgctggc cacctaccac atcttcttcc aaaactgcaa gatcccctc tcctgccgcg    26280
ccaaccgcac ccgcgccgac aagacgctgg ccctgcggca gggcgcccac atacctgata   26340
tcgcctctct ggaggaggtg cccaagatct tcgagggtct cggtcgcgac gagaaacggg   26400
cggcgaacgc tctgcaagga gacagcgaaa acgagagtca ctcggggtg ctggtggagc    26460
tcgagggcga caacgcgcgc ctggccgtgc tcaagcgcag catcgaagtc acccacttcg   26520
cctaccggc gctcaacctg cccccaagg tcatgagtgt ggtcatgagt gagctcatca     26580
tgcgccgcgc ccagcccctg gacgcggatg caaacttgca agagccctcc gaggaaggcc   26640
tgcccgcggt cagcgacgag cagctggcgc gctggctgga gacccgcgac ccgcccagc    26700
tggaggagcg gcgcaagctc atgatggccg cggtgctcgt caccgtggag ctcgagtgtc   26760
tgcagcgctt cttcggggac cccgagatgc agcgcaagct cgaggagacc ctgcactaca   26820
ccttccgcca gggctacgtg cgccaggcct gcaagatctc caacgtggag ctctgcaacc   26880
tggtctccta cctgggcatc ctgcacgaga accgcctcgg gcagaacgtc ctgcactcca   26940
ccctcaaagg ggaggcgcgc cgcgactacg tccgcgactg cgtctacctc ttcctctgct   27000
acacgtggca gacggccatg gggtctggc agcagtgcct ggaggagcgc aacctcaagg    27060
agctggagaa gctcctccgg cgcgccctca gggacctctg gacgggcttc aacgagcgct   27120
cggtggccgc cgcgctggcg gacatcatct tccccgagcg cctgctcaaa accctgcagc   27180
agggcctgcc cgacttcacc agccagagca tgctgcagaa cttcaggacc ttcatcctgg   27240
agcgctcggg catcctgccg gccacctgct gcgcgctgcc cagcgacttc gtgcccatca   27300
ggtacaggga gtgcccgccg ccgctctggg gccactgcta cctcttccag ctggccaact   27360
acctcgccta ccactcggat ctcatggaag acgtgagcgg cgagggcctg ctcgagtgcc   27420
actgccgctg caacctgtgc acgccccacc gctctctagt ctgcaatccg cagctgctca   27480
gcgagagtca gattatcggt accttcgagc tgcagggtcc ctcgcccgac gaaaagtccg   27540
cggctccggg gttgaaactc actccggggc tgtggacttc cgcctaccta cgcaaatttg   27600
tacctgaaga ctaccacgcc cacgagatca ggttttacga agaccaatcc cgcccgccca   27660
aggcggagct caccgcctgc gtcattaccc agggccacat cctgggccaa ttgcaagcca   27720
tcaacaaagc ccgccaagag ttcttgctga aaaagggtcg gggggtgtac ctggaccccc   27780
agtccggcga ggagctaaac ccgctacccc cgccgccgcc ccagcagcgg gaccttgctt   27840
cccaggatgg cacccagaaa gaagcagccg ccgccgccgc cagcatacat gcttctggag   27900
gaagaggagg actgggacag tcaggcagag gaggtttcgg acgaggacga ggaggaggag   27960
atgatggaag actgggagga ggacagccta gacgaggaag cttcagaggc cgaagaggtg   28020
gcagacgcaa caccatcacc ctcggccgca gcccctcgc cggcgccccc gaaatcctcc    28080
gaccccagca gcagcgctat aacctccgct cctccggcgc cggcgcccac ccgcagcaga   28140
cccaaccgta gatgggacac tacaggaacc ggggtcggta agtccaagtg ccccccagcg   28200
ccgcccccgc aacaggagca acagcagcag cagcggcgac agggctaccg ctcgtggcgc   28260
ggacacaaga acgccatagt cgcctgcttg caagactgcg ggggcaacat ctccttcgcc   28320
cgccgcttcc tgctcttcca ccacgggggtg gcttttcccc gcaatgtcct gcattactac  28380
```

```
cgtcatctct acagcccta ctgcggcggc agcggcgacc cagagggagc ggcggcagca    28440
gcagcgccag ccacagcggc gaccacctag gaagacctcc gcgggcaaga cggcgggagc    28500
cgggagaccc gcggcggcgg cggtagcggc ggcggcgggc gcactgcgcc tctcgcccaa    28560
cgaacccctc tcgacccggg agctcagaca caggatcttc cccactctgt atgctatctt    28620
ccagcagagc agaggccagg aacaggagct caaaataaaa aacagatctc tgcgctccct    28680
cacccgcagc tgtctgtatc acaaaagcga agatcagctt cggcgcacgc tggaggacgc    28740
ggaggcactc ttcagcaaat actgcgcgct gactcttaag gactagccgc gcgcccttct    28800
cgaatttagg cgggagaaag actacgtcat cgccgaccgc cgcccagccc acccagccga    28860
catgagcaaa gagattccca cgccctacat gtggagctac cagccgcaga tgggactcgc    28920
ggcgggagcg gcccaagact actccacccg catgaactac atgagcgcgg gcccccacat    28980
gatctcacgg gttaatggga tccgcgccca gcgaaaccaa atactgctgg aacaggcggc    29040
cataaccgcc acacccgtc atgacctcaa tccccgaaat tggcccgccg ccctcgtgta    29100
ccaggaaacc ccctctgcca ccaccgtggt acttccgcgt gacacccagg ccgaagtcca    29160
gatgactaac tcaggggcgc agctcgcggg cggctttcgt cacggggtgc ggccgcaccg    29220
gccgggtata ttacacctgg cgatcagagg ccgaggtatt cagctcaacg acgagtcggt    29280
gagctcttcg ctcggtctcc gtccggacgg aaccttccag atcgccggat caggtcgctc    29340
ctcattcacg cctcgccagg cgtatctgac tctgcagacc tcctcctcgg agcctcgctc    29400
cggcggcatc ggcaccctcc agttcgtgga ggagttcgtg ccctcggtct acttcaaccc    29460
cttctcggga cctcccggac gctaccccga ccagttcatc ccgaactttg acgcggtgaa    29520
ggactcggcg gacggctacg actgaatgtc aagtgctgag gcagagagcg ttcgcctgaa    29580
acacctccag cactgccgcc gcttcgcctg cttttgcccgc agctccggtg agttctgcta    29640 cttcagctg cccgaggagc ataccgaagg gccggcgcac ggcgtccgcc taaccaccca    29700
gggcgaggtt acctgtaccc ttatccggga gtttacccct cgtcccctgc tagtggagcg    29760
ggagcggggt tcttgtgtca taactatcgc ctgcaactgc cctaaccctg gattacatca    29820
agatctttgt tgtcacctgt gcgctgagta taataaacgc tgagatcaga ctctactggg    29880
gctcctgtcg ccatcctgtg aacgccaccg tcttcaccca ccccgagcag ccccaggcga    29940
acctcacctg cggcctgcgt cggagggcca agaagtacct cacctggtac ttcaacggca    30000
ccccctttgt ggtttacaac agcttcgacc aggacggagt tgccttgaga gacgaccttt    30060
ccggtctcag ctactccatt cacaagaaca ccacccctcca cctcttccct ccctacctgc    30120
cgggaaccta cgagtgcgtc accggccgct gcacccacct cctccgcctg atcgtaaacc    30180 agaccttttcc gggaacacac ctcttcccca gaacaggagg tgagctcagg aaaccccctg    30240
gggcccaggg cggagactta ccttcgaccc ttgtggggtt aggattttt atcgccgggt    30300 tgctggctct cctgatcaaa gcttccttca gatttgttct ctcccttac ttttatgaac    30360 agctcaactt ctaataacgc taccttttct caggaatcga gtagtaactt ctcttccgaa    30420
atcgggctgg gtgtgctgct tactctgttg atttttttcc ttatcatact tagccttctg    30480
tgcctcaggc tcgccgcctg ctgcgcacat atctacatct acagccggtt gcttaactgc    30540
tggggtcgcc atccaagatg aacggggctc aggtgctatg tctgctggcc ctggtggcct    30600
gcagtgccgc cgtcaatttt gaggaacccg cttgcaatgt gactttcaag cctgagggcg    30660
cacattgcac cactctggtt aaatgtgtga cctctcatga aaaactgctc atcgcctaca    30720
```

```
aaaacaaaac aggccagatc gcagtctata gcgagtggct acccggagac cataataact    30780
actcagtcac cgtcttcgag ggtgcggagt ctaagaaatt cgattacacc tttcccttcg    30840
aggagatgtg tgatgcggtc atgtacctgt ccaaacagta caagctgtgg ccccccaccc    30900
ccaaggcgtg tgtggaaaac actgggtctt tctgctgtct ctctctggca atcactgtgc    30960
ttgctctaat ctgcacgctg ctatacatga gattcaggca gaggcgaatc tttatcgatg    31020
agaaaaaaat gccttgatcg ctaacaccgg ctttctgtct gcagaatgaa agcaatcacc    31080
tccctactaa tcagcaccac cctccttgcg attgcccatg ggttgacacg aatcgaagtg    31140
ccagtggggt ccaatgtcac catggtgggc ccgccggca attcctccct gatgtgggaa    31200
aaatatgtcc gtaatcaatg ggatcattac tgctctaatc gaatctgtat caagcccaga    31260
gccacctgcg acgggcaaaa tctaactttg attgatgtgc aaatgacgga tgctgggtac    31320
tattacgggc agcggggaga aatgattaat tactggcgac cccacaagga ctacatgctg    31380
catgtagtca aggcagtccc aactactacc accccccacca ctaccactcc cactaccacc    31440 accccccacca ctaccactag cactgctact accgctgccc gcaaagctat acccgcaaa    31500 agcaccatgc ttagcaccaa gccccattct cactcccacg ccggcgggcc caccggtgcg    31560
gcctcagaaa ccaccgagct ttgcttctgc caatgcacta acgccagcgc ccacgaactg    31620
ttcgacctgg agaatgagga cgatgaccag ctgagctccg cttgcccggt cccgctgccc    31680
gcagagccgg tcgccctgaa gcagctcggt gatccattta atgactctcc tgtttatccc    31740
tctcccgaat accctcccga ctctaccttc cacatcacgg gcaccaaaga ccccaacctc    31800
tccttctacc tgatgctgct gctctgtatc tctgtggtat cttccgcgct catgttactg    31860
ggcatgttct gctgcctcat ctgccgcaga aaaagaaagt ctcgctctca gggccaacca    31920
ctgatgccct tccccctaccc cccagatttt gcagataaca agatatgagc acgctgctga    31980
cactaaccgc tttactcgcc tgcgctctaa cccttgtcgc ttgcgaatcc agataccaca    32040
atgtcacagt tgtgacagga gaaaatgtta cattcaactc cacggccgac acccagtggt    32100
cgtggagtgg ccacggtagc tatgtataca tctgcaatag ctccacctcc cctagcatgt    32160
cctctcccaa gtaccactgc aatgacagcc tgttcaccct catcaacgcc tccacctcgg    32220
acaatggact ctatgtaggc tatgtgacac ccggtgggca gggaaagacc cacgcctaca    32280
acctgcaagt tcgccacccc tccaccaccg ccaccacctc tgccgcccct acccgcagca    32340
gcagcagcag cagcagcagc agcagcagca gcagcagcag attcctgact ttaatcctag    32400
ccagctcaac aaccaccgcc accgctgaga ccacccacag ctccgcgccc gaaaccaccc    32460
acacccacca cccagagacg accgcggcct ccagcgacca gatgtcggcc aacatcaccg    32520
cctcgggtct tgaacttgct tcaaccccca ccccaaaacc agtggatgca gccgacgtct    32580
ccgccctcgt caatgactgg gcggggctgg gaatgtggtg gttcgccata ggcatgatgg    32640
cgctctgcct gcttctgctc tggctcatct gctgcctcaa ccgcaggcgg gccagaccca    32700
tctatagacc catcattgtt ctcaaccccg ctgatgatgg gatccataga ttggatggtc    32760
tgaaaaacct actttctctct tttacagtat gataaattga gacatgcctc gcattttcat    32820
gtacttgaca cttctcccac tttttctggg gtgttctacg ctggccgccg tctctcacct    32880
cgaggtagac tgcctcacac ccttcactgt ctacctgatt tacggattgg tcaccctcac    32940
tctcatctgc agcctaatca cagtagtcat cgccttcatc cagtgcattg actacatctg    33000
tgtgcgcctc gcatacctga gacaccaccc gcagtaccga gacaggaaca ttgcccaact    33060
cctaagactg ctctaatcat gcataagact gtgatctgcc tcctcatcct cctctcccctg    33120
```

```
cccgctctcg tctcatgcca gcccaccaca aaacctccac gaaaaagaca tgcctcctgt   33180
cgcttgagcc aactgtggaa tattcccaaa tgctacaatg aaaagagcga gctttccgaa   33240
gcctggctat atgcggtcat gtgtgtcctt gtcttctgca gcacaatctt tgccctcatg   33300 atctacccc  actttgattt gggatggaat gcggtcgatg ccatgaatta ccctacctttc  33360 cccgcgcccg atatgattcc actccgacag gttgtggtgc ccgtcgccct caatcaacgc   33420
cccccatccc ctacacccac tgaggtcagc tactttaatc taacaggcgg agatgactga   33480
cactctagat ctagaaatgg acggcatcgg caccgagcag cgtctcctac agaggcgcaa   33540
gcaggcggct gaacaagagc gcctcaatca ggagctccga gatctcatta acctgcacca   33600
gtgcaaaaaa ggcatctttt gcctggtcaa gcaggccgat gtcacctacg agaaaccgg    33660 taacagccac cgcctcagct acaagctgcc cacccaacgc cagaagttgg tgctcatggt   33720
gggtcagaat cccatcaccg tcacccagca ctcggtggag accgaggggt gtctgcactc   33780
cccctgtcag ggtccggaag acctctgcac cctggtaaag accctgtgtg gtcttagaga   33840
tttaatcccc tttaactaat caaacactgg aatcaataaa agaatcact  tactttaaat   33900 cagtcagcag gtctctgtcc actttattca gcagcacctc cttcccctcc tcccaactct   33960
ggtactccaa acgcctcctg gcggcaaact tcctccacac cctgaaggga atgtcagatt   34020
cttgctcctg tccctccgca cccactatct tcatgttgtt gcagatgaag cgcgccaaaa   34080
cgtctgacga gaccttcaac cccgtgtacc cctatgacac ggaaaacggg cctccctccg   34140
ttcctttcct cacccctccc ttcgtgtccc ccgacggatt tcaagaaagc cccccagggg   34200
tcctgtctct gcgcctgtca gagcccctgg tcacttccca cggcatgctt gccctgaaaa   34260
tgggaaatgg cctctccctg gatgacgccg gcaacctcac ctctcaagat gtcaccaccg   34320
tcacccctcc cctcaaaaaa accaagacca acctcagcct ccagacctca gcccccctga   34380
ccgttagctc tgggtccctc accgtcgcgg ccgccgctcc actggcggtg gccggcacct   34440
ctctcaccat gcaatctcag gccccctga cggtgcaaga tgcaaaactg ggtctggcca    34500
cccagggacc cctgaccgtg tctgaaggca aactcacctt gcagacatcg gctccactga   34560
cggccgccga cagcagcact ctcactgttg gcaccacacc gccaatcagt gtgagcagtg   34620
gaagtctagg cttagatatg gaagacccca tgtatactca cgatggaaaa ctgggaatca   34680
gaattggtgg cccactgcaa gtagtagaca gcttgcacac actcactgta gttactgaa    34740 acggaataac tgtagctaac aatgcccttc aaactaaagt tgcgggtgcc ctgggttatg   34800
actcatctgg caatctagaa ttgcgagccg caggggggtat gcgaattaac acaggggtc   34860 aactcattct tgatgtggct tatccatttg atgctcagaa caatctcagc cttagactcg   34920
gccagggacc tttatatgtg aacaccaatc acaacctaga tttaaattgc aacagaggtc   34980
tgaccacaac caccagcagt aacacaacca aacttgaaac taaaatcgat tcgggcttag   35040
actataacgc caatgggct  atcattgcta aacttggcac tgggttaacc tttgacaaca   35100
caggtgccat aactgtggga aacactgggg atgacaaact cactctgtgg actaccccag   35160
atccctctcc taactgcaga attcacgcag acaaagactg caagtttact ctagtcctga   35220
ctaagtgtgg aagtcaaatt ctggcctccg tcgccgccct ggcggtgtct ggaaacctat   35280
catcaatgac aggcactgtc tccagcgtta ccatcttcct cagattcgat cagaatggag   35340
ttcttatgga aaaattcctc gctagacaagg agtactggaa cttcagaaat ggtaattcca   35400
ccaatgccac cccctacacc aatgcggttg ggttcatgcc caacctcagc gcctacccca   35460
```

```
aaacccagag tcaaactgca aaaaacaaca ttgtaagtga ggtttactta catggggaca   35520
aatctaaacc catgatcctt accattaccc ttaatggcac aaatgaatcc agtgaaacta   35580
gtcaggtgag tcactactcc atgtcattta catggtcgag ggacagtggg aaatatgcca   35640
ccgaaacctt tgccaccaac tcttttacct tctcctacat tgctgaacaa taaagaagca   35700
taacgctgct gttcatttgt aatcaagtgt tactttttta tttttcaatt acaacagaat   35760
cattcaagtc attctccatt tagcttaata gaccccagta gtgcaaagcc ccatactagc   35820
ttatttcagc aattgggaga agtactcgcc tacatggggg tagagtcata atcgtgcatc   35880
aggatagggc ggtggtgctg cagcagcgcg cgaataaact gctgccgccg ccgctccgtc   35940
ctgcaggaat acaacatggc agtggtctcc tcagcgatga ttcgcaccgc ccgcagcata   36000
aggcgccttg tcctccgggc acagcagcgc accctgatct cacttaaatc agcacagtaa   36060
ctgcagcaca gcaccacaat attgttcaaa atcccacagt gcaaggcgct gtatccaaag   36120
ctcatggcgg ggaccacaga acccacgtgg ccatcatacc acaagcgcag gtagattaag   36180
tggcgacccc tcataaacac gctggacata acattacct cttttggcat gttgtaattc   36240
accacctccc ggtaccatat aaacctctga ttaaacatgg cgccatccac caccatccta   36300
aaccagctgg ccaaaacctg cccgccggct atacactgca gggaaccggg actgaacaa   36360 tgacagtgga gagcccagga ctcgtaacca tggatcatca tgctcgtcat gatatcaatg   36420
ttggcacaac acaggcacac gtgcatacac ttcctcagga ttacaagctc ctcccgcgtt   36480
agaaccatat cccagggaac aacccattcc tgaatcagcg taaatcccac actgcaggga   36540
agacctcgca cgtaactcac gttgtgcatt gtcaaagtgt tacattcggg cagcagcgga   36600
tgatcctcca gtatggtagc gcgggtttct gtctcaaaag gaggtagacg atccctactg   36660
tacggagtgc gccgagacaa ccgagatcgt gttggtcgta gtgtcatgcc aaatggaacg   36720
ccggacgtag tcatatttcc tgaagtcttg gcgcgccaga cccgagtctt accaggaaaa   36780
ttttaaaaaa gattcctcaa cgcagcacca gcaccaacac ctgtcagtgt aaaatgccaa   36840
gcgccgagcg agtatatata ggaataaaaa gtgacgtaaa cggttaaagt ccagaaaacg   36900
cccagaaaaa ccgcacgcga acctacgccc gaaacgaaa gccaaaaaac agtgaacacg   36960 cccttttcggc gtcaacttcc gctttcccac ggtacgtcac ttccgcatat agtaaaacta   37020
cgctacccaa catgcaagaa gccacgcccc aaaacacgtc acacctcccg gcccgccccg   37080
cgccgccgct cctccccgcc ccgccccgct ccgcccacct cattatcata ttggcttcaa   37140
tccaaaataa ggtatattat tgatgatg                                     37168
```

<210> SEQ ID NO 8
<211> LENGTH: 36397
<212> TYPE: DNA
<213> ORGANISM: Artificial Sequence
<220> FEATURE:
<223> OTHER INFORMATION: synthetic chimpanzee adenovirus serotype PanAd3
      with Ebola virus Sudan/Gulu codon optimized
      transmembrane envelope glycoprotein (GP) insert
      (PanAd3 GP Ebola S/G (PB/6611))
<220> FEATURE:
<221> NAME/KEY: CDS
<222> LOCATION: (1624)...(3654)
<223> OTHER INFORMATION: Ebola virus Sudan/Gulu codon optimized
      transmembrane envelope glycoprotein (GP) insert in PanAd3 GP Ebola
      S/G (PB/6611)
<220> FEATURE:
<221> NAME/KEY: CDS
<222> LOCATION: (14671)...(16425)
<223> OTHER INFORMATION: chimpanzee adenovirus serotype ChAd63 penton
<220> FEATURE:

```
<221> NAME/KEY: CDS
<222> LOCATION: (19516)...(22410)
<223> OTHER INFORMATION: chimpanzee adenovirus serotype ChAd63 hexon
<220> FEATURE:
<221> NAME/KEY: CDS
<222> LOCATION: (33294)...(34922)
<223> OTHER INFORMATION: chimpanzee adenovirus serotype ChAd63 fiber

<400> SEQUENCE: 8
```

| | | | | | |
|---|---|---|---|---|---|
| catcatcaat | aatatacctt | attttggatt | gaagccaata | tgataatgag | gtgggcggag | 60 |
| cggggcgggg | cggggaggag | cggcggcgcg | gggcgggccg | ggaggtgtgg | cggaagttga | 120 |
| gtttgtaagt | gtggcggatg | tgacttgcta | gcgccggatg | tggtaaaagt | gacgttttt | 180 |
| ggagtgcgac | aacgcccacg | ggaagtgaca | ttttccgc | ggttttacc | ggatgtcgta | 240 |
| gtgaatttgg | gcgttaccaa | gtaagatttg | gccattttcg | cgggaaaact | gaaatgggga | 300 |
| agtgaaatct | gattaatttc | gcgttagtca | taccgcgtaa | tatttgccga | gggccgaggg | 360 |
| actttgaccg | attacgtgga | ggaatcgccc | aggtgttttt | tgaggtgaat | ttccgcgttc | 420 |
| cgggtcaaag | tctccgtttt | attattatag | gtatacccat | tgcatacgtt | gtatccatat | 480 |
| cataatatgt | acatttatat | tggctcatgt | ccaacattac | cgccatgttg | acattgatta | 540 |
| ttgactagtt | attaatagta | atcaattacg | gggtcattag | ttcatagccc | atatatggag | 600 |
| ttccgcgtta | cataacttac | ggtaaatggc | ccgcctggct | gaccgcccaa | cgaccccgc | 660 |
| ccattgacgt | caataatgac | gtatgttccc | atagtaacgc | caatagggac | tttccattga | 720 |
| cgtcaatggg | tggagtattt | acggtaaact | gcccacttgg | cagtacatca | agtgtatcat | 780 |
| atgccaagta | cgccccctat | tgacgtcaat | gacggtaaat | ggcccgcctg | gcattatgcc | 840 |
| cagtacatga | ccttatggga | cttcctact | tggcagtaca | tctacgtatt | agtcatcgct | 900 |
| attaccatgg | tgatgcggtt | ttggcagtac | atcaatgggc | gtggatagcg | gtttgactca | 960 |
| cggggatttc | caagtctcca | ccccattgac | gtcaatggga | gtttgttttg | gaaccaaaat | 1020 |
| caacgggact | ttccaaaatg | tcgtaacaac | tccgccccat | tgacgcaaat | gggcggtagg | 1080 |
| cgtgtacggt | gggaggtcta | tataagcaga | gctctcccta | tcagtgatag | agatctccct | 1140 |
| atcagtgata | gagatcgtcg | acgagctcgt | ttagtgaacc | gtcagatcgc | ctggagacgc | 1200 |
| catccacgct | gttttgacct | ccatagaaga | caccgggacc | gatccagcct | ccatcggctc | 1260 |
| gcatctctcc | ttcacgcgcc | cgccgcccta | cctgaggccg | ccatccacgc | cggttgagtc | 1320 |
| gcgttctgcc | gcctcccgcc | tgtggtgcct | cctgaactgc | gtccgccgtc | taggtaagtt | 1380 |
| taaagctcag | gtcgagaccg | ggcctttgtc | cggcgctccc | ttggagccta | cctagactca | 1440 |
| gccggctctc | cacgctttgc | ctgaccctgc | ttgctcaact | ctagttaacg | gtggagggca | 1500 |
| gtgtagtctg | agcagtactc | gttgctgccg | cgcgcgccac | cagacataat | agctgacaga | 1560 |
| ctaacagact | gttcctttcc | atgggtcttt | tctgcagtca | ccgtcgtcga | cgatatcgcc | 1620 |
| gccatggagg | gcctgagcct | gctgcagctg | cccaggaca | agttcaggaa | gagcagcttc | 1680 |
| ttcgtgtggg | tgatcatcct | gttccagaag | gccttcagca | tgccctggg | cgtggtgacc | 1740 |
| aacagcaccc | tggaggtgac | cgagatcgac | cagctggtgt | gcaaggacca | cctggccagc | 1800 |
| accgaccagc | tgaagagcgt | gggcctgaac | ctggagggca | cgcgcgtgag | caccgacatc | 1860 |
| cccagcgcca | ccaagaggtg | gggcttcagg | agcggcgtgc | ctcccaaggt | ggtgagctac | 1920 |
| gaggccggcg | agtgggccga | gaactgctac | aacctggaga | tcaagaagcc | cgacggcagc | 1980 |
| gagtgcctgc | ctcctcctcc | tgacggcgtg | aggggcttcc | ccaggtgcag | gtacgtgcac | 2040 |
| aaggcccagg | gcaccggccc | ctgccccggc | gactacgcct | tccacaagga | cggcgccttc | 2100 |

```
ttcctgtacg acaggctggc cagcaccgtg atctacaggg gcgtgaactt cgccgagggc    2160
gtgatcgcct tcctgatcct ggccaagccc aaggagacct tcctgcagag ccctcccatc    2220
agggaggccg tgaactacac cgagaacacc agcagctact acgccaccag ctatctagag    2280
tacgagatcg agaacttcgg cgcccagcac agcaccaccc tgttcaagat cgacaacaac    2340
accttcgtga ggctggacag gccccacacc cctcagttcc tgttccagct gaacgacacc    2400
atccacctgc accagcagct gagcaacacc accggcaggc tgatctggac cctggacgcc    2460
aacatcaacg ccgacatcgg cgagtgggcc ttctgggaga caagaagaa cctgagcgag    2520
cagctgaggg gcgaggagct gagcttcgag gccctgagcc tgaacgagac cgaggacgac    2580
gacgccgcca gcagcaggat caccaagggc aggatcagcg acagggccac caggaagtac    2640
agcgacctgg tgcccaagaa cagccccggc atggtgcccc tgcacatccc cgagggcgag    2700
accaccctgc ccagccagaa cagcaccgag ggcaggaggg tgggcgtgaa cacccaggag    2760
accatcaccg agaccgccgc caccatcatc ggcaccaacg gcaaccacat gcagatcagc    2820
accatcggca tcaggcccag cagcagccag atccccagca gcagccccac caccgcccct    2880
agccccgagg cccagacccc caccacccac accagcggac ccagcgtgat ggccaccgag    2940
gagcccacca cccctcccgg cagcagcccc ggacccacca ccgaggcccc taccctgacc    3000
accccctgaga acatcaccac cgccgtgaag accgtgctgc cccaggagag caccagcaac    3060
ggcctgatca ccagcaccgt gaccggcatc ctgggcagcc tgggcctgag gaagaggagc    3120
aggaggcaga ccaacaccaa ggccaccggc aagtgcaacc ccaacctgca ctactggacc    3180
gcccaggagc agcacaacgc cgccggcatc gcctggattc cctacttcgg ccccggcgcc    3240
gagggcatct acaccgaggg cctgatgcac aaccagaacg ccctggtgtg cggcctgagg    3300
cagctggcca acgagaccac ccaggccctg cagctgttcc tgagggccac caccgagctg    3360
aggacctaca ccatcctgaa caggaaggcc atcgacttcc tgctgaggag gtggggcggc    3420
acctgcagga ttctgggccc cgactgctgc atcgagcccc acgactggac caagaacatc    3480
accgacaaga tcaaccagat catccacgac ttcatcgaca ccctctgcc caaccaggac    3540
aacgacgaca actggtggac cggctggcgg cagtggatac ctgccggcat cggcatcacc    3600
ggcatcatca tcgccatcat cgctctgctg tgcgtgtgca agctgctgtg ctgagaattc    3660
agatctgctg tgccttctag ttgccagcca tctgttgttt gcccctcccc cgtgccttcc    3720
ttgaccctgg aaggtgccac tcccactgtc ctttcctaat aaaatgagga aattgcatcg    3780
cattgtctga gtaggtgtca ttctattctg ggggtgggg tggggcagga cagcaagggg    3840
gaggattggg aagacaatag caggcatgct ggggatgcgg tgggctctag atatcagcga    3900
tcgctgaggt gggtgagtgg gcgtggtctg ggggtgggaa gcaatatata agttgggggt    3960
cttagggtct ctgtgtctgt tttgcagagg accgccggc gccatgagcg ggagcagtag    4020
cagcaacgcc ttggatggca gcatcgtgag cccttatttg acgacgcgca tgccccactg    4080
ggccggggtg cgtcagaatg tgatgggctc cagcatcgac ggacgacccg tgctgcccgc    4140
aaattccgcc acgctgacct acgcgaccgt cgcggggacc ccgttggacg ccaccgccgc    4200
cgccgccgcc accgccgccg cctcggccgt gcgcagcctg ccacggact ttgcattctt    4260
gggacccttg gccaccgggg cggccgcccg tgccgccgtt cgcgatgaca agctgaccgc    4320
cctgctggcg cagttggatg cgcttacccg ggaactgggt gacctttcgc agcaggtcgt    4380
ggccctgcgc cagcaggtct ccgccctgca ggctagcggg aatgcttctc ctgcaaatgc    4440
```

-continued

```
cgtttaagat aaataaaacc agactctgtt gataaataaa accagactct gtttggatta    4500
aagaaaagta gcaagtgcat tgctctcttt atttcataat tttccgcgcg cgataggccc    4560
gagtccagcg ttctcggtcg ttgagggtgc ggtgtatctt ctccaggacg tggtagaggt    4620
ggctctggac gttgagatac atgggcatga gcccgtcccg ggggtggagg tagcaccact    4680
gcagagcttc atgctccggg gtggtgttgt agatgatcca gtcgtagcag gagcgctggg    4740
catggtgcct aaaaatgtcc ttaagcagca ggccgatggc caggggagg cccttggtgt     4800
aagtgtttac aaaacggttg agttgggaag ggtgcatgcg gggtgagatg atgtgcatct    4860
tagattgtat ttttagattg gcgatgtttc ctcccagatc ccttctggga ttcatgttgt    4920
ggaggaccac cagcacagta tatccggtgc acttgggaaa tttgtcatgc agcttagagg    4980
gaaatgcgtg gaagaacttg gagacgccct tgtggcctcc cagattctcc atgcattcgt    5040
ccatgatgat ggcaatgggc ccgcgggagg cggcctgggc aaagatgttt ctggggtcac    5100
tgacatcgta gttgtgttcc agggtgagat cgtcataggc cattttttata aagcgcgggc    5160
ggagggtgcc cgactggggg atgatggttc cctcgggccc cggggcgtag ttgccttcgc    5220
agatctgcat ttcccaggcc ttaatctctg agggggaat catatccact tgcggggcga    5280
tgaagaaaac ggtttccgga ccgggagag ttaactggga tgagagcagg tttctcagca    5340
gctgtgactt tccacagccg gtgggtccat aaataacacc tataaccggc tgcagctggt    5400
agttgagcga gctgcagctg ccgtcgtccc ggaggagggg ggccacctca ttgagcatgt    5460
cccggacgcg cttgttctcc tcgaccaggt ccgccagaag gcgctcgccg cccagggaca    5520
gcagctcttg caaggaagca agttttttca gcggtttgag gccgtccgcc gtgggcatgt    5580
ttttcagggt ctggccgagc agctccaggc ggtcccagag ctcggtgacg tgctctacgg    5640
catctctatc cagcatatct cctcgtttcg cggttggggg cggctttcgc tgtagggcac    5700
caggcgatgg tcgtccagcg cggccagagt catgtccttc catgggcgca gggtcctcgt    5760
cagggtggtc tgggtcacgg tgaaggggtg cgccccgggc tgggcgctgg ccagggtgcg    5820
cttgagactg gtcctgctgg tgctgaagcg ctgccggtct tcgccctgcg cgtcggccag    5880
gtagcatttg accatggtgt cgtagtccag ccctcggcg gcgtgtccct tggcgcgcag    5940
cttgcccttg gaggtggcgc cgcacgcggg gcactgcagg ctcttgagcg cgtagagctt    6000
gggggcgagg aagaccgatt cggggggagta ggcgtccgcg ccgcaggccc cgcacacggt    6060
ctcgcactcc accagccagg tgagctcggg gcgctcgggg tcaaaaacca ggtttccccc    6120
atgctttttg atgcgtttct tacctcgggt ctccatgagg cggtgtcccc gttcggtgac    6180
gaagaggctg tccgtgtctc cgtagaccga cttgaggggt ctgtcctcca gggggtccc    6240
tcggtcctct tcgtagagaa actcggacca ctctgagaca aaggcccgcg tccaggccag    6300
gacgaaggag gccaggtggg aggggtaccg gtcgttgtcc actaggggt ccaccttctc    6360
caaggtgtga agacacatgt cgccctcctc ggcgtccagg aaggtgattg gcttgtaggt    6420
gtaggccacg tgacccgggg ttccggacgg gggggtataa aaggggggtgg gggcgcgctc    6480
gtcctcactc tcttccgcat cgctgtctgc gagggccagc tgctggggtg agtattccct    6540
ctcgaaggcg ggcatgacct cagcgctgag gctgtcagtt tctaaaaacg aggaggattt    6600
gatgttcacc tgtcccgagc tgatgccttt gagggtgccc gcgtccatct ggtcagaaaa    6660
cacgatcttt ttattgtcca gcttggtggc gaacgacccg tagagggcgt tggagagcag    6720
cttggcgatg gagcgcaggg tctgattctt gtcccggtcg gcgcgctcct tggccgcgat    6780
gttgagctgc acgtactcgc gcgcgacgca gcgccactcg gggaagacgg tggtgcgctc    6840
```

```
gtcgggcacc aggcgcacgc gccagccgcg gttgtgcagg gtgacgaggt ccacgctggt    6900
ggcgacctcg ccgcgcaggc gctcgttggt ccagcagagg cgcccgccct tgcgcgagca    6960 gaagggggc aggggtcga gttgggtttc gtccggggg tccgcgtcca ccgtgaagac       7020 cccgggcgc aggcgcgcgt cgaagtagtc gatcttgcat ccttgcaagt ccagcgcccg    7080
ctgccagtcg cgggcggcga gcgcgcgctc gtaggggttg agcggcgggc cccagggcat    7140
ggggtgggtg agcgcggagg cgtacatgcc gcagatgtca tagacgtaga ggggctcccg    7200
gaggatgccc aggtaggtgg ggtagcagcg gccgccgcgg atgctggcgc gcacgtagtc    7260
gtagagctcg tgcgaggggg cgaggaggtc gggggcccagg ttggtgcggg cggggcgctc   7320
cgcgcggaag acgatctgcc tgaagatggc atgcgagttg aagagatgg tggggcgctg    7380 gaagacgttg aagctggcgt cctgcaggcc gacggcgtcg cgcacgaagg aggcgtagga    7440
ctcgcgcagc ttgtgcacca gctcggcggt gacctgcacg tcgagcgcgc agtagtcgag    7500
ggtctcgcgg atgatgtcat acttagcctg cccttctttt ttccacagct cgcggttgag    7560
gacgaactct tcgcggtctt ccagtactc ttggatcggg aaaccgtccg gctccgaacg     7620
gtaagagccc agcatgtaga actggttgac ggcctggtag gcgcagcagc ccttctccac    7680
gggcagggcg taggcctgcg cggccttgcg gagcgaggtg tgggtcaggg cgaaggtgtc    7740
cctgaccatg accttgaggt actggtgttt gaagtcggag tcgtcgcagc cgcccgctc    7800 ccagagcgag aagtcggtgc gcttttgga gcggggttg ggcagcgcga aggtgacatc     7860
gttgtagagg atcttgcccg cgcgaggcat gaagttgcgg gtgatgcgga agggccccgg   7920
cacttccgag cggttgttga tgacctgggc ggcgagcacg atctcgtcga agccgttgat    7980
gttgtggccc acgatgtaga gttccaggaa gcggggccgg cccttgacgc tgggcagctt    8040
ctttagctct tcgtaggtga gctcctcggg cgaggcgagg ccgtgctcgg ccagggccca    8100
gtccgccagg tgcgggttgt ccgcgaggaa ggaccgccag aggtcgcggg ccaggagggt    8160
ctgcaggcgg tccctgaagg tcctgaactg gcggcctacg gccatctttt cggggtgac    8220 gcagtagaag gtgagggggt cttgctgcca ggggtcccag tcgagctcca gggcgaggtc    8280
gcgcgcggcg gcgaccaggc gctcgtcgcc cccgaatttc atgaccagca tgaagggcac    8340
gagctgcttt ccgaaggcgc ccatccaagt gtaggtctct acatcgtagg tgacaaagag    8400
acgttccgtg cgaggatgcg agccgatcgg gaagaactg atctcccgcc accagttgga    8460
ggagtggctg ttgatgtggt gaaagtagaa gtcccgtcgg cgggccgagc actcgtgctg    8520
gcttttgtaa aagcgagcgc agtactgca gcgctgcacg gctgtacct cttgcacgag     8580 atgcacctgc cgaccgcgga cgaggaagct gagtgggaat ctgagccccc cgcatggctc    8640
gcggcctggc tggtgctctt ctactttgga tgcgtggccg tcaccgtctg gctcctcgag    8700
gggtgttacg gtggagcgga tcaccacgcc gcgcgagccg caggtccaga tatcggcgcg    8760
cggcggtcgg agtttgatga cgacatcgcg cagctgggag ctgtccatgg tctgagctc    8820 ccgcggcggc ggcaggtcag ccgggagttc ttgcaggttt acctcgcaga gacgggccag    8880
ggcgcggggc aggtccaggt ggtacttgaa ttcgagaggc gtgttggtgg cggcgtcgat    8940
ggcttgcagt atgccgcagc cccggggcgc gacgacggtg ccccgcgggg cggtgaagct    9000 ccgccgccg ctcctgctgt cgccgccggt ggcggggctt agaagcggtg ccgcggtcgg    9060 gccccggag gtaggggggg ctccggtccc gcgggcaggg gcgcagcgg cacgtcggcg     9120 ccgcgcgcgg gcaggagctg gtgctgcgcc cggaggttgc tggcgaaggc gacgacgcgg   9180
```

```
cggttgatct cctggatctg gcgcctctgc gtgaagacga cgggtccggt gagcttgaac    9240
ctgaaagaga gttcgacaga atcaatctcg gtgtcattga ccgcgacctg gcgcaggatc    9300
tcctgcacgt cgcccgagtt gtcttggtag gcgatctcgg ccatgaactg ttcaatctct    9360
tcctcctgga ggtctccgcg tccggcgcgc tccacggtgg ccgccaggtc gttggagatg    9420
cgcgccatga gctgcgagaa ggcgttgagt ccgccctcgt tccacactcg gctgtagacc    9480
acgccgccct ggtcgtcgcg ggcgcgcatg accacctgcg cgaggttgag ttccacgtgg    9540
cgcgcaaaga cggcgtagtt gcgcaggcgc tggaagaggt agttgagggt ggtggcggtg    9600
tgctcggcca caaagaagta catgacccag cggcgcaacg tggattcgtt gatgtccccc    9660
aaggcctcca gtcgctccat ggcctcgtag aagtccacgg cgaagttgaa aaactgggag    9720
ttgcgcgccg acacggtcaa ctcctcctcc agaagacgga tgagctcggc gacggtgtcg    9780
cgcacctcgc gctcgaaggc tatgggaatc tcttcctccg ccagcatcac cacctcttcc    9840
tcttcttcct cctctggcac ttccatgatg gcttcctcct cttcgggggg tggcggcggg    9900
ggaggggcg ctcggcgccg gcggcggcgc accgggaggc ggtccacgaa gcgctcgatc    9960
atctccccgc ggcggcgacg catggtctcg gtgacggcgc ggccgttctc tcggggacgc   10020
agctggaaga cgccgccggt catctggtgc tgggcgggt ggccgtgggg cagcgagacc   10080
gcgctgacga tgcatcttaa caattgctgc gtaggtacgc cgccgaggga cctgagggag   10140
tccagatcca ccggatccga aaacctttcg aggaaggcat ctaaccagtc gcagtcgcaa   10200
ggtaggctga gcaccgtggc gggcggcggg gggtggggg agtgtctggc ggaggtgctg   10260
ctgatgatgt aattgaagta ggcggtcttg acacggcgga tggtcgacag gagcaccatg   10320
tctttgggcc cggcctgctg gatgcggagg cggtcggcca tgccccaggc ttcgttctgg   10380
catctgcgca ggtcttttgta gtagtcttgc atgagccttt ccaccggcac ctcttctcct   10440
tcttcttctg acatctctgc tgcatctgcg gccctggggc gacggcgcgc gcccctgccc   10500
cccatgcgcg tcaccccgaa ccccctgagc ggctggagca gggccaggtc ggcgacgacg   10560
cgctcggcca ggatggcctg ctggacctgc gtgagggtgg tttggaagtc atccaagtcc   10620
acgaagcggt ggtaggcgcc cgtgttgatg gtgtaggtgc agttggccat gacgaccag   10680
ttgacggtct ggtggcccgg ttgcgtcatc tcggtgtacc tgaggcgcga gtaggcgcgc   10740
gagtcgaaga tgtagtcgtt gcaagtccgc accaggtact ggtagcccac caggaagtgc   10800
ggcggcggct ggcggtagag gggccagcgg agggtggcgg gggctccggg ggccaggtct   10860
tccagcatga ggcggtggta ttcgtagatg tacctggaca tccaggtgat gcccgcggcg   10920
gtggtggagg cgcgcgggaa gtcgcgcacc cggttccaga tgttgcgcag cggcagaaag   10980
tgctccatgt taggcgtgct ctggccggtc aggcgcgcgc agtcgttgat actctagacc   11040
agggaaaacg aaagccggtc agcgggcact cttccgtggt ctggtggata aattcgcaag   11100
ggtatcatgg cggagggcct cggttcgagc cccgggcccg ggccgacgg tccgccatga   11160
tccacgcggt taccgcccgc gtgtcgaacc caggtggcga cgtcagacaa cggtggagtg   11220
ttcctttttgg gttttttttcc aaatttttct ggccgggcgc cgacgccgcc gcgtaagaga   11280
ctagagtgca aaagcgaaag cagtaagtgg ctcgctccct gtagcccgga ggatccttgc   11340
taagggttgc gttgcggcga accccggttc gagtctggct ctcgctgggc cgctcgggtc   11400
ggccggaacc gcggctaagg cgggattggc ctccccctca ttaaagaccc cgcttgcgga   11460
ttcctccgga cacaggggac gagccccttt ttactttgc ttttctcaga tgcatccggt   11520
gctgcggcag atgcgccccc cgccccagca gcagcagcag caacatcagc aagagcggca   11580
```

```
ccagcagcag cgggagtcat gcagggcccc ctcgcccacg ctcggcggtc cggcgacctc    11640
ggcgtccgcg gccgtgtctg gagccggcgg cggtgggctg gcggacgacc cggaggagcc    11700
cccgcggcgc agggccagac agtacctgga cctggaggag ggcgagggcc tggcgcgact    11760
gggggcgccg tccccgagc gccacccgcg ggtgcagctg aagcgcgact cgcgcgaggc     11820
gtacgtgcct cggcagaacc tgttcagaga ccgcgcgggc gaggagcccg aggagatgcg    11880
ggaccgcagg ttcgccgcgg ggcgggagct cggcagggg ctgaaccggg agcggctgct     11940
gcgcgaggag gactttgagc ccgacgcgcg gacgggatc agccccgcgc gcgcgcacgt     12000
ggcggccgcc gacctggtga cggcgtacga gcagacggtg aaccaggaga tcaacttcca    12060
aaaaagcttc aacaaccacg tgcgcacgct ggtggcgcgc gaggaggtga ccatcggcct    12120
gatgcacctg tgggactttg tgagcgcgct ggagcagaac cccaacagca agcctctgac    12180
ggcgcagctg ttcctgatag tgcagcacag cagggacaac gaggcgttca gggacgcgct    12240
gctgaacatc accgagcccg agggtcggtg gctgctggac ctgattaaca tcttgcagag    12300
catagtggtg caggagcgca gcctgagcct ggccgacaag gtggcggcca tcaattactc    12360
gatgctcagt ctgggcaagt tttacgcgcg caagatctac cagacgccgt acgtgcccat    12420
agacaaggag gtgaagatcg acggcttcta catgcgcatg gcgctgaagg tgctgacccct   12480 gagcgacgac ctgggcgtgt accgcaacga gcgcatccac aaggccgtga gcgtgagccg    12540
gcggcgcgag ctgagcgacc gcgagctgat gcacagcctg cagcgggcgc tggcggggc     12600 cggcagcggc gacagggagg ccgagtccta cttcgaggcg ggggcggacc tgcgctgggt    12660
gcccagccgg agggccctgg aggccgcggg ggcccgccgc gaggactatg cagacgagga    12720
ggaggaggat gacgaggagt acgagctaga ggagggcgag tacctggact aaaccgcagg    12780
tggtgttttt ggtagatgca agacccgaac gtggtggacc cggcgctgcg ggcggctctg    12840
cagagccagc cgtccggcct taactctaca gacgactggc gacaggtcat ggaccgcatc    12900
atgtcgctga cggcgcgcaa tccggacgcg ttccggcagc agccgcaggc caacaggctc    12960
tccgccatct tggaggcggt ggtgcctgcg cgcgcgaacc ccacgcacga aaggtgctg     13020 gccatagtga acgcgctggc cgagaacagg gccatccgcc cggacgaggc cgggctggtg    13080
tacgacgcgc tgctgcagcg cgtggcccgc tacaacagcg gcaacgtgca gaccaacctg    13140
gaccggctgg tggggacgt gcgcgaggcg gtggcgcagc gggagcgcgc ggagcggcag     13200
ggaaacctgg gctccatggt ggcgctgaac gccttcctga gcacgcagcc ggccaacgtg    13260
ccgcgggggc aggaggacta caccaacttt gtgagcgcgc tgcggctgat ggtgaccgag    13320 acccccccaga gcgaggtgta ccagtcgggg ccggactact ttttccagac cagcagacag    13380
ggcctgcaga cggtgaacct gagccaggct ttcaagaacc tgcgggggct gtggggcgtg    13440
aaggcgccca ccggggaccg ggcgacggtg tccagcctgc tgacgcccaa ctcgcgcctg    13500
ctgctgctgc tgatcgcgcc gttcacggac agcggcagcg tgtcccggga gacctacctc    13560
gggcacctgc tgacgctgta ccgcgaggcc atcgggcaga cccaggtgga cgagcacacc    13620
ttccaggaga tcaccagcgt gagccgcgcg ctggggcagg aggacacggg cagcctggag    13680
gcgaccctga actacctgct gaccaaccgg cggcagaaga tccccctcgct gcatagtttg    13740 accaccgagg aggagcgcat cctgcgctac gtgcagcaga gcgtgagcct gaacctgatg    13800
cgcgacgggg tgacgcccag cgtggcgctg gacatgaccg cgcgcaacat ggaacccggc    13860
atgtacgccg cgcatcggcc ttacatcaac cgcctgatgg actacttgca tcgcgcggcg    13920
```

```
gccgtgaacc ccgagtactt caccaacgcc atcctgaacc cgcactggct cccgccgccc    13980
gggttctaca gcgggggctt cgaggtcccc gaggccaacg acggcttcct gtgggacgac    14040
atggacgaca gcgtgttctc cccgcggccg caggcgctgg cggaggcgtc gctgctccgc    14100
ctcccccaaga aagaagagag ccgccggccc agcagcgcgg cggcctctct gtccgagctg    14160
ggggcggcgg ccgcgcggcc cgggtccctg ggggcagcc cctttcccag tctggtgggg    14220
tctctgcaga gcgggcgcac cacccggccc cggctgctgg gcgaggacga gtacctgaac    14280
aactccctga tgcagccggt gcgggagaaa aacctgcccc ccgccttccc caacaacggg    14340
atagagagcc tggtagacaa gatgagcaga tggaagacct atgcgcagga gcacagggac    14400
tcgcccgtgc tccgtccgcc cacgcggcgc cagcgccacg accggcagcg ggggctggta    14460
tgggatgacg aggactccgc ggacgatagc agcgtgctgg acctgggggg gagcggcggt    14520
aacccgttcg cgcacctgcg cccccgcctg gggaggatgt ttcaataaga aaaatcaagc    14580
atgatgcaag gttttttaag cggataaata aaaaactcac caaggccatg gcgaccgagc    14640
gttgttggtt tcttgttgtg ttcccttagt atgcggcgcg cggcgatgta ccacgaggga    14700
cctcctccct cttatgagag cgtggtgggc gcggcggcgg cctctcccct tgcgtcgcag    14760
ctggagccgc cgtacgtgcc tccgcggtac ctgcggccta cggggggaag aaacagcatc    14820
cgttactcgg agctggcgcc cctgtacgac accacccggg tgtacctggt ggacaacaag    14880
tcggcggacg tggcctccct gaactaccag aacgaccaca gcaattttt gaccacggtc    14940
atccagaaca atgactacac cccgagcgag gccagcaccc agaccatcaa tctggatgac    15000
cggtcgcact ggggcggcga cctgaaaacc atcctgcaca ccaacatgcc caacgtgaac    15060
gagttcatgt tcaccaataa gttcaaggcg cgggtgatgg tgtcgcgttc gcacaccaag    15120
gacgaccggg tggagctgaa gtacgagtgg gtagagttcg agctgcccga gggcaactac    15180
tcggagacca tgaccataga cctgatgaac aacgcgatcg tggagcacta tctgaaagtg    15240
ggcaggcaga acgggtcct ggagagcgac atcggggtca agttcgacac caggaacttc    15300
cgcctggggc tggacccggt caccgggctg gtcatgcccg ggtctacac caacgaggcc    15360
ttccaccccg acatcatcct gctgcccggc tgcggggtgg acttcaccta cagccgcctg    15420
agcaacctgc tgggcatccg caagcggcag cccttccagg agggctttag gatcacctac    15480
gaggacctgg aggggggcaa catccccgcg ctcctggatg tggaggccta ccaggatagc    15540
ttgaaggaag aagaggcggg agagggcagc ggcggcggcg gcggcgccgg tcaggaggag    15600
ggcggggcct cctctgaggc ctctgcggac gccgccgctg ccgccgaggc ggaggcggcc    15660
gaccccgcga tggtggtaga ggaagagaag gatatgaatg acgaggcggt gcgcggcgac    15720
acctttgcca cccgggggga ggagaagaaa gcggaggccg aggccgcggc agaggaggcg    15780
gcagcggcgg cggcggcggc agtagaggcg gcggccgagg cggagaagcc ccccaaggag    15840
cccgtgatta aggccctgac cgaagatagc aagaagcgca gttacaacgt gctcaaggac    15900
agcaccaaca ccgcgtaccg cagctggtac ctggcctaca actacggcga cccggcgacg    15960
ggggtgcgct cctggaccct gctgtgtacg ccggacgtga cctgcggctc ggagcaggtg    16020
tactggtcgc tgcccgacat gatgcaagac cccgtgacct tccgctccac gcggcaggtc    16080
agcaacttcc cggtggtggg cgccgagctg ctgcccgtgc actccaagag cttctacaac    16140
gaccaggccg tctactccca gctcatccgc cagttcacct ctctgacccca cgtgttcaat    16200
cgcttcctg agaaccagat tctggcgcgc ccgcccgccc ccaccatcac caccgtcagt    16260
gaaaacgttc ctgctctcac agatcacggg acgctaccgc tgcgcaacag catcggagga    16320
```

```
gtccagcgag tgaccgtaac tgacgccaga cgccgcacct gtccctacgt ttacaaggcc    16380
ctgggcatag tctcgccgcg cgtcctttcc agccgcactt tttaagcatg tccatcctca    16440
tctcgcccag caataacacc ggctggggcc tgctgcgcgc gcccagcaag atgtttggag    16500
gggcgaggaa gcgctccgac cagcaccccg tgcgcgtgcg cgggcactac cgcgcccct    16560 ggggcgcgca caaacgcggg cgcaccggca ccgcggggcg caccaccgtg gacgaagcca    16620
tcgactcggt ggtggagcag gcgcgcaact acacgcccgc ggtctccacc gtggacgcgg    16680
ctatcgagag cgtggtgcga ggcgcgcggc ggtacgccaa ggcgaagagc cgccggaggc    16740
gcgtggcccg ccgccaccgc cgtcgacccg gaagcgccgc caagcgcgcc gccgccgcct    16800
tgcttcgtcg ggccagacgc acgggccgcc gcgccgccat gagggccgcg cgccgcctgg    16860
ccgccggcat caccaccgtg gccccccgcg ccagaagacg cgcggccgct gccgccgccg    16920
cggccatcag cgacctggcc accaggcgcc ggggcaacgt gtactgggtg cgcgactcgg    16980
tgagcggcac gcgcgtgccc gtgcgcttcc gccccccgcg gacttgagag gagaggacag    17040
gaaaaaagca tcaacaacac caccactgag tctcctgctg ttgtgtgtat cccagcggcg    17100
cgcgcgcaca cggcgacatg tccaagcgca aaatcaaaga agagatgctc caggtcgtcg    17160
cgccggaaat ctatgggccc ccgaagaagg aagagcagga tttcaagccc cgcaagataa    17220
agcgggtcaa aaagaaaaag aaagatgacg atgatggcga ggtggagttt ctgcgcgcca    17280
cggcgcccag gcgcccgctg cagtggaagg gtcggcgcgt aaagcgcgtt ctgcgccccg    17340
gcaccgcggt ggtcttcacg cccggcgagc gctccaccg cactttcaag cgcgtctatg    17400
acgaggtgta cggcgacgaa gacctgctgg agcaggccaa cgatcgctcc ggagagtttg    17460
cttacgggaa gcggcaccgg gcgatggaga aggacgaggt gctggcgctg ccgctggacc    17520
ggggcaaccc caccccagc ctgaagcccg tgaccctgca gcaggtgctg ccggccagcg    17580
cgccctccga gatgaagcgg ggcctgaagc gcgagggcgg cgacctggcg cccaccgtgc    17640
agctgatggt gcccaagcgg cagaggctgg aggacgtgct ggagaaaatg aaagtagacc    17700
ccggcctgca gccggacatc agggtccgcc ccatcaagca ggtggcgccg ggcctcggcg    17760
tgcagaccgt ggacgtggtc atccccaccg gcgcctcctc ttccagcgcc gccgccgcca    17820
ctagcaccgc ggacatggag acgcagacta gctccgccct cgccgccccc gcggccgccg    17880
ccgccgccac ctcctcggcg gaggtacaga cggacccctg gatgccgccg ccggcggccg    17940 cccctcgcg cgcacgccgc gggcgcagga agtacggcgc cgccagcgcg ctcatgcccg    18000
agtacgcctt gcatccttcc atcgcgccca ccccgcgcta ccgaggctac agctaccgcc    18060
cgcgaagagc caagggctcc acccgccgca gccgccgcgc cgccacctct acccgccgcc    18120
gcagtcgccg ccgccgccgg cagcccgcgc tggctccgat ctccgtgagg agagtggcgc    18180
gcaacgggga caccttggtg ctgcccaggg cgcgctacca ccccagcatc gtttaaaagc    18240
ctgttgtggt tcttgcagat atggccctca cttgccgcct ccgtttccg gtgccgggat    18300 accgaggaag atcgcgccgt agaaggggta tggccggacg cggcctgagc ggaggcagcc    18360
gccgtgcgca ccggcggcga cgcgccacca gccgacgcat gcgcggcggg gtgctgcctc    18420
tgctgatccc cctgatcgcc gcggcgatcg gcgccgtgcc cggatcgcc tccgtggcct    18480 tgcaggcgtc ccagaggcgt tgacacagac ttcttgcaag cttgcaaaaa tatggaaaaa    18540
atccccccaa taaaaagtc tagactctca cgctcgcttg gtcctgtgac tattttgtag    18600
aaaaaaagat ggaagacatc aactttgcgt cgctggcccc gcgtcacggc tcgcgcccgt    18660
```

```
tcctgggaca ctggaacgat atcggcacca gcaacatgag cggtggcgcc ttcagttggg   18720
gctctctgtg gagcggcatt aaaaatatcg gttctgccgt taagaattac ggctccaagg   18780
cctggaacag cagcacgggc cagatgttga gagacaagtt gaaagagcag aacttccagc   18840
agaaggtggt ggagggcctg gcctccggca tcaacgggt ggtggacctg gccaatcagg    18900
ccgtgcaaaa taagatcaac agcagactgg accccggcc gccggtggaa gagctgccgc    18960
cggcgctgga cacggtgtcc cccgatgggc gggcgaaaa cgcccgcgg cccgacaggg     19020 aagagaccac tctggtcacg cacaccgatg agccgcccc ctacgaggaa gctctgaagc     19080
aaggcttgcc caccactcgg cccatcgcgc ccatggccac cggggtggtg ggccgccaca   19140
cccccgccag gctggacctg cctcctcctc ctgtttcttc ttcggccgcc gatgcgcagc   19200
agcagaaggc ggcgctgccc ggtccgcccg cggccgcccc ccgtcccacc gccagtcgag   19260
cgccgctgcg tcgcgcggcc agcggccccc gcggggtcgc gaggcacagc agcggcaact   19320
ggcagaacac gctgaacagc atcgtgggtc tgggggtgca gtccgtgaag cgccgccgat   19380
gctactgaat agcttagcta acggtgttgt atgtgtgtat gcgtcctatg tcaccgccag   19440
aggagctgct gagtcgccgc cgttcgcgcg cccaccgcca ctaccaccgc cggtaccact   19500
ccagcgcccc tcaagatggc gacccccatcg atgatgccgc agtggtcgta catgcacatc   19560
tcgggccagg acgcctcgga gtacctgagc cccgggctgg tgcagttcgc ccgcgccacc   19620
gacagctact tcagcctgag taacaagttt aggaaccccca cggtggcgcc cacgcacgat   19680
gtgaccaccg accggtccca gcgcctgacg ctgcggttca tccccgtgga ccgcgaggac   19740
accgcgtact cttacaaggc gcggttcacc ctggccgtgg cgacaaccg cgtgctggac    19800 atggcctcca cctactttga catccgcggc gtgctggaca ggggcccccac cttcaagccc   19860 tactccggca ccgcctacaa ctccctggcc ccaagggcg ccccaactc ctgcgagtgg     19920 gagcaagagg agactcagac agctgaagag gcacaagacg aagaagaaga tgaagctgaa   19980
gctgaggagg aaatgcctca ggaagagcaa gcacctgtca aaaagactca tgtatatgct   20040
caggctcccc tttctggcga aaaaattact aaagacggtc tgcagatagg aacggacgct   20100
acagctaccg aacaaaaacc tatttatgca gatcccacat tccagccaga accccaaatt   20160
ggtgaatctc agtggaatga ggcagatgct tcagttgccg gcggtagagt gctgaagaaa   20220
actactccca tgaaaccctg ttatggttcc tatgccaggc ccacaaatgc caatggaggt   20280
cagggtgtat tggtggagaa agacggtgga aagatggaaa gccaagtaga tatgcaattc   20340
ttttcgactt ctgaaaacgc ccgtaacgag gctaacaaca ttcagcccaa attggtgctg   20400
tacagcgagg atgtgcatat ggagacccca gacacacaca tttcttacaa gcctgcaaaa   20460
agcgatgata attcgaaagt catgctgggt cagcagtcca tgcccaacag gccaaattac   20520
atcggcttca gagacaactt tatcgggctc atgtattaca acagcactgg caacatgggg   20580
gtgctggcag gtcaggcctc acagttgaat gcggtggtgg acttgcaaga cagaaacaca   20640
gaactgtcct accagctctt gcttgattcc atggagacag aaccagata cttttccatg   20700 tggaatcagg cggtggacag ttatgatcca gatgtcagaa ttattgaaaa tcatggaact   20760
gaagatgagc tgcccaacta ttgtttccct ctggaggca taggggtaac tgacacttac   20820
caggccatta agactaatgg caatggcaac ggcggggca ataccacttg gaccaaggat    20880 gaaactttttg cagaccgcaa cgagatagg gtgggaaaca atttcgccat ggagatcaac    20940
ctcagtgcca acctgtggag gaacttcctc tactccaacg tggccctgta cctgccagac    21000
aagcttaagt acaacccctc caacgtggaa atctctgaca accccaacac ctacgactac    21060
```

```
atgaacaagc gagtggtggc cccggggctg gtggactgct acatcaacct gggcgcgcgc   21120
tggtccctgg actacatgga caacgtcaac cccttcaacc accaccgcaa cgcgggcctg   21180
cgctaccgct ccatgcttct gggcaacggg cgctacgtgc ccttccacat ccaggtgccc   21240
cagaagttct ttgccatcaa gaacctcctc ctcctgccgg gctcctacac ctacgagtgg   21300
aacttcagga aggatgtcaa catggtcctc cagagctctc tgggtaacga cctcagggtc   21360
gacggggcca gcatcaagtt cgagagcatc tgcctctacg ccaccttctt ccccatggcc   21420
cacaacacgg cctccacgct cgaggccatg ctcaggaacg acaccaacga ccagtccttc   21480
aacgactacc tctccgccgc caacatgctc taccccatcc ccgccaacgc caccaacgtt   21540
cccatctcca tccctcgcg caactgggcg ccttccgcg ctgggcctt cacccgcctc   21600 aagaccaagg agaccccctc cctgggctcg ggtttcgacc cctactacac ctactcgggc   21660
tccataccct acctggacgg aaccttctac ctcaaccaca ctttcaagaa ggtctcggtc   21720
accttcgact cctcggtcag ctggccgggc aacgatcgcc tgctcacccc caacgagttc   21780
gagatcaagc gctcggtcga cggggagggc tacaacgtgg cccagtgcaa catgaccaag   21840
gactggttcc tcatccaaat gctggccaac tacaacatcg gctatcaggg cttctacatc   21900
ccagagagct acaaggacag gatgtactcc ttctttagga acttccagcc catgagccgg   21960
caggtggtgg acgaaaccaa gtacaaggac taccagcagg tgggcatcat ccaccagcac   22020
aacaactcgg gcttcgtggg ctacctcgcc cccaccatgc gcgagggaca ggcctacccc   22080
gccaacttcc cctacccgct cattggcaag accgcggtcg acagcgtcac ccagaaaaag   22140
ttcctctgcg accgcaccct ctggcgcatc cccttctcca gcaacttcat gtccatgggt   22200
gcgctcacgg acctgggcca gaacctgctc tatgccaact ccgcccacgc gctcgacatg   22260
accttcgagg tcgaccccat ggacgagccc acccttctct atgttctgtt cgaagtcttt   22320
gacgtggtcc gggtccacca gccgcaccgc ggcgtcatcg agaccgtgta cctgcgcacg   22380
cccttctcgg ccggcaacgc caccacctaa agaagcaagc cgccaccgcc accacctgca   22440
tgtcgtcggg ttccaccgag caggagctca aggccatcgt cagagacctg ggatgcgggc   22500
cctatttttt gggcaccttc gacaaacgct tcccgggctt cgtcgcccg cacaagctgg   22560 cctgcgccat cgtcaacacg gccggccgcg agaccggggg cgtgcactgg ctggccttcg   22620
cctggaaccc gcgctccaaa acatgctacc tctttgaccc cttcggattc tcggaccagc   22680
ggctcaagca gatctaccag ttcgagtacg agggcctgct gcgccgcagc gccatcgcct   22740
cctcgcccga ccgctgcgtc accctcgaga agtccaccca ccgtgcag gggccccgact   22800 cggccgcctg cggtctcttc tgctgcatgt tcctgcatgc ctttgtgcac tggccccaga   22860
gtcccatgga ccgcaacccc accatgaact tgctgacggg gatccccaac tccatgctcc   22920
agagccccca ggtcgcgccc accctgcgcc gcaaccagga gcggctctac agcttcctgg   22980
aacgccactc gccctacttc cgccgccaca gcgcgcagat cagggggggcc acctcttttct   23040 gccgcatgca agagatgcaa gggaaaatgc aatgatgtac acagacactt tttctttttct   23100 caataaatgg caactttatt tatacatgct ctctctcggg tattcatttc cccaccaccc   23160
accacccgcc gccgccgtaa ccatctgctg ctggcttttt tttttttttt taaaaatcga   23220
aagggttctg ccgggaatcg ccgtgcgcca cgggcaggga cacgttgcgg aactggtagc   23280 gggtgccca cttgaactcg ggcaccacca tgcggggcaa gtcggggaag ttgtcggccc   23340
acaggctgcg ggtcagcacc agcgcgttca ttaggtcggg cgccgagatc ttgaagtcgc   23400
```

```
agttggggcc gccgccctgc gcgcgcgagt tgcggtacac cgggttgcaa cactggaaca   23460
ccagcagcgc cggataattc acactggcca gcacgctccg gtcggagatc agctcggcgt   23520
ccaggtcctc cgcgttgctc agcgcgaacg gggtcagctt gggcacctgc cgccccagga   23580
agggagcgtg ccccggcttc gagttgcagt cgcagcgcag cgggatcagc aggtgcccgc   23640
ggccggactc ggcgttgggg tacagcgcgc gcatgaaggc ctccatctgg cggaaggcca   23700
tctgggcctt ggcgccctcc gagaagaaca tgccgcagga cttgcccgag aactggttcg   23760
cggggcagct agcgtcgtgc aggcagcagc gcgcgtcggt gttggcgatc tgcaccacgt   23820
tgcgccccca ccggttcttc acgattttgg ccttggaagc ctgctccttc agcgcgcgct   23880
gcccgttctc gctggtcaca tccatctcga tcacgtgctc cttgttcacc atgctgctgc   23940
cgtgcagaca cttcagctcg ccctccacct cggtgcagcg gtgctgccat agcgcgcagc   24000
ccgtgggctc gaaatgcttg taggtcacct ccgcgtagga ctgcaggtag gcctgcagga   24060
agcgccccat catggtcacg aaggtcttgt tgctgctgaa ggtcagctgc agcccgcggt   24120
gctcctcgtt cagccaggcc ttgcacacgg ccgccagcgc ctccacctgg tcgggcagca   24180
tcttgaagtt cagcttcagc tcattctcca catggtactt gtccatcagc gcgcgcgcag   24240
cctccatgcc cttctcccag gccgacacca gcggcaggct caaggggttc accaccgtcg   24300
cagccgccgc tgcgctttcg ctttccgctc cgctgttctc ttcttcctcc tcctcttctt   24360
cctcgccgcc cgcgcgcagc ccccgcacca cggggtcgtc ttcctgcagg cgccgcaccg   24420
agcgcttgcc gctcctgccc tgcttgatac gcacgggcgg gttgctgaag cctaccatca   24480
ccagcgcggc ctcttcttgc tcgtcctcgc tgtccactat gacctcgggg gagggcgacc   24540
tcagaaccgt ggcgcgctgc ctcttctttt cctgggggc gtttgccagc tccgcggccg   24600
cggccgccgc cgaggtcgaa ggccgagggc tgggcgtgcg cggcaccagc gcgtcctgcg   24660
agccgtcctc gtcctcggac tcgaggcggc agcgagcccg cttcttcggg ggcgcgcggg   24720
gcggcggcgg cggggcggc ggcgacggag acggggacga gacatcgtcc agggtgggag   24780
gacggcgggc cgcgccgcgt ccgcgctcgg gggtggtttc gcgctggtcc tcttcccgac   24840
tggccatctc ccactgctcc ttctcctata ggcagaaaga gatcatggag tctctcatgc   24900
aagtcgagaa ggaggaggac agcctaacca ccaccgcccc ctctgagccc tccgccgccg   24960
ccgcggacga cgcgcccacc accaccgccg ccgccaccac caccattacc accctacccg   25020
gcgacgcagc cccgatcgag aaggaagtgt tgatcgagca ggacccgggt tttgtgagcg   25080
aagaggagga tgaggaggat gaaaaggaga aggataccgc cgcctcagtg ccaaaagagg   25140
ataaaaagca agaccaggac gacgcagaga cagatgaggc agcagtcggg cgggggacg   25200
gaaggcatga tgatgatgac ggctacctag acgtgggaga cgacgtgctg cttaagcacc   25260
tgcaccgcca gtgcgtcatc gtctgcgacg cgctgcagga gcgctgcgaa gtgcccctgg   25320
acgtggcgga ggtcagccgc gcctacgagc ggcacctctt cgcgccacac gtgccccca   25380
agcgccggga gaacggcacc tgcgagccca acccgcgcct caacttctac ccggtcttcg   25440
cggtacccga ggtgctggcc acctaccaca tcttcttcca aaactgcaag atccccctct   25500
cctgccgcgc caaccgcacc cgcgccgaca agacgctggc cctgcggcag ggcgccaca   25560
tacctgatat cgcctctctg gaggaggtgc ccaagatctt cgagggtctc ggtcgcgacg   25620
agaaacgggc ggcgaacgct ctgcaaggag acagcgaaaa cgagagtcac tcgggggtgc   25680
tggtggagct cgagggcgac aacgcgcgcc tggccgtgct caagcgcagc atcgaagtca   25740
cccacttcgc ctaccccggcg ctcaacctgc cccccaaggt catgagtgtg gtcatgagtg   25800
```

```
agctcatcat gcgccgcgcc cagcccctgg acgcggatgc aaacttgcaa gagccctccg   25860
aggaaggcct gcccgcggtc agcgacgagc agctggcgcg ctggctggag acccgcgacc   25920
ccgcccagct ggaggagcgg cgcaagctca tgatggccgc ggtgctcgtc accgtggagc   25980
tcgagtgtct gcagcgcttc ttcggggacc ccgagatgca cgcaagctc gaggagaccc    26040 tgcactacac cttccgccag ggctacgtgc gccaggcctg caagatctcc aacgtggagc   26100
tctgcaacct ggtctcctac ctgggcatcc tgcacgagaa ccgcctcggg cagaacgtcc   26160
tgcactccac cctcaaaggg gaggcgcgcc gcgactacgt ccgcgactgc gtctacctct   26220
tcctctgcta cacgtggcag acggccatgg gggtctggca gcagtgcctg gaggagcgca   26280
acctcaagga gctggagaag ctcctccggc gcgccctcag ggacctctgg acgggcttca   26340
acgagcgctc ggtggccgcc gcgctggcgg acatcatctt ccccgagcgc ctgctcaaaa   26400
ccctgcagca gggcctgccc gacttcacca gccagagcat gctgcagaac ttcaggacct   26460
tcatcctgga gcgctcgggc atcctgccgg ccacctgctg cgcgctgccc agcgacttcg   26520
tgcccatcag gtacagggag tgcccgccgc cgctctgggg ccactgctac ctcttccagc   26580
tggccaacta cctcgcctac cactcggatc tcatggaaga cgtgagcggc gagggcctgc   26640
tcgagtgcca ctgccgctgc aacctgtgca cgccccaccg ctctctagtc tgcaatccgc   26700
agctgctcag cgagagtcag attatcggta ccttcgagct gcagggtccc tcgcccgacg   26760
aaaagtccgc ggctccgggg ttgaaactca ctccggggct gtggacttcc gcctacctac   26820
gcaaatttgt acctgaagac taccacgccc acgagatcag gttttacgaa gaccaatccc   26880
gcccgcccaa ggcggagctc accgcctgcg tcattaccca gggccacatc ctgggccaat   26940
tgcaagccat caacaaagcc cgccaagagt tcttgctgaa aaagggtcgg ggggtgtacc   27000
tggaccccca gtccggcgag gagctaaacc cgctacccc gccgccgccc cagcagcggg    27060
accttgcttc ccaggatggc acccagaaaag aagcagccgc cgccgccgcc agcatacatg   27120
cttctggagg aagaggagga ctgggacagt caggcagagg aggtttcgga cgaggacgag   27180
gaggaggaga tgatggaaga ctgggaggag acagcctag acgaggaagc ttcagaggcc    27240
gaagaggtgg cagacgcaac accatcaccc tcggccgcag cccctcgcc ggcgcccccg     27300 aaatcctccg accccagcag cagcgctata acctccgctc ctccggcgcc ggcgcccacc   27360
cgcagcagac ccaaccgtag atgggacact acaggaaccg gggtcggtaa gtccaagtgc   27420 ccccagcgc cgccccgca acaggagcaa cagcagcagc agcggcgaca gggctaccgc      27480
tcgtggcgcg gacacaagaa cgccatagtc gcctgcttgc aagactgcgg gggcaacatc   27540
tccttcgccc gccgcttcct gctcttccac cacgggtgg cttttccccg caatgtcctg    27600
cattactacc gtcatctcta cagccccta tgcggcggca gcggcgaccc agagggagcg     27660
gcggcagcag cagcgccagc cacagcggcg accacctagg aagacctccg cgggcaagac   27720
ggcgggagcc gggagacccg cggcggcggc ggtagcggcg gcgcggggcg cactgcgcct   27780
ctcgcccaac gaacccctct cgacccggga gctcagacac aggatcttcc ccactctgta   27840
tgctatcttc cagcagagca gaggccagga acaggagctc aaaataaaaa acagatctct   27900
gcgctccctc acccgcagct gtctgtatca caaaagcgaa gatcagcttc ggcgcacgct   27960
ggaggacgcg gaggcactct tcagcaaata ctgcgcgctg actcttaagg actagccgcg   28020 cgccttctc gaatttaggc gggagaaaga ctacgtcatc gccgaccgcc gcccagccca   28080
cccagccgac atgagcaaag agattcccac gccctacatg tggagctacc agccgcagat   28140
```

```
gggactcgcg gcgggagcgg cccaagacta ctccacccgc atgaactaca tgagcgcggg   28200
gccccacatg atctcacggg ttaatgggat ccgcgcccag cgaaaccaaa tactgctgga   28260
acaggcggcc ataaccgcca caccccgtca tgacctcaat ccccgaaatt ggcccgccgc   28320
cctcgtgtac caggaaaccc cctctgccac caccgtggta cttccgcgtg acacccaggc   28380
cgaagtccag atgactaact cagggggcgca gctcgcgggc ggctttcgtc acgggtgcg   28440 gccgcaccgg ccgggtatat tacacctggc gatcagaggc cgaggtattc agctcaacga   28500
cgagtcggtg agctcttcgc tcggtctccg tccggacgga accttccaga tcgccggatc   28560
aggtcgctcc tcattcacgc ctcgccaggc gtatctgact ctgcagacct cctcctcgga   28620
gcctcgctcc ggcggcatcg gcaccctcca gttcgtggag gagttcgtgc cctcggtcta   28680
cttcaacccc ttctcgggac ctcccggacg ctaccccgac cagttcatcc cgaactttga   28740
cgcggtgaag gactcggcgg acggctacga ctgaatgtca agtgctgagg cagagagcgt   28800
tcgcctgaaa caccccagc actgccgccg cttcgcctgc tttgcccgca gctccggtga   28860
gttctgctac tttcagctgc ccgaggagca taccgaaggg ccggcgcacg gcgtccgcct   28920
aaccacccag ggcgaggtta cctgtaccct tatccgggag tttaccctcc gtcccctgct   28980
agtggagcgg gagcggggtt cttgtgtcat aactatcgcc tgcaactgcc ctaaccctgg   29040
attacatcaa gatctttgtt gtcacctgtg cgctgagtat aataaacgct gagatcagac   29100
tctactgggg ctcctgtcgc catcctgtga acgccaccgt cttcacccac ccgagcagc   29160 cccaggcgaa cctcacctgc ggcctgcgtc ggagggccaa gaagtacctc acctggtact   29220
tcaacggcac ccccttttgtg gtttacaaca gcttcgacca ggacggagtt gccttgagag   29280
acgacctttc cggtctcagc tactccattc acaagaacac caccctccac ctcttccctc   29340
cctacctgcc gggaacctac gagtgcgtca ccggccgctg cacccacctc ctccgcctga   29400 tcgtaaaacca gaccttttccg ggaacacacc tcttccccag aacaggaggt gagctcagga   29460
aaccccctgg ggcccagggc ggagacttac cttcgaccct tgtggggtta ggattttta   29520 tcgccgggtt gctggctctc ctgatcaaag cttccttcag atttgttctc tcccttact   29580 tttatgaaca gctcaacttc taataacgct accttttctc aggaatcgag tagtaacttc   29640
tcttccgaaa tcgggctggg tgtgctgctt actctgttga ttttttttcct tatcatactt   29700 agccttctgt gcctcaggct cgccgcctgc tgcgcacata tctacatcta cagccggttg   29760
cttaactgct ggggtcgcca tccaagatga acggggctca ggtgctatgt ctgctggccc   29820
tggtggcctg cagtgccgcc gtcaattttg aggaacccgc ttgcaatgtg actttcaagc   29880
ctgagggcgc acattgcacc actctggtta aatgtgtgac ctctcatgaa aaactgctca   29940
tcgcctacaa aaacaaaaca ggccagatcg cagtctatag cgagtggcta cccggagacc   30000
ataataacta ctcagtcacc gtcttcgagg gtgcggagtc taagaaattc gattacacct   30060
ttcccttcga ggagatgtgt gatgcggtca tgtacctgtc caaacagtac aagctgtggc   30120
cccccacccc caaggcgtgt gtggaaaaca ctgggtctttt ctgctgtctc tctctggcaa   30180
tcactgtgct tgctctaatc tgcacgctgc tatacatgag attcaggcag aggcgaatct   30240
ttatcgatga gaaaaaaatg ccttgatcgc taacaccggc tttctgtctg cagaatgaaa   30300
gcaatcacct ccctactaat cagcaccacc ctccttgcga ttgcccatgg gttgacacga   30360
atcgaagtgc cagtggggtc caatgtcacc atggtgggcc ccgccggcaa ttcctccctg   30420
atgtgggaaa aatatgtccg taatcaatgg gatcattact gctctaatcg aatctgtatc   30480
aagcccagag ccacctgcga cgggcaaaat ctaactttga ttgatgtgca aatgacggat   30540
```

```
gctgggtact attacgggca gcggggagaa atgattaatt actggcgacc ccacaaggac  30600
tacatgctgc atgtagtcaa ggcagtccca actactacca cccccaccac taccactccc  30660
actaccacca cccccaccac taccactagc actgctacta ccgctgcccg caaagctatt  30720
acccgcaaaa gcaccatgct tagcaccaag ccccattctc actcccacgc cggcgggccc  30780
accggtgcgg cctcagaaac caccgagctt tgcttctgcc aatgcactaa cgccagcgcc  30840
cacgaactgt tcgacctgga gaatgaggac gatgaccagc tgagctccgc ttgcccggtc  30900
ccgctgcccg cagagccggt cgccctgaag cagctcggtg atccatttaa tgactctcct  30960
gtttatccct ctcccgaata ccctcccgac tctaccttcc acatcacggg caccaaagac  31020
cccaacctct ccttctacct gatgctgctg ctctgtatct ctgtggtatc ttccgcgctc  31080
atgttactgg gcatgttctg ctgcctcatc tgccgcagaa aagaaagtc tcgctctcag  31140
ggccaaccac tgatgccctt cccctacccc ccagattttg cagataacaa gatatgagca  31200
cgctgctgac actaaccgct ttactcgcct gcgctctaac ccttgtcgct tgcgaatcca  31260
gataccacaa tgtcacagtt gtgacaggag aaaatgttac attcaactcc acggccgaca  31320
cccagtggtc gtggagtggc cacggtagct atgtatacat ctgcaatagc tccacctccc  31380
ctagcatgtc ctctcccaag taccactgca atgacagcct gttcaccctc atcaacgcct  31440
ccacctcgga caatggactc tatgtaggct atgtgacacc cggtgggcag ggaaagaccc  31500
acgcctacaa cctgcaagtt cgccaccccct ccaccaccgc caccacctct gccgccccta  31560
cccgcagcag cagcagcagc agcagcagca gcagcagcag cagcagcaga ttcctgactt  31620
taatcctagc cagctcaaca accaccgcca ccgctgagac cacccacagc tccgcgcccg  31680
aaaccaccca cacccaccac ccagagacga ccgcggcctc cagcgaccag atgtcggcca  31740
acatcaccgc ctcgggtctt gaacttgctt caaccccccac cccaaaacca gtggatgcag  31800
ccgacgtctc cgccctcgtc aatgactggg cggggctggg aatgtggtgg ttcgccatag  31860
gcatgatggc gctctgcctg cttctgctct ggctcatctg ctgcctcaac cgcaggcggg  31920
ccagacccat ctatagaccc atcattgttc tcaaccccgc tgatgatggg atccatagat  31980
tggatggtct gaaaaaccta cttttctctt ttacagtatg ataaattgag acatgcctcg  32040
cattttcatg tacttgacac ttctcccact ttttctgggg tgttctacgc tggccgccgt  32100
ctctcacctc gaggtagact gcctcacacc cttcactgtc tacctgattt acggattggt  32160
cacccctcact ctcatctgca gcctaatcac agtagtcatc gccttcatcc agtgcattga  32220
ctacatctgt gtgcgcctcg catacctgag acaccacccg cagtaccgag acaggaacat  32280
tgcccaactc ctaagactgc tctaatcatg cataagactg tgatctgcct cctcatcctc  32340
ctctccctgc ccgctctcgt tcatgccag cccaccacaa aacctccacg aaaaagacat  32400
gcctcctgtc gcttgagcca actgtggaat attcccaaat gctacaatga aaagagcgag  32460
cttttccgaag cctggctata tgcggtcatg tgtgtccttg tcttctgcag cacaatcttt  32520
gccctcatga tctaccccca ctttgatttg ggatggaatg cggtcgatgc catgaattac  32580
cctacctttc ccgcgcccga tatgattcca ctccgacagg ttgtggtgcc cgtcgccctc  32640
aatcaacgcc cccatccccc tacacccact gaggtcagct actttaatct aacaggcgga  32700
gatgactgac actctagatc tagaaatgga cggcatcggc accgagcagc gtctcctaca  32760
gaggcgcaag caggcggctg aacaagagcg cctcaatcag gagctccgag atctcattaa  32820
cctgcaccag tgcaaaaaag gcatcttttg cctggtcaag caggccgatg tcacctacga  32880
```

```
gaaaaccggt aacagccacc gcctcagcta caagctgccc acccaacgcc agaagttggt  32940
gctcatggtg ggtcagaatc ccatcaccgt cacccagcac tcggtggaga ccgaggggtg  33000
tctgcactcc ccctgtcagg gtccggaaga cctctgcacc ctggtaaaga ccctgtgtgg  33060
tcttagagat ttaatcccct ttaactaatc aaacactgga atcaataaaa agaatcactt  33120
actttaaatc agtcagcagg tctctgtcca ctttattcag cagcacctcc ttcccctcct  33180
cccaactctg gtactccaaa cgcctcctgg cggcaaactt cctccacacc ctgaagggaa  33240
tgtcagattc ttgctcctgt ccctccgcac ccactatctt catgttgttg cagatgaagc  33300
gcgccaaaac gtctgacgag accttcaacc ccgtgtaccc ctatgacacg aaaacgggc   33360 ctccctccgt tcctttcctc acccctccct tcgtgtcccc cgacggattt caagaaagcc  33420
ccccaggggg cctgtctctg cgcctgtcag agccctggt cacttcccac ggcatgcttg    33480
ccctgaaaat gggaaatggc ctctccctgg atgacgccgg caacctcacc tctcaagatg  33540
tcaccaccgt caccctccc ctcaaaaaaa ccaagaccaa cctcagcctc cagacctcag    33600
cccccctgac cgttagctct gggtccctca ccgtcgcggc cgccgctcca ctggcggtgg  33660
ccggcacctc tctcaccatg caatctcagg ccccccttgac ggtgcaagat gcaaaactgg 33720
gtctggccac ccagggaccc ctgaccgtgt ctgaaggcaa actcaccttg cagacatcgg  33780
ctccactgac ggccgccgac agcagcactc tcactgttgg caccacaccg ccaatcagtg  33840
tgagcagtgg aagtctaggc ttagatatgg aagaccccat gtatactcac gatggaaaac  33900
tgggaatcag aattggtggc ccactgcaag tagtagacag cttgcacaca ctcactgtag  33960
ttactggaaa cggaataact gtagctaaca atgcccttca aactaaagtt gcgggtgccc  34020
tgggttatga ctcatctggc aatctagaat tgcgagccgc aggggggtatg cgaattaaca  34080 caggggggtca actcattctt gatgtggctt atccatttga tgctcagaac aatctcagcc  34140
ttagactcgg ccagggacct ttatatgtga acaccaatca caacctagat ttaaattgca  34200
acagaggtct gaccacaacc accagcagta acacaaccaa acttgaaact aaaatcgatt  34260
cgggcttaga ctataacgcc aatgggggcta tcattgctaa acttggcact gggttaaacct 34320 ttgacaacac aggtgccata actgtgggaa acactgggga tgacaaactc actctgtgga  34380
ctaccccaga tccctctcct aactgcagaa ttcacgcaga caaagactgc aagtttactc  34440
tagtcctgac taagtgtgga agtcaaattc tggcctccgt cgccgccctg gcggtgtctg  34500
gaaacctatc atcaatgaca ggcactgtct ccagcgttac catcttctc agattcgatc    34560 agaatggagt tcttatggaa aattcctcgc tagacaagga gtactggaac ttcagaaatg  34620
gtaattccac caatgccacc ccctacacca atgcggttgg gttcatgccc aacctcagcg  34680
cctaccccaa aacccagagt caaactgcaa aaaacaacat tgtaagtgag gtttacttac  34740
atggggacaa atctaaaccc atgatcctta ccattaccct taatggcaca aatgaatcca  34800
gtgaaactag tcaggtgagt cactactcca tgtcatttac atggtcgagg acagtgggaa  34860
aatatgccac cgaaaccttt gccaccaact ctttttacctt ctcctacatt gctgaacaat  34920
aaagaagcat aacgctgctg ttcatttgta atcaagtgtt acttttttat ttttcaatta  34980
caacagaatc attcaagtca ttctccattt agcttaatag accccagtag tgcaaagccc  35040
catactagct tatttcagca attgggagaa gtactcgcct acatgggggt agagtcataa   35100
tcgtgcatca ggatagggcg gtggtgctgc agcagcgcgc gaataaactg ctgccgccgc   35160
cgctccgtcc tgcaggaata caacatggca gtggtctcct cagcgatgat tcgcaccgcc   35220
cgcagcataa ggcgccttgt cctccgggca cagcagcgca ccctgatctc acttaaatca   35280
```

```
gcacagtaac tgcagcacag caccacaata ttgttcaaaa tcccacagtg caaggcgctg    35340
tatccaaagc tcatggcggg gaccacagaa cccacgtggc catcatacca caagcgcagg    35400
tagattaagt ggcgacccct cataaacacg ctggacataa acattacctc ttttggcatg    35460
ttgtaattca ccacctcccg gtaccatata aacctctgat taaacatggc gccatccacc    35520
accatcctaa accagctggc caaaacctgc ccgccggcta tacactgcag ggaaccggga    35580
ctggaacaat gacagtggag agcccaggac tcgtaaccat ggatcatcat gctcgtcatg    35640
atatcaatgt tggcacaaca caggcacacg tgcatacact tcctcaggat tacaagctcc    35700
tcccgcgtta gaaccatatc ccagggaaca acccattcct gaatcagcgt aaatcccaca    35760
ctgcagggaa gacctcgcac gtaactcacg ttgtgcattg tcaaagtgtt acattcgggc    35820
agcagcggat gatcctccag tatggtagcg cgggtttctg tctcaaaagg aggtagacga    35880
tccctactgt acggagtgcg ccgagacaac cgagatcgtg ttggtcgtag tgtcatgcca    35940
aatggaacgc cggacgtagt catatttcct gaagtcttgg cgcgccagac ccgagtctta    36000
ccaggaaaat tttaaaaaag attcctcaac gcagcaccag caccaacacc tgtcagtgta    36060
aaatgccaag cgccgagcga gtatatatag gaataaaaag tgacgtaaac ggttaaagtc    36120
cagaaaacgc ccagaaaaac cgcacgcgaa cctacgcccc gaaacgaaag ccaaaaaaca    36180
gtgaacacgc cctttcggcg tcaacttccg ctttcccacg gtacgtcact tccgcatata    36240
gtaaaactac gctacccaac atgcaagaag ccacgcccca aaacacgtca cacctcccgg    36300
cccgccccgc gccgccgctc ctccccgccc cgccccgctc cgcccacctc attatcatat    36360
tggcttcaat ccaaaataag gtatattatt gatgatg                             36397
```

<210> SEQ ID NO 9
<211> LENGTH: 36445
<212> TYPE: DNA
<213> ORGANISM: Artificial Sequence
<220> FEATURE:
<223> OTHER INFORMATION: synthetic chimpanzee adenovirus serotype PanAd3
      with Marburg virus Angola codon optimized
      transmembrane envelope glycoprotein (GP) insert
      (PanAd3 GP Marburg (PB/6712))
<220> FEATURE:
<221> NAME/KEY: CDS
<222> LOCATION: (1656)...(3698)
<223> OTHER INFORMATION: Marburg virus Angola codon optimized
      transmembrane envelope glycoprotein (GP) insert in PanAd3 GP
      Marburg (PB/6712)
<220> FEATURE:
<221> NAME/KEY: CDS
<222> LOCATION: (14719)...(16473)
<223> OTHER INFORMATION: chimpanzee adenovirus serotype ChAd63 penton
<220> FEATURE:
<221> NAME/KEY: CDS
<222> LOCATION: (19564)...(22458)
<223> OTHER INFORMATION: chimpanzee adenovirus serotype ChAd63 hexon
<220> FEATURE:
<221> NAME/KEY: CDS
<222> LOCATION: (33342)...(34970)
<223> OTHER INFORMATION: chimpanzee adenovirus serotype ChAd63 fiber

<400> SEQUENCE: 9

```
catcatcaat aatatacctt attttggatt gaagccaata tgataatgag gtgggcggag      60
cggggcgggg cggggaggag cggcggcgcg gggcggccg ggaggtgtgg cggaagttga     120
gtttgtaagt gtggcggatg tgacttgcta gcgccggatg tggtaaaagt gacgtttttt     180
ggagtgcgac aacgcccacg ggaagtgaca ttttcccgc ggttttttacc ggatgtcgta    240 gtgaatttgg gcgttaccaa gtaagatttg gccattttcg cggaaaaact gaaatgggga     300
```

```
agtgaaatct gattaatttc gcgttagtca taccgcgtaa tatttgccga gggccgaggg      360
actttgaccg attacgtgga ggaatcgccc aggtgttttt tgaggtgaat ttccgcgttc      420
cgggtcaaag tctccgtttt attattatag gtatacccat tgcatacgtt gtatccatat      480
cataatatgt acatttatat tggctcatgt ccaacattac cgccatgttg acattgatta      540
ttgactagtt attaatagta atcaattacg gggtcattag ttcatagccc atatatggag      600
ttccgcgtta cataacttac ggtaaatggc ccgcctggct gaccgcccaa cgaccccgc       660 ccattgacgt caataatgac gtatgttccc atagtaacgc caatagggac tttccattga      720
cgtcaatggg tggagtattt acggtaaact gcccacttgg cagtacatca agtgtatcat      780
atgccaagta cgccccctat tgacgtcaat gacggtaaat ggcccgcctg gcattatgcc      840
cagtacatga ccttatggga ctttcctact tggcagtaca tctacgtatt agtcatcgct      900
attaccatgg tgatgcggtt ttggcagtac atcaatgggc gtggatagcg gtttgactca      960
cggggatttc caagtctcca ccccattgac gtcaatggga gtttgttttg gaaccaaaat     1020
caacgggact ttccaaaatg tcgtaacaac tccgccccat tgacgcaaat gggcggtagg     1080
cgtgtacggt gggaggtcta taagcaga gctctcccta tcagtgatag agatctccct       1140
atcagtgata gagatcgtcg acgagctcgt ttagtgaacc gtcagatcgc ctggagacgc     1200
catccacgct gttttgacct ccatagaaga caccgggacc gatccagcct catcggctc      1260 gcatctctcc ttcacgcgcc cgccgcccta cctgaggccg ccatccacgc cggttgagtc     1320
gcgttctgcc gcctcccgcc tgtggtgcct cctgaactgc gtccgccgtc taggtaagtt     1380
taaagctcag gtcgagaccg ggcctttgtc cggcgctccc ttggagccta cctagactca     1440
gccggctctc cacgctttgc ctgacccctgc ttgctcaact ctagttaacg gtggagggca     1500
gtgtagtctg agcagtactc gttgctgccg cgcgcgccac cagacataat agctgacaga     1560
ctaacagact gttcctttcc atgggtcttt tctgcagtca ccgtcgtcga cacgtgtgat     1620
cagatatcgc ggccgctcta gagatatcgg ccgccatgaa gaccacctgc ctgctgatca     1680
gcctgatcct gatccagggc gtgaagaccc tgcccatcct ggagatcgcc agcaacatcc     1740 agcccccagaa cgtggacagc gtgtgcagcg gcaccctgca agaccgag gacgtgcacc      1800 tgatgggctt caccctgagc ggccagaagg tggccgacag ccctctggag gccagcaaga     1860
ggtgggcctt cagggccggc gtgccccca agaacgtgga gtacaccgag ggcgaggagg      1920
ccaagacctg ctacaacatc agcgtgaccg accccagcgg caagagcctg ctgctggacc     1980
ctcccaccaa catcagggac taccctaagt gcaagaccat ccaccacatc cagggccaga     2040
accctcacgc ccagggcatc gccctgcacc tgtgggcgc cttcttcctg tacgacagga      2100
tcgccagcac caccatgtac agaggaaaag tgttcacaga gggaaacatc gctgctatga     2160
tcgtgaacaa gaccgtgcat aagatgatct tcagcagaca gggacaggga tatagacata     2220
tgaacctgac atccacaaac aagtactgga caagcagcaa cggaacacag acaaacgata     2280
caggatgttt tggaacactg caggaataca actccaccaa gaaccagaca tgtgccccta     2340
gcaagaagcc tctgcctctg cctacagctc atcctgaagt gaagctgaca tccacaagca     2400
cagatgccac aaagctgaac acaacagatc ctaatagcga cgacgaggat ctgacaacaa     2460
gcggatccgg atccggagaa caggaacctt atacaacaag cgacgctgct acaaaacagg     2520
gactgtcctc cacaatgcct cctacaccta gccctcagcc tagcacacct cagcaggag      2580 gcaacaacac aaaccattcc cagggagtgg tgacagaacc tggaaagaca aacacaacag     2640
```

| | |
|---|---|
| cccagcctag catgcctcct cataacacaa caacaatcag cacaaacaac acctccaagc | 2700 |
| acaatctgag cacacctagc gtgcctattc agaatgccac caactacaac acacagtcca | 2760 |
| cagcccctga aaacgaacag acctccgccc cttccaaaac aaccctgctg cctacagaaa | 2820 |
| accctacaac agccaagagc acaaacagca caaagagccc tacaacaaca gtgcctaaca | 2880 |
| caacaaacaa gtatagcaca agccctagcc ctacacctaa ttccacagct cagcatctgg | 2940 |
| tgtattttag aagaaagaga acatcctgt ggagagaagg agatatgttc ccttttctgg | 3000 |
| atggactgat caacgctcct atcgattttg atcctgtgcc taacacaaag acaatctttg | 3060 |
| atgaaagcag cagcagcgga gcctccgccg aagaagatca gcatgcctcc cctaacatca | 3120 |
| gcctgacact gagctatttt cctaaggtga acgaaaacac agcccattcc ggagaaaacg | 3180 |
| aaaacgattg tgatgccgaa ctgagaatct ggagcgtgca ggaagatgat ctggccgccg | 3240 |
| gactgagctg gatccctttt tttgggcccg gaattgaagg actgtacacc gccggcctga | 3300 |
| tcaagaacca gaacacctg tgtgcaggc tgaggaggct ggccaaccag accgccaaga | 3360 |
| gcctggagct gctgctgagg gtgaccaccg aggagggac cttcagcctg atcaacaggc | 3420 |
| acgccatcga cttcctgctg gctaggtggg gcggcacctg caaggtgctg ggccccgact | 3480 |
| gctgcatcgg catcgaggac ctgagcagga acatcagcga gcagatcgac cagatcaaga | 3540 |
| aggacgagca aaggagggc accggctggg gcctgggcgg caagtggtgg accagcgact | 3600 |
| ggggagtgct gacaaacctg ggaatcctgc tgctgctgag cattgccgtg ctcattgctc | 3660 |
| tgtcctgtat ctgtagaatc tttaccaagt acatcggatg atagatccag atctgctgtg | 3720 |
| ccttctagtt gccagccatc tgttgtttgc ccctcccccg tgccttcctt gaccctggaa | 3780 |
| ggtgccactc ccactgtcct ttcctaataa aatgaggaaa ttgcatcgca ttgtctgagt | 3840 |
| aggtgtcatt ctattctggg gggtggggtg gggcaggaca gcaagggga ggattgggaa | 3900 |
| gacaatagca ggcatgctgg ggatgcggtg ggctctagat atcagcgatc gctgaggtgg | 3960 |
| gtgagtgggc gtggtctggg ggtgggaagc aatatataag ttgggggtct tagggtctct | 4020 |
| gtgtctgttt tgcagaggga ccgccggcgc catgagcggg agcagtagca gcaacgcctt | 4080 |
| ggatggcagc atcgtgagcc cttatttgac gacgcgcatg ccccactggg ccggggtgcg | 4140 |
| tcagaatgtg atgggctcca gcatcgacgg acgacccgtg ctgcccgcaa attccgccac | 4200 |
| gctgacctac gcgaccgtcg cggggacccc gttggacgcc accgccgccg ccgccgccac | 4260 |
| cgccgccgcc tcggccgtgc gcagcctggc cacggacttt gcattcttgg gaccccttggc | 4320 |
| caccggggcg gccgcccgtg ccgccgttcg cgatgacaag ctgaccgccc tgctggcgca | 4380 |
| gttggatgcg cttacccggg aactgggtga cctttcgcag caggtcgtgg ccctgcgcca | 4440 |
| gcaggtctcc gccctgcagg ctagcgggaa tgcttctcct gcaaatgccg tttaagataa | 4500 |
| ataaaaccag actctgttga taaataaaac cagactctgt ttggattaaa gaaaagtagc | 4560 |
| aagtgcattg ctctctttat ttcataattt tccgcgcgcg ataggcccga gtccagcgtt | 4620 |
| ctcggtcgtt gagggtgcgg tgtatcttct ccaggacgtg gtagaggtgg ctctggacgt | 4680 |
| tgagatacat gggcatgagc ccgtcccggg ggtggaggta gcaccactgc agagcttcat | 4740 |
| gctccggggt ggtgttgtag atgatccagt cgtagcagga gcgctgggca tggtgcctaa | 4800 |
| aaatgtcctt aagcagcagg ccgatggcca gggggaggcc cttggtgtaa gtgtttacaa | 4860 |
| aacggttgag ttgggaaggg tgcatgcggg gtgagatgat gtgcatctta gattgtattt | 4920 |
| ttagattggc gatgtttcct cccagatccc ttctgggatt catgttgtgg aggaccacca | 4980 |
| gcacagtata tccggtgcac ttgggaaatt tgtcatgcag cttagaggga aatgcgtgga | 5040 |

```
agaacttgga gacgcccttg tggcctccca gattctccat gcattcgtcc atgatgatgg    5100
caatgggccc gcgggaggcg gcctgggcaa agatgtttct ggggtcactg acatcgtagt    5160
tgtgttccag ggtgagatcg tcataggcca tttttataaa gcgcgggcgg agggtgcccg    5220
actgggggat gatggttccc tcgggccccg ggcgtagtt gccttcgcag atctgcattt    5280
cccaggcctt aatctctgag gggggaatca tatccacttg cggggcgatg aagaaaacgg    5340
tttccggagc cggggagatt aactgggatg agagcaggtt tctcagcagc tgtgactttc    5400
cacagccggt gggtccataa ataacaccta taaccggctg cagctggtag ttgagcgagc    5460
tgcagctgcc gtcgtcccgg aggaggggg ccacctcatt gagcatgtcc cggacgcgct    5520
tgttctcctc gaccaggtcc gccagaaggc gctcgccgcc cagggacagc agctcttgca    5580
aggaagcaaa gttttcagc ggtttgaggc cgtccgccgt gggcatgttt tcagggtct    5640 ggccgagcag ctccaggcgg tcccagagct cggtgacgtg ctctacggca tctctatcca    5700
gcatatctcc tcgtttcgcg ggttgggcg gctttcgctg tagggcacca ggcgatggtc    5760
gtccagcgcg gccagagtca tgtccttcca tgggcgcagg gtcctcgtca gggtggtctg    5820
ggtcacggta aaggggtgcg cccgggctg ggcgctggcc agggtgcgct tgagactggt    5880
cctgctggtg ctgaagcgct gccggtcttc gccctgcgcg tcggccaggt agcatttgac    5940
catggtgtcg tagtccagcc cctccgcggc gtgtccttg gcgcgcagct tgcccttgga    6000
ggtggcgccc cacgcgggc actgcaggct cttgagcgcg tagagcttgg gggcgaggaa    6060
gaccgattcg ggggagtagg cgtccgcgcc gcaggcccg cacacggtct cgcactccac    6120
cagccaggtg agctcggggc gctcggggtc aaaaaccagg tttcccccat gcttttgat    6180 gcgtttctta cctcgggtct ccatgaggcg gtgtccccgt tcggtgacga agaggctgtc    6240
cgtgtctccg tagaccgact tgagggggtct gtcctccagg ggggtccctc ggtcctcttc    6300
gtagagaaac tcggaccact ctgagacaaa ggcccgcgtc caggccagga cgaaggaggc    6360
caggtgggag gggtaccggt cgttgtccac taggggtcc accttctcca aggtgtgaag    6420
acacatgtcg ccctcctcgg cgtccaggaa ggtgattggc ttgtaggtgt aggccacgtg    6480
acccggggtt ccggacgggg gggtataaaa ggggtgggg gcgcgctcgt cctcactctc    6540
ttccgcatcg ctgtctgcga gggccagctg ctggggtgag tattccctct cgaaggcggg    6600
catgacctca gcgctgaggc tgtcagtttc taaaaacgag gaggatttga tgttcacctg    6660
tcccgagctg atgcctttga gggtgcccgc gtccatctgg tcagaaaaca cgatcttttt    6720
attgtccagc ttggtggcga acgacccgta gagggcgttg gagagcagct tggcgatgga    6780
gcgcagggtc tgattcttgt cccggtcggc gcgctccttg gccgcgatgt tgagctgcac    6840
gtactcgcgc gcgacgcagc gccactcggg gaagacggtg gtgcgctcgt cgggcaccag    6900
gcgcacgcgc cagccgcggt tgtgcagggt gacgaggtcc acgctggtgg cgacctcgcc    6960
gcgcaggcgc tcgttggtcc agcagaggcg cccgcccttg cgcgagcaga agggggggcag    7020 ggggtcgagt tgggtttcgt ccgggggggtc cgcgtccacc gtgaagaccc cggggcgcag    7080
gcgcgcgtcg aagtagtcga tcttgcatcc ttgcaagtcc agcgcccgct gccagtcgcg    7140
ggcggcgagc gcgcgctcgt aggggttgag cggcggccc cagggcatgg ggtgggtgag    7200
cgcggaggcg tacatgccgc agatgtcata gacgtagagg ggctcccgga ggatgcccag    7260
gtaggtgggg tagcagcggc cgccgcggat gctggcgcgc acgtagtcgt agagctcgtg    7320 cgaggggcg aggaggtcgg ggcccaggtt ggtgcggggcg gggcgctccg cgcggaagac    7380
```

```
gatctgcctg aagatggcat gcgagttgga agagatggtg gggcgctgga agacgttgaa    7440
gctggcgtcc tgcaggccga cggcgtcgcg cacgaaggag gcgtaggact cgcgcagctt    7500
gtgcaccagc tcggcggtga cctgcacgtc gagcgcgcag tagtcgaggg tctcgcggat    7560
gatgtcatac ttagcctgcc ccttcttttt ccacagctcg cggttgagga cgaactcttc    7620
gcggtctttc cagtactctt ggatcgggaa accgtccggc tccgaacggt aagagcccag    7680
catgtagaac tggttgacgg cctggtaggc gcagcagccc ttctccacgg gcagggcgta    7740
ggcctgcgcg gccttgcgga gcgaggtgtg ggtcagggcg aaggtgtccc tgaccatgac    7800
cttgaggtac tggtgtttga agtcggagtc gtcgcagccg ccccgctccc agagcgagaa    7860
gtcggtgcgc ttttttggagc gggggttggg cagcgcgaag gtgacatcgt tgtagaggat    7920
cttgcccgcg cgaggcatga agttgcgggt gatgcggaag gccccggca cttccgagcg    7980
gttgttgatg acctgggcgg cgagcacgat ctcgtcgaag ccgttgatgt tgtggcccac    8040
gatgtagagt tccaggaagc ggggccggcc cttgacgctg gcagcttct ttagctcttc    8100
gtaggtgagc tcctcgggcg aggcgaggcc gtgctcggcc agggcccagt ccgccaggtg    8160
cggggttgtcc gcgaggaagg accgccagag gtcgcgggcc aggagggtct gcaggcggtc    8220
cctgaaggtc ctgaactggc ggcctacggc catcttttcg ggggtgacgc agtagaaggt    8280
gaggggggtct tgctgccagg gtcccagtc gagctccagg gcgaggtcgc gcgcggcggc    8340
gaccaggcgc tcgtcgcccc cgaatttcat gaccagcatg aagggcacga gctgctttcc    8400
gaaggcgccc atccaagtgt aggtctctac atcgtaggtg acaaagagac gttccgtgcg    8460
aggatgcgag ccgatcggga agaactggat ctcccgccac cagttggagg agtggctgtt    8520
gatgtggtga agtagaagt cccgtcggcg ggccgagcac tcgtgctggc ttttgtaaaa    8580
gcgagcgcag tactggcagc gctgcacggg ctgtacctct tgcacgagat gcacctgccg    8640
accgcggacg aggaagctga gtgggaatct gagccccccg catggctcgc ggcctggctg    8700
gtgctcttct actttggatg cgtggccgtc accgtctggc tcctcgaggg gtgttacggt    8760
ggagcggatc accacgccgc gcgagccgca ggtccagata tcggcgcgcg gcggtcggag    8820
tttgatgacg acatcgcgca gctgggagct gtccatggtc tggagctccc gcggcggcgg    8880
caggtcagcc gggagttctt gcaggtttac ctcgcagaga cgggccaggg cgcggggcag    8940
gtccaggtgg tacttgaatt cgagaggcgt gttggtggcg gcgtcgatgg cttgcagtat    9000
gccgcagccc cggggcgcga cgacggtgcc ccgcggggcg gtgaagctcc gccgccgct    9060
cctgctgtcg ccgccggtgg cggggcttag aagcggtgcc gcggtcgggc ccccggaggt    9120
agggggggct ccggtcccgc gggcaggggc ggcagcggca cgtcggcgcc gcgcgcgggc    9180
aggagctggt gctgcgcccg gaggttgctg gcgaaggcga cgacgcggcg gttgatctcc    9240
tggatctggc gcctctgcgt gaagacgacg ggtccggtga gcttgaacct gaaagagagt    9300
tcgacagaat caatctcggt gtcattgacc gcgacctggc gcaggatctc ctgcacgtcg    9360
cccgagttgt cttggtaggc gatctcggcc atgaactgtt caatctcttc ctcctggagg    9420
tctccgcgtc cggcgcgctc acggtggcc gccaggtcgt tggagatgcg cgccatgagc    9480
tgcgagaagg cgttgagtcc gccctcgttc cacactcggc tgtagaccac gccgccctgg    9540
tcgtcgcggg cgcgcatgac cacctgcgcg aggttgagtt ccacgtggcg cgcaaagacg    9600
gcgtagttgc gcaggcgctg gaagaggtag ttgagggtgg tggcggtgtg ctcggccaca    9660
aagaagtaca tgacccagcg gcgcaacgtg gattcgttga tgtcccccaa ggcctccagt    9720
cgctccatgg cctcgtagaa gtccacggcg aagttgaaaa actgggagtt gcgcgccgac    9780
```

```
acggtcaact cctcctccag aagacggatg agctcggcga cggtgtcgcg cacctcgcgc    9840
tcgaaggcta tgggaatctc ttcctccgcc agcatcacca cctcttcctc ttcttcctcc    9900
tctggcactt ccatgatggc ttcctcctct tcgggggtg gcggcggggg aggggcgct     9960
cggcgccggc ggcggcgcac cgggaggcgg tccacgaagc gctcgatcat ctccccgcgg   10020
cggcgacgca tggtctcggt gacggcgcgg ccgttctctc ggggacgcag ctggaagacg   10080
ccgccggtca tctggtgctg gggcgggtgg ccgtggggca gcgagaccgc gctgacgatg   10140
catcttaaca attgctgcgt aggtacgccg ccgagggacc tgagggagtc cagatccacc   10200
ggatccgaaa acctttcgag gaaggcatct aaccagtcgc agtcgcaagg taggctgagc   10260
accgtggcgg gcggcggggg gtgggggag tgtctggcgg aggtgctgct gatgatgtaa    10320
ttgaagtagg cggtcttgac acggcggatg gtcgacagga gcaccatgtc tttgggcccg   10380
gcctgctgga tgcggaggcg gtcggccatg ccccaggctt cgttctggca tctgcgcagg   10440
tctttgtagt agtcttgcat gagccttttcc accggcacct cttctccttc ttcttctgac  10500
atctctgctg catctgcggc cctggggcga cggcgcgcgc ccctgccccc catgcgcgtc   10560
accccgaacc ccctgagcgg ctggagcagg gccaggtcgg cgacgacgcg ctcggccagg   10620
atggcctgct ggacctgcgt gagggtggtt tggaagtcat ccaagtccac gaagcggtgg   10680
taggcgcccg tgttgatggt gtaggtgcag ttggccatga cggaccagtt gacggtctgg   10740
tggcccggtt gcgtcatctc ggtgtacctg aggcgcgagt aggcgcgcga gtcgaagatg   10800
tagtcgttgc aagtccgcac caggtactgg tagcccacca ggaagtgcgg cggcggctgg   10860
cggtagaggg gccagcggag ggtggcgggg gctccggggg ccaggtcttc cagcatgagg   10920
cggtggtatt cgtagatgta cctggacatc caggtgatgc ccgcggcggt ggtggaggcg   10980
cgcgggaagt cgcgcacccg gttccagatg ttgcgcagcg gcagaaagtg ctccatggta   11040
ggcgtgctct ggccggtcag gcgcgcgcag tcgttgatac tctagaccag ggaaaacgaa   11100
agccggtcag cgggcactct tccgtggtct ggtggataaa ttcgcaaggg tatcatggcg   11160
gagggcctcg gttcgagccc cgggcccggg ccggacggtc cgccatgatc cacgcggtta   11220
ccgcccgcgt gtcgaaccca ggtggcgacg tcagacaacg gtggagtgtt ccttttgggt   11280
ttttttccaa attttctgg ccgggcgccg acgccgccgc gtaagagact agagtgcaaa   11340
agcgaaagca gtaagtggct cgctccctgt agcccgagg atccttgcta agggttgcgt    11400
tgcggcgaac cccggttcga gtctggctct cgctgggccg ctcgggtcgg ccggaaccgc   11460
ggctaaggcg ggattggcct ccccctcatt aaagaccccg cttgcggatt cctccggaca   11520
caggggacga gccccttttt acttttgctt ttctcagatg catccggtgc tgcggcagat   11580
gcgcccccg ccccagcagc agcagcagca acatcagcaa gagcggcacc agcagcagcg    11640
ggagtcatgc agggccccct cgcccacgct cggcggtccg gcgacctcgg cgtccgcggc   11700
cgtgtctgga gccggcggcg gtgggctggc ggacgacccg gaggagcccc gcggcgcag    11760
ggccagacag tacctggacc tggaggaggg cgagggcctg gcgcgactgg gggcgccgtc   11820
ccccgagcgc cacccgcggg tgcagctgaa gcgcgactcg cgcgaggcgt acgtgcctcg   11880
gcagaacctg ttcagagacc gcgcgggcga ggagcccgag gagatgcggg accgcaggtt   11940
cgccgcgggg cggagctgc ggcaggggct gaaccgggag cggctgctgc gcgaggagga    12000
ctttgagccc gacgcgcgga cggggatcag cccccgcgcgc gcgcacgtgg cggccgccga   12060
cctggtgacg gcgtacgagc agacggtgaa ccaggagatc aacttccaaa aaagcttcaa   12120
```

```
caaccacgtg cgcacgctgg tggcgcgcga ggaggtgacc atcggcctga tgcacctgtg   12180
ggactttgtg agcgcgctgg agcagaaccc caacagcaag cctctgacgg cgcagctgtt   12240
cctgatagtg cagcacagca gggacaacga ggcgttcagg gacgcgctgc tgaacatcac   12300
cgagcccgag ggtcggtggc tgctggacct gattaacatc ttgcagagca tagtggtgca   12360
ggagcgcagc ctgagcctgg ccgacaaggt ggcggccatc aattactcga tgctcagtct   12420
gggcaagttt tacgcgcgca agatctacca gacgccgtac gtgcccatag acaaggaggt   12480
gaagatcgac ggcttctaca tgcgcatggc gctgaaggtg ctgaccctga gcgacgacct   12540
gggcgtgtac cgcaacgagc gcatccacaa ggccgtgagc gtgagccggc ggcgcgagct   12600
gagcgaccgc gagctgatgc acagcctgca gcgggcgctg gcggggccg gcagcggcga   12660 cagggaggcc gagtcctact tcgaggcggg ggcggacctg cgctgggtgc ccagccggag   12720
ggccctggag gccgcggggg cccgccgcga ggactatgca gacgaggagg aggaggatga   12780
cgaggagtac gagctagagg agggcgagta cctggactaa accgcaggtg gtgttttgg   12840 tagatgcaag acccgaacgt ggtggacccg gcgctgcggg cggctctgca gagccagccg   12900
tccggcctta actctacaga cgactggcga caggtcatgg accgcatcat gtcgctgacg   12960
gcgcgcaatc cggacgcgtt ccggcagcag ccgcaggcca acaggctctc cgccatcttg   13020
gaggcggtgg tgcctgcgcg cgcgaacccc acgcacgaga aggtgctggc catagtgaac   13080
gcgctggccg agaacagggc catccgcccg gacgaggccg ggctggtgta cgacgcgctg   13140
ctgcagcgcg tggcccgcta acagcggc aacgtgcaga ccaacctgga ccggctggtg   13200
ggggacgtgc gcgaggcggt ggcgcagcgg gagcgcgcgg agcggcaggg aaacctgggc   13260
tccatggtgg cgctgaacgc cttcctgagc acgcagccgg ccaacgtgcc gcggggcag   13320 gaggactaca ccaactttgt gagcgcgctg cggctgatgg tgaccgagac ccccagagc   13380 gaggtgtacc agtcggggcc ggactacttt ttccagacca gcagacaggg cctgcagacg   13440
gtgaacctga gccaggcttt caagaacctg cggggctgt ggggcgtgaa ggcgcccacc   13500
ggggaccggg cgacggtgtc cagcctgctg acgcccaact cgcgcctgct gctgctgctg   13560
atcgcgccgt tcacggacag cggcagcgtg tcccgggaga cctacctcgg gcacctgctg   13620
acgctgtacc gcgaggccat cgggcagacc caggtggacg agcacacctt ccaggagatc   13680
accagcgtga gccgcgcgct ggggcaggag gacacgggca gcctggaggc gaccctgaac   13740
tacctgctga ccaaccggcg gcagaagatc ccctcgctgc atagtttgac caccgaggag   13800
gagcgcatcc tgcgctacgt gcagcagagc gtgagcctga acctgatgcg cgacggggtg   13860
acgcccagcg tggcgctgga catgaccgcg cgcaacatgg aaccgggcat gtacgccgcg   13920
catcggcctt acatcaaccg cctgatggac tacttgcatc gcgcggcggc cgtgaacccc   13980
gagtacttca ccaacgccat cctgaacccg cactggctcc cgccgccgg gttctacagc   14040 gggggcttcg aggtccccga ggccaacgac ggcttcctgt gggacgacat ggacgacagc   14100
gtgttctccc cgcggccgca ggcgctggcg gaggcgtcgc tgctccgcct ccccaagaaa   14160
gaagagagcc gccggcccag cagcgcggcg gcctctctgt ccgagctggg ggcggcggcc   14220
gcgcggcccg ggtccctggg gggcagcccc tttcccagtc tggtggggtc tctgcagagc   14280
gggcgcacca cccggccccg gctgctgggc gaggacgagt acctgaacaa ctccctgatg   14340
cagccggtgc gggagaaaaa cctgcccccc gccttcccca acaacgggat agagagcctg   14400
gtagacaaga tgagcagatg gaagacctat gcgcaggagc acagggactc gcccgtgctc   14460
cgtccgccca cgcggcgcca gcgccacgac cggcagcggg ggctggtatg ggatgacgag   14520
```

```
gactccgcgg acgatagcag cgtgctggac ctggggggga gcggcggtaa cccgttcgcg    14580
cacctgcgcc cccgcctggg gaggatgttt caataagaaa aatcaagcat gatgcaaggt    14640
tttttaagcg gataaataaa aaactcacca aggccatggc gaccgagcgt tgttggtttc    14700
ttgttgtgtt cccttagtat gcggcgcgcg gcgatgtacc acgagggacc tcctccctct    14760
tatgagagcg tggtgggcgc ggcggcggcc tctcccttlg cgtcgcagct ggagccgccg    14820
tacgtgcctc cgcggtacct gcggcctacg gggggaagaa acagcatccg ttactcggag    14880
ctggcgcccc tgtacgacac cacccgggtg tacctggtgg acaacaagtc ggcggacgtg    14940
gcctccctga actaccagaa cgaccacagc aattttttga ccacggtcat ccagaacaat    15000
gactacaccc cgagcgaggc cagcacccag accatcaatc tggatgaccg gtcgcactgg    15060
ggcggcgacc tgaaaaccat cctgcacacc aacatgccca acgtgaacga gttcatgttc    15120
accaataagt tcaaggcgcg ggtgatggtg tcgcgttcgc acaccaagga cgaccgggtg    15180
gagctgaagt acgagtgggt agagttcgag ctgcccgagg gcaactactc ggagaccatg    15240
accatagacc tgatgaacaa cgcgatcgtg gagcactatc tgaaagtggg caggcagaac    15300
ggggtcctgg agagcgacat cggggtcaag ttcgacacca ggaacttccg cctggggctg    15360
gacccggtca ccgggctggt catgcccggg gtctacacca acgaggcctt ccaccccgac    15420
atcatcctgc tgcccggctg cggggtggac ttcacctaca gccgcctgag caacctgctg    15480
ggcatccgca agcggcagcc cttccaggag ggctttagga tcacctacga ggacctggag    15540
gggggcaaca tccccgcgct cctggatgtg gaggcctacc aggatagctt gaaggaagaa    15600
gaggcgggag agggcagcgg cggcgcggc ggcgccggtc aggaggaggg cggggcctcc    15660
tctgaggcct ctgcggacgc cgccgctgcc gccgaggcgg aggcggccga ccccgcgatg    15720
gtggtagagg aagagaagga tatgaatgac gaggcggtgc gcggcgacac ctttgccacc    15780
cggggggagg agaagaaagc ggaggccgag gccgcggcag aggaggcggc agcggcggcg    15840
gcggcggcag tagaggcggc ggccgaggcg gagaagcccc ccaaggagcc cgtgattaag    15900
gccctgaccg aagatagcaa gaagcgcagt acaacgtgc tcaaggacag caccaacacc    15960
gcgtaccgca gctggtacct ggcctacaac tacgcgaccc ggcgacggg ggtgcgctcc    16020 tggaccctgc tgtgtacgcc ggacgtgacc tgcggctcgg agcaggtgta ctggtcgctg    16080
cccgacatga tgcaagaccc cgtgaccttc cgctccacgc ggcaggtcag caacttcccg    16140
gtggtgggcg ccgagctgct gcccgtgcac tccaagagct ctacaacga ccaggccgtc    16200 tactcccagc tcatccgcca gttcacctct ctgacccacg tgttcaatcg ctttcctgag    16260
aaccagattc tggcgcgccc gcccgccccc accatcacca ccgtcagtga aaacgttcct    16320
gctctcacag atcacgggac gctaccgctg cgcaacagca tcgaggagt ccagcgagtg    16380 accgtaactg acgccagacg ccgcacctgt ccctacgttt acaaggccct gggcatagtc    16440
tcgccgcgcg tcctttccag ccgcactttt taagcatgtc catcctcatc tcgcccagca    16500
ataacaccgg ctgggccctg ctgcgcgcgc ccagcaagat gtttggaggg gcgaggaagc    16560
gctccgacca gcacccgtg cgcgtgcgcg ggcactaccg cgcccctgg ggcgcgcaca    16620 aacgcgggcg caccggcacc gcggggcgca ccaccgtgga cgaagccatc gactcggtgg    16680
tggagcaggc gcgcaactac acgcccgcgg tctccaccgt ggacgcggct atcgagagcg    16740
tggtgcgagg cgcgcggcgg tacgccaagg cgaagagccg ccggaggcgc gtggcccgcc    16800
gccaccgccg tcgacccgga agcgccgcca agcgcgccgc cgccgccttg cttcgtcggg    16860
```

```
ccagacgcac gggccgccgc gccgccatga gggccgcgcg ccgcctggcc gccggcatca    16920
ccaccgtggc cccccgcgcc agaagacgcg cggccgctgc cgccgccgcg gccatcagcg    16980
acctggccac caggcgccgg ggcaacgtgt actgggtgcg cgactcggtg agcggcacgc    17040
gcgtgcccgt gcgcttccgc cccccgcgga cttgagagga gaggacagga aaaaagcatc    17100
aacaacacca ccactgagtc tcctgctgtt gtgtgtatcc cagcggcgcg cgcgcacacg    17160
gcgacatgtc caagcgcaaa atcaaagaag agatgctcca ggtcgtcgcg ccggaaatct    17220
atgggccccc gaagaaggaa gagcaggatt tcaagcccccg caagataaag cgggtcaaaa    17280
agaaaaagaa agatgacgat gatggcgagg tggagtttct gcgcgccacg gcgcccaggc    17340
gcccgctgca gtggaagggt cggcgcgtaa agcgcgttct gcgccccggc accgcggtgg    17400
tcttcacgcc cggcgagcgc tccacccgca ctttcaagcg cgtctatgac gaggtgtacg    17460
gcgacgaaga cctgctggag caggccaacg atcgctccgg agagtttgct tacgggaagc    17520
ggcaccgggc gatggagaag gacgaggtgc tggcgctgcc gctggaccgg ggcaacccca    17580
cccccagcct gaagcccgtg accctgcagc aggtgctgcc ggccagcgcg ccctccgaga    17640
tgaagcgggg cctgaagcgc gagggcggcg acctggcgcc caccgtgcag ctgatggtgc    17700
ccaagcggca gaggctggag gacgtgctgg agaaaatgaa agtagacccc ggcctgcagc    17760
cggacatcag ggtccgcccc atcaagcagg tggcgccggg cctcggcgtg cagaccgtgg    17820
acgtggtcat ccccaccggc gcctcctctt ccagcgccgc cgccgccact agcaccgcgg    17880
acatggagac gcagactagc tccgccctcg ccgcccccgc ggccgccgcc gccgccacct    17940
cctcggcgga ggtacagacg gacccctgga tgccgccgcc ggcggccgcc ccctcgcgcg    18000
cacgccgcgg gcgcaggaag tacggcgccg ccagcgcgct catgcccgag tacgccttgc    18060
atccttccat cgcgcccacc cccggctacc gaggctacag ctaccgcccg cgaagagcca    18120
agggctccac ccgccgcagc cgccgcgccg ccacctctac ccgccgccgc agtcgccgcc    18180
gccgccggca gcccgcgctg gctccgatct ccgtgaggag agtggcgcgc aacggggaca    18240
ccttggtgct gcccagggcg cgctaccacc ccagcatcgt ttaaaagcct gttgtggttc    18300
ttgcagatat ggccctcact tgccgcctcc gtttcccggt gccgggatac cgaggaagat    18360
cgcgccgtag aaggggtatg gccggacgcg gcctgagcgg aggcagccgc cgtgcgcacc    18420
ggcggcgacg cgccaccagc cgacgcatgc gcggcggggt gctgcctctg ctgatccccc    18480
tgatcgccgc ggcgatcggc gccgtgcccg ggatcgcctc cgtggccttg caggcgtccc    18540
agaggcgttg acacagactt cttgcaagct tgcaaaaata tggaaaaaat cccccccaata    18600
aaaaagtcta gactctcacg ctcgcttggt cctgtgacta ttttgtagaa aaaagatgg     18660
aagacatcaa ctttgcgtcg ctggccccgc gtcacggctc gcgcccgttc ctgggacact    18720
ggaacgatat cggcaccagc aacatgagcg gtggcgcctt cagttggggc tctctgtgga    18780
gcggcattaa aaatatcggt tctgccgtta agaattacgg ctccaaggcc tggaacagca    18840
gcacgggcca gatgttgaga gacaagttga aagagcagaa cttccagcag aaggtggtgg    18900
agggcctggc ctccggcatc aacgggGtgg tggacctggc caatcaggcc gtgcaaaata    18960
agatcaacag cagactggac ccccggccgc cggtggaaga gctgccgccg gcgctggaga    19020
cggtgtcccc cgatgggcgg ggcgaaaagc gcccgcggcc cgacagggaa gagaccactc    19080
tggtcacgca caccgatgag ccgccccccct acgaggaagc tctgaagcaa ggcttgccca    19140
ccactcggcc catcgcgccc atggccaccg gggtggtggg ccgccacacc cccgccaggc    19200
tggacctgcc tcctcctcct gtttcttctt cggccgccga tgcgcagcag cagaaggcgg    19260
```

```
cgctgcccgg tccgcccgcg gccgccccccc gtcccaccgc cagtcgagcg ccccctgcgtc    19320
gcgcggccag cggcccccgc ggggtcgcga ggcacagcag cggcaactgg cagaacacgc    19380
tgaacagcat cgtgggtctg ggggtgcagt ccgtgaagcg ccgccgatgc tactgaatag    19440
cttagctaac ggtgttgtat gtgtgtatgc gtcctatgtc accgccagag gagctgctga    19500
gtcgccgccg ttcgcgcgcc caccgccact accaccgccg gtaccactcc agcgcccctc    19560
aagatggcga ccccatcgat gatgccgcag tggtcgtaca tgcacatctc gggccaggac    19620
gcctcggagt acctgagccc cgggctggtg cagttcgccc gcgccaccga cagctacttc    19680
agcctgagta acaagtttag gaaccccacg gtggcgccca cgcacgatgt gaccaccgac    19740
cggtcccagc gcctgacgct gcggttcatc cccgtggacc gcgaggacac cgcgtactct    19800
tacaaggcgc ggttcaccct ggccgtgggc gacaaccgcg tgctggacat ggcctccacc    19860
tactttgaca tccgcggcgt gctggacagg ggccccacct tcaagcccta ctccggcacc    19920
gcctacaact ccctggcccc caagggcgcc cccaactcct gcgagtggga gcaagaggag    19980
actcagacag ctgaagaggc acaagacgaa gaagaagatg aagctgaagc tgaggaggaa    20040
atgcctcagg aagagcaagc acctgtcaaa aagactcatg tatatgctca ggctccccttt    20100
tctggcgaaa aaattactaa agacggtctg cagataggaa cggacgctac agctaccgaa    20160
caaaaaccta tttatgcaga tcccacattc cagccagaac cccaaattgg tgaatctcag    20220
tggaatgagg cagatgcttc agttgccggc ggtagagtgc tgaagaaaac tactcccatg    20280
aaaccctgtt atggttccta tgccaggccc acaaatgcca atggaggtca gggtgtattg    20340
gtggagaaag acggtggaaa gatggaaagc caagtagata tgcaattctt ttcgacttct    20400
gaaaacgccc gtaacgaggc taacaacatt cagcccaaat tggtgctgta cagcgaggat    20460
gtgcatatgg agaccccaga cacacacatt tcttacaagc ctgcaaaaag cgatgataat    20520
tcgaaagtca tgctgggtca gcagtccatg cccaacaggc caaattacat cggcttcaga    20580
gacaacttta tcgggctcat gtattacaac agcactggca catggggggt gctggcaggt    20640
caggcctcac agttgaatgc ggtggtggac ttgcaagaca gaaacacaga actgtcctac    20700
cagctcttgc ttgattccat gggagacaga accagatact tttccatgtg gaatcaggcg    20760
gtggacagtt atgatccaga tgtcagaatt attgaaaatc atggaactga agatgagctg    20820
cccaactatt gtttccctct gggaggcata ggggtaactg acacttacca ggccattaag    20880
actaatggca atggcaacgg cggggggcaat accacttgga ccaaggatga aactttttgca    20940
gaccgcaacg agatagggggt gggaaacaat ttcgccatgg agatcaacct cagtgccaac    21000
ctgtggagga acttcctcta ctccaacgtg gccctgtacc tgccagacaa gcttaagtac    21060
aaccccctcca acgtggaaat ctctgacaac cccaacacct acgactacat gaacaagcga    21120
gtggtggccc cgggggctggt ggactgctac atcaacctgg gcgcgcgctg gtccctggac    21180
tacatggaca acgtcaaccc cttcaaccac caccgcaacg cgggcctgcg ctaccgctcc    21240
atgcttctgg gcaacggccg ctacgtgccc ttccacatcc aggtgcccca gaagttcttt    21300
gccatcaaga acctcctcct cctgccgggc tcctacaccct acgagtggaa cttcaggaag    21360
gatgtcaaca tggtcctcca gagctctctg ggtaacgacc tcagggtcga cggggccagc    21420
atcaagttcg agagcatctg cctctacgcc accttcttcc ccatggccca caacacggcc    21480
tccacgctcg aggccatgct caggaacgac accaacgacc agtccttcaa cgactacctc    21540
tccgccgcca acatgctcta cccccatcccc gccaacgcca ccaacgttcc catctccatc    21600
```

```
ccctcgcgca actgggcggc cttccgcggc tgggccttca cccgcctcaa gaccaaggag    21660
accccctccc tgggctcggg tttcgacccc tactacacct actcgggctc catccctac     21720
ctggacggaa ccttctacct caaccacact ttcaagaagg tctcggtcac cttcgactcc    21780
tcggtcagct ggccgggcaa cgatcgcctg ctcaccccca acgagttcga gatcaagcgc    21840
tcggtcgacg gggagggcta caacgtggcc cagtgcaaca tgaccaagga ctggttcctc    21900
atccaaatgc tggccaacta caacatcggc tatcagggct tctacatccc agagagctac    21960
aaggacagga tgtactcctt ctttaggaac ttccagccca tgagccggca ggtggtggac    22020
gaaaccaagt acaaggacta ccagcaggtg ggcatcatcc accagcacaa caactcgggc    22080
ttcgtgggct acctcgcccc caccatgcgc gagggacagg cctaccccgc caacttcccc    22140
tacccgctca ttggcaagac cgcggtcgac agcgtcaccc agaaaaagtt cctctgcgac    22200
cgcaccctct ggcgcatccc cttctccagc aacttcatgt ccatgggtgc gctcacggac    22260
ctgggccaga acctgctcta tgccaactcc gcccacgcgc tcgacatgac cttcgaggtc    22320
gaccccatgg acgagcccac ccttctctat gttctgttcg aagtctttga cgtggtccgg    22380
gtccaccagc cgcaccgcgg cgtcatcgag accgtgtacc tgcgcacgcc cttctcggcc    22440
ggcaacgcca ccacctaaag aagcaagccg ccaccgccac cacctgcatg tcgtcgggtt    22500
ccaccgagca ggagctcaag gccatcgtca gagacctggg atgcgggccc tattttttgg    22560
gcaccttcga caaacgcttc ccgggcttcg tcgccccgca caagctggcc tgcgccatcg    22620
tcaacacggc cggccgcgag accgggggcg tgcactggct ggccttcgcc tggaacccgc    22680
gctccaaaac atgctacctc tttgaccct tcggattctc ggaccagcgg ctcaagcaga    22740
tctaccagtt cgagtacgag ggcctgctgc gccgcagcgc catcgcctcc tcgcccgacc    22800
gctgcgtcac cctcgagaag tccacccaga ccgtgcaggg gcccgactcg gccgcctgcg    22860
gtctcttctg ctgcatgttc ctgcatgcct ttgtgcactg gccccagagt cccatggacc    22920
gcaaccccac catgaacttg ctgacgggga tccccaactc catgctccag agcccccagg    22980
tcgcgcccac cctgcgccgc aaccaggagc ggctctacag cttcctggaa cgccactcgc    23040
cctacttccg ccgccacagc gcgcagatca gggggggccac ctctttctgc cgcatgcaag    23100
agatgcaagg gaaaatgcaa tgatgtacac agacactttt tcttttctca ataaatggca    23160
acttttattta tacatgctct ctctcgggta ttcatttccc caccacccac cacccgccgc    23220
cgccgtaacc atctgctgct ggcttttttt ttttttttta aaaatcgaaa gggttctgcc    23280
gggaatcgcc gtgcgccacg ggcagggaca cgttgcggaa ctggtagcgg gtgccccact    23340
tgaactcggg caccaccatg cggggcaagt cggggaagtt gtcggcccac aggctgcggg    23400
tcagcaccag cgcgttcatt aggtcgggcg ccgagatctt gaagtcgcag ttggggccgc    23460
cgccctgcgc gcgcgagttg cggtacaccg ggttgcaaca ctggaacacc agcagcgccg    23520
gataattcac actggccagc acgctccggt cggagatcag ctcggcgtcc aggtcctccg    23580
cgttgctcag cgcgaacggg gtcagcttgg gcacctgccg ccccaggaag ggagcgtgcc    23640
ccggcttcga gttgcagtcg cagcgcagcg ggatcagcag gtgcccgcgg ccggactcgg    23700
cgttggggta cagcgcgcgc atgaaggcct ccatctggcg gaaggccatc tgggccttgg    23760
cgccctccga gaagaacatg ccgcaggact tgcccgagaa ctggttcgcg gggcagctag    23820
cgtcgtgcag gcagcagcgc gcgtcggtgt ggcgatctg caccacgttg cgcccccacc    23880
ggttcttcac gattttggcc ttggaagcct gctccttcag cgcgcgctgc ccgttctcgc    23940
tggtcacatc catctcgatc acgtgctcct tgttcaccat gctgctgccg tgcagacact    24000
```

```
tcagctcgcc ctccacctcg gtgcagcggt gctgccatag cgcgcagccc gtgggctcga   24060
aatgcttgta ggtcacctcc gcgtaggact gcaggtaggc ctgcaggaag cgccccatca   24120
tggtcacgaa ggtcttgttg ctgctgaagg tcagctgcag cccgcggtgc tcctcgttca   24180
gccaggcctt gcacacggcc gccagcgcct ccacctggtc gggcagcatc ttgaagttca   24240
gcttcagctc attctccaca tggtacttgt ccatcagcgc gcgcgcagcc tccatgccct   24300
tctcccaggc cgacaccagc ggcaggctca aggggttcac caccgtcgca gccgccgctg   24360
cgctttcgct ttccgctccg ctgttctctt cttcctcctc ctcttcttcc tcgccgcccg   24420
cgcgcagccc ccgcaccacg gggtcgtctt cctgcaggcg ccgcaccgag cgcttgccgc   24480
tcctgccctg cttgatacgc acgggcgggt tgctgaagcc taccatcacc agcgcggcct   24540
cttcttgctc gtcctcgctg tccactatga cctcggggga gggcgacctc agaaccgtgg   24600
cgcgctgcct cttcttttc ctgggggcgt ttgccagctc cgcggccgcg ccgccgccg    24660
aggtcgaagg ccgagggctg ggcgtgcgcg caccagcgc gtcctgcgag ccgtcctcgt   24720
cctcggactc gaggcggcag cgagcccgct tcttcggggg cgcgcggggc ggcggcggcg   24780
ggggcggcgg cgacggagac ggggacgaga catcgtccag ggtgggagga cggcgggccg   24840
cgccgcgtcc gcgctcgggg gtggtttcgc gctggtcctc ttcccgactg gccatctccc   24900
actgctcctt ctcctatagg cagaaagaga tcatggagtc tctcatgcaa gtcgagaagg   24960
aggaggacag cctaaccacc accgccccct ctgagccctc cgccgccgcc gcggacgacg   25020
cgcccaccac caccgccgcc gccaccacca ccattaccac cctacccggc gacgcagccc   25080
cgatcgagaa ggaagtgttg atcgagcagg acccgggttt tgtgagcgaa gaggaggatg   25140
aggaggatga aaaggagaag gataccgccg cctcagtgcc aaaagaggat aaaaagcaag   25200
accaggacga cgcagagaca gatgaggcag cagtcgggcg gggggacgga aggcatgatg   25260
atgatgacgg ctacctagac gtgggagacg acgtgctgct taagcacctg caccgccagt   25320
gcgtcatcgt ctgcgacgcg ctgcaggagc gctgcgaagt gccccctggac gtggcggagg   25380
tcagccgcgc ctacgagcgg cacctcttcg cgccacacgt gccccccaag cgccgggaga   25440
acggcacctg cgagcccaac ccgcgcctca acttctaccc ggtcttcgcg gtacccgagg   25500
tgctggccac ctaccacatc ttcttccaaa actgcaagat cccccctctcc tgccgcgcca   25560
accgcacccg cgccgacaag acgctggccc tgcggcaggg cgcccacata cctgatatcg   25620
cctctctgga ggaggtgccc aagatcttcg agggtctcgg tcgcgacgag aaacgggcgg   25680
cgaacgctct gcaaggagac agcgaaaacg agagtcactc gggggtgctg gtggagctcg   25740
agggcgacaa cgcgcgcctg gccgtgctca gcgcagcat cgaagtcacc cacttcgcct   25800
acccggcgct caacctgccc cccaaggtca tgagtgtggt catgagtgag ctcatcatgc   25860
gccgcgccca gcccctggac gcggatgcaa acttgcaaga gccctccgag gaaggcctgc   25920
ccgcggtcag cgacgagcag ctggcgcgct ggctggagac ccgcgacccc gcccagctgg   25980
aggagcggcg caagctcatg atggccgcgg tgctcgtcac cgtggagctc gagtgtctgc   26040
agcgcttctt cggggacccc gagatgcagc gcaagctcga ggagaccctg cactacacct   26100
tccgccaggg ctacgtgcgc caggcctgca agatctccaa cgtggagctc tgcaacctgg   26160
tctcctacct gggcatcctg cacgagaacc gcctcgggca gaacgtcctg cactccaccc   26220
tcaaaggga ggcgcgccgc gactacgtcc gcgactgcgt ctacctcttc ctctgctaca   26280
cgtggcagac ggccatgggg gtctggcagc agtgcctgga ggagcgcaac ctcaaggagc   26340
```

```
tggagaagct cctccggcgc gccctcaggg acctctggac gggcttcaac gagcgctcgg   26400
tggccgccgc gctggcggac atcatcttcc ccgagcgcct gctcaaaacc ctgcagcagg   26460
gcctgcccga cttcaccagc cagagcatgc tgcagaactt caggaccttc atcctggagc   26520
gctcgggcat cctgccggcc acctgctgcg cgctgcccag cgacttcgtg cccatcaggt   26580
acagggagtg cccgccgccg ctctggggcc actgctacct cttccagctg gccaactacc   26640
tcgcctacca ctcggatctc atggaagacg tgagcggcga gggcctgctc gagtgccact   26700
gccgctgcaa cctgtgcacg ccccaccgct ctctagtctg caatccgcag ctgctcagcg   26760
agagtcagat tatcggtacc ttcgagctgc agggtccctc gcccgacgaa aagtccgcgg   26820
ctccggggtt gaaactcact ccgggggctgt ggacttccgc ctacctacgc aaatttgtac   26880
ctgaagacta ccacgcccac gagatcaggt tttacgaaga ccaatcccgc ccgcccaagg   26940
cggagctcac cgcctgcgtc attacccagg gccacatcct gggccaattg caagccatca   27000
acaaagcccg ccaagagttc ttgctgaaaa agggtcgggg ggtgtacctg gaccccccagt   27060 ccggcgagga gctaaacccg ctaccccgc cgccgcccca gcagcgggac cttgcttccc   27120
aggatggcac ccagaaagaa gcagccgccg ccgccgccag catacatgct tctggaggaa   27180
gaggaggact gggacagtca ggcagaggag gtttcggacg aggacgagga ggaggagatg   27240
atggaagact gggaggagga cagcctagac gaggaagctt cagaggccga agaggtggca   27300
gacgcaacac catcaccctc ggccgcagcc ccctcgccgg cgcccccgaa atcctccgac   27360
cccagcagca gcgctataac ctccgctcct ccggcgccgg cgcccacccg cagcagaccc   27420
aaccgtagat gggacactac aggaaccggg gtcggtaagt ccaagtgccc cccagcgccg   27480
cccccgcaac aggagcaaca gcagcagcag cggcgacagg gctaccgctc gtggcgcgga   27540
cacaagaacg ccatagtcgc ctgcttgcaa gactgcgggg gcaacatctc cttcgcccgc   27600
cgcttcctgc tcttccacca cggggtggct tttccccgca atgtcctgca ttactaccgt   27660
catctctaca gcccctactg cggcggcagc ggcgacccag agggagcggc ggcagcagca   27720
gcgccagcca cagcggcgac cacctaggaa gacctccgcg ggcaagacgg cgggagccgg   27780
gagacccgcg gcggcggcgg tagcggcggc ggcgggcgca ctgcgcctct cgcccaacga   27840
acccctctcg acccgggagc tcagacacag gatcttcccc actctgtatg ctatcttcca   27900
gcagagcaga ggccaggaac aggagctcaa aataaaaaac agatctctgc gctccctcac   27960
ccgcagctgt ctgtatcaca aaagcgaaga tcagcttcgg cgcacgctgg aggacgcgga   28020
ggcactcttc agcaaatact gcgcgctgac tcttaaggac tagccgcgcg cccttctcga   28080
atttaggcgg gagaaagact acgtcatcgc cgaccgccgc ccagcccacc cagccgacat   28140
gagcaaagag attcccacgc cctacatgtg gagctaccag ccgcagatgg gactcgcggc   28200
gggagcggcc caagactact ccacccgcat gaactacatg agcgcggggc cccacatgat   28260
ctcacgggtt aatgggatcc gcgcccagcg aaaccaaata ctgctggaac aggcggccat   28320
aaccgccaca ccccgtcatg acctcaatcc ccgaaattgg cccgccgccc tcgtgtacca   28380
ggaaaccccc tctgccacca ccgtggtact tccgcgtgac acccaggccg aagtccagat   28440
gactaactca ggggcgcagc tcgcgggcgg ctttcgtcac ggggtgcggc cgcaccggcc   28500
gggtatatta cacctggcga tcagaggccg aggtattcag ctcaacgacg agtcggtgag   28560
ctcttcgctc ggtctccgtc cggacggaac cttccagatc gccggatcag gtcgctcctc   28620
attcacgcct cgccaggcgt atctgactct gcagacctcc tcctcggagc ctcgctccgg   28680
cggcatcggc accctccagt tcgtggagga gttcgtgccc tcggtctact tcaaccccctt   28740
```

```
ctcgggacct cccggacgct accccgacca gttcatcccg aactttgacg cggtgaagga    28800
ctcggcggac ggctacgact gaatgtcaag tgctgaggca gagagcgttc gcctgaaaca    28860
cctccagcac tgccgccgct tcgcctgctt tgcccgcagc tccggtgagt tctgctactt    28920
tcagctgccc gaggagcata ccgaagggcc ggcgcacggc gtccgcctaa ccacccaggg    28980
cgaggttacc tgtaccctta tccgggagtt taccctccgt cccctgctag tggagcggga    29040
gcggggttct tgtgtcataa ctatcgcctg caactgccct aaccctggat tacatcaaga    29100
tctttgttgt cacctgtgcg ctgagtataa taaacgctga gatcagactc tactggggct    29160
cctgtcgcca tcctgtgaac gccaccgtct tcacccaccc cgagcagccc caggcgaacc    29220
tcacctgcgg cctgcgtcgg agggccaaga agtacctcac ctggtacttc aacggcaccc    29280
cctttgtggt ttacaacagc ttcgaccagg acggagttgc cttgagagac gacctttccg    29340
gtctcagcta ctccattcac aagaacacca ccctccacct cttccctccc tacctgccgg    29400
gaacctacga gtgcgtcacc ggccgctgca cccacctcct ccgcctgatc gtaaaccaga    29460
cctttccggg aacacacctc ttccccagaa caggaggtga gctcaggaaa ccccctgggg    29520
cccagggcgg agacttacct tcgacccttg tggggttagg attttttatc gccgggttgc    29580
tggctctcct gatcaaagct tccttcagat ttgttctctc cctttacttt tatgaacagc    29640
tcaacttcta ataacgctac cttttctcag gaatcgagta gtaacttctc ttccgaaatc    29700
gggctgggtg tgctgcttac tctgttgatt tttttcctta tcatacttag ccttctgtgc    29760
ctcaggctcg ccgcctgctg cgcacatatc tacatctaca gccggttgct taactgctgg    29820
ggtcgccatc caagatgaac ggggctcagg tgctatgtct gctggccctg gtggcctgca    29880
gtgccgccgt caattttgag gaacccgctt gcaatgtgac tttcaagcct gagggcgcac    29940
attgcaccac tctggttaaa tgtgtgacct ctcatgaaaa actgctcatc gcctacaaaa    30000
acaaaacagg ccagatcgca gtctatagcg agtggctacc cggagaccat aataactact    30060
cagtcaccgt cttcgagggt gcggagtcta agaaattcga ttacaccttt cccttcgagg    30120
agatgtgtga tgcggtcatg tacctgtcca aacagtacaa gctgtggccc cccaccccca    30180
aggcgtgtgt ggaaaacact gggtctttct gctgtctctc tctggcaatc actgtgcttg    30240
ctctaatctg cacgctgcta tacatgagat tcaggcagag gcgaatcttt atcgatgaga    30300
aaaaaatgcc ttgatcgcta acaccggctt tctgtctgca gaatgaaagc aatcacctcc    30360
ctactaatca gcaccaccct ccttgcgatt gcccatgggt tgacacgaat cgaagtgcca    30420
gtggggtcca atgtcaccat ggtgggcccc gccggcaatt cctccctgat gtgggaaaaa    30480
tatgtccgta atcaatggga tcattactgc tctaatcgaa tctgtatcaa gcccagagcc    30540
acctgcgacg gcaaaatct aactttgatt gatgtgcaaa tgacggatgc tgggtactat    30600
tacgggcagc ggggagaaat gattaattac tggcgacccc acaaggacta catgctgcat    30660
gtagtcaagg cagtcccaac tactaccacc cccaccacta ccactcccac taccaccacc    30720
cccaccacta ccactagcac tgctactacc gctgcccgca aagctattac ccgcaaaagc    30780
accatgctta gcaccaagcc ccattctcac tcccacgccg gcgggcccac cggtgcggcc    30840
tcagaaacca ccgagctttg cttctgccaa tgcactaacg ccagcgccca cgaactgttc    30900
gacctggaga atgaggacga tgaccagctg agctccgctt gcccggtccc gctgcccgca    30960
gagccggtcg ccctgaagca gctcggtgat ccatttaatg actctcctgt ttatccctct    31020
cccgaatacc ctcccgactc taccttccac atcacgggca ccaaagaccc caacctctcc    31080
```

```
ttctacctga tgctgctgct ctgtatctct gtggtatctt ccgcgctcat gttactgggc    31140
atgttctgct gcctcatctg ccgcagaaaa agaaagtctc gctctcaggg ccaaccactg    31200
atgcccttcc cctaccccccc agattttgca gataacaaga tatgagcacg ctgctgacac   31260
taaccgcttt actcgcctgc gctctaaccc ttgtcgcttg cgaatccaga taccacaatg    31320
tcacagttgt gacaggagaa aatgttacat tcaactccac ggccgacacc cagtggtcgt    31380
ggagtggcca cggtagctat gtatacatct gcaatagctc cacctcccct agcatgtcct    31440
ctcccaagta ccactgcaat gacagcctgt tcaccctcat caacgcctcc acctcggaca    31500
atggactcta tgtaggctat gtgacacccg gtgggcaggg aaagacccac gcctacaacc    31560
tgcaagttcg ccacccctcc accaccgcca ccacctctgc cgcccctacc cgcagcagca    31620
gcagcagcag cagcagcagc agcagcagca gcagcagatt cctgacttta atcctagcca    31680
gctcaacaac caccgccacc gctgagacca cccacagctc cgcgcccgaa accacccaca    31740
cccaccaccc agagacgacc gcggcctcca gcgaccagat gtcggccaac atcaccgcct    31800
cgggtcttga acttgcttca accccaccc caaaaccagt ggatgcagcc gacgtctccg    31860
ccctcgtcaa tgactgggcg gggctgggaa tgtggtggtt cgccataggc atgatggcgc    31920
tctgcctgct tctgctctgg ctcatctgct gcctcaaccg caggcgggcc agacccatct    31980
atagacccat cattgttctc aaccccgctg atgatgggat ccatagattg gatggtctga    32040
aaaacctact tttctctttt acagtatgat aaattgagac atgcctcgca ttttcatgta    32100
cttgacactt ctcccacttt ttctggggtg ttctacgctg ccgccgtct ctcacctcga    32160 ggtagactgc ctcacaccct tcactgtcta cctgatttac ggattggtca ccctcactct    32220
catctgcagc ctaatcacag tagtcatcgc cttcatccag tgcattgact acatctgtgt    32280
gcgcctcgca tacctgagac accacccgca gtaccgagac aggaacattg cccaactcct    32340
aagactgctc taatcatgca taagactgtg atctgcctcc tcatcctcct ctccctgccc    32400
gctctcgtct catgccagcc caccacaaaa cctccacgaa aaagacatgc ctcctgtcgc    32460
ttgagccaac tgtggaatat tcccaaatgc tacaatgaaa agagcgagct ttccgaagcc    32520
tggctatatg cggtcatgtg tgtccttgtc ttctgcagca caatcttgc cctcatgatc    32580 taccccccact ttgatttggg atggaatgcg gtcgatgcca tgaattaccc tacctttccc    32640
gcgcccgata tgattccact ccgacaggtt gtggtgcccg tcgccctcaa tcaacgcccc    32700
ccatccccta cacccactga ggtcagctac tttaatctaa caggcggaga tgactgacac    32760
tctagatcta gaaatggacg gcatcggcac cgagcagcgt ctcctacaga ggcgcaagca    32820
ggcggctgaa caagagcgcc tcaatcagga gctccgagat ctcattaacc tgcaccagtg    32880
caaaaaaggc atcttttgcc tggtcaagca ggccgatgtc acctacgaga aaacggtaa    32940 cagccaccgc ctcagctaca agctgcccac ccaacgccag aagttggtgc tcatggtggg    33000
tcagaatccc atcaccgtca cccagcactc ggtggagacc gaggggtgtc tgcactcccc    33060
ctgtcagggt ccggaagacc tctgcaccct ggtaaagacc ctgtgtggtc ttagagattt    33120 aatcccctt aactaatcaa acactggaat caataaaaag aatcacttac tttaaatcag    33180
tcagcaggtc tctgtccact ttattcagca gcacctcctt cccctcctcc caactctggt    33240
actccaaacg cctcctggcg gcaaacttcc tccacaccct gaagggaatg tcagattctt    33300
gctcctgtcc ctccgcaccc actatcttca tgttgttgca gatgaagcgc gccaaaacgt    33360
ctgacgagac cttcaacccc gtgtacccct atgcacggaa aaacgggcct ccctccgttc    33420 cttttcctcac ccctcccttc gtgtcccccg acggatttca agaaagcccc ccagggtcc    33480
```

```
tgtctctgcg cctgtcagag cccctggtca cttcccacgg catgcttgcc ctgaaaatgg   33540
gaaatggcct ctccctggat gacgccggca acctcacctc tcaagatgtc accaccgtca   33600
cccctcccct caaaaaaacc aagaccaacc tcagcctcca gacctcagcc cccctgaccg   33660
ttagctctgg gtccctcacc gtcgcggccg ccgctccact ggcggtggcc ggcacctctc   33720
tcaccatgca atctcaggcc cccttgacgg tgcaagatgc aaaactgggt ctggccaccc   33780
agggacccct gaccgtgtct gaaggcaaac tcaccttgca gacatcggct ccactgacgg   33840
ccgccgacag cagcactctc actgttggca ccacaccgcc aatcagtgtg agcagtggaa   33900
gtctaggctt agatatggaa gaccccatgt atactcacga tggaaaactg ggaatcagaa   33960
ttggtggccc actgcaagta gtagacagct tgcacacact cactgtagtt actggaaacg   34020
gaataactgt agctaacaat gcccttcaaa ctaaagttgc gggtgccctg ggttatgact   34080
catctggcaa tctagaattg cgagccgcag ggggtatgcg aattaacaca gggggtcaac   34140
tcattcttga tgtggcttat ccatttgatg ctcagaacaa tctcagcctt agactcggcc   34200
agggaccttt atatgtgaac accaatcaca acctagattt aaattgcaac agaggtctga   34260
ccacaaccac cagcagtaac acaaccaaac ttgaaactaa aatcgattcg ggcttagact   34320
ataacgccaa tgggctatc attgctaaac ttggcactgg gttaacccttt gacaacacag   34380 gtgccataac tgtgggaaac actggggatg acaaactcac tctgtggact accccagatc   34440
cctctcctaa ctgcagaatt cacgcagaca aagactgcaa gtttactcta gtcctgacta   34500
agtgtggaag tcaaattctg gcctccgtcg ccgccctggc ggtgtctgga aacctatcat   34560
caatgacagg cactgtctcc agcgttacca tctttctcag attcgatcag aatggagttc   34620
ttatggaaaa ttcctcgcta gacaaggagt actggaactt cagaaatggt aattccacca   34680
atgccacccc ctacaccaat gcggttgggt tcatgcccaa cctcagcgcc taccccaaaa   34740
cccagagtca aactgcaaaa aacaacattg taagtgaggt ttacttacat ggggacaaat   34800
ctaaacccat gatccttacc attaccctta atggcacaaa tgaatccagt gaaactagtc   34860
aggtgagtca ctactccatg tcatttacat ggtcgaggga cagtgggaaa tatgccaccg   34920
aaacctttgc caccaactct tttaccttct cctacattgc tgaacaataa agaagcataa   34980
cgctgctgtt catttgtaat caagtgttac ttttttattt ttcaattaca acagaatcat   35040
tcaagtcatt ctccatttag cttaatagac cccagtagtg caaagcccca tactagctta   35100
tttcagcaat tgggagaagt actcgcctac atgggggtag agtcataatc gtgcatcagg   35160 ataggcggt ggtgctgcag cagcgcgcga ataaactgct gccgccgccg ctccgtcctg   35220
caggaataca acatggcagt ggtctcctca gcgatgattc gcaccgcccg cagcataagg   35280
cgccttgtcc tccgggcaca gcagcgcacc ctgatctcac ttaaatcagc acagtaactg   35340
cagcacagca ccacaatatt gttcaaaatc ccacagtgca aggcgctgta tccaaagctc   35400
atggcgggga ccacagaacc cacgtggcca tcataccaca agcgcaggta gattaagtgg   35460
cgacccctca taaacacgct ggacataaac attacctctt ttggcatgtt gtaattcacc   35520
acctcccggt accatataaa cctctgatta aacatggcgc catccaccac catcctaaac   35580
cagctggcca aaacctgccc gccggctata cactgcaggg aaccgggact ggaacaatga   35640
cagtggagag cccaggactc gtaaccatgg atcatcatgc tcgtcatgat atcaatgttg   35700
gcacaacaca ggcacacgtg catacacttc ctcaggatta caagctcctc ccgcgttaga   35760
accatatccc agggaacaac ccattcctga atcagcgtaa atcccacact gcagggaaga   35820
```

-continued

| | |
|---|---|
| cctcgcacgt aactcacgtt gtgcattgtc aaagtgttac attcgggcag cagcggatga | 35880 |
| tcctccagta tggtagcgcg ggtttctgtc tcaaaaggag gtagacgatc cctactgtac | 35940 |
| ggagtgcgcc gagacaaccg agatcgtgtt ggtcgtagtg tcatgccaaa tggaacgccg | 36000 |
| gacgtagtca tatttcctga agtcttggcg cgccagaccc gagtcttacc aggaaaattt | 36060 |
| taaaaaagat tcctcaacgc agcaccagca ccaacacctg tcagtgtaaa atgccaagcg | 36120 |
| ccgagcgagt atatatagga ataaaaagtg acgtaaacgg ttaaagtcca gaaaacgccc | 36180 |
| agaaaaaccg cacgcgaacc tacgccccga aacgaaagcc aaaaaacagt gaacacgccc | 36240 |
| tttcggcgtc aacttccgct ttcccacggt acgtcacttc cgcatatagt aaaactacgc | 36300 |
| tacccaacat gcaagaagcc acgccccaaa acacgtcaca cctcccggcc cgccccgcgc | 36360 |
| cgccgctcct ccccgccccg ccccgctccg cccacctcat tatcatattg gcttcaatcc | 36420 |
| aaaataaggt atattattga tgatg | 36445 |

<210> SEQ ID NO 10
<211> LENGTH: 2302
<212> TYPE: DNA
<213> ORGANISM: Ebola virus
<220> FEATURE:
<223> OTHER INFORMATION: Ebola virus Zaire wild type transmembrane
      envelope glycoprotein (GP) (EBOV GP Zaire wild type)

<400> SEQUENCE: 10

| | |
|---|---|
| cgtcgtcgac acgtgtgatc agatatcgcg gccgctctag accaggccct ggatcgatcc | 60 |
| aacaacacaa tgggcgttac aggaatattg cagttacctc gtgatcgatt caagaggaca | 120 |
| tcattctttc tttgggtaat tatccttttc caaagaacat tttccatccc acttggagtc | 180 |
| atccacaata gcacattaca ggttagtgat gtcgacaaac tagtttgtcg tgacaaactg | 240 |
| tcatccacaa atcaattgag atcagttgga ctgaatctcg aagggaatgg agtggcaact | 300 |
| gacgtgccat ctgcaactaa agatgggggc ttcaggtccg tgtgtccacc aaaggtggtc | 360 |
| aattatgaag ctggtgaatg ggctgaaaac tgctacaatc ttgaaatcaa aaaacctgac | 420 |
| gggagtgagt gtctaccagc agcgccagac gggattcggg gcttcccccg gtgccggtat | 480 |
| gtgcacaaag tatcaggaac gggaccgtgt gccggagact tgccttcca taagagggt | 540 |
| gctttcttcc tgtatgatcg acttgcttcc acagttatct accgaggaac gactttcgct | 600 |
| gaaggtgtcg ttgcatttct gatactgccc caagctaaga aggacttctt cagctcacac | 660 |
| cccttgagag agccggtcaa tgcaacggag gaccgtctag tggctacta ttctaccaca | 720 |
| attagatatc aggctaccgg tttttggaacc aatgagacag agtacttgtt cgaggttgac | 780 |
| aatttgacct acgtccaact tgaatcaaga ttcacaccac agtttctgct ccagctgaat | 840 |
| gagacaatat atacaagtgg aaaaggagc aataccacgg aaaactaat ttggaaggtc | 900 |
| aaccccgaaa ttgatacaac aatcggggag tgggccttct gggaaactaa aaaaaacctc | 960 |
| actagaaaaa ttcgcagtga agagttgtct ttcacagttg tatcaaacgg agccaaaaac | 1020 |
| atcagtggtc agagtccggc gcgaacttct tccgacccag ggaccaacac aacaactgaa | 1080 |
| gaccacaaaa tcatggcttc agaaaattc tctgcaatgg ttcaagtgca cagtcaagga | 1140 |
| agggaagctg cagtgtcgca tctaacaacc cttgccacaa tctccacgag tccccaatcc | 1200 |
| ctcacaacca aaccaggtcc ggacaacagc acccataata cacccgtgta taaacttgac | 1260 |
| atctctgagg caactcaagt tgaacaacat caccgcagaa cagacaacga cagcacagcc | 1320 |
| tccgacactc cctctgccac gaccgcagcc ggacccccaa aagcagagaa caccaacacg | 1380 |

| | |
|---|---|
| agcaagagca ctgacttcct ggaccccgcc accacaacaa gtccccaaaa ccacagcgag | 1440 |
| accgctggca acaacaacac tcatcaccaa gataccggag aagagagtgc cagcagcggg | 1500 |
| aagctaggct taattaccaa tactattgct ggagtcgcag gactgatcac aggcgggaga | 1560 |
| agaactcgaa gagaagcaat tgtcaatgct caacccaaat gcaaccctaa tttacattac | 1620 |
| tggactactc aggatgaagg tgctgcaatc ggactggcct ggataccata tttcgggcca | 1680 |
| gcagccgagg gaatttacat agaggggcta atgcacaatc aagatggttt aatctgtggg | 1740 |
| ttgagacagc tggccaacga gacgactcaa gctcttcaac tgttcctgag agccacaact | 1800 |
| gagctacgac cctttcaat cctcaaccgt aaggcaattg atttcttgct gcagcgatgg | 1860 |
| ggcggcacat gccacattct gggaccggac tgctgtatcg aaccacatga ttggaccaag | 1920 |
| aacataacag acaaaattga tcagattatt catgattttg ttgataaaac ccttccggac | 1980 |
| caggggaca atgacaattg gtggacagga tggagacaat ggataccggc aggtattgga | 2040 |
| gttacaggcg ttgtaattgc agttatcgct ttattctgta tatgcaaatt tgtctttag | 2100 |
| tttttcttca gattgcttca tggaaaagct cagcctcaaa tcaatgaaac caggatttaa | 2160 |
| ttatatggat tacttgaatc taagattact tgacaaatga taatataata cactggagct | 2220 |
| ttaaacatag ccaatgtgat tctaactcct ttaaactcac agttaatcat aaacaaggtt | 2280 |
| tgaggtaccg agctcgaatt ga | 2302 |

<210> SEQ ID NO 11
<211> LENGTH: 2031
<212> TYPE: DNA
<213> ORGANISM: Artificial Sequence
<220> FEATURE:
<223> OTHER INFORMATION: synthetic Ebola virus Sudan/Gulu codon optimized transmembrane envelope glycoprotein (GP) (EBOV GP Sudan/Gulu codon optimized)

<400> SEQUENCE: 11

| | |
|---|---|
| atggagggcc tgagcctgct gcagctgccc agggacaagt tcaggaagag cagcttcttc | 60 |
| gtgtgggtga tcatcctgtt ccagaaggcc ttcagcatgc ccctgggcgt ggtgaccaac | 120 |
| agcaccctgg aggtgaccga gatcgaccag ctggtgtgca aggaccacct ggccagcacc | 180 |
| gaccagctga agagcgtggg cctgaacctg gagggcagcg gcgtgagcac cgacatcccc | 240 |
| agcgccacca gaggtggggg cttcaggagc ggcgtgcctc ccaaggtggt gagctacgag | 300 |
| gccggcgagt gggccgagaa ctgctacaac ctggagatca agaagcccga cggcagcgag | 360 |
| tgcctgcctc ctcctcctga cggcgtgagg ggcttcccca ggtgcaggta cgtgcacaag | 420 |
| gcccagggca ccggccctg ccccggcgac tacgccttcc acaaggacgg cgccttcttc | 480 |
| ctgtacgaca gcctggccag caccgtgatc tacaggggcg tgaacttcgc cgagggcgtg | 540 |
| atcgccttcc tgatcctggc caagcccaag gagaccttcc tgcagagccc tcccatcagg | 600 |
| gaggccgtga actacaccga gaacaccagc agctactacg ccaccagcta tctagagtac | 660 |
| gagatcgaga acttcggcgc ccagcacagc accaccctgt tcaagatcga caacaacacc | 720 |
| ttcgtgaggc tggacaggcc ccacaccccct cagttcctgt tccagctgaa cgacaccatc | 780 |
| cacctgcacc agcagctgag caacaccacc ggcaggctga tctggaccct ggacgccaac | 840 |
| atcaacgccg acatcggcga gtgggccttc tgggagaaca gaagaacct gagcgagcag | 900 |
| ctgaggggcg aggagctgag cttcgaggcc ctgagcctga acgagaccga ggacgacgac | 960 |
| gccgccagca cagggatcac caagggcagg atcagcgaca gggccaccag gaagtacagc | 1020 |
| gacctggtgc ccaagaacag ccccggcatg gtgcccctgc acatccccga gggcgagacc | 1080 |

```
accctgccca gccagaacag caccgagggc aggagggtgg gcgtgaacac ccaggagacc    1140
atcaccgaga ccgccgccac catcatcggc accaacggca accacatgca gatcagcacc    1200
atcggcatca ggcccagcag cagccagatc ccagcagca gccccaccac cgccccctagc    1260 cccgaggccc agaccccac cacccacacc agcggaccca gcgtgatggc caccgaggag    1320
cccaccaccc ctcccggcag cagccccgga cccaccaccg aggcccctac cctgaccacc    1380
cctgagaaca tcaccaccgc cgtgaagacc gtgctgcccc aggagagcac cagcaacggc    1440
ctgatcacca gcaccgtgac cggcatcctg ggcagcctgg gcctgaggaa gaggagcagg    1500
aggcagacca caccaaggc caccggcaag tgcaaccca acctgcacta ctggaccgcc    1560
caggagcagc acaacgccgc cggcatcgcc tggattccct acttcggccc cggcgccgag    1620
ggcatctaca ccgagggcct gatgcacaac agaacgccc tggtgtgcgg cctgaggcag    1680
ctggccaacg agaccaccca ggccctgcag ctgttcctga gggccaccac cgagctgagg    1740
acctacacca tcctgaacag gaaggccatc gacttcctgc tgaggaggtg gggcggcacc    1800
tgcaggattc tgggccccga ctgctgcatc gagccccacg actggaccaa gaacatcacc    1860
gacaagatca accagatcat ccacgacttc atcgacaacc tctgcccaa ccaggacaac    1920 gacgacaact ggtggaccgg ctggcggcag tggataccctg ccggcatcgg catcaccggc    1980
atcatcatcg ccatcatcgc tctgctgtgc gtgtgcaagc tgctgtgctg a            2031
```

<210> SEQ ID NO 12  
<211> LENGTH: 2043  
<212> TYPE: DNA  
<213> ORGANISM: Artificial Sequence  
<220> FEATURE:  
<223> OTHER INFORMATION: synthetic Marburg virus Angola codon optimized transmembrane envelope glycoprotein (GP) (Marburg virus Angola codon optimized)

<400> SEQUENCE: 12

```
atgaagacca cctgcctgct gatcagcctg atcctgatcc agggcgtgaa gaccctgccc     60
atcctggaga tcgccagcaa catccagccc cagaacgtgg acagcgtgtg cagcggcacc    120
ctgcagaaga ccgaggacgt gcacctgatg ggcttcaccc tgagcggcca gaaggtggcc    180
gacagccctc tggaggccag caagaggtgg gccttcaggg ccggcgtgcc ccccaagaac    240
gtggagtaca ccgagggcga ggaggccaag acctgctaca cactcagcgt gaccgacccc    300
agcggcaaga gcctgctgct ggaccctccc accaacatca gggactaccc taagtgcaag    360
accatccacc acatccaggg ccagaaccct acgcccagg gcatcgccct gcacctgtgg    420
ggcgccttct tcctgtacga caggatcgcc agcaccacca tgtacagagg aaaagtgttc    480
acagagggaa acatcgctgc tatgatcgtg aacaagaccg tgcataagat gatcttcagc    540
agacagggac agggatatag acatatgaac ctgacatcca aaacaagta ctggacaagc    600 agcaacggaa cacagacaaa cgatacagga tgtttttggaa cactgcagga atacaactcc    660
accaagaacc agacatgtgc ccctagcaag aagcctctgc ctctgcctac agctcatcct    720
gaagtgaagc tgcatccac aagcacagat gccacaaagc tgaacacaac agatcctaat    780
agcgacgacg aggatctgac aacaagcgga tccggatccg agaacagga accttataca    840 acaagcgacg ctgctacaaa acagggactg tcctccacaa tgcctcctac acctagccct    900
cagcctagca cacctcagca gggaggcaac aacacaaacc attccagggg agtggtgaca    960
gaacctggaa agacaaacac aacagcccag cctagcatgc tcctcataa cacaacaaca   1020
```

```
atcagcacaa acaacacctc caagcacaat ctgagcacac ctagcgtgcc tattcagaat    1080
gccaccaact acaacacaca gtccacagcc cctgaaaacg aacagacctc cgccccttcc    1140
aaaacaaccc tgctgcctac agaaaaccct acaacagcca gagcacaaa cagcacaaag     1200
agccctacaa caacagtgcc taacacaaca aacaagtata gcacaagccc tagccctaca    1260
cctaattcca cagctcagca tctggtgtat tttagaagaa agagaaacat cctgtggaga    1320
gaaggagata tgttcccttt tctggatgga ctgatcaacg ctcctatcga ttttgatcct    1380
gtgcctaaca caaagacaat ctttgatgaa agcagcagca gcggagcctc cgccgaagaa    1440
gatcagcatg cctcccctaa catcagcctg acactgagct attttcctaa ggtgaacgaa    1500
aacacagccc attccggaga aaacgaaaac gattgtgatg ccgaactgag aatctggagc    1560
gtgcaggaag atgatctggc cgccggactg agctggatcc cttttttggg gcccggaatt    1620
gaaggactgt acaccgccgg cctgatcaag aaccagaaca acctggtgtg caggctgagg    1680
aggctggcca accagaccgc caagagcctg gagctgctgc tgagggtgac caccgaggag    1740
aggaccttca gcctgatcaa caggcacgcc atcgacttcc tgctggctag gtggggcggc    1800
acctgcaagg tgctgggccc cgactgctgc atcggcatcg aggacctgag caggaacatc    1860
agcgagcaga tcgaccagat caagaaggac gagcagaagg agggcaccgg ctggggcctg    1920
ggcggcaagt ggtggaccag cgactgggga gtgctgacaa acctgggaat cctgctgctg    1980
ctgagcattg ccgtgctcat tgctctgtcc tgtatctgta gaatctttac caagtacatc    2040
gga                                                                  2043
```

<210> SEQ ID NO 13  
<211> LENGTH: 2028  
<212> TYPE: DNA  
<213> ORGANISM: Ebola virus  
<220> FEATURE:  
<223> OTHER INFORMATION: Ebola virus Sudan/Gulu wild type transmembrane envelope glycoprotein (GP) (EBOV GP Sudan/Gulu wild type)

<400> SEQUENCE: 13

```
atgggggtc ttagcctact ccaattgccc agggacaaat tcggaaaag ctctttcttt     60
gtttgggtca tcatcttatt ccaaaaggcc ttttccatgc ctttgggtgt tgtgactaac    120
agcactttag aagtaacaga gattgaccag ctagtctgca aggatcatct tgcatctact    180
gaccagctga atcagttgg tctcaacctc gaggggagcg gagtatctac tgatatccca    240
tctgcaacaa agcgttgggg cttcagatct ggtgttcctc caaggtggt cagctatgaa    300
gcgggagaat gggctgaaaa ttgctacaat cttgaaataa agaagccgga cgggagcgaa    360
tgcttacccc caccgccaga tggtgtcaga ggctttccaa ggtgccgcta tgttcacaaa    420
gcccaaggaa ccgggccctg cccaggtgac tacgcctttc acaaggatgg agctttcttc    480
ctctatgaca ggctggcttc aactgtaatt tacagaggag tcaattttgc tgaggggta    540
attgcattct tgatattggc taaaccaaaa gaaacgttcc ttcagtcacc cccattcga    600
gaggcagtaa actacactga aatacatca agttattatg ccacatccta cttggagtat    660
gaaatcgaaa attttggtgc tcaacactcc acgaccattt tcaaaattga caataatact    720
tttgttcgtc tggacaggcc ccacacgcct cagttccttt tccagctgaa tgataccatt    780
caccttcacc aacagttgag taatacaact gggagactaa tttggacact agatgctaat    840
atcaatgctg atattggtga atgggctttt tggaaaaata aaaaaatct ctccgaacaa    900
ctacgtggag aagagctgtc tttcgaagct ttatcgctca cgagacaga agacgatgat    960
```

```
gcggcatcgt cgagaattac aaagggaaga atctccgacc gggccaccag gaagtattcg   1020
gacctggttc caaagaattc ccctgggatg gttccattgc ataccaga aggggaaaca    1080 acattgccgt ctcagaattc gacagaaggt cgaagagtag gtgtgaacac tcaggagacc   1140
attacagaga cagctgcaac aattataggc actaacggca accatatgca gatctccacc   1200
atcgggataa gaccgagctc cagccaaatc ccgagttcct caccgaccac ggcaccaagc   1260
cctgaggctc agaccccac aacccacaca tcaggtccat cagtgatggc caccgaggaa    1320
ccaacaacac caccgggaag ctcccccggc ccaacaacag aagcacccac tctcaccacc   1380
ccagaaaata taacaacagc ggttaaaact gtcctgccac aggagtccac aagcaacggt   1440
ctaataactt caacagtaac agggattctt gggagtcttg ggcttcgaaa acgcagcaga   1500
agacaaacta acaccaaagc cacgggtaag tgcaatccca acttacacta ctggactgca   1560
caagaacaac ataatgctgc tgggattgcc tggatcccgt actttggacc gggtgcggaa   1620
ggcatataca ctgaaggcct gatgcataac caaaatgcct tagtctgtgg acttaggcaa   1680
cttgcaaatg aaacaactca agctctgcag ctttttcttaa gagccacaac ggagctgcgg   1740
acatatacca tactcaatag gaaggccata gatttccttc tgcgacgatg gggcgggaca   1800
tgcaggatcc tgggaccaga ttgttgcatt gagccacatg attggacaaa aaacatcact   1860
gataaaatca accaaatcat ccatgatttc atcgacaacc ccttacctaa tcaggataat   1920
gatgataatt ggtggacggg ctggagacag tggatccctg caggaatagg cattactgga   1980
attattattg caattattgc tcttctttgc gtttgcaagc tgctttgc              2028
```

<210> SEQ ID NO 14
<211> LENGTH: 2031
<212> TYPE: DNA
<213> ORGANISM: Artificial Sequence
<220> FEATURE:
<223> OTHER INFORMATION: synthetic Ebola virus Zaire codon optimized
      transmembrane envelope glycoprotein (GP) (EBOV GP
      Zaire codon optimized)

<400> SEQUENCE: 14

```
atgggcgtga ccggcatcct gcagctgccc agggacaggt tcaagaggac cagcttcttc     60
ctgtgggtga tcatcctgtt ccagagggacc ttcagcatcc ccctgggcgt gatccacaac   120
agcaccctgc aggtgagcga cgtggacaag ctggtgtgca gggacaagct gagcagcacc   180
aaccagctga ggagcgtggg cctgaacctg gagggcaacg cgtggccac cgacgtgccc   240 agcgccacca gaggtggggg cttcaggagc ggcgtgcctc ccaaggtggt gaactacgag   300
gccggcgagt gggccgagaa ctgctacaac ctggagatca agaagcccga cggcagcgag   360
tgcctgcccg ccgcccctga cggcatcagg ggcttcccca ggtgcaggta cgtgcacaag   420
gtgagcggca ccggcccctg cgccggcgac ttcgccttcc acaaggaggg cgccttcttc   480
ctgtacgaca ggctggccag caccgtgatc tacaggggca ccaccttcgc cgagggcgtg   540
gtggccttcc tgatcctgcc ccaggccaag aaggacttct cagcagcca ccctctgagg   600 gagcccgtga cgccaccga ggaccccagc agcggctact acagcaccac catcaggtac   660
caggccaccg gcttcggcac caacgagacc gagtacctgt cgaggtgga caacctgacc   720 tacgtgcagc tggagtctag attcacccct cagttcctgc tgcagctgaa cgagaccatc   780
tacaccagcg gcaagaggag caacaccacc ggcaagctga tctggaaggt gaaccccgag   840
atcgacacca ccatcggcga gtgggccttc tgggagacca agaagaacct gaccaggaag   900
```

```
atcaggagcg aggagctgag cttcaccgtc gtgagcaacg gggccaagaa catcagcggc      960
cagagccccg ccaggaccag cagcgacccc ggcaccaaca ccaccaccga ggaccacaag     1020
atcatggcca gcgagaacag cagcgccatg gtgcaggtgc acagccaggg cagggaggcc     1080
gccgtgagcc acctgaccac cctggccacc atcagcacca gccctcagtc tttaaccacc     1140
aagcccggcc ccgacaacag cacccacaac acccctgtgt acaagctgga catcagcgag     1200
gccacccagg tggagcagca ccacaggagg accgacaacg acagcaccgc cagcgacacc     1260
ccttccgcca ccaccgccgc cggccctccg aaggccgaga acaccaacac cagcaagagc     1320
accgactttc tggatcccgc caccaccacc agccctcaga accacagcga gaccgccggc     1380
aacaacaaca cccaccacca ggacaccggc gaggagagcg ccagcagcgg caagctgggc     1440
ctgatcacca acaccatcgc cggcgtggcc ggcctgatca ccggcggcag gaggaccagg     1500
agggaggcca tcgtgaacgc ccagcccaag tgcaaccca acctgcacta ctggaccacc     1560
caggacgagg gcgccgccat cggcctggcc tggattccct acttcggccc cgccgccgag     1620
ggcatctaca tcgagggcct gatgcacaac caggacggcc tgatctgcgg cctgaggcag     1680
ctggccaacg agaccaccca ggccctgcag ctgttcctga gggccaccac cgagctgagg     1740
accttcagca tcctgaacag gaaggccatc gacttcctgc tgcagaggtg gggcggcacc     1800
tgccacatcc tgggccccga ctgctgcatc gagccccacg actggaccaa gaacatcacc     1860
gacaagatcg accagatcat ccacgacttc gtggacaaga ccctgccaga ccagggcgac     1920
aacgacaact ggtggaccgg ctggcggcag tggatacctg ccggcatcgg cgtgaccggc     1980
gtggtgatcg ccgtgatcgc tctgttctgc atctgcaagt tcgtgttctg a              2031
```